US012655114B2

(12) United States Patent
Zhang et al.

(10) Patent No.: US 12,655,114 B2
(45) Date of Patent: Jun. 16, 2026

(54) IONIZABLE LIPID COMPOUNDS AND LIPID NANOPARTICLE COMPOSITIONS

(71) Applicant: SunVax mRNA Therapeutics Inc., Beverly, MA (US)

(72) Inventors: Libin Zhang, Lynnfield, MA (US); Yingzhong Li, Reading, MA (US)

(73) Assignee: SunVax mRNA Therapeutics Inc., Beverly, MA (US)

( * ) Notice: Subject to any disclaimer, the term of this patent is extended or adjusted under 35 U.S.C. 154(b) by 0 days.

(21) Appl. No.: 18/296,742

(22) Filed: Apr. 6, 2023

(65) Prior Publication Data

US 2023/0322689 A1 Oct. 12, 2023

Related U.S. Application Data

(60) Provisional application No. 63/429,468, filed on Dec. 1, 2022, provisional application No. 63/329,200, filed on Apr. 8, 2022.

(51) Int. Cl.
*C07D 251/04* (2006.01)
*B82Y 40/00* (2011.01)
*C07C 229/12* (2006.01)

(52) U.S. Cl.
CPC ............ *C07D 251/04* (2013.01); *B82Y 40/00* (2013.01); *C07C 229/12* (2013.01)

(58) Field of Classification Search
None
See application file for complete search history.

(56) References Cited

U.S. PATENT DOCUMENTS

| | | | |
|---|---|---|---|
| 2,615,887 | A | 10/1952 | Zerner et al. |
| 3,323,884 | A | 6/1967 | Thompson et al. |
| 3,676,143 | A | 7/1972 | Himmelmann et al. |
| 9,339,461 | B2 | 5/2016 | Quay et al. |
| 9,499,763 | B2 | 11/2016 | Loper et al. |
| 2005/0238556 | A1 | 10/2005 | Pakulski et al. |
| 2012/0277289 | A1 | 11/2012 | Fam et al. |
| 2015/0119488 | A1 | 4/2015 | Jin |
| 2015/0258022 | A1 | 9/2015 | Navarro Y Garcia et al. |
| 2016/0264744 | A1 | 9/2016 | Boday et al. |

FOREIGN PATENT DOCUMENTS

| | | | |
|---|---|---|---|
| CN | 101674853 | A | 3/2010 |
| CN | 102665761 | A | 9/2012 |
| CN | 103881790 | A | 6/2014 |
| CN | 101941952 | B | 4/2015 |
| CN | 104684543 | A | 6/2015 |
| CN | 103706397 | B | 7/2015 |
| CN | 111574467 | A | 8/2020 |
| CN | 114904002 | A | 8/2022 |
| CN | 114904003 | A | 8/2022 |
| CN | 114904004 | A | 8/2022 |
| DE | 1148866 | B | 5/1963 |
| DE | 1942562 | A1 | 4/1971 |
| DE | 3140635 | A1 | 4/1983 |
| EP | 0008186 | A1 | 2/1980 |
| FR | 2864964 | A1 | 7/2005 |
| JP | S6263570 | A | 3/1987 |
| JP | 2008247749 | A | 10/2008 |
| JP | 2014189668 | A | 10/2014 |
| KR | 20140069931 | A | 6/2014 |
| WO | 2003082809 | A1 | 10/2003 |
| WO | 2008/095069 | A2 | 8/2008 |
| WO | 2013/063468 | A1 | 5/2013 |
| WO | 2013/128003 | A1 | 9/2013 |
| WO | 2014/028487 | A1 | 2/2014 |
| WO | 2014/179562 | A1 | 11/2014 |
| WO | 2015/184256 | A2 | 12/2015 |
| WO | 2017/112865 | A1 | 6/2017 |
| WO | 2021/077066 | A1 | 4/2021 |
| WO | 2022170833 | A1 | 8/2022 |
| WO | 2022170834 | A1 | 8/2022 |
| WO | 2022170835 | A1 | 8/2022 |
| WO | 2023133089 | A1 | 7/2023 |
| WO | 2023/142167 | A1 | 8/2023 |
| WO | WO2023142167 | * | 8/2023 |

OTHER PUBLICATIONS

Chemical Abstract Registry No. 1833441-61-4, indexed in the Registry File on STN CAS Online Dec. 20, 2015.*
Chemical Abstract Registry No. 137499-90-2, indexed in the Registry File on STN CAS Online Nov. 22, 1991.*
Choi et al., Single-cell, real-time detection of oxidative stress induced in*Escherichia coli* by the antimicrobial peptide CM15. PNAS, 2015, 112, E303-E310.*
CAPLUS printout of "Choi et al., Single-cell, real-time detection of oxidative stress induced in *Escherichia coli* by the antimicrobial peptide CM15. PNAS, 2015, 112, E303-E310."*
Ren Long-Fan et al, "Synthesis and Properties of Hydroxyl-terminated Hyperbranched Poly Isocyanurate-ester Retanning Agents"; Journal of the American Leather Chemists Association, (Jan. 1, 2017), pp. 240-249, vol. 112, No. 07.
Sato et al, "Original plate for lithographic plate having multifunctional polymerization inhibitor-containing image-recording layer and method for platemaking", Database Caplus, (Apr. 27, 2014), retrieved from STNext accession No. 160524312; database accession No. 2014488614 abstract; compounds 1585160-97-9, Chemical Abstracts Service, Columbus, OH.
Provisional Opinion Accompanying the Partial Search Result in PCT/US2023/017777, Jul. 27, 2023 (13 pages).
Written Opinion and International Search Report for International Application No. PCT/US2023/017777 mailed Nov. 3, 2023. (34 pages).
Neubacher et al: "In Situ Cyclization of Proteins (INCYPRO): Cross-Link Derivatization Modulates Protein Stability", The Journal of Organic Chemistry, vol. 85, No. 3, Dec. 2, 2019, pp. 1476-1483.

(Continued)

*Primary Examiner* — Po-Chih Chen
(74) *Attorney, Agent, or Firm* — ROTHWELL, FIGG, ERNST & MANBECK, P.C.

(57) ABSTRACT

Novel ionizable lipids, compositions, and methods of using the novel ionizable lipids and compositions are disclosed. Lipid nanoparticle compositions include a novel ionizable lipid as well as additional lipids such as phospholipids, structural lipids, and PEG lipids. Lipid nanoparticle compositions further including biologically active agents such as mRNA or DNA are useful in the delivery of biologically active agents to mammalian cells or organs.

21 Claims, 29 Drawing Sheets

(56) References Cited

OTHER PUBLICATIONS

Huang et al: "Synthesis, characterization and complexation behavior investigations of novel starburst-like tris-crown ethers", New Journal of Chemistry, vol. 29, No. 12, Jan. 1, 2005, p. 1616.
Feuerstein et al: "Palladium-tetraphosphine catalysed allylic substitution in water", Tetrahedron Letters, vol. 42, No. 12, Jan. 25, 2001, pp. 2313-2315.
Leadbeater et al: "Microwave-assisted Mannich-type three-component reactions", Molecular Diversity, vol. 7, No. 2-4, Jan. 1, 2003, pp. 135-144.
Petasis et al: "A New and Practical Synthesis of .alpha.-Amino Acids from Alkenyl Boronic Acids", Journal of the American Chemical Society, American Chemical Society, vol. 119, No. 2, Jan. 1, 1997, pp. 445-446.
Database Registry, Aurora Fine Chemicals LLC "Hexadecanamide, N-(1-oxohexadecyl)-N-(1-phenylpropyl)-" Chemical Abstracts Service, Columbus, OH, US; Aug. 31, 2021, retrieved from STNext Database accession No. 2685752-45-6.
Database Registry, Aurora Fine Chemicals LLC "Decanoic acid, 2-(1-oxohexadecyl) (1-phenylpropyl)amino]-" Chemical Abstracts Service, Columbus, OH, US; Aug. 27, 2021, retrieved from STNext Database accession No. 2683006-24-6.
Tremblay-Morin et al: "Lewis acid-catalyzed Mannich type reactions with potassium organotrifluoroborates", Tetrahedron Letters, vol. 45, No. 17, Apr. 19, 2004, pp. 3471-3474.
Stachurski et al: "Effect of self-assembly on antimicrobial activity of double-chain short cationic lipopeptides", Bioorganic & Medicinal Chemistry, vol. 27, No. 23, Oct. 17, 2019.
Fouad et al: "Two decades of recent advances of Ugi reactions: synthetic and pharmaceutical applications", RSC Advances, vol. 10, No. 70, Jan. 1, 2020, pp. 42644-42681.
Lin et al: "Rapid synthesis of diketopiperazine macroarrays via Ugi four-component reactions on planar solid supports", Chemical Communications, No. 27, Jan. 1, 2006, p. 2884.
Mercer et al: "Design, synthesis, and solution behaviour of small polyamines as switchable water additives", Green Chemistry, vol. 14, No. 3, Jan. 1, 2012, p. 832.
Pérez-Labrada et al: "Multicomponent Synthesis of Ugi-Type Ceramide Analogues and Neoglycolipids from Lipidic Isocyanides", The Journal of Organic Chemistry, vol. 77, No. (10), Apr. 25, 2012, pp. 4660-4670 (Abstract).
Furuta et al. "Nutrient-Based Chemical Library as a Source of Energy Metabolism Modulators", ACS Chem Biol., vol. 14, No. (9), Aug. 22, 2019, pp. 1860-1865, p. S3, S27-S30.
Douy, A. et al: "New Amphipathic Lipopeptides. 1 Synthesis and Mesomorphic Structures of Lipopeptides with Polysarcosine Peptidic Chains." Makromol. Chem., vol. 187, No. (3), Mar. 31, 1986, pp. 465-483 (Abstract).
Previdi et al: "Synthesis and Antileishmanial Activity of Some Functionalized Peptoids" J. Braz. Chem. Soc., vol. 30, No. (6), Feb. 7, 2019, p. 1334-1340.
Molla et al: Combinatorial Synthesis of a Lipidoid Library by Thiolactone Chemistry: in Vitro Screening and in Vivo Validation for siRNA Delivery, Bioconjugate Chem., vol. 31, No. (3), Feb. 18, 2020, pp. 852-860.
Galetti et al: "Multicomponent Synthesis of Acylated Short Peptoids with Antifungal Activity against Plant Pathogens", Molecular Diversity, vol. 16, No. (1), Sep. 16, 2011, pp. 113-119. S1-S2 (Abstract).
Chrisment et al: "Proton Transfers on Amphiphilic Molecules. A Nonionic Alkyllipopeptide in Dimethyl Sulfoxide", Langmuir, vol. 12, No. (10), Dec. 31, 1996, pp. 2441-2445.

* cited by examiner

TAb-9

TAb-13

TP1A11

TP3G11

TP4G11

TP3F11

(D7)

(C7)

(E6)

(E2)

IONIZABLE LIPID COMPOUNDS AND LIPID NANOPARTICLE COMPOSITIONS

CROSS-REFERENCE TO RELATED APPLICATIONS

This application claims priority benefit of U.S. provisional application Nos. 63/329,200, filed Apr. 8, 2022 and 63/429,468, filed Dec. 1, 2022, the disclosures of which are incorporated herein by reference in their entireties.

TECHNICAL FIELD

The present disclosure provides novel compounds, compositions comprising such compounds, and methods to deliver one or more biologically active agents to mammalian cells or organs.

BACKGROUND

Delivery of biologically active substances such as small molecule drugs, proteins, and nucleic acids, including DNA and mRNA, is a medical challenge. In particular, the delivery of nucleic acids to cells is made difficult by the relative instability and low cell permeability of such molecules. Furthermore, components of lipid nanoparticle delivery systems (LNPs) approved by FDA are currently synthesized using a multiple step method. Thus, there exists a need to develop compounds, compositions, and methods for improving the delivery of biologically active molecules, including nucleic acids, into cells or organs and to synthesize such compounds in a time efficient, cost effective, and high-throughput manner.

SUMMARY OF THE INVENTION

The present disclosure provides novel compounds and compositions and methods involving the same.

In one aspect, the present disclosure provides compounds of Formula (I):

(I)

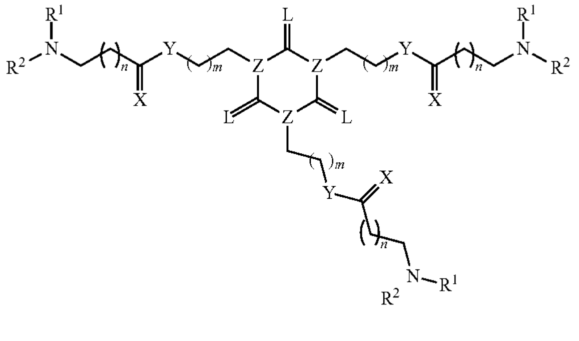

or a salt or isomer thereof, wherein m and n are each independently an integer from 0-10, e.g., 0, 1, 2, 3, 4, 5, 6, 7, 8, 9, or 10, or any subrange selected from within the range of 0-10, e.g., 2-9, 3-8, 4-7, 1-5, 1-4, 5-9, etc.;

each $R^1$ and $R^2$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

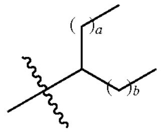,
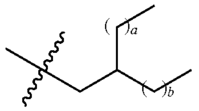,

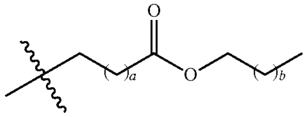,

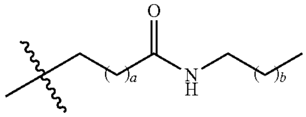,

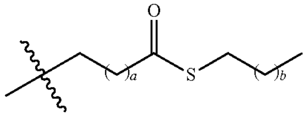,

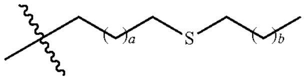,

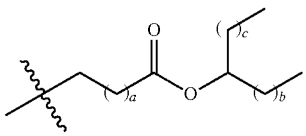,

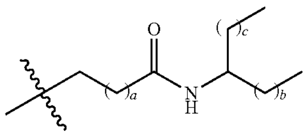,

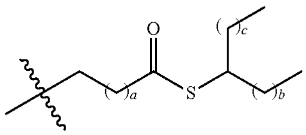,

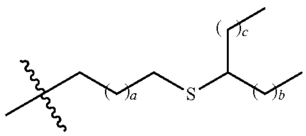,

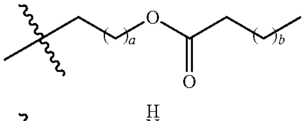,

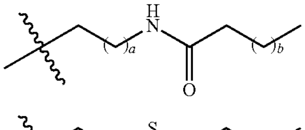,

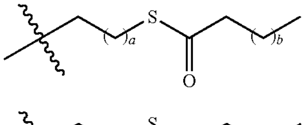,

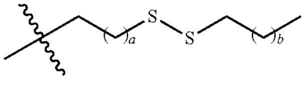,

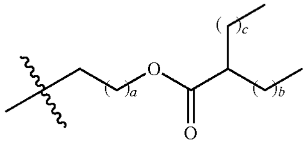,

-continued

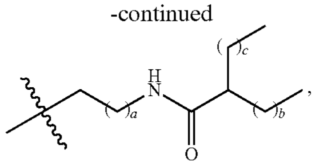

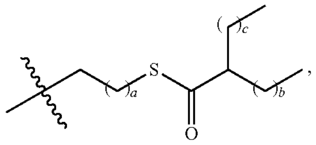

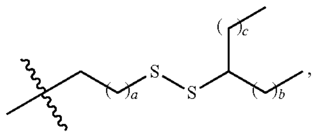

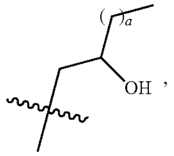

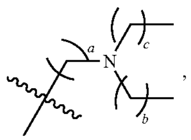

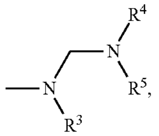

each a, b and c in $R^1$ or $R^2$ is independently an integer selected from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24 each $R^3$, $R^4$ and $R^5$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

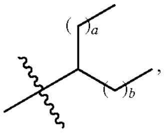

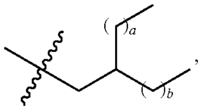

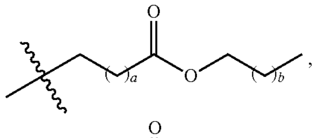

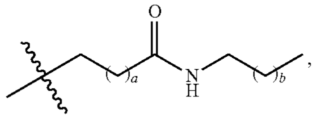

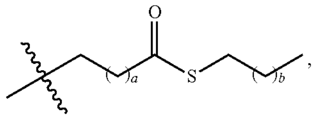

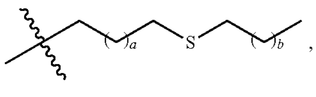

-continued

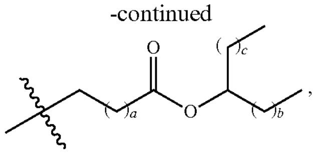

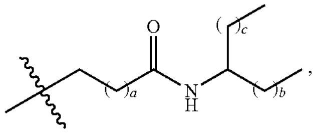

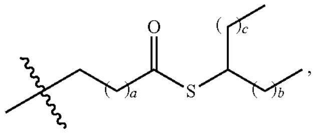

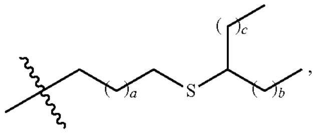

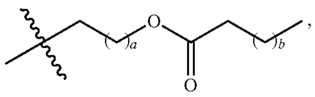

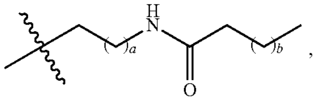

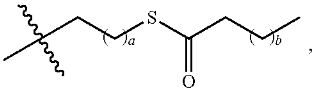

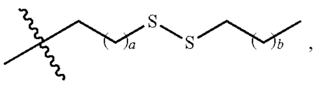

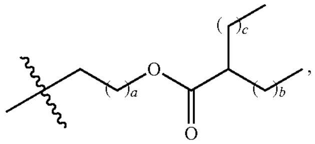

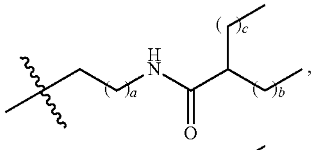

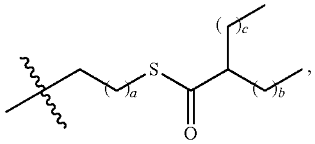

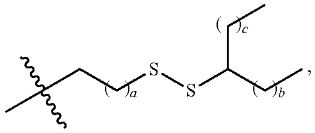

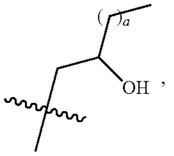

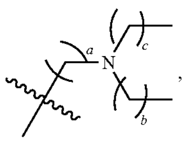

a, b and c in $R^3$, $R^4$ and $R^5$ are each independently an integer from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24;

each X is independently selected from $CH_2$, NH, O, or S;

each Y is independently selected from $CH_2$, NH, O, or S;

each Z is independently selected from CH or N; and each L is independently selected from $CH_2$, NH, O, or S.

In certain aspects, compounds of Formula I may comprise, for example, the following formula:

I-1

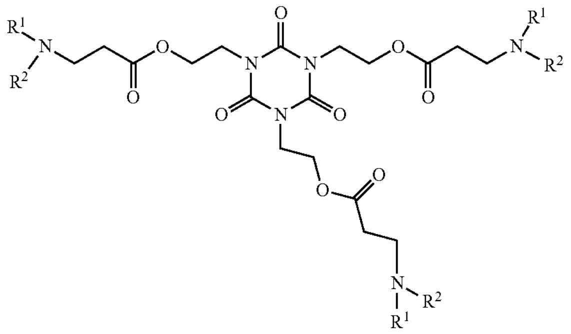

or a salt or isomer thereof, wherein each $R^1$ and $R^2$ are as defined above.

General synthesis route for the synthesis of compounds of Formula I-1:

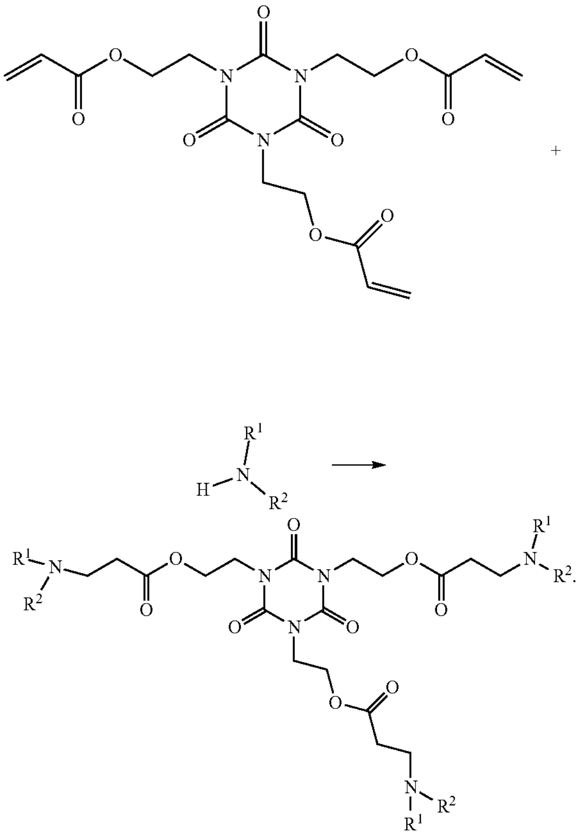

In certain aspects, compounds of Formula I may include, for example, the following compounds:

(Ia)

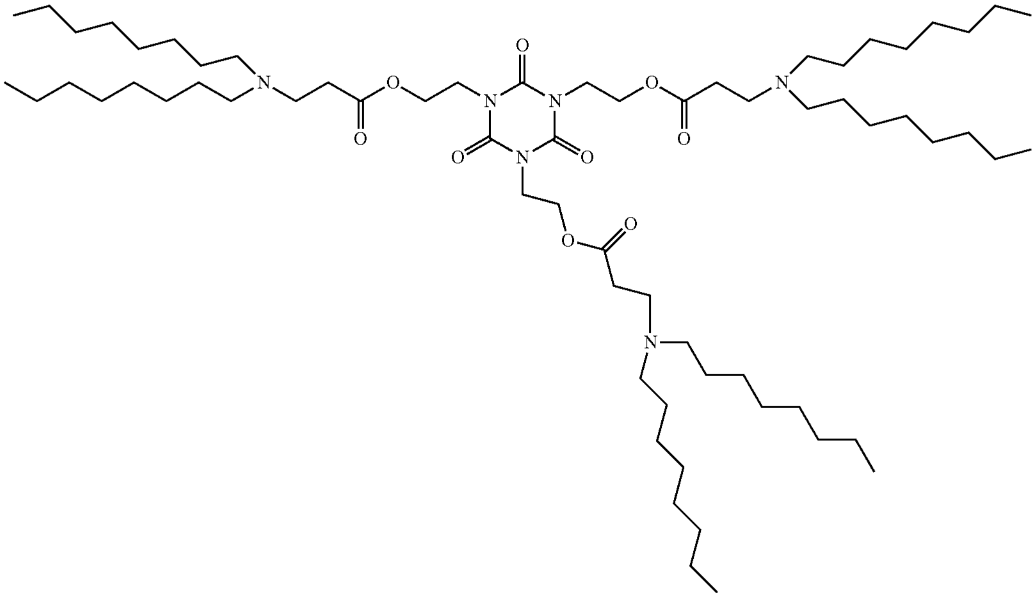

also referred to as C7;

(Ib)

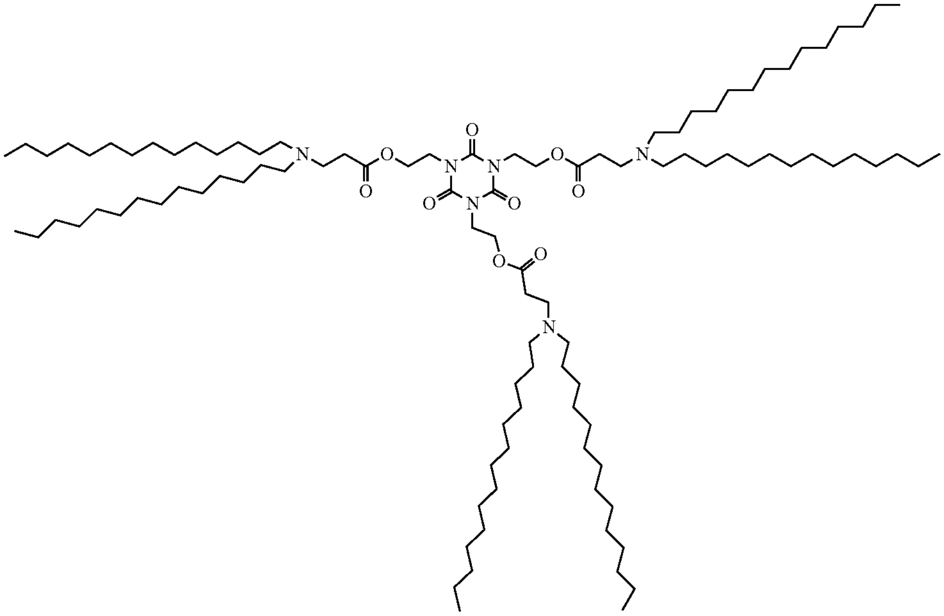

also referred to as D7.

In another aspect, the present disclosure provides compounds of Formula (II):

(II)

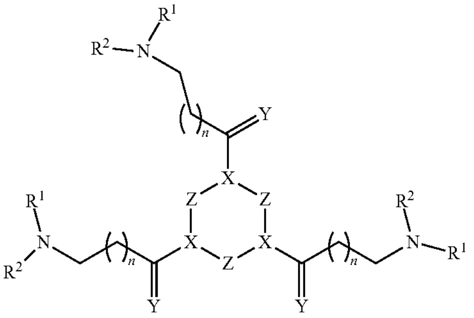

or a salt or isomer thereof, wherein each n is independently an integer from 0-10, e.g., 0, 1, 2, 3, 4, 5, 6, 7, 8, 9, or 10, or any subrange selected from within the range of 0-10, e.g., 2-9, 3-8, 4-7, 1-5, 1-4, 5-9, etc.;

each $R^1$ and $R^2$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

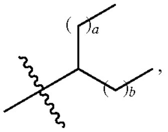

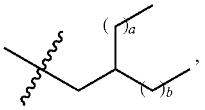

-continued

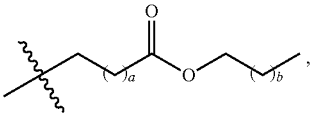

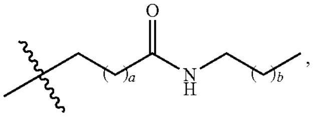

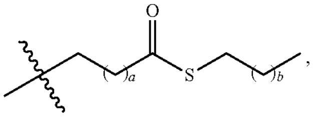

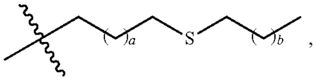

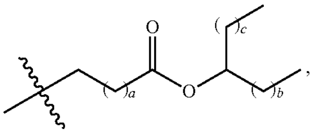

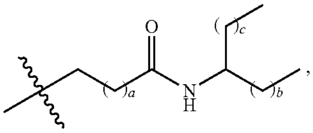

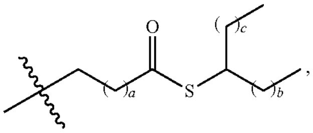

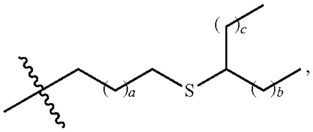

-continued
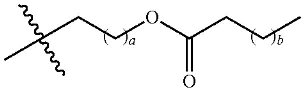,
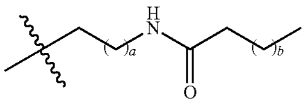,
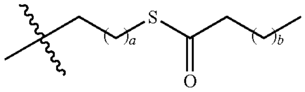,
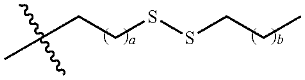,
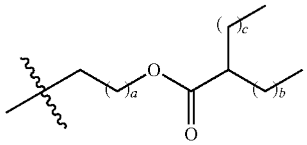,
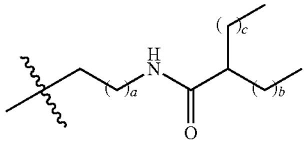,
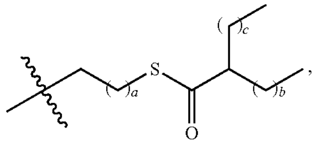,
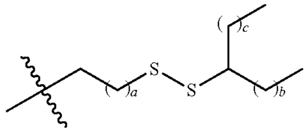,
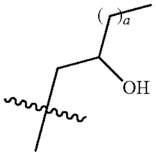, 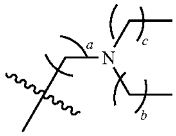,
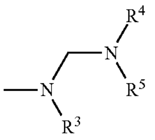
a, b and c in $R^1$ or $R^2$ are each independently an integer from 0-24;
each $R^3$, $R^4$ and $R^5$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,
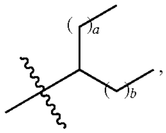, 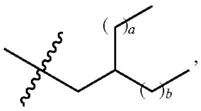,
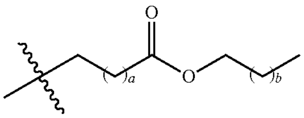,
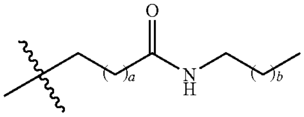,
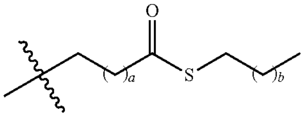,
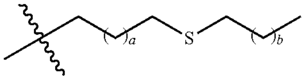,
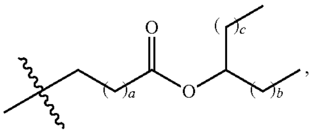,
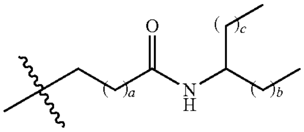,
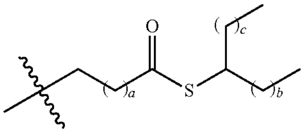,
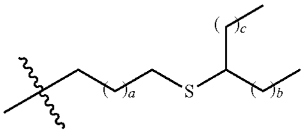, -continued

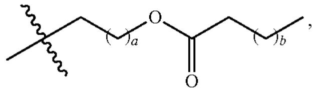,

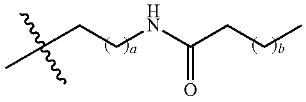,

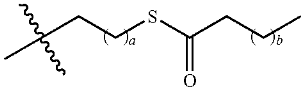,

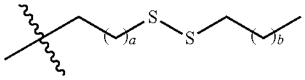,

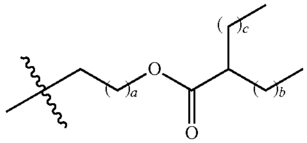,

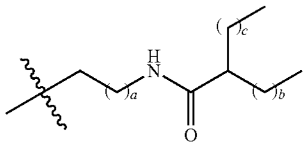,

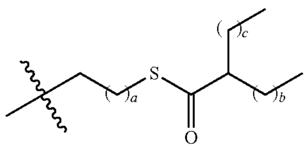,

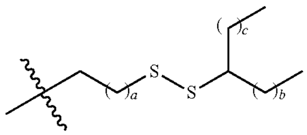,

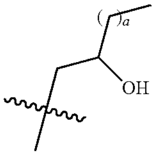, 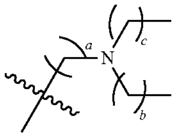, a, b and c in $R^3$, $R^4$ or $R^5$ are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24;

each X is independently selected from CH, or N;

each Y is independently selected from $CH_2$, NH, O, or S; and each Z is independently selected from $CH_2$, NH, O, or S.

In certain aspects, compounds of Formula II may comprise, for example, the following formula:

II-1

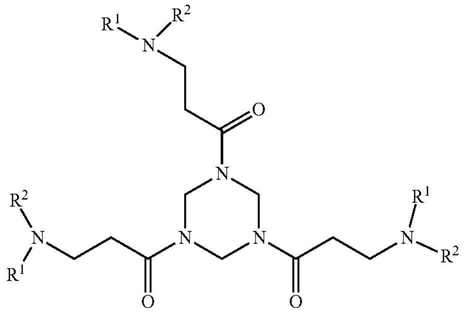

or a salt or isomer thereof, wherein each $R^1$ and $R^2$ are as defined above.

General synthesis route for the synthesis of compounds of Formula II-1:

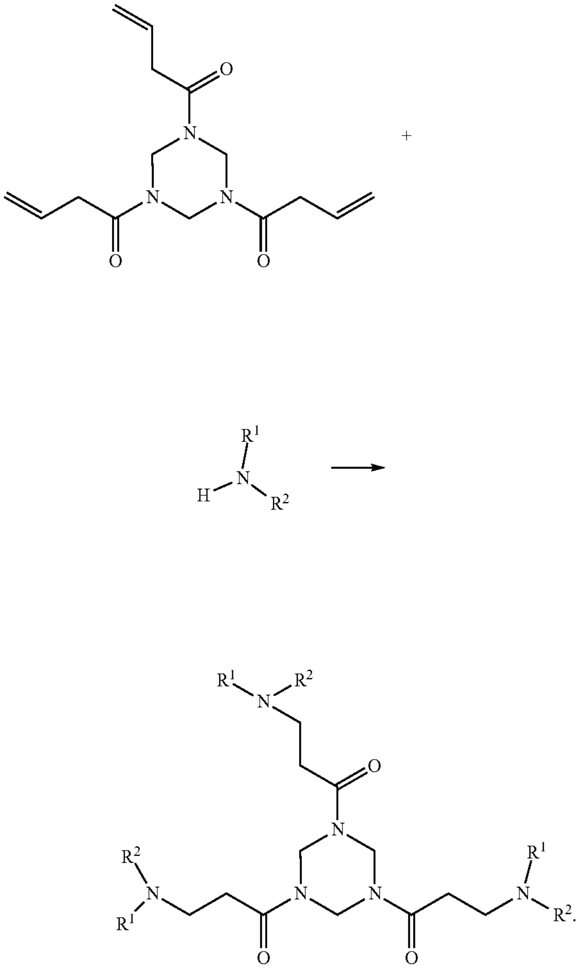

In certain aspects, compounds of Formula II may include, for example, the following compounds:
(IIa)
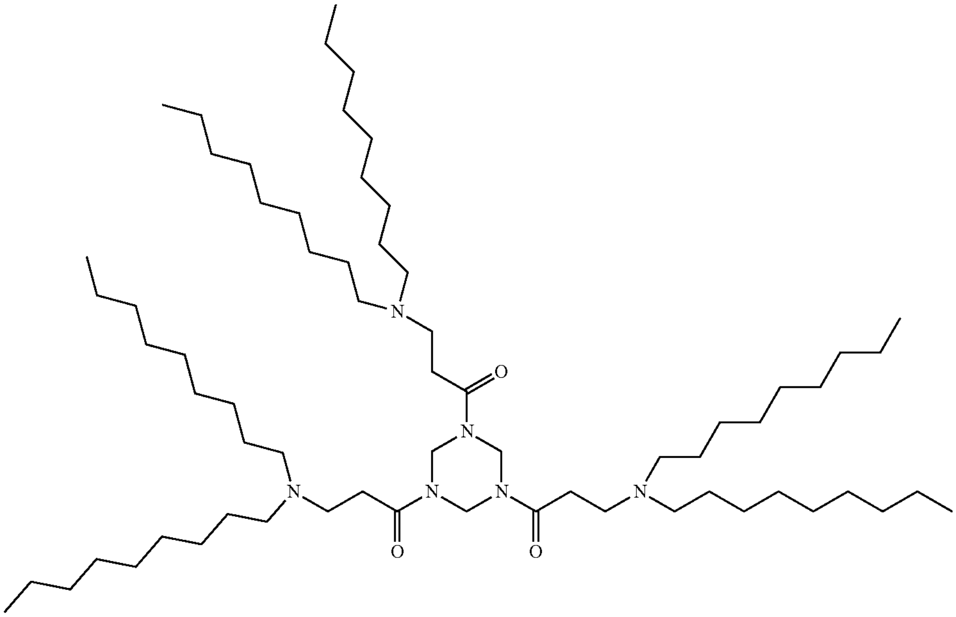
;
also referred to as TAb-9 or E2;
(IIb)
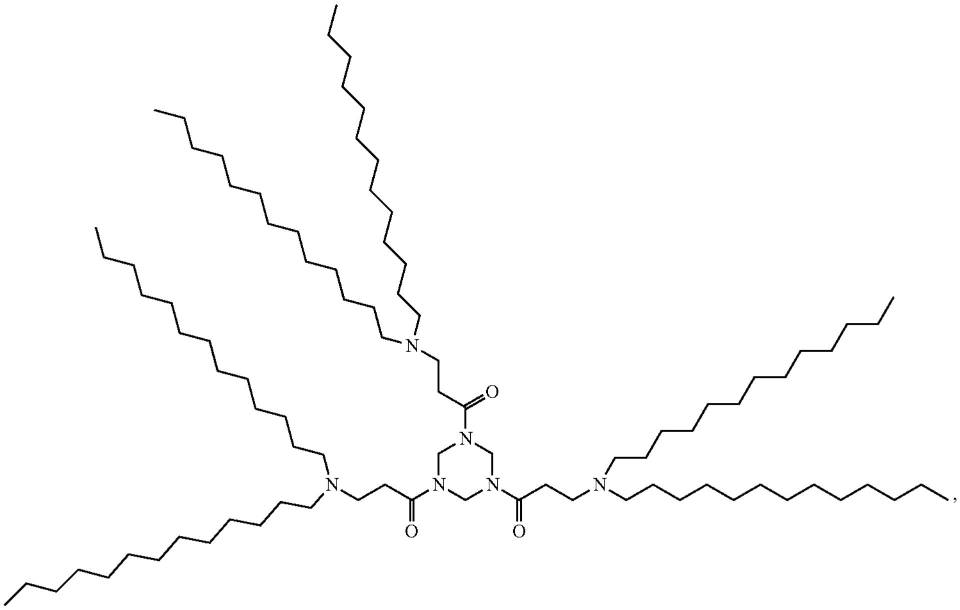
,
also referred to as TAb-13 or E6;
or a salt or isomer thereof.

In another aspect, the present disclosure provides compounds of Formula (III):

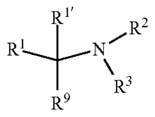

(III)

or a salt or isomer thereof, wherein each $R^1$, $R^{1'}$, $R^2$ and $R^3$ are independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

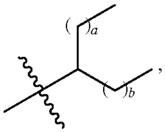,
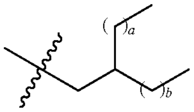,
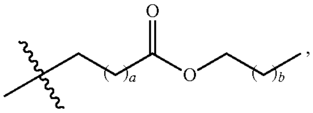,
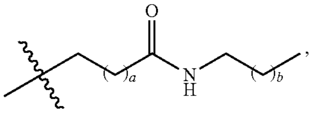,
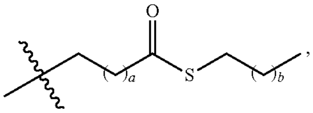,
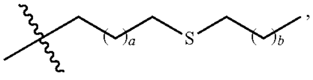,
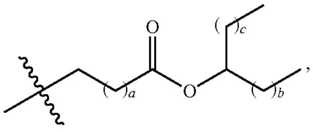,
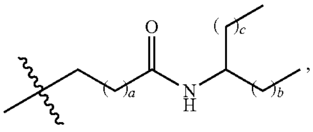,
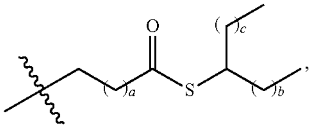,
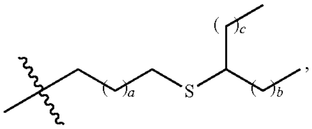,
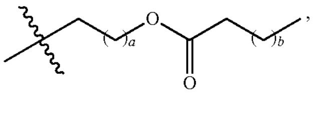, -continued

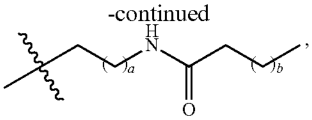,
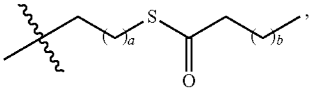,
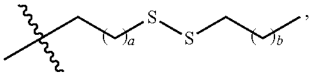,
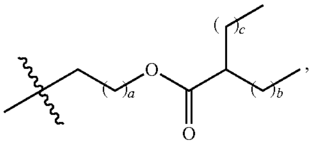,
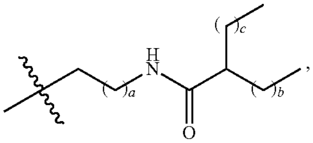,
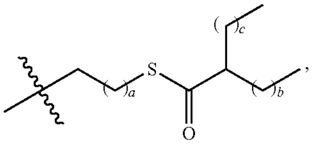,
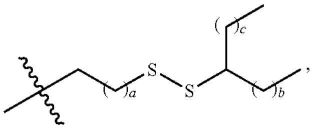,
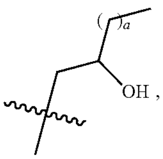,
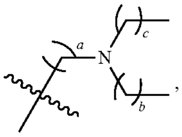,
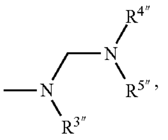, a, b and c are each independently an integer from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24;

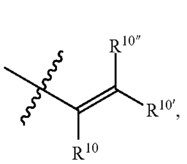,
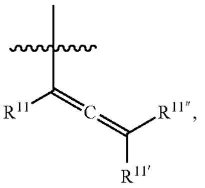, or
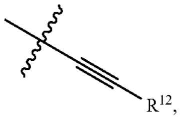, each $R^9$ is independently selected from wherein each $R^{10}$, $R^{10'}$, $R^{10''}$, $R^{11}$, $R^{11'}$, $R^{11''}$, and $R^{12}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

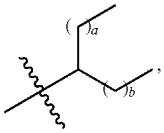, 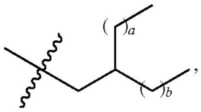,

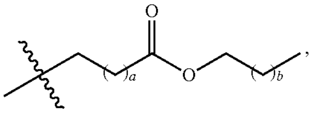,

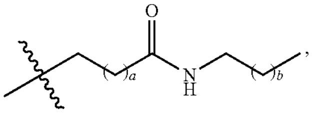,

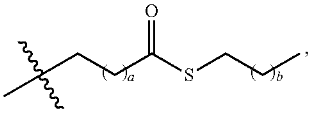,

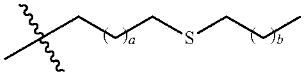,

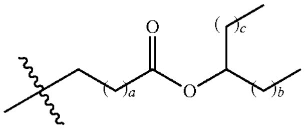,

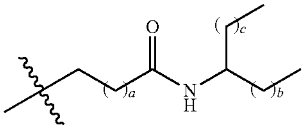,

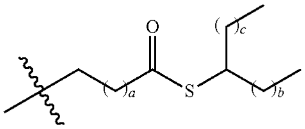,

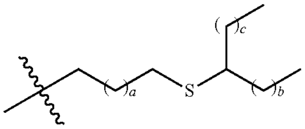,

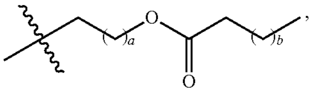,

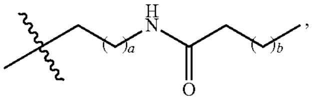,

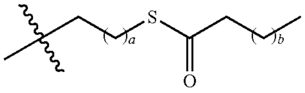,

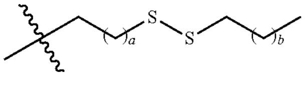,

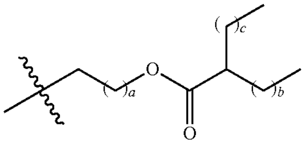,

-continued

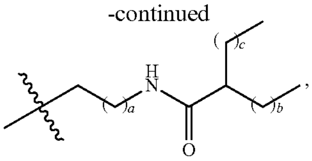,

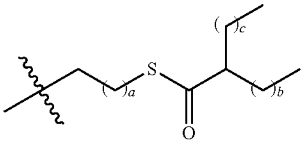,

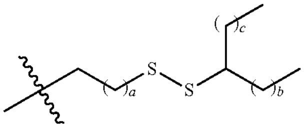,

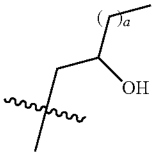, 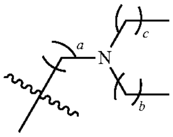, 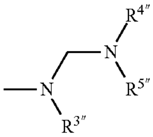, a, b and c are each independently an integer from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24;

$R^{3''}$, $R^{4''}$, and $R^{5''}$ are independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

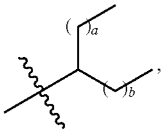, 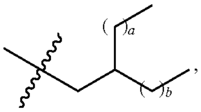,

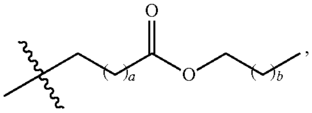,

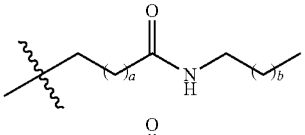,

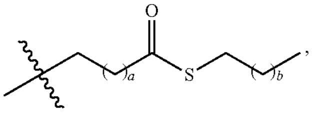,

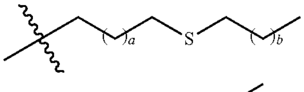,

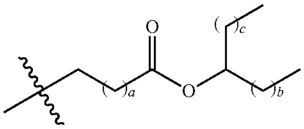,

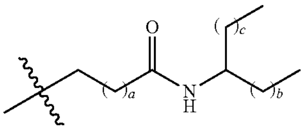,

-continued

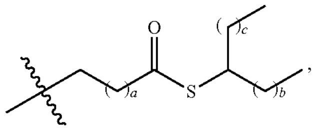

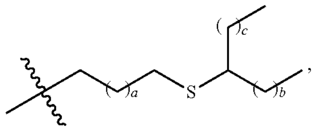

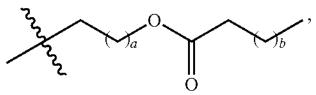

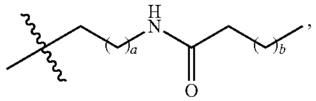

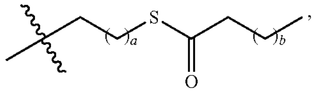

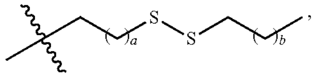

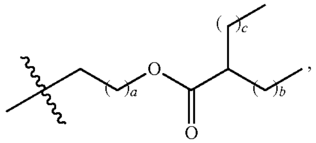

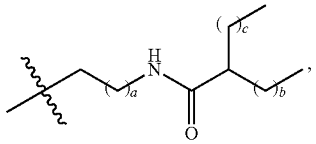

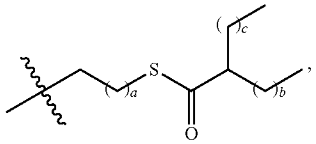

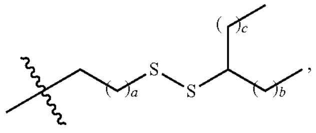

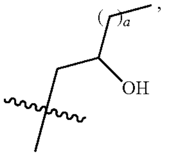

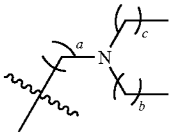

a, b and c are each independently an integer from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24.

In certain aspects, compounds of Formula III may comprise, for example, the following formula:

(III-1)

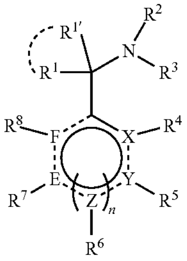

or a salt or isomer thereof, each $R^1$, $R^{1'}$, $R^2$, $R^3$, $R^4$, $R^5$, $R^6$, $R^7$ and $R^8$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

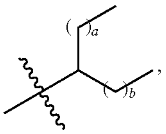

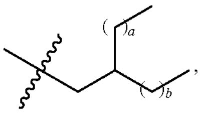

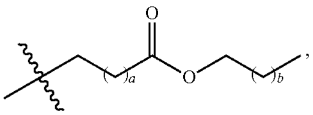

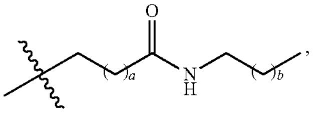

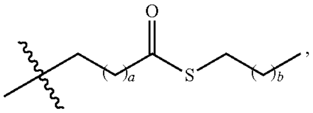

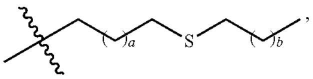

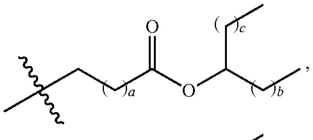

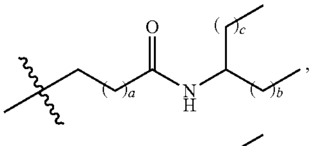

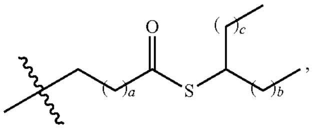

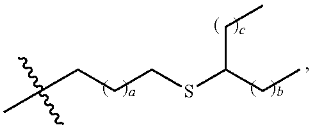

-continued
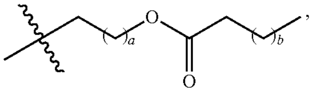
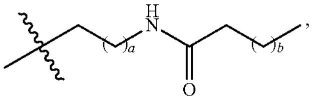
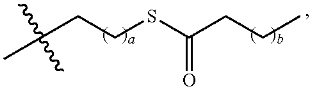
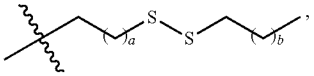
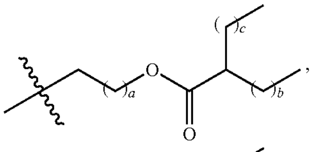
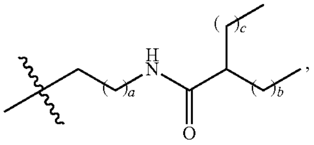
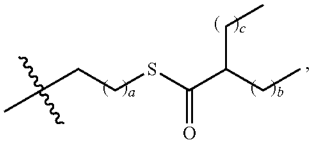
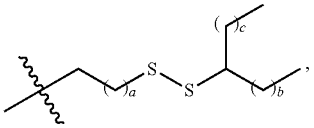
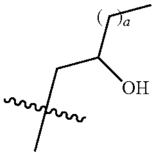 , 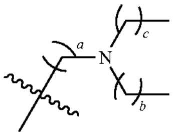 , 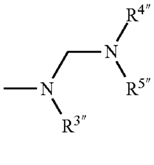
a, b and c are each independently an integer from 0-24;
each $R^{3''}$, $R^{4''}$, and $R^{5''}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,
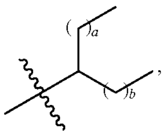 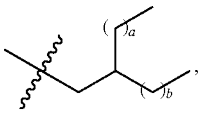
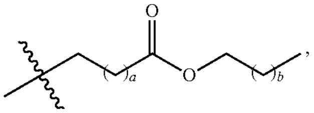
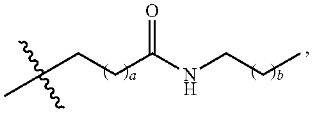
-continued
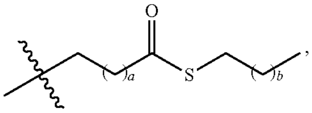
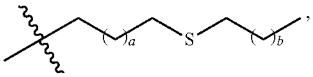
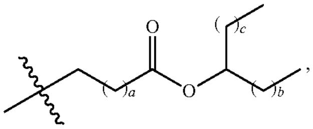
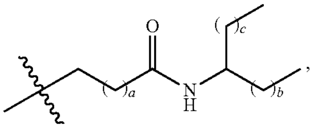
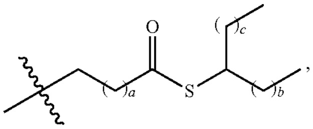
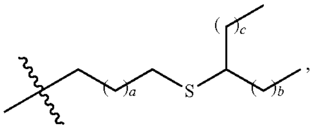
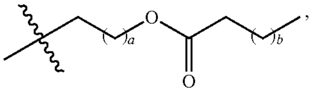
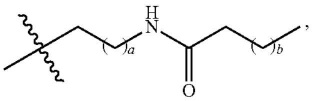
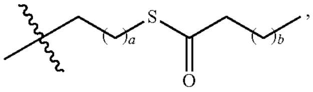
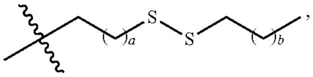
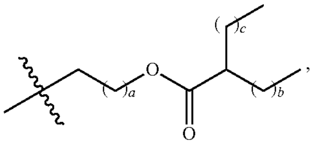
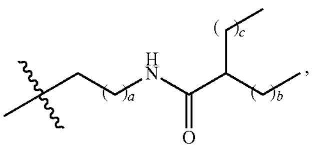
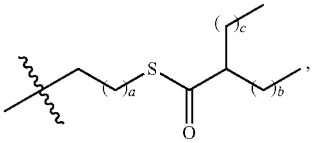
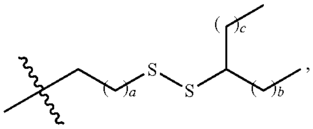

-continued

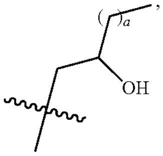

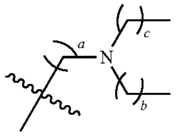

a, b and c are each independently an integer from 0-24; or wherein each $R^4$, $R^5$, $R^6$, $R^7$ and $R^8$ is independently:

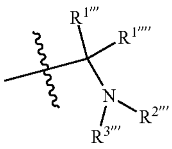

wherein $R^{1'''}$, $R^{1''''}$, $R^{2'''}$ and $R^{3'''}$ are independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

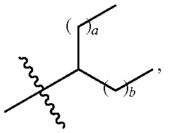

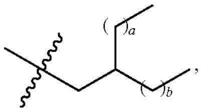

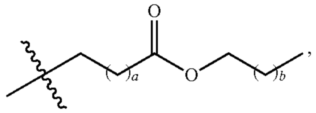

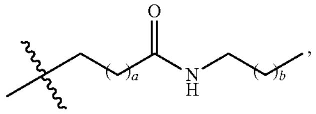

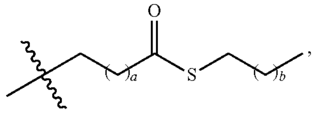

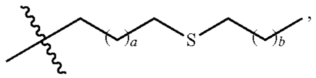

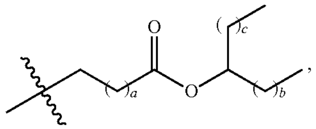

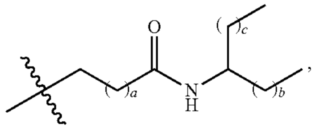

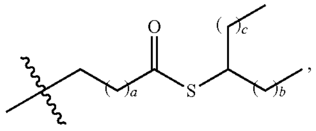

-continued

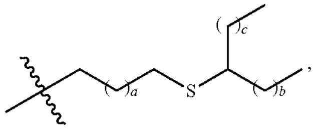

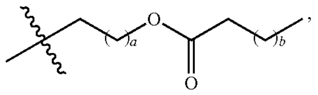

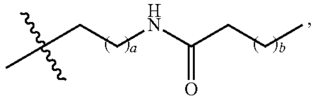

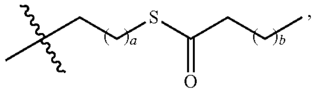

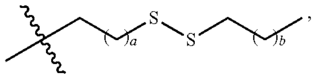

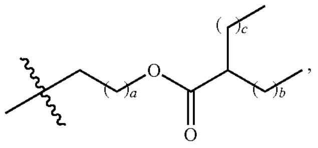

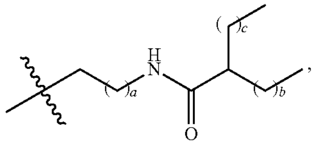

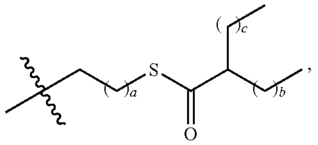

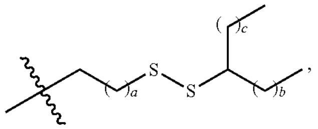

each a, b, and c are independently an integer selected from 0-24;

each X is independently CH, N, O or S;

each Y is independently CH, N, O or S each Z is independently CH, N, O or S each F is independently CH, N, O or S and each E is independently CH, N, O or S.

General synthesis route for the synthesis of compounds of Formula III-1:

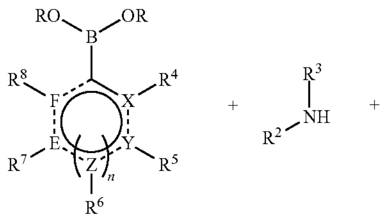

-continued
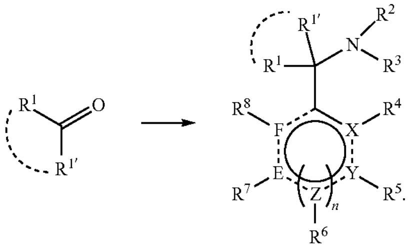
In certain aspects, compounds of Formula III may include, for example, the following compounds:
(IIIa)
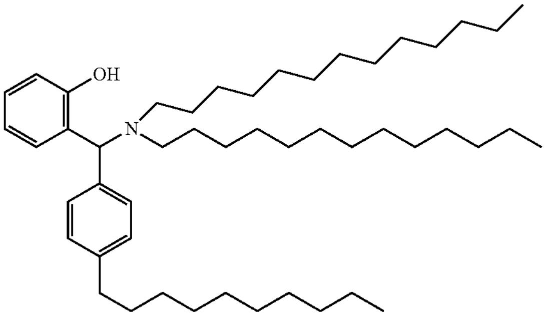
;
(IIIb)
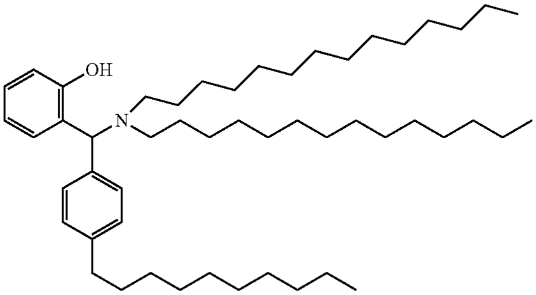
;
(IIIc)
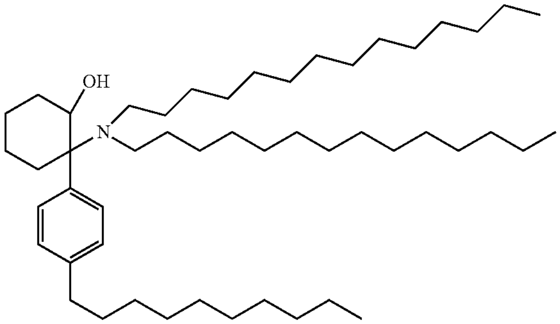
;
-continued
(IIId)
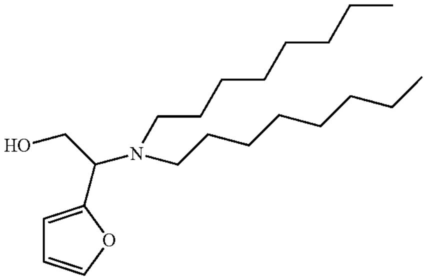
;
(IIIe)
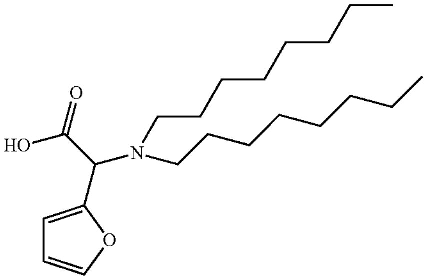
;
(IIIf)
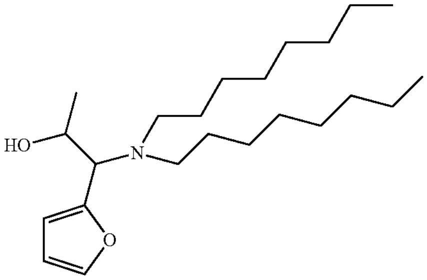
;
(IIIg)
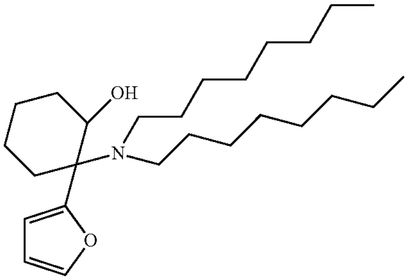
;
(IIIh)
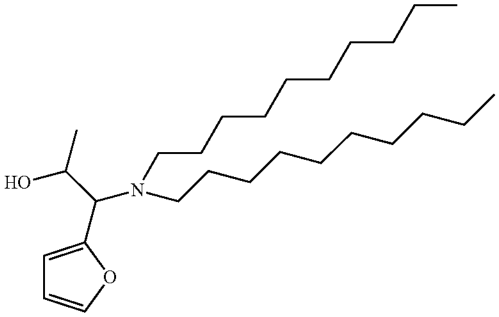
;

-continued
(IIIi)
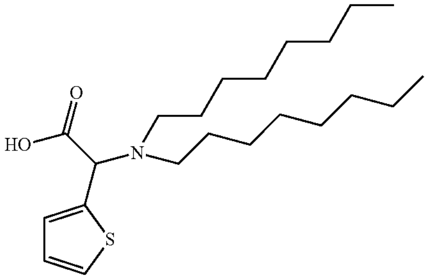
;
(IIIj)
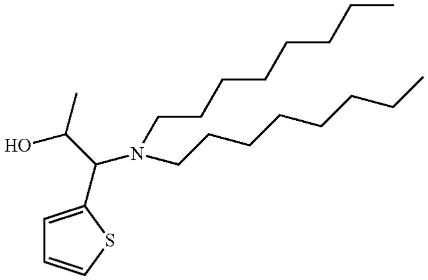
;
(IIIk)
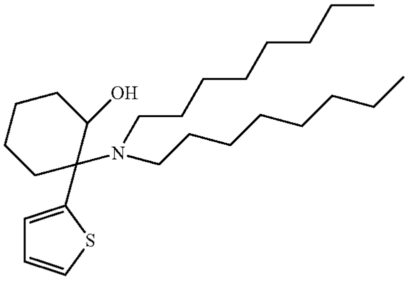
;
(IIIl)
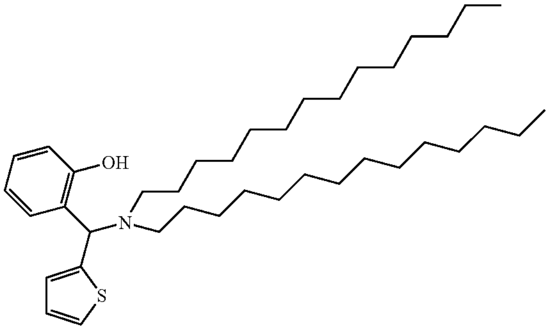
also referred to as TP4G11;
(IIIm)
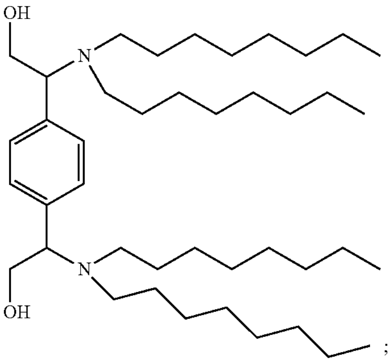
;
(IIIm)
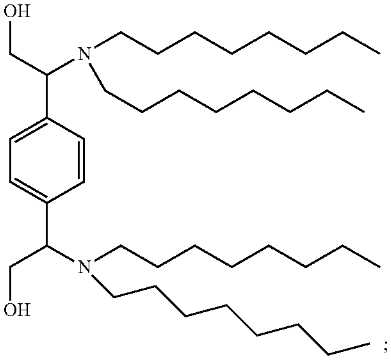
;
(IIIn)
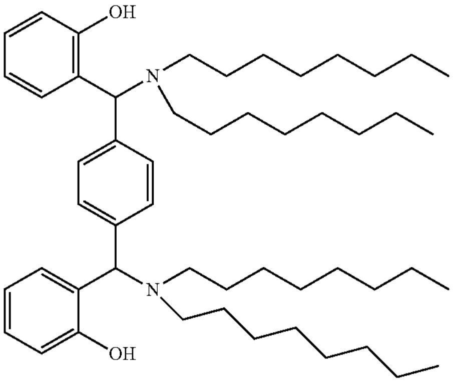

also referred to as TP1A11;
(IIIo)
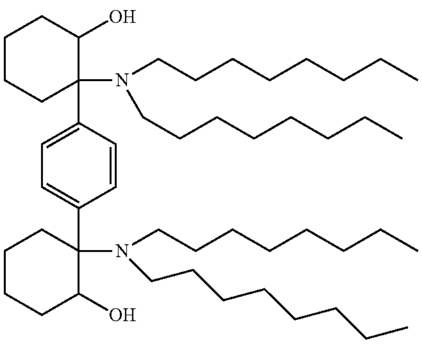
;
(IIIp)
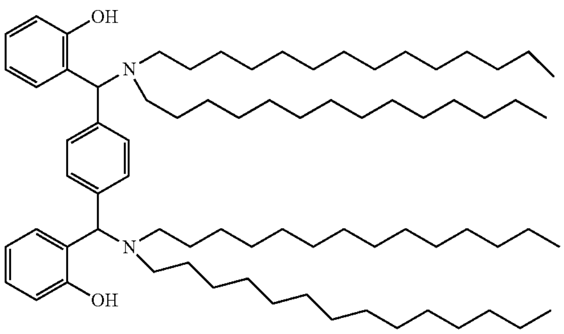
;
(IIIq)
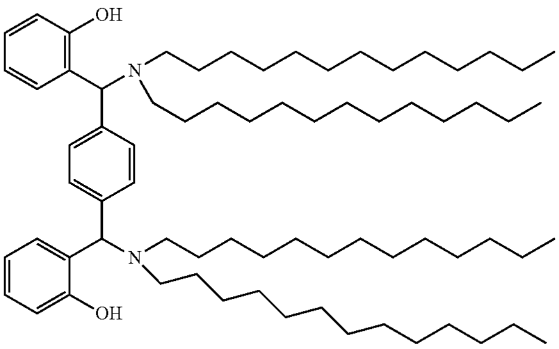
;
(IIIr)
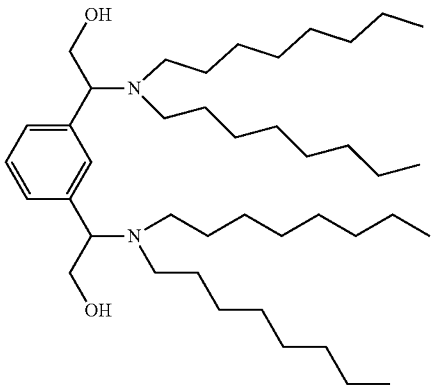
;
(IIIs)
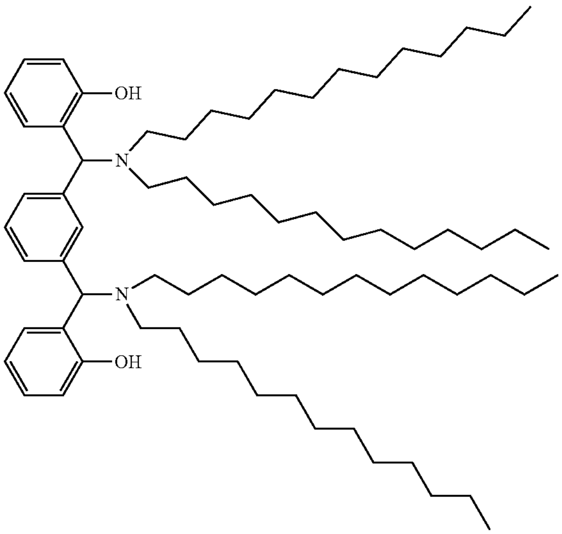
;
(IIIt)
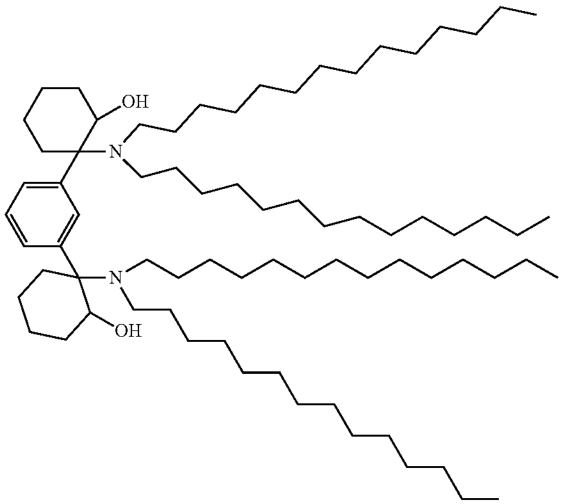
;

-continued
(IIIu)
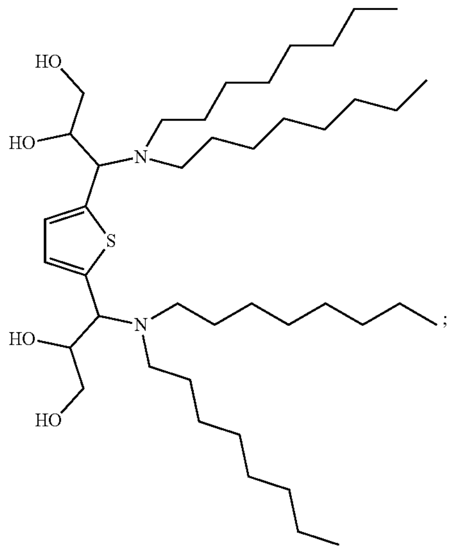
(IIIv)
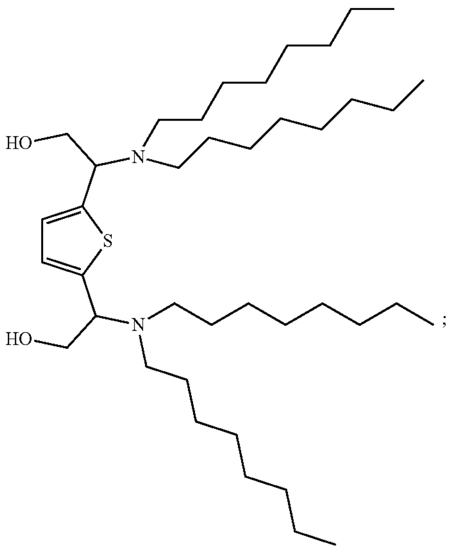
(IIIw)
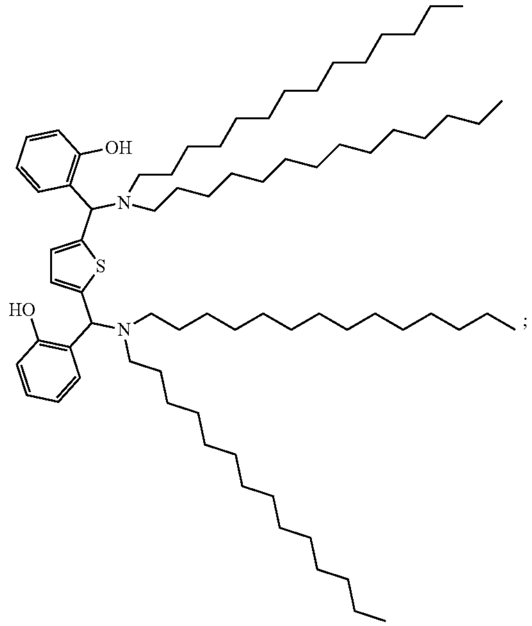

-continued
(IIIx)
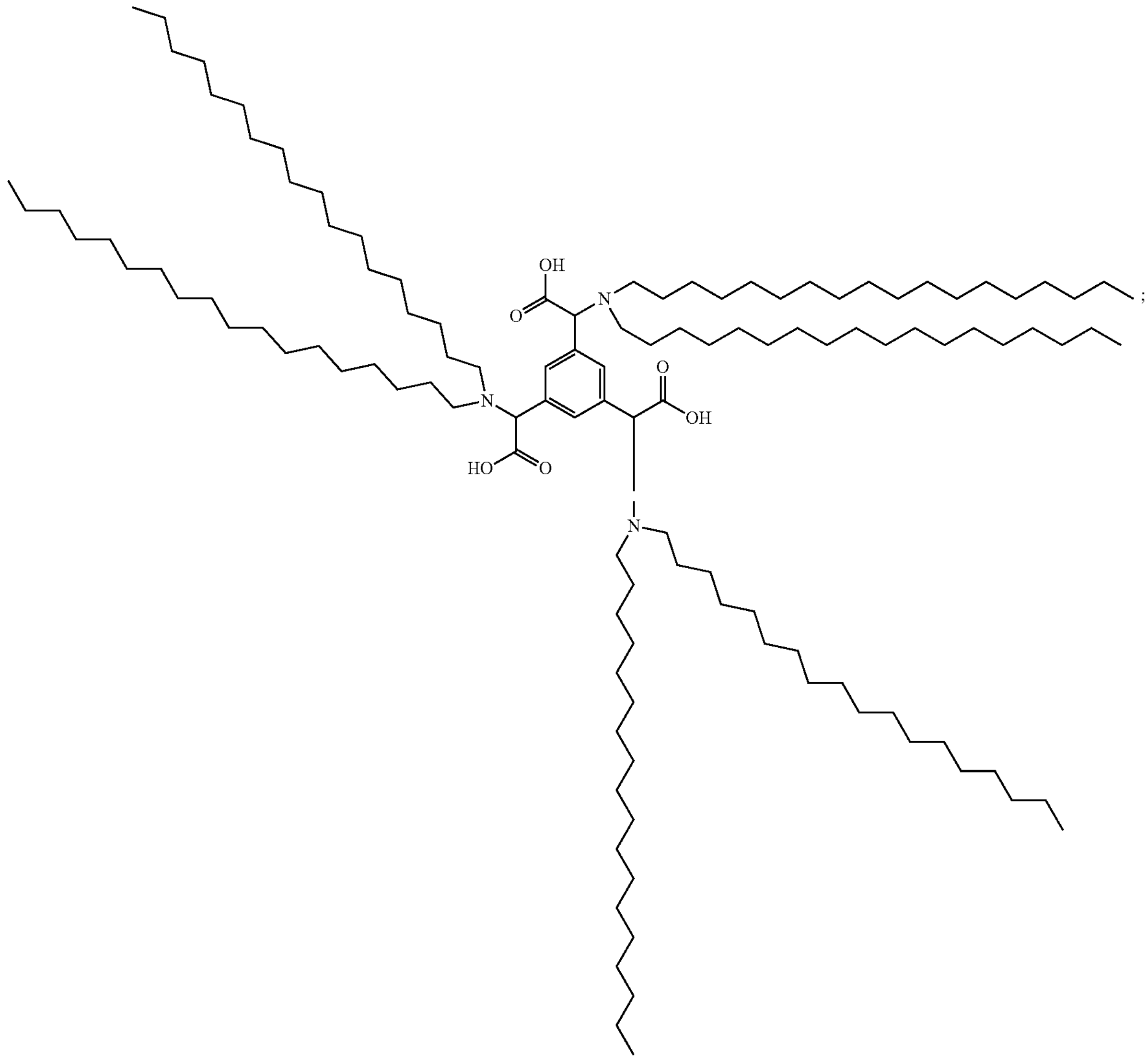
;

-continued
(IIIy)
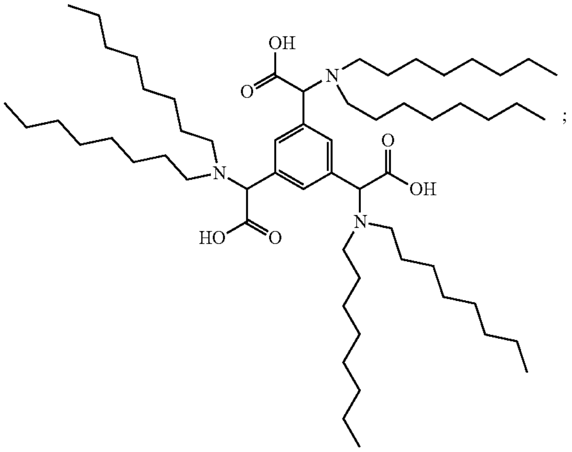
(IIIz)
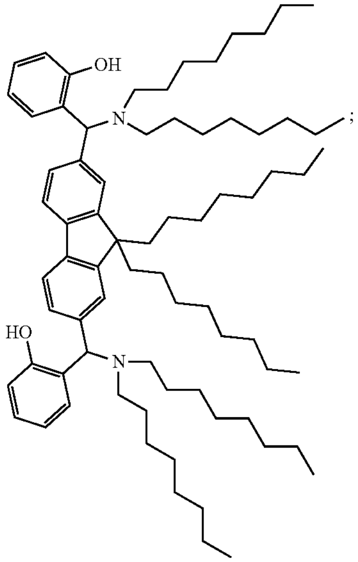
(III-2)
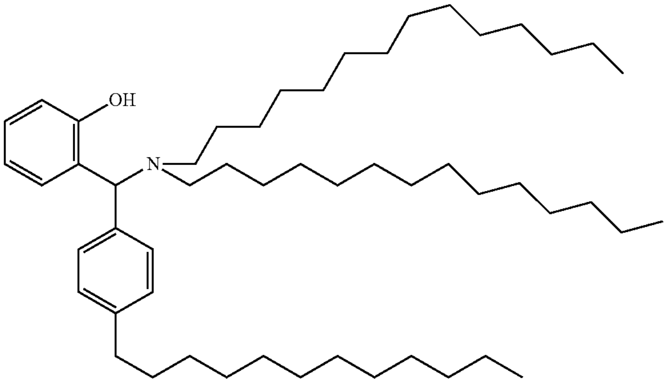
also referred to as TP3G11;
also referred to as TP3F11;
(III-3)
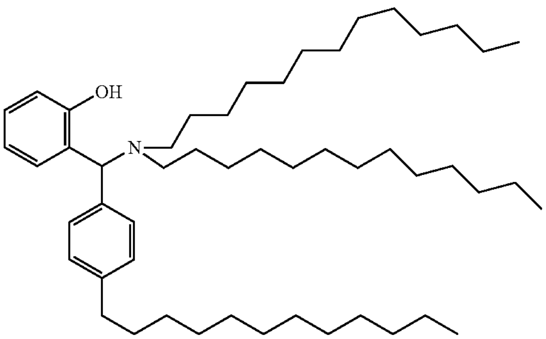
(III-4)
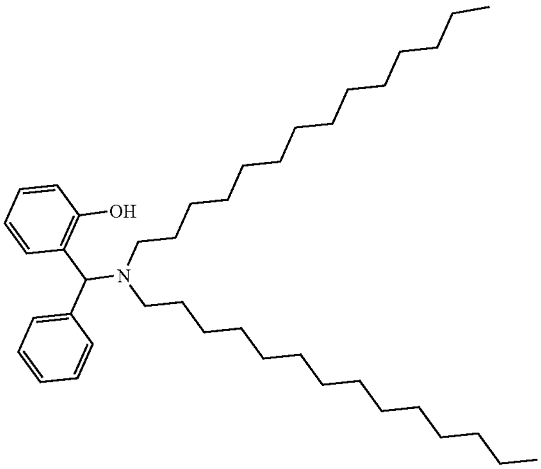
also referred to as TP5A1;
or a salt or isomer thereof.

In another aspect, the present disclosure provides compounds of Formula (IV):

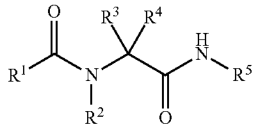

(IV)

or a salt or isomer thereof, wherein each $R^1$, $R^2$, $R^3$, $R^4$ and $R^5$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

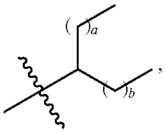

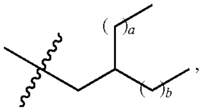

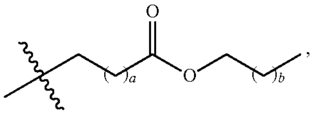

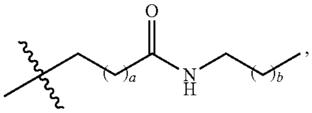

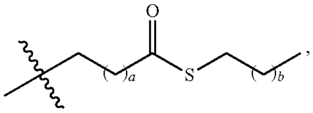

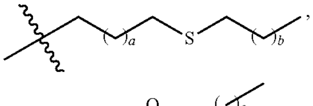

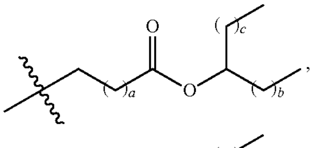

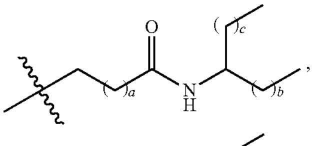

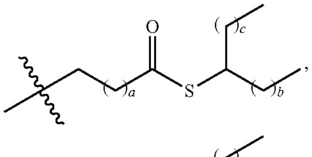

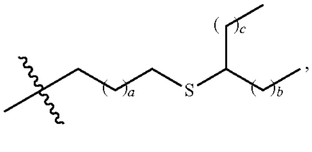

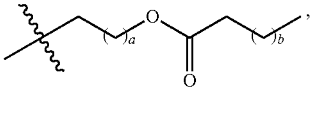

-continued

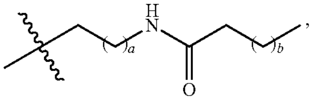

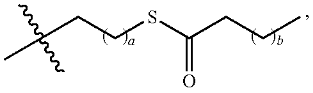

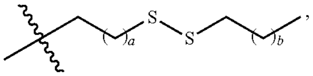

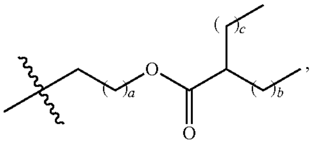

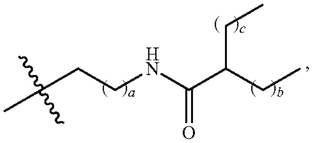

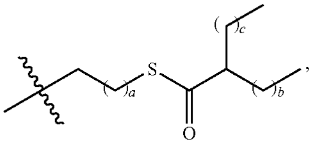

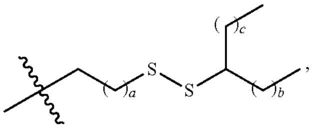

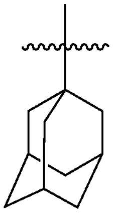

,

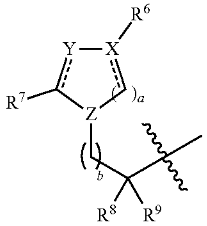

,

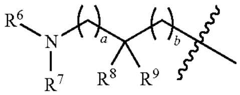

a, b and c are each independently an integer from 0-24;

each $R^6$, $R^7$, $R^8$ and $R^9$ are independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

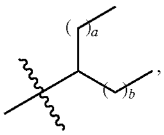

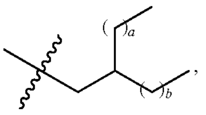

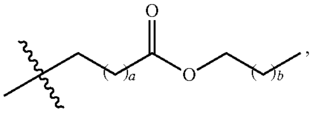

-continued
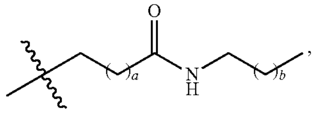
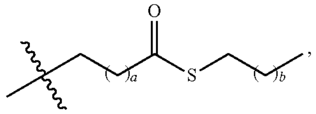
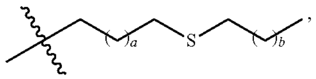
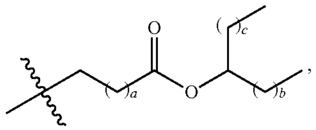
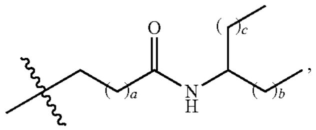
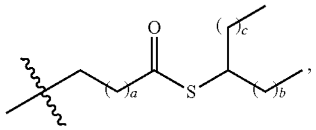
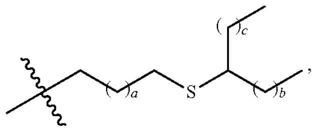
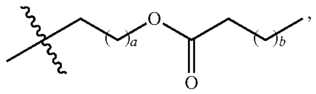
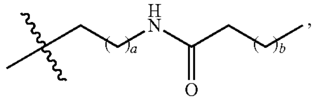
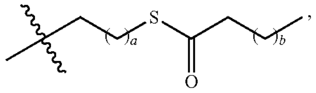
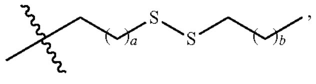
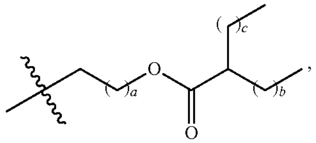
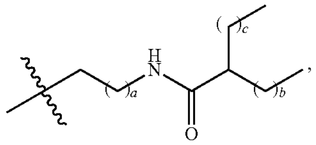
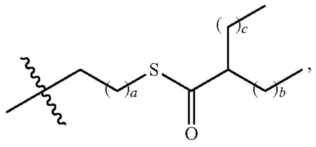
-continued
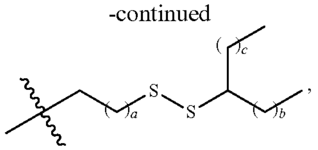
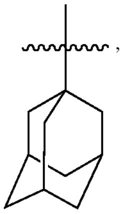
a, b and c are each independently an integer from 0-24;
each X is independently selected from CH, N;
each Y is independently selected from $CH_2$, NH, O, or S;
each Z is independently selected from CH or N.
In certain aspects, compounds of Formula IV may include, for example, the following compounds:
(IVa)
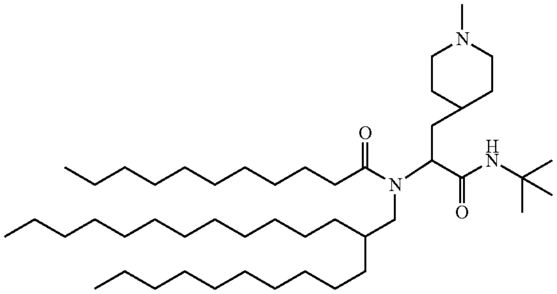
also referred to as P53F12;
(IVb)
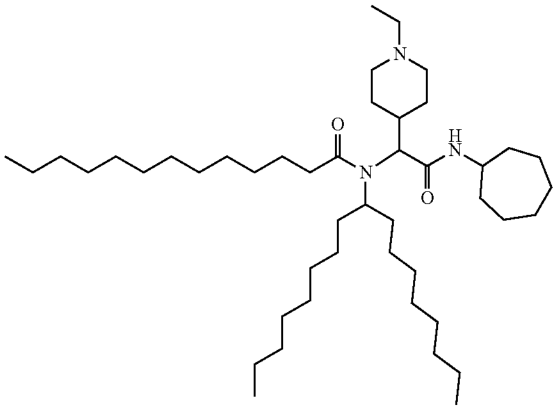

also referred to as P38C2;
(IVc)
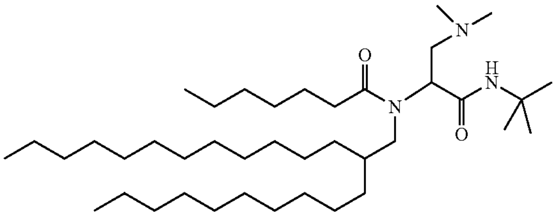
also referred to as P55H12;
(IVd)
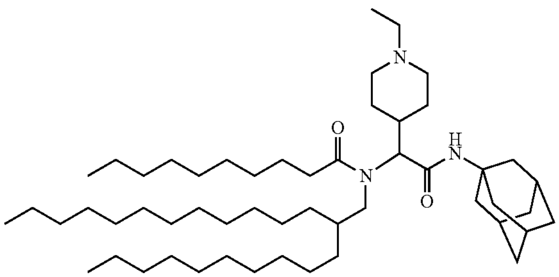
also referred to as P54A6;
(IVe)
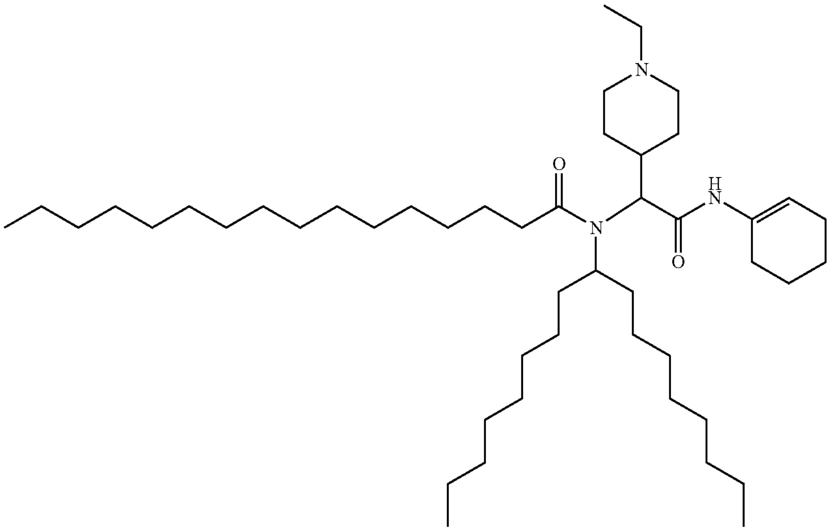
also referred to as P6A2;
(IVf)
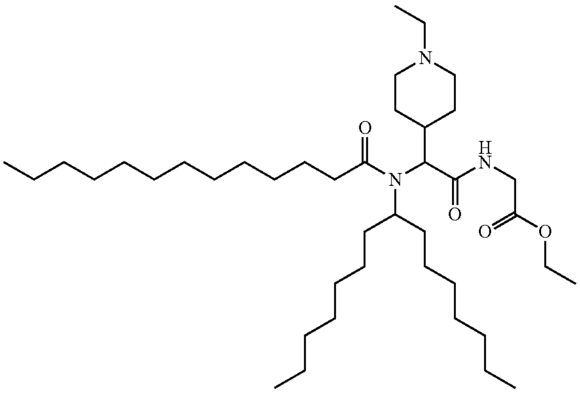

also referred to as P1C1;
(IVg)
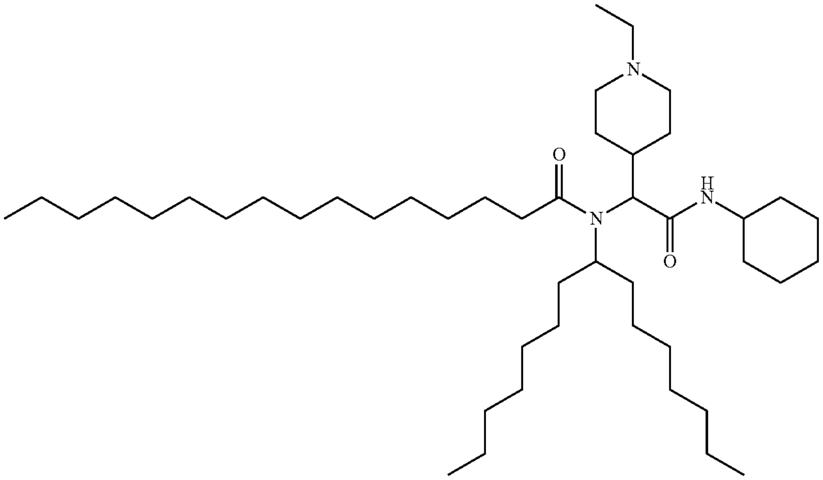
also referred to as P30A1;
(IVh)
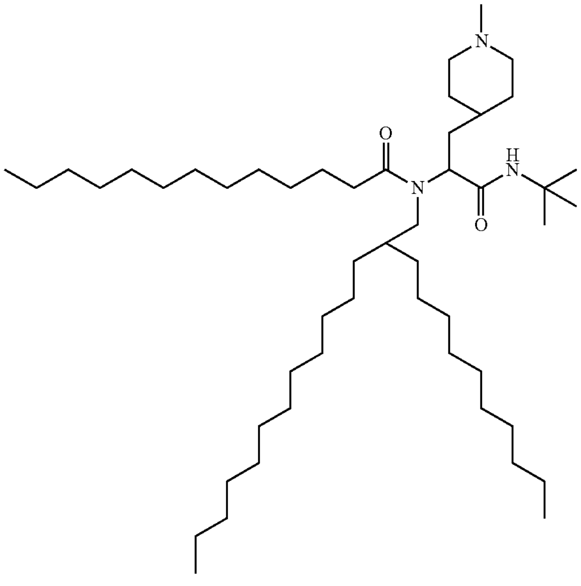
also referred to as P51C12;
(IVi)
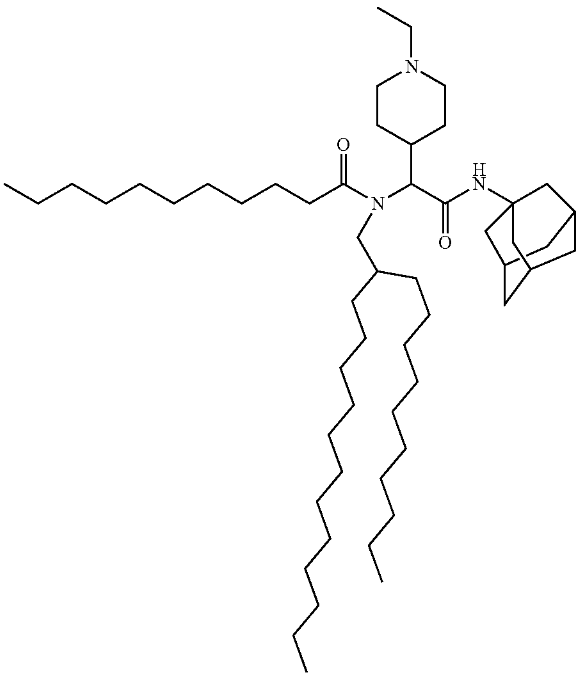

also referred to as P54B4;
(IVj)
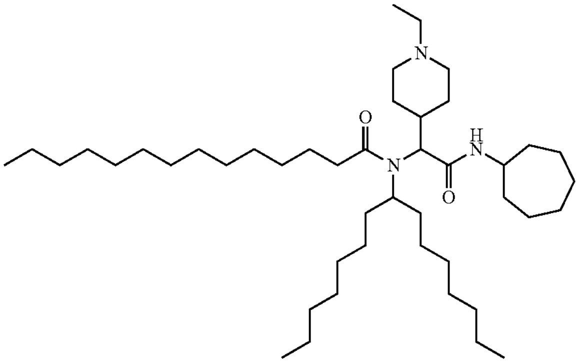
also referred to as P38D1;
(IVk)
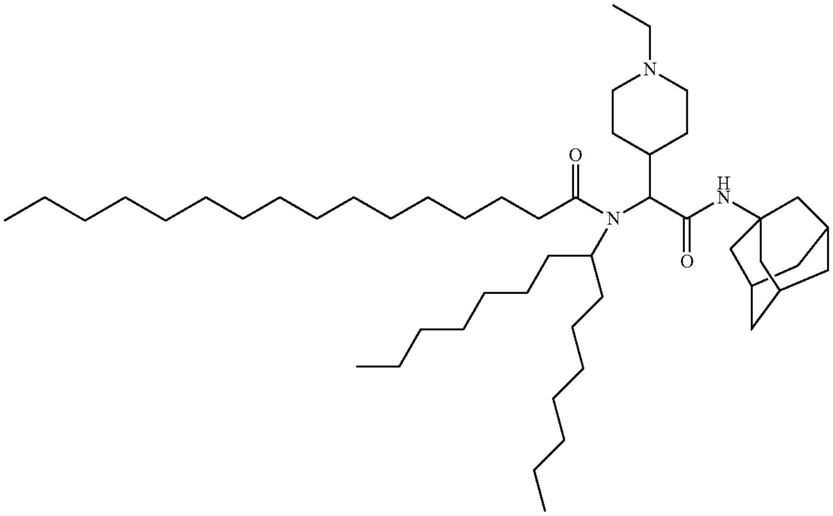

also referred to as P56A1;
(IVl)
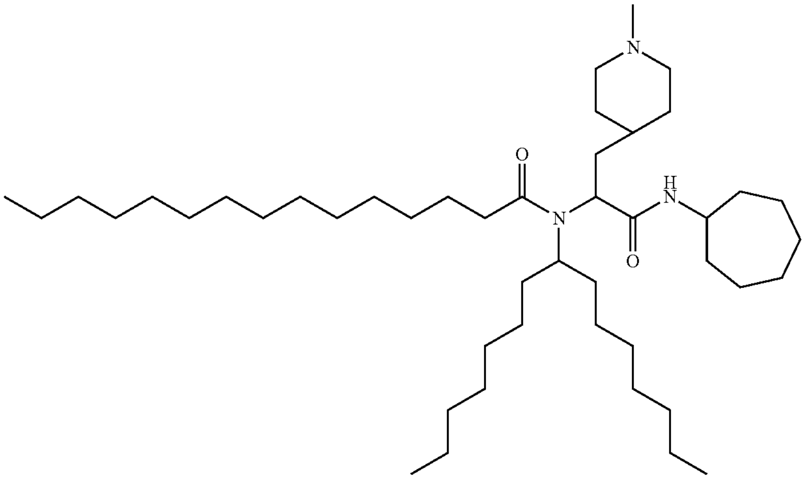
also referred to as P40D7;
(IVm)
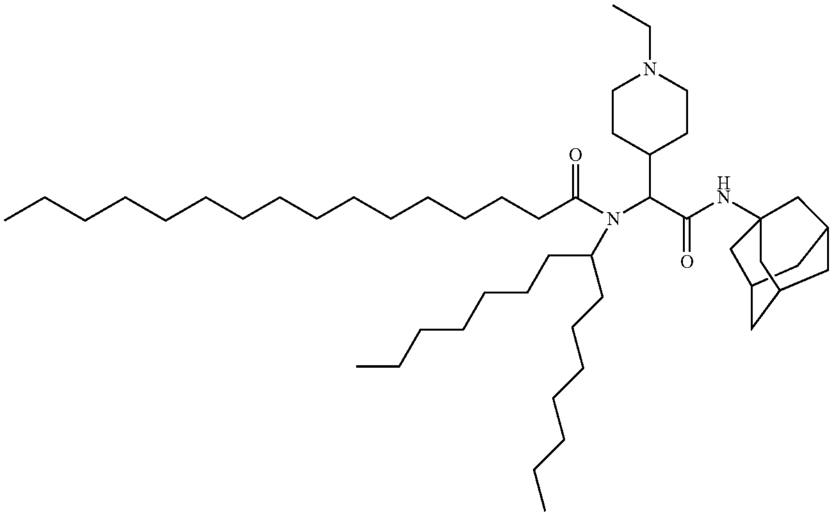

also referred to as P56B1;
(IVn)
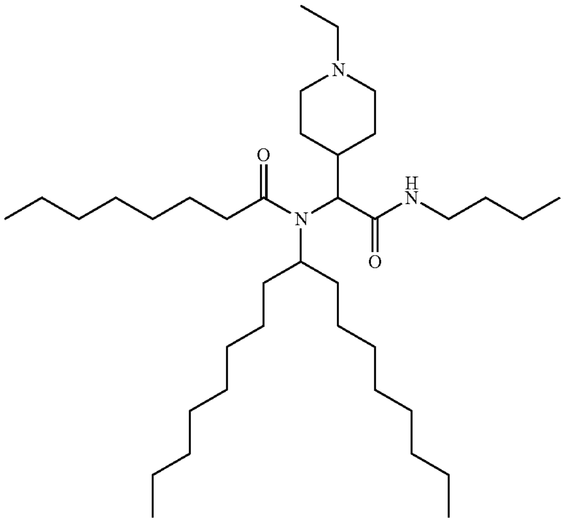
also referred to as P14A2;
(IVo)
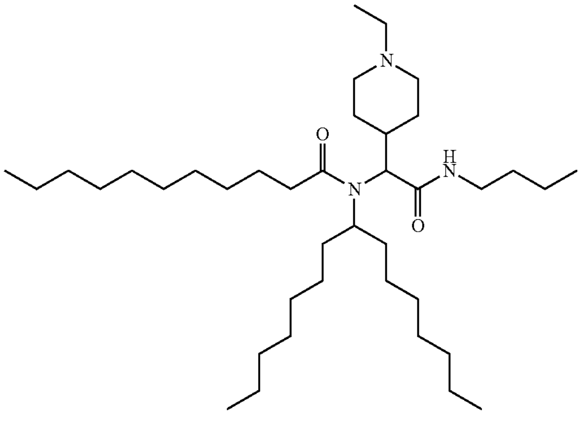
also referred to as P16B1;
(IVp)
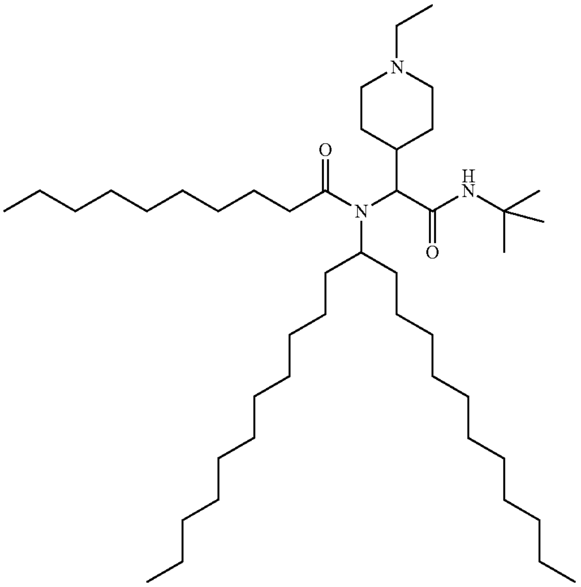
also referred to as P53A5;
(IVq)
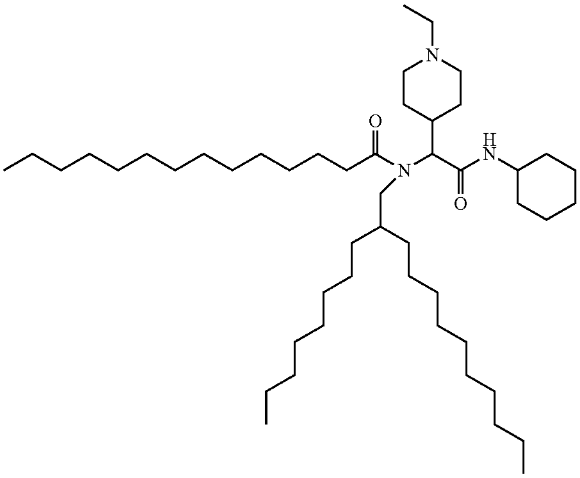

also referred to as P26D4;
(IVr)
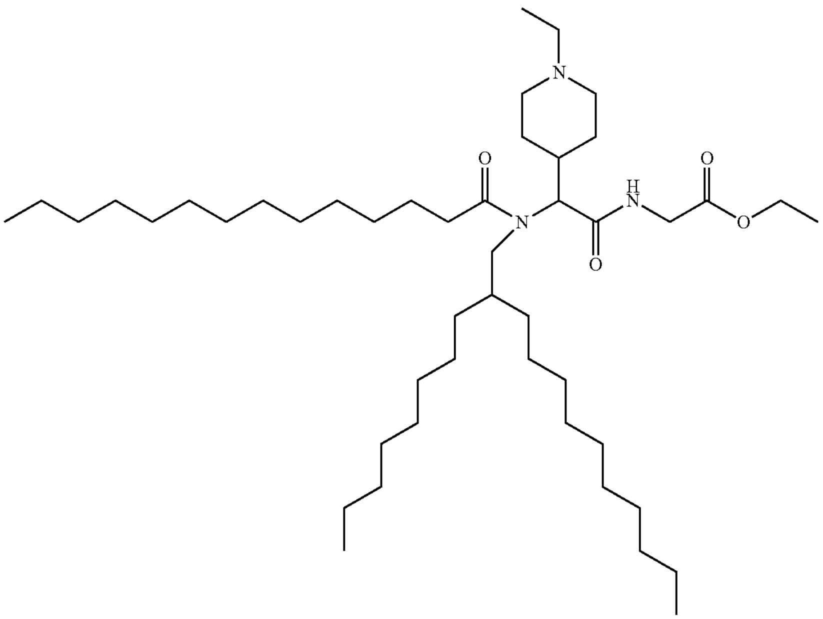
also referred to as P1D4;
(IVs)
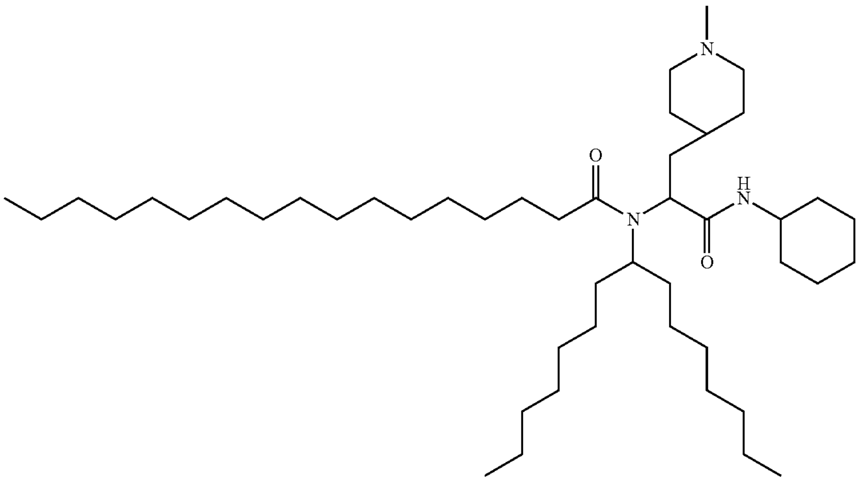

also referred to as P30B7;
(IVt)
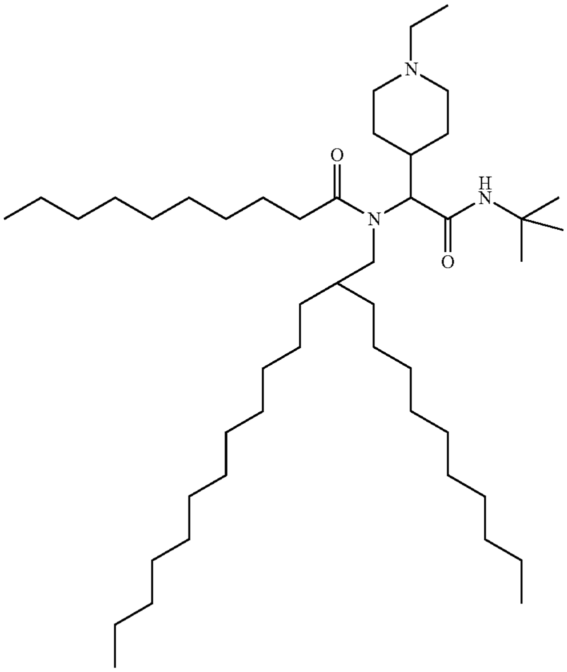
also referred to as P53A6;
(IVu)
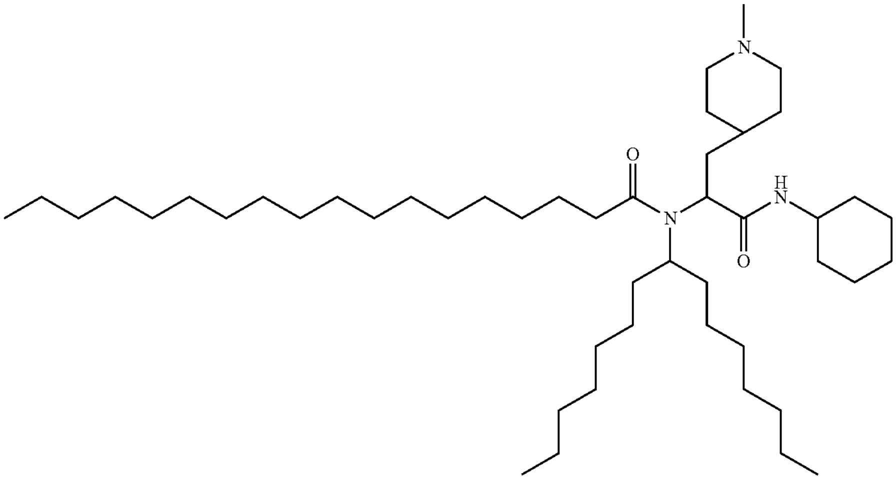
also referred to as P30C7;
(IVv)
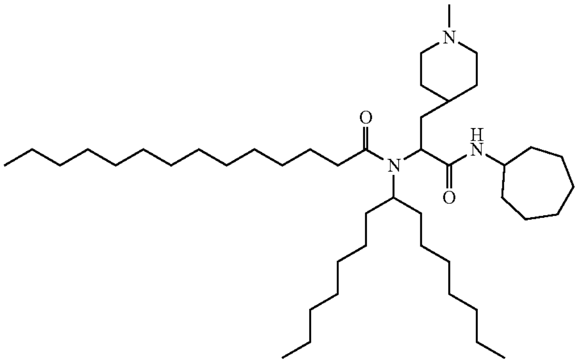

also referred to as P38D7;
(IVw)
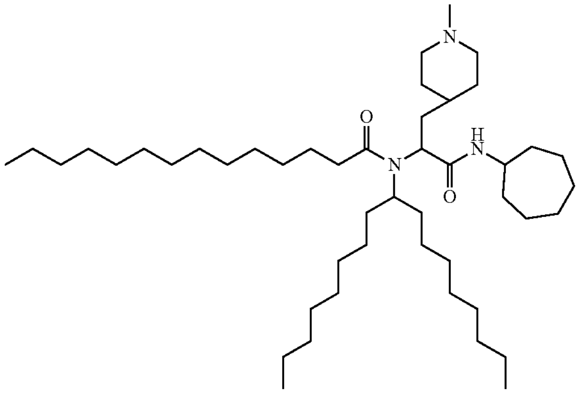
also referred to as P38D8;
(IVx)
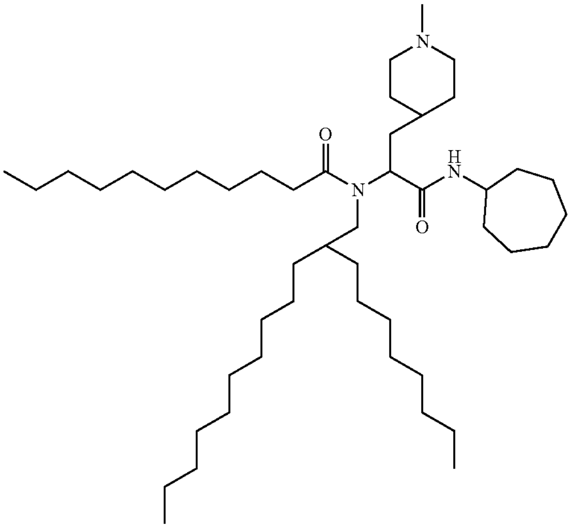
also referred to as P40B10;
(IVy)
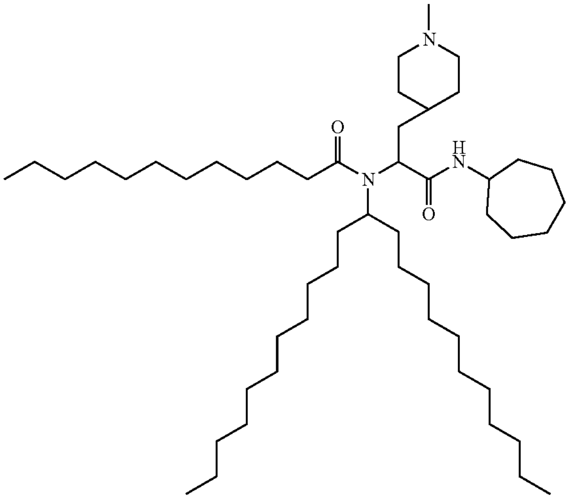
also referred to as P40C11;
(IVz)
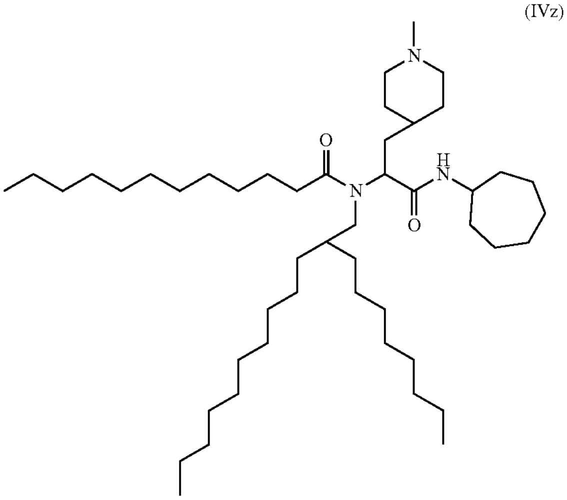 [SMILES: CCCCCCCCCCCC(=O)N(CC(CCCCCCCC)CCCCCCCCCC)C(CC1CCN(C)CC1)C(=O)NC1CCCCCC1]

also referred to as P40C10;
(IVaa)
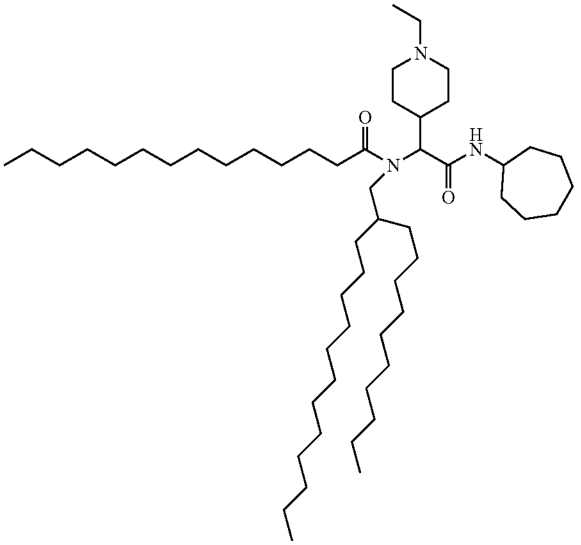
also referred to as P38D4;
also referred to as P56A2;
(IVac)
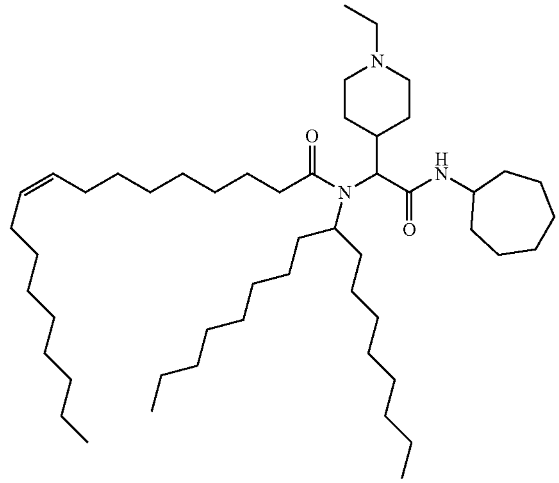
(IVab)
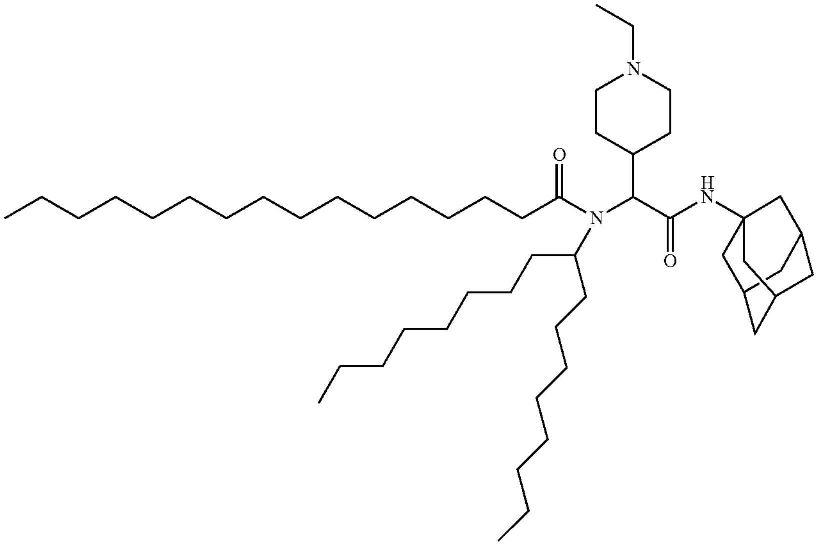

also referred to as P149A2;

(IVad)

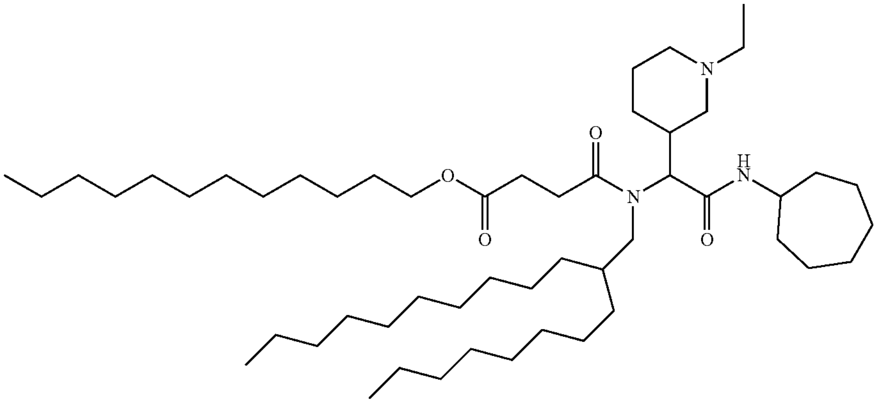

also referred to as P159C10;

(IVae)

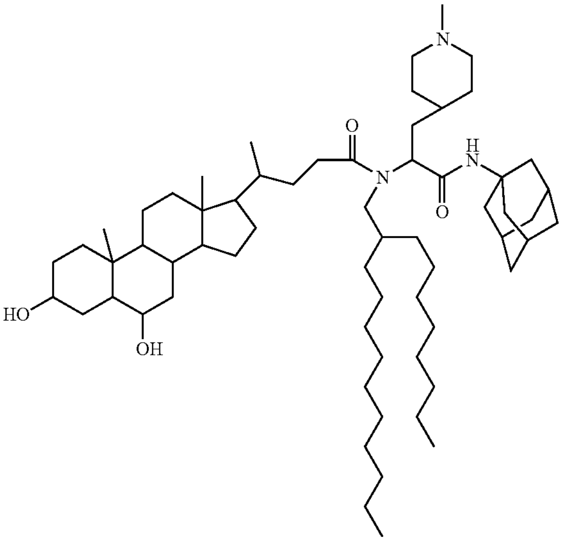

also referred to as P161F10;

or a salt or isomer thereof.

In another aspect, the present disclosure provides compounds of Formula (V):

(V)

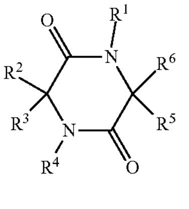

or a salt or isomer thereof, wherein each $R^1$, $R^2$, $R^3$, $R^4$, $R^5$ and $R^6$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

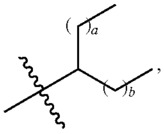

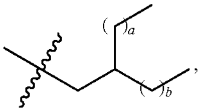

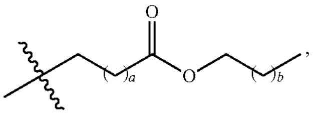

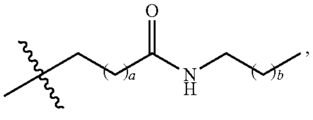

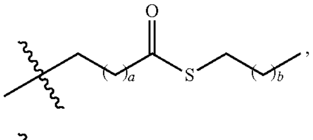

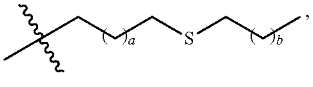

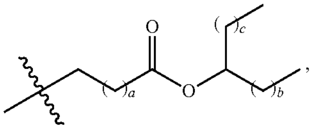

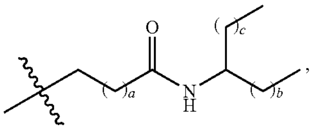

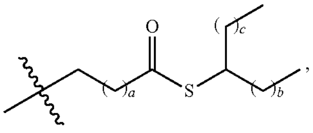

-continued
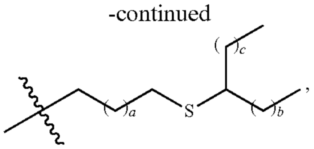
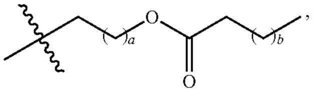
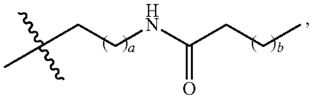
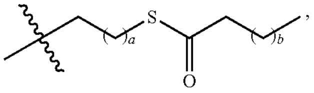
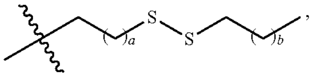
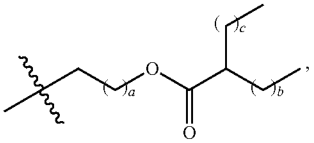
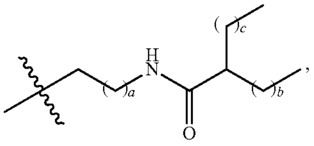
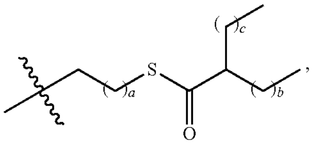
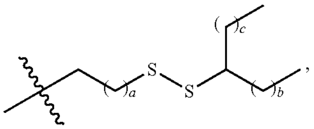
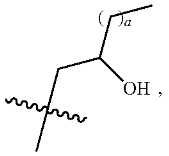
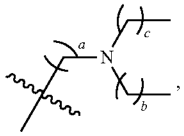
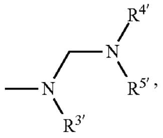
a, b and c are each independently an integer from 0-24; each R3', R4' and R5' is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,
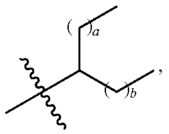
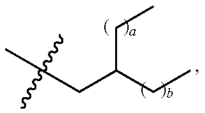
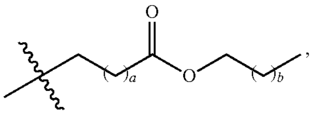
-continued
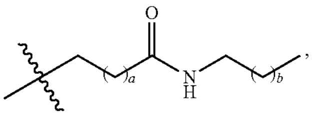
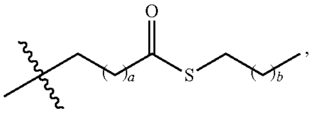
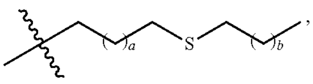
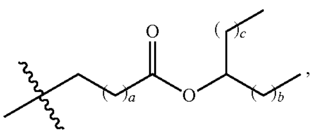
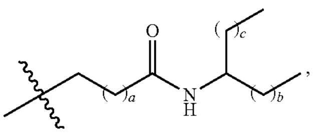
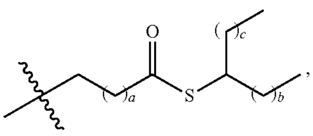
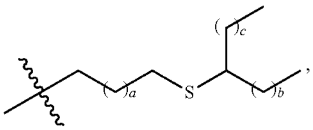
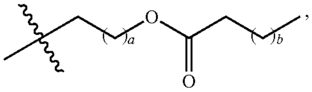
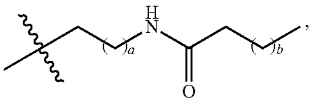
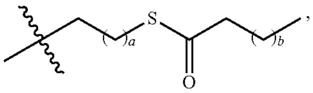
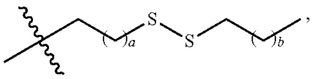
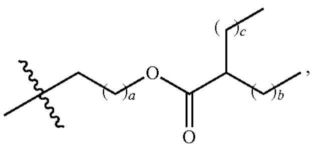
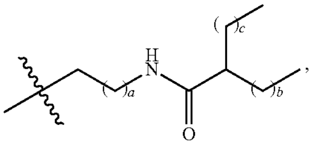
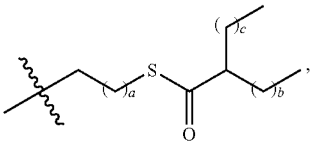

-continued

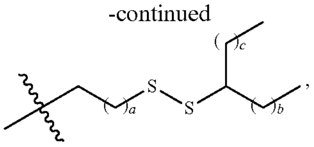

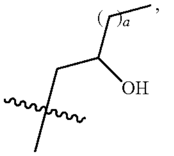

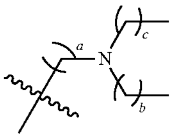

a, b and c are each independently an integer from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24.

In certain aspects, compounds of Formula V may include, for example, the following compounds:

or a salt or isomer thereof, wherein each n is independently an integer from 0-10, e.g., 0, 1, 2, 3, 4, 5, 6, 7, 8, 9, or 10, or any subrange selected from the range of 0-10, e.g., 2-9, 3-8, 4-7, 1-5, 1-4, 5-9, etc.;

each $R^1$ and $R^2$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

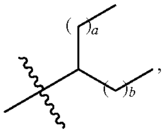

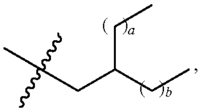

(Va)

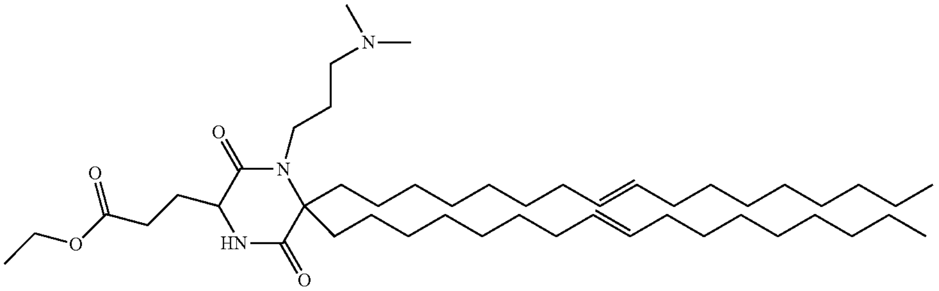

; or (Vb)

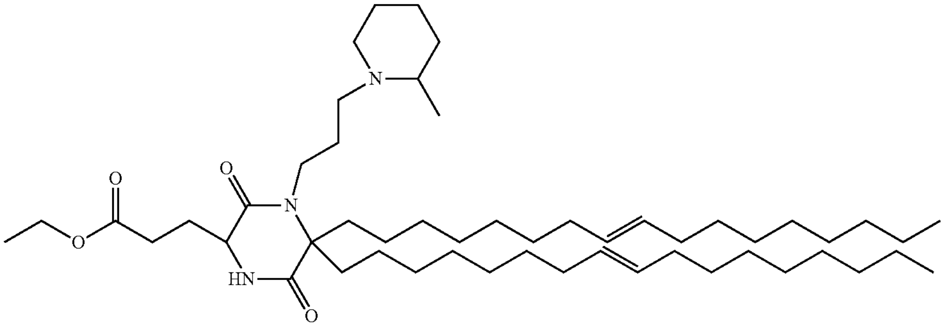

, or a salt or isomer thereof.

In another aspect, the present disclosure provides compounds of Formula (VI):

(VI)

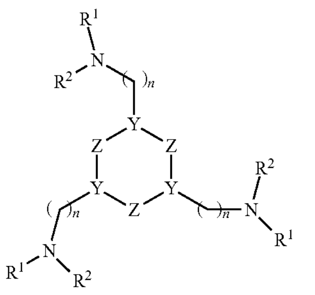

-continued

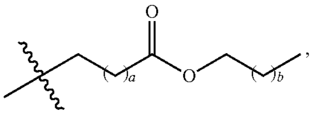

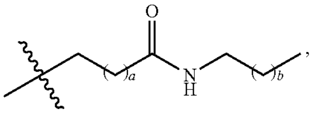

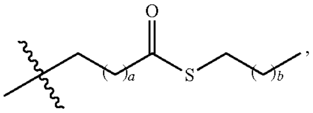

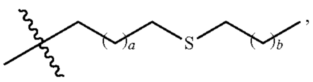

-continued
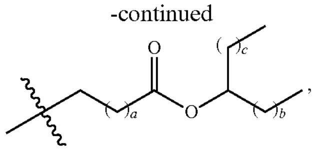
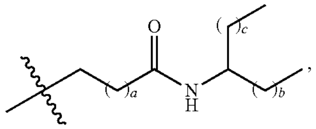
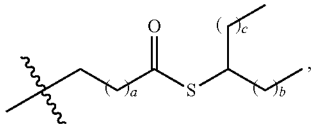
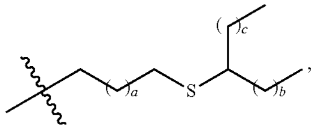
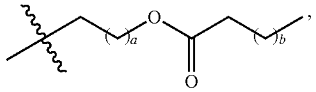
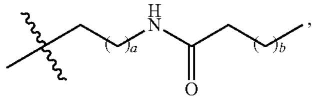
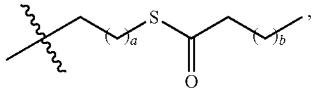
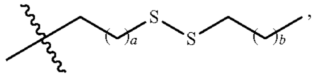
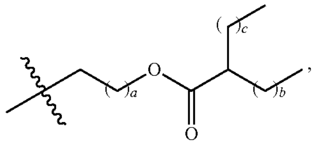
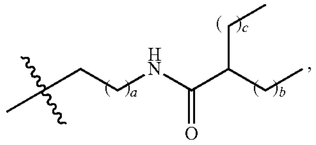
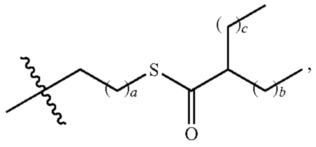
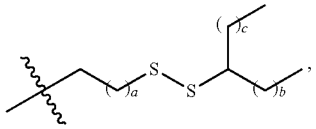
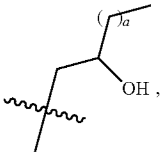
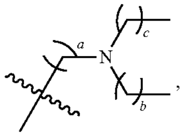
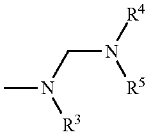
a, b and c are each independently an integer from 0-24; each $R^3$, $R^4$ and $R^5$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,
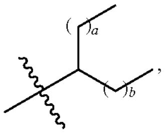
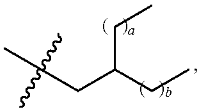
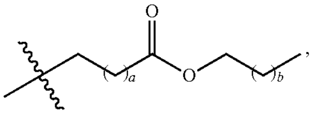
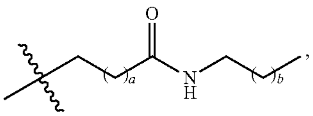
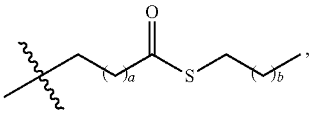
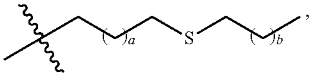
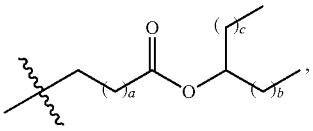
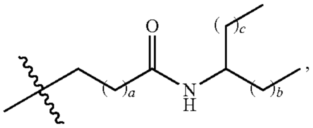
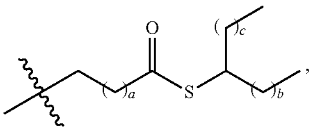
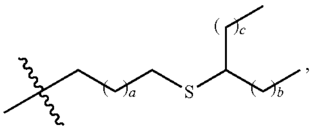
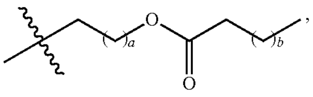
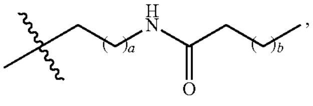
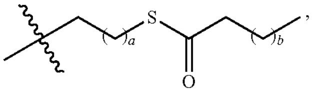
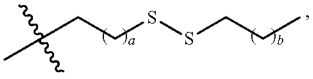
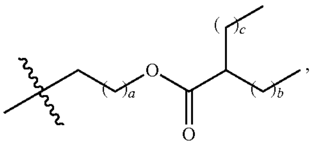

-continued

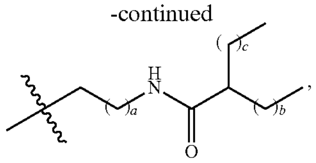

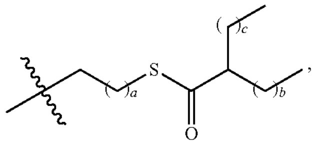

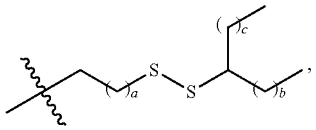

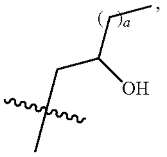

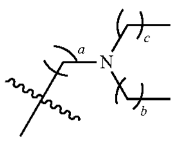

a, b and c are each independently an integer from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24;

each Y is independently selected from CH or N;

each Z is independently selected from $CH_2$, NH, O, or S.

In certain aspects, compounds of Formula VI may comprise, for example, the following formula:

VI-1

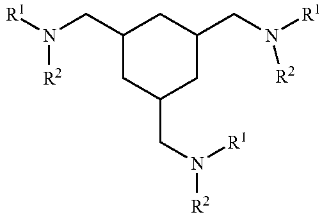

or a salt or isomer thereof, wherein each $R^1$ and $R^2$ are as defined above.

General synthesis route for the synthesis of compounds of Formula VI-1:

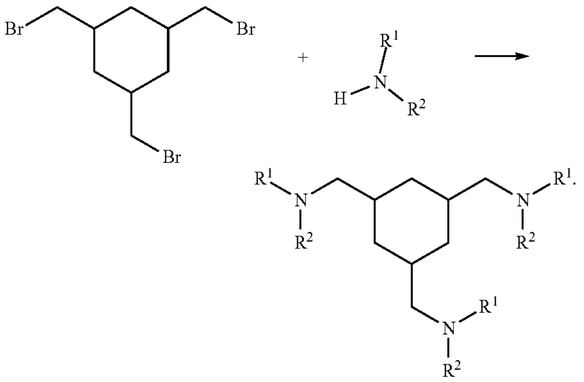

In certain aspects, compounds of Formula VI may include, for example, the following compounds:

(VIa)

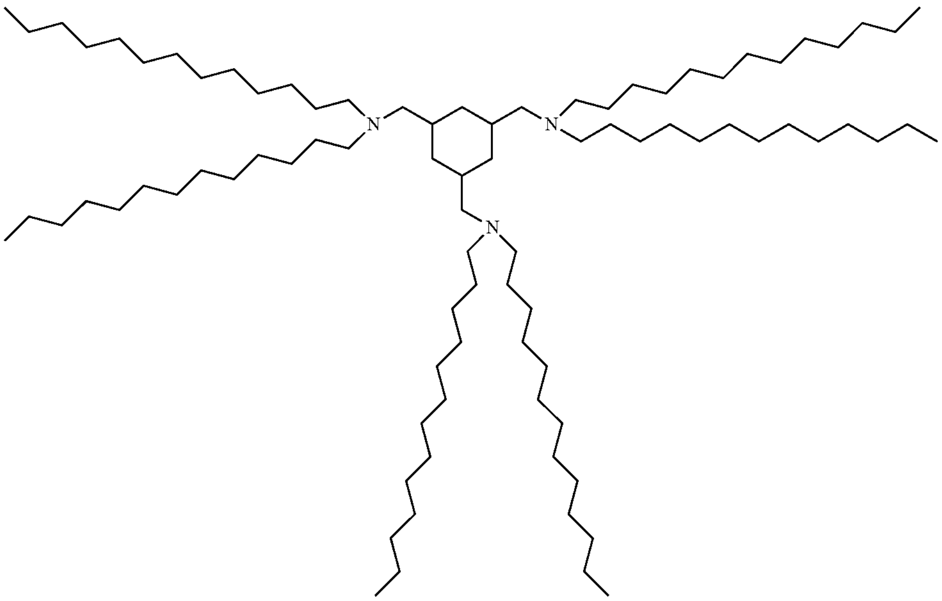

;

-continued
(VIb)
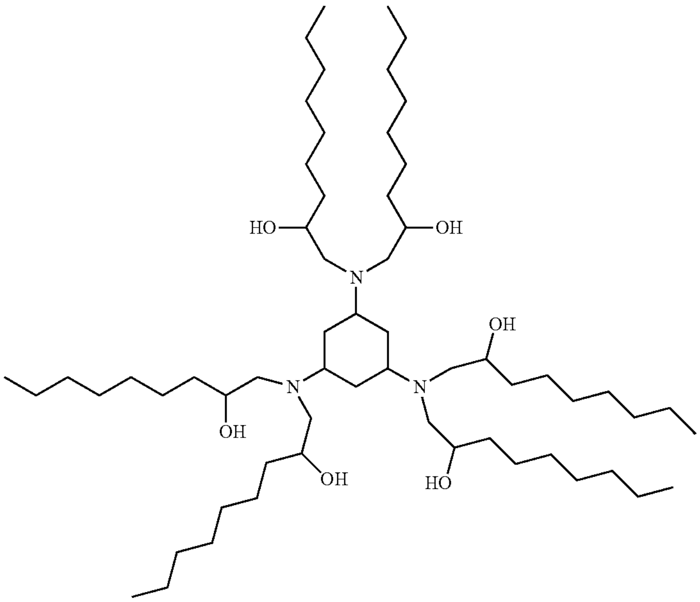
;
(VIc)
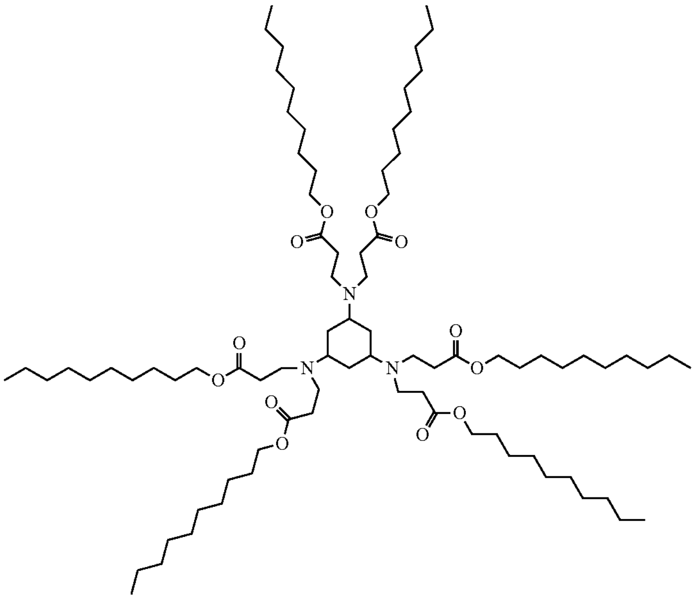
;
or a salt or isomer thereof.

In another aspect, the present disclosure provides compounds of Formula (VII):

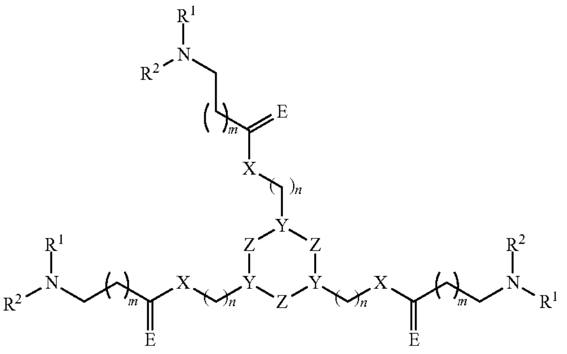

or a salt or isomer thereof, wherein each n is independently an integer from 0-10, e.g., 0, 1, 2, 3, 4, 5, 6, 7, 8, 9, or 10, or any subrange selected from the range of 0-10, e.g., 2-9, 3-8, 4-7, 1-5, 1-4, 5-9, etc.;

each $R^1$ and $R^2$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

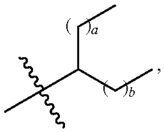
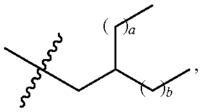

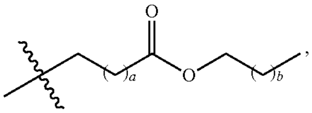

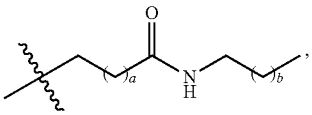

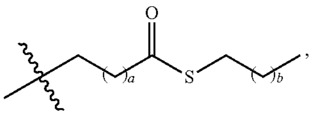

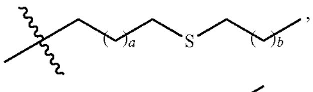

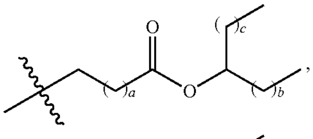

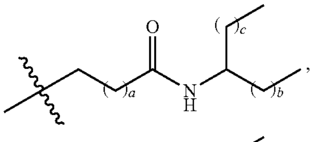

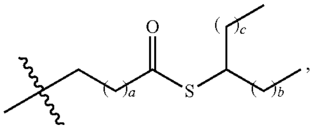

-continued

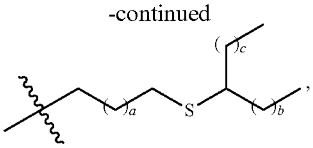

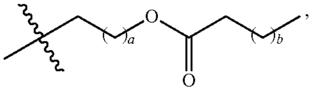

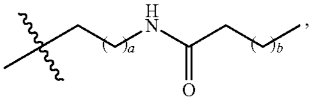

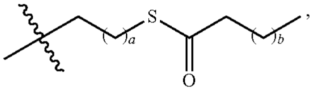

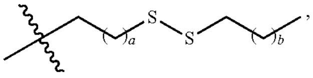

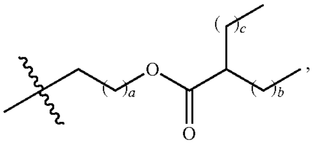

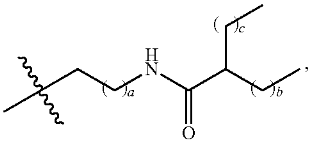

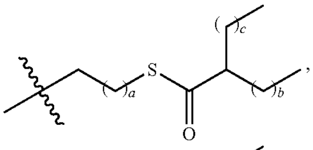

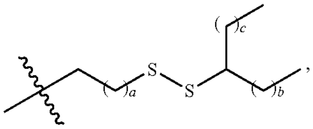

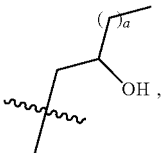
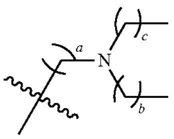
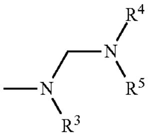

a, b and c are each independently an integer from 0-24;

each $R^3$, $R^4$ and $R^5$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

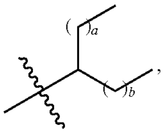
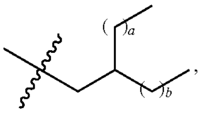

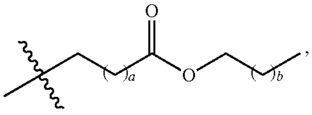

-continued

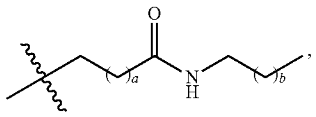

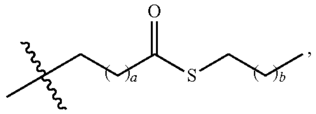

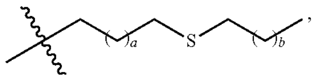

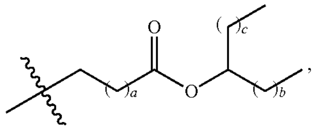

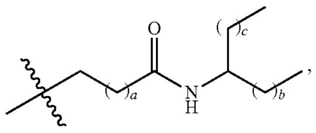

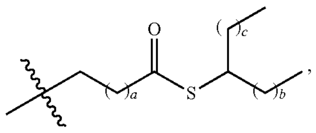

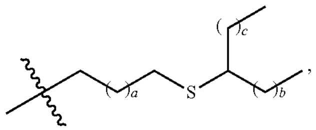

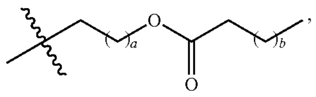

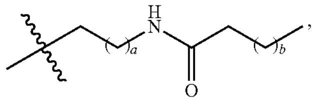

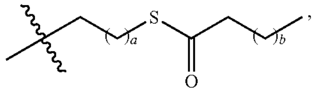

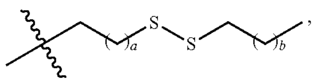

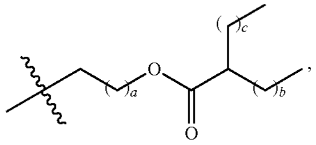

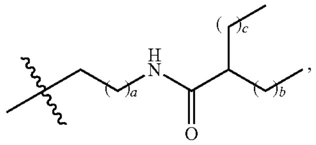

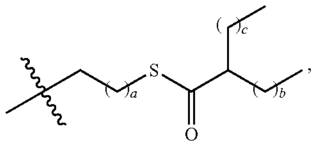

-continued

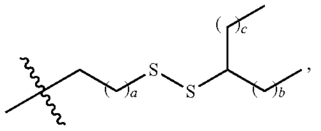

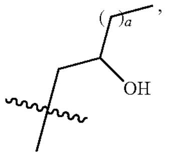

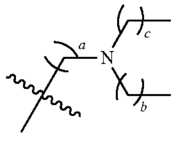

a, b and c are each independently an integer from 0-24;

each X is independently selected from $CH_2$, NH, O, or S;

each Y is independently selected from CH, N;

each Z is independently selected from $CH_2$, NH, O, or 5; and each E is independently selected from $CH_2$, NH, O, or S.

In certain aspects, compounds of Formula VII may comprise, for example, the following formula:

VII-1

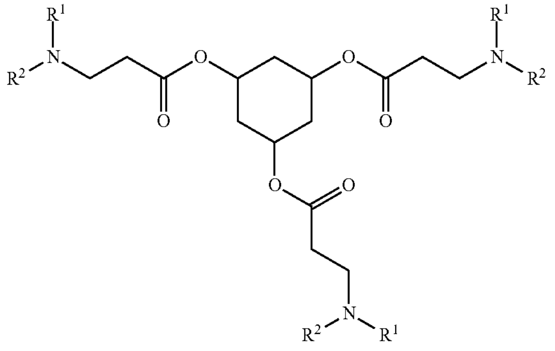

wherein each $R^1$ and $R^2$ are as defined above.

General synthesis route for the synthesis of compounds of Formula VII-1:

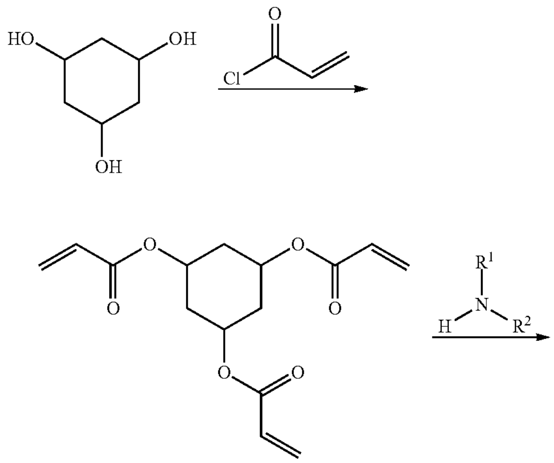

-continued
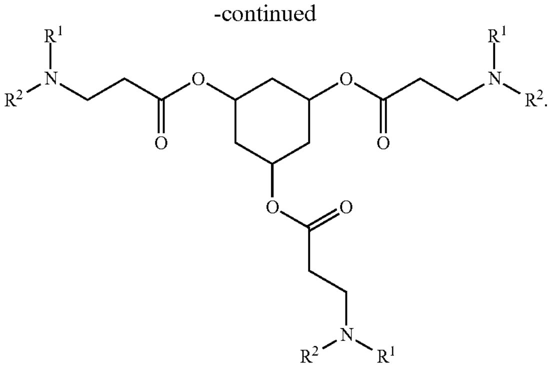
In certain aspects, compounds of Formula VII may include, for example, the following compounds:
(VIIa)
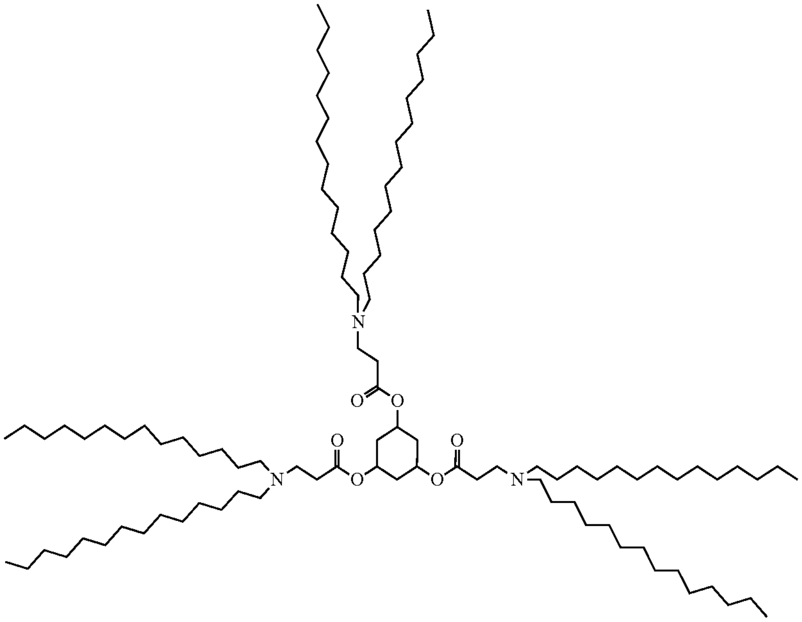

also referred to as T7;

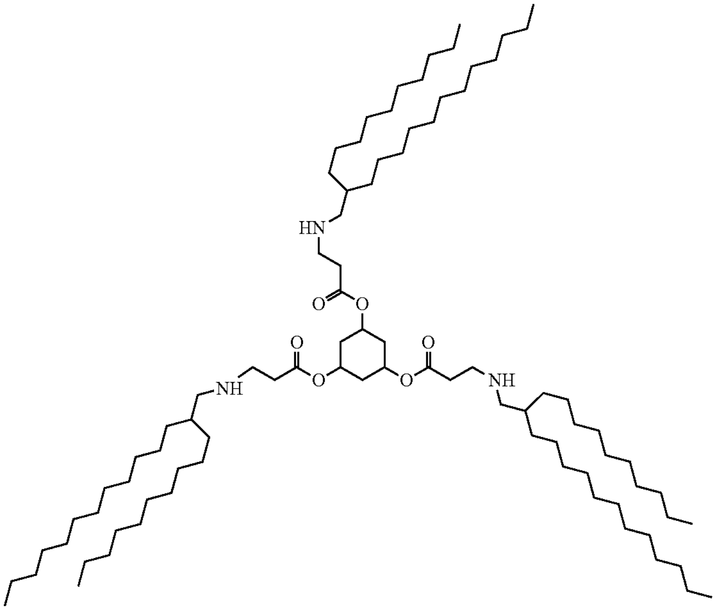

(VIIb)

also referred to as P7;
or a salt or isomer thereof.

In another aspect, the present disclosure provides a composition including a lipid component comprising the compound of Formula (I), (II), (III), (IV), (V), (VI), and/or (VII). In some aspects, the composition may include one or more cationic and/or ionizable lipids, an anionic lipid, phospholipids including polyunsaturated lipids, PEG lipids, structural lipids, and/or biologically active molecules.

In another aspect, the present disclosure provides methods of making a nanoparticle composition including a lipid component comprising the compound of Formula (I), (II), (III), (IV), (V), (VI), and/or (VII).

In another aspect, the present disclosure provides a method of delivering a biologically active agent (e.g., an mRNA) to a cell (e.g., a mammalian cell) by administering a nanoparticle composition including (i) a lipid component, including at least one of a phospholipid, a PEG lipid, a structural lipid, and an ionizable lipid of Formulae (I), (II), (III), (IV), (V), (VI), and (VII); and (ii) a biologically active agent to a subject, in which administering involves contacting the cell with the nanoparticle composition such that biologically active agent is delivered to the cell.

In another aspect, the present disclosure provides a method of producing a polypeptide of interest in a cell (e.g., a mammalian cell) by contacting the cell with a nanoparticle composition including (i) a lipid component, including at least one of a phospholipid, a PEG lipid, a structural lipid, and an ionizable lipid of Formulae (I), (II), (III), (IV), (V), (VI), and (VII); and (ii) a mRNA encoding a polypeptide of interest to a subject, whereby the mRNA is capable of being translated in the cell to produce the polypeptide.

In another aspect, the present disclosure provides a method of introducing a gene to a cell (e.g., a mammalian cell) by contacting the cell with a nanoparticle composition including (i) a lipid component, including at least one of a phospholipid, a PEG lipid, a structural lipid, and an ionizable lipid of Formulae (I), (II), (III), (IV), (V), (VI), and (VII); and (ii) a DNA encoding the gene of interest, whereby the cell becomes capable of expressing the introduced gene.

In some aspects, the nanoparticles of the present invention are employed with another therapeutic compound separate from the nanoparticle for treatment of the same indication in the individual. In particular cases, the nanoparticles and the therapeutic compound are delivered separately or together. When delivered together, they may or may not be in the same formulation, and they may or may not be delivered by the same route.

In another aspect, the present disclosure provides methods of synthesizing a compound of Formulae (I), (II), (III), (IV), (V), (VI), and (VII).

DETAILED DESCRIPTION

Figure 1:
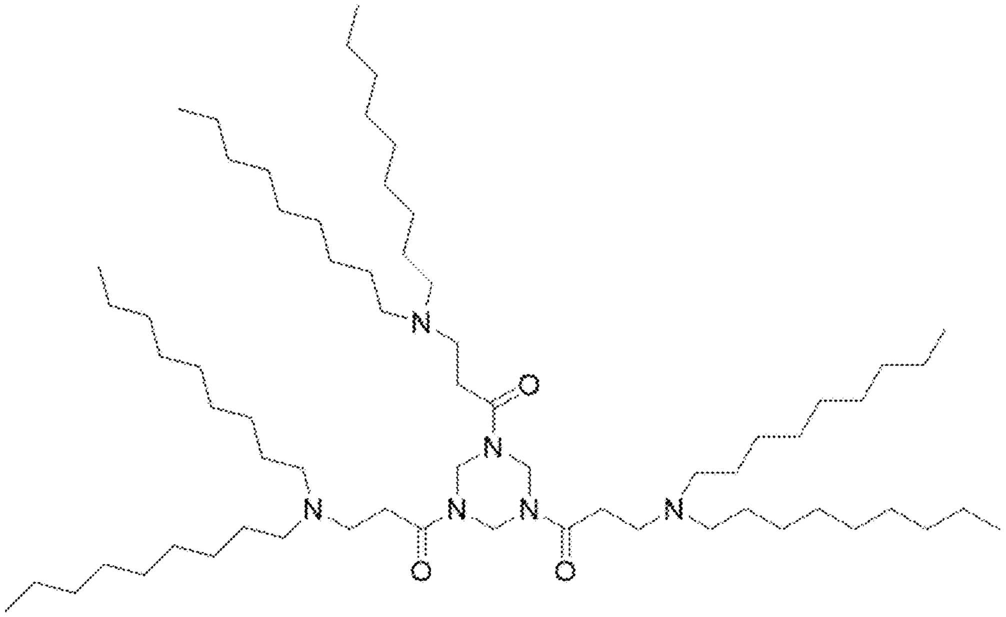
FIG. 1 shows structures of TAb-9 and TAb-13 and Fluorescence-activated cell sorting (FACS) of TAb-9 and TAb-13 formulated LNPs encapsulated with self-amplifying mRNA encoding with GFP, which transfect and express GFP-mRNA in C2C12 cells.
Figure 1:
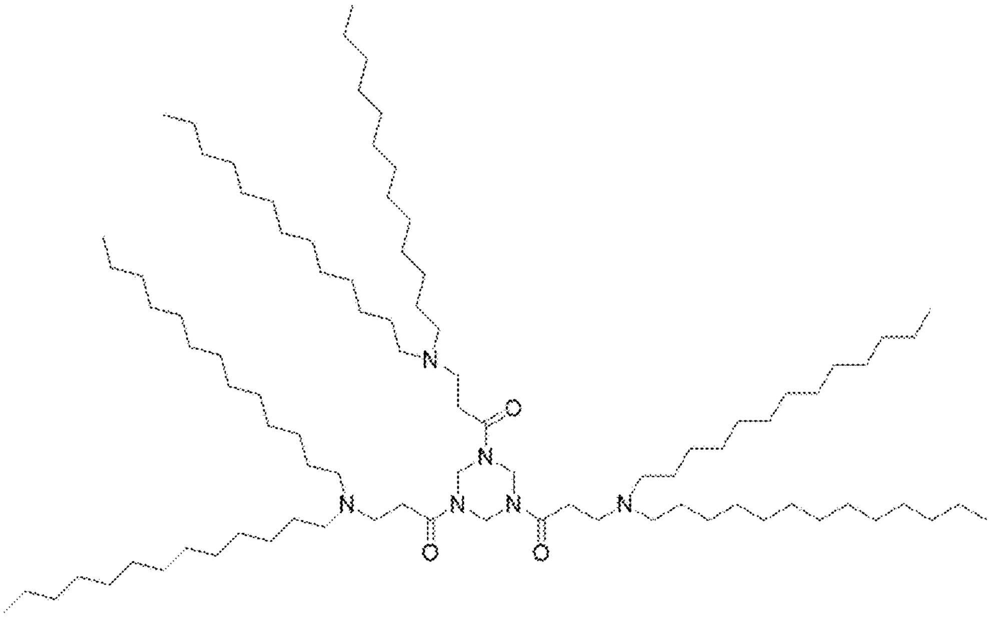
Figure 1:
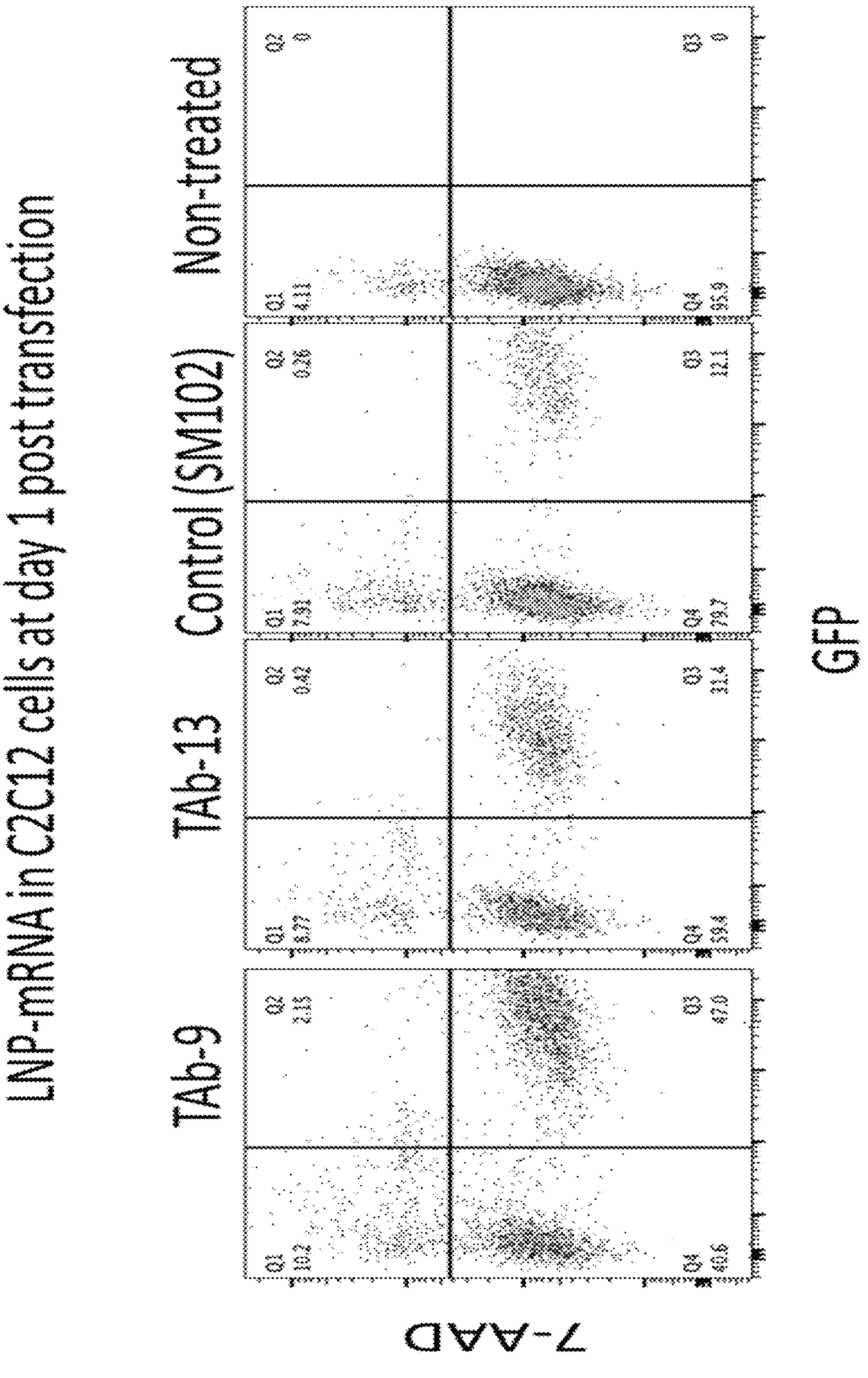
Figure 2:
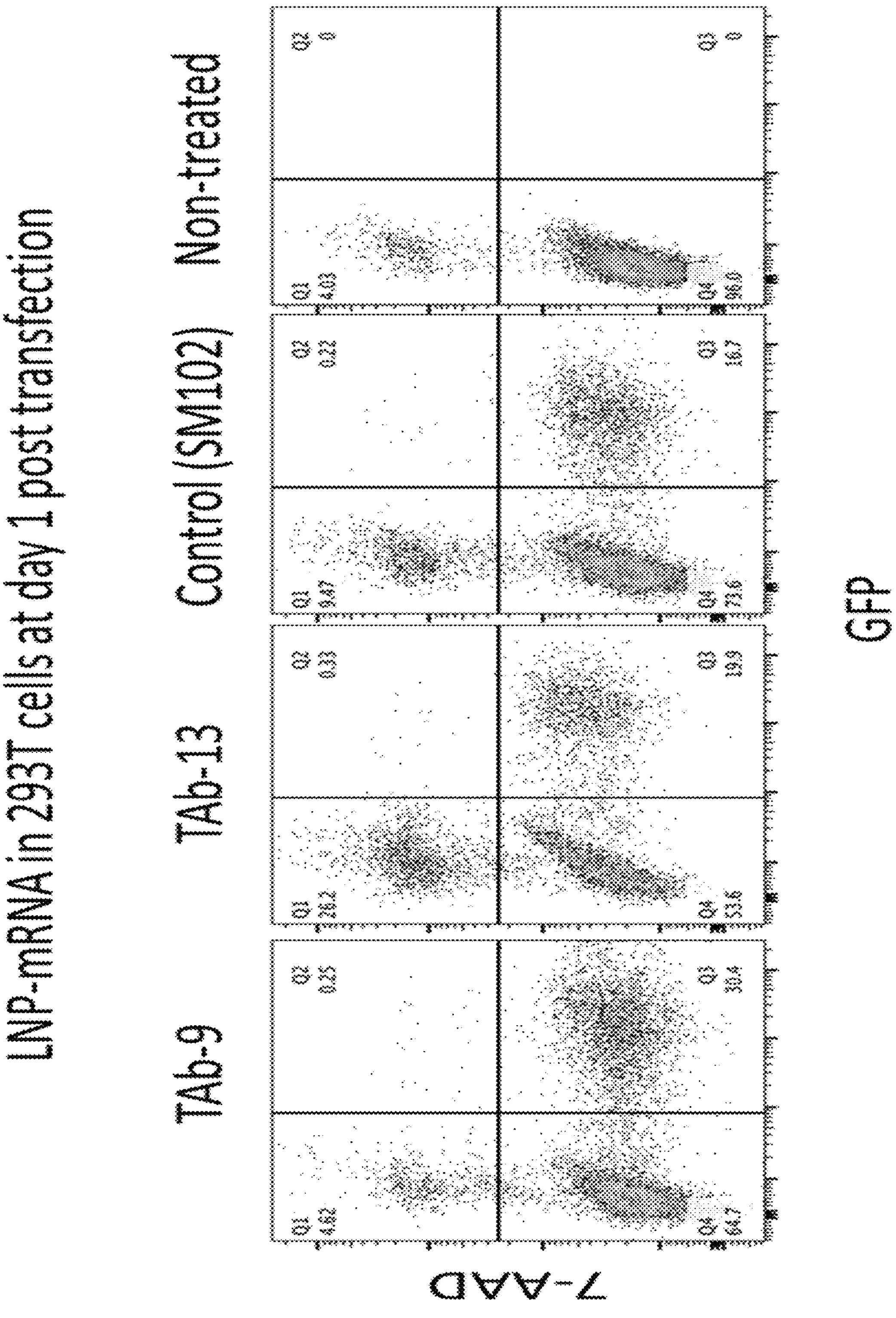
FIG. 2 shows FACS of TAb-9 and TAb-13 formulated LNPs encapsulated with self-amplifying mRNA encoding with GFP, which transfect and express GFP-mRNA in 293T cells.
Figure 3:
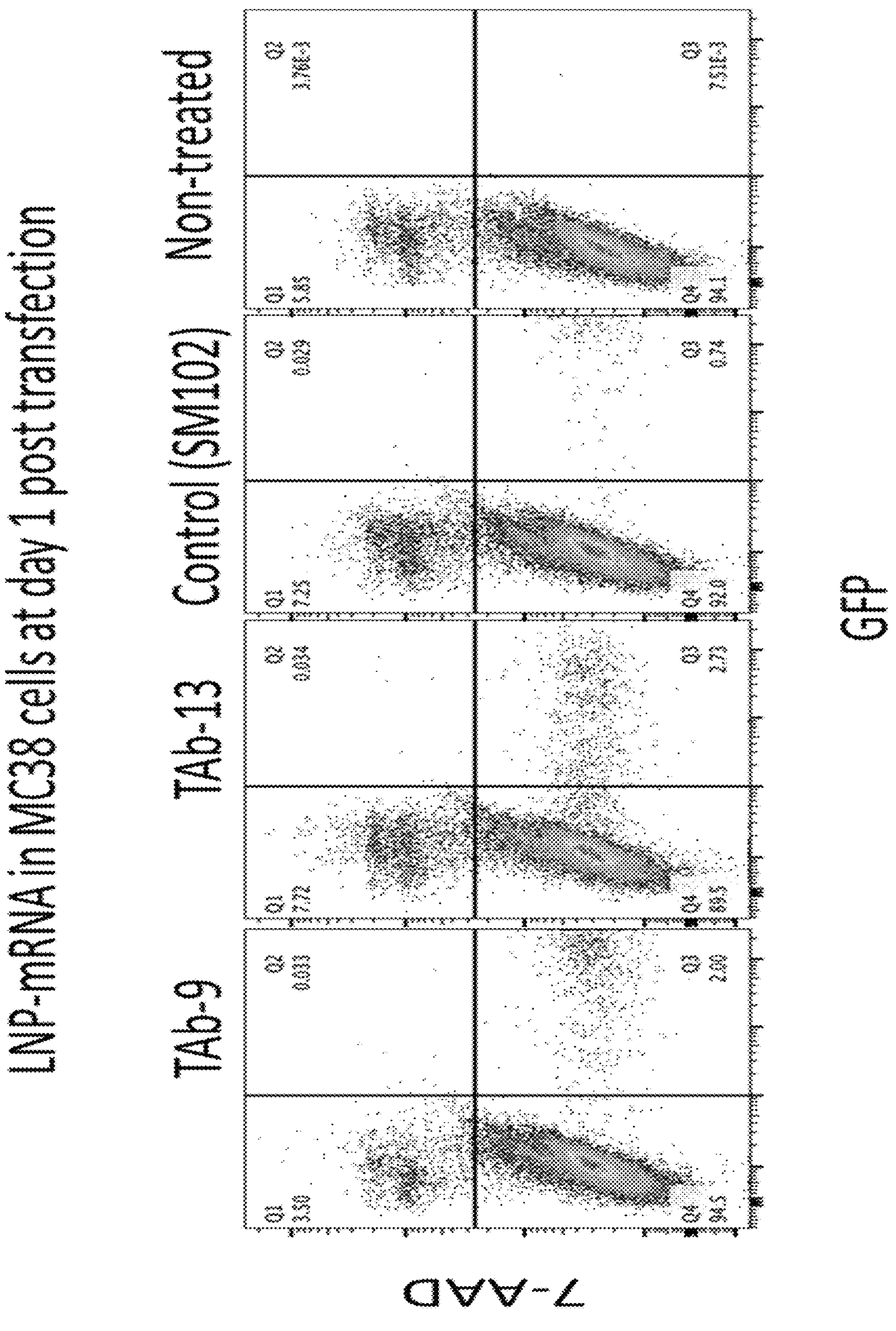
FIG. 3 shows FACS of TAb-9 and TAb-13 formulated LNPs encapsulated with self-amplifying mRNA encoding with GFP, which transfect and express GFP-mRNA in MC38 cells.

The disclosure relates to novel ionizable lipids and lipid nanoparticle compositions including a novel ionizable lipid. The disclosure also provides methods of delivering a biologically active agent to a cell, and treating a disease or disorder in a mammal in need thereof. For example, a method of producing a polypeptide of interest in a cell involves contacting a nanoparticle composition comprising an mRNA, such as modified mRNA, circular mRNA, or self-amplifying mRNA, with a cell, whereby the mRNA may be translated to produce the polypeptide or regulatory structure of interest.

In the present specification, the structural formula of the compound represents a certain isomer for convenience in some cases, but the present disclosure includes all isomers, it being understood that not all isomers may have the same level of activity. In addition, a crystal polymorphism may be present for the compounds represented by the formula. Any crystal form, crystal form mixture, or anhydride or hydrate thereof is included in the scope of the present disclosure.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates.

In the reaction schemes described herein, multiple stereoisomers may be produced. When no particular stereoisomer is indicated, it is understood to mean all possible stereoisomers that could be produced from the reaction. Enantiomeric and stereometric mixtures of compounds and means of resolving them into their component enantiomers or stereoisomers are well-known, for example, techniques such as preparative thin layer chromatography, preparative HPLC, preparative chiral HPLC, or preparative SFC may be used to separate the isomers.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "C1-C24 alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_1$-$C_{24}$ alkenyl" means an optionally substituted linear or branched hydrocarbon including 1-24 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_1$-$C_{24}$ alkynyl" means an optionally substituted linear or branched hydrocarbon including 1-24 carbon atoms and at least one carbon-carbon triple bond. An alkynyl group may include one, two, three, four, or more carbon-carbon triple bonds. For example, $C_{18}$ alkynyl may include one or more carbon-carbon triple bonds. Unless otherwise specified, an alkynyl group described herein refers to both unsubstituted and substituted alkynyl groups.

Alkyl, alkenyl, alkynyl, acyl, aryl, heteroaryl and cyclyl (e.g., carbocyclyl and heterocyclyl) groups may be optionally substituted unless otherwise specified.

About, Approximately: As used herein, the terms "approximately" and "about," as applied to one or more values of interest, refer to a value that is ±20% of the recited value.

As used herein, the term "contacting" means establishing a physical connection between two or more entities. For example, contacting a cell with a nanoparticle composition means that the cell and the nanoparticle composition are made to share a physical connection. Methods of contacting cells with external entities both in vivo and ex vivo are well known in the relevant arts. Moreover, more than one cell may be contacted by the nanoparticle composition.

As used herein, the term "delivering" means providing an entity to a destination. For example, delivering a biologically active agent to a subject may involve administering a LNP including the biologically active agent to the subject (e.g., by an intravenous, intramuscular, intradermal, or subcutaneous route). Administration of a nanoparticle composition to a subject or cell may involve contacting one or more cells with the nanoparticle composition.

As used herein, "encapsulation efficiency" refers to the amount of a biologically active agent that becomes part of a nanoparticle composition, relative to the initial total amount of biologically active agent used in the preparation of a nanoparticle composition. For example, if 97 mg of biologically active agent are encapsulated in a nanoparticle composition out of a total 100 mg of therapeutic and/or prophylactic initially provided to the composition, the encapsulation efficiency may be given as 97%. The encapsulation efficiency may be measured, for example, by encapsulating mRNA encoding GFP (green fluorescent protein) sequences in the nanoparticle composition and then measuring the encapsulation efficiency of the RFP sequence using flow cytometry. As used herein, "encapsulation" may refer to complete, substantial, or partial enclosure, confinement, surrounding, or encasement.

As used herein, "expression" of a nucleic acid sequence refers to translation of an mRNA into a polypeptide or protein and/or post-translational modification of a polypeptide or protein.

As used herein, a "lipid component" is that component of a nanoparticle composition that includes one or more lipids. For example, the lipid component may include one or more ionizable, PEGylated, structural, or phospholipids.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, "naturally occurring" means existing in nature without artificial aid.

As used herein, a "nanoparticle composition" is a composition comprising one or more lipids and biologically active agents. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

As used herein, a "lipid" refers to a group of organic compounds that include, for example, esters of fatty acids that are characterized by being less soluble in water but more soluble in many organic solvents.

As used herein, the term "subject" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants. As used herein, "patient" refers to an individual who may seek or be in need of treatment, requires treatment, is receiving treatment, will receive treatment, or under care by a trained professional for a particular disease or condition.

As used herein, a "PEG lipid" or "PEGylated lipid" refers to a lipid comprising a polyethylene glycol component.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, in some aspects, the term "structural lipid" refers to a compound comprising the following carbon skeleton:

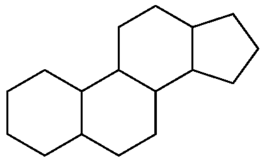 [SMILES: C1CCC2C(C1)CCC1C3CCCC3CCC21]

As used herein, "cationic lipid" and "ionizable lipid" refer to compounds that comprise both a polar (hydrophilic) head-group or moiety and a non-polar (hydrophobic or lipophilic) tail-group or moiety and may have a positive or partial positive charge at physiological pH. In certain aspects, such polar head-group and non-polar tail-group are bound (e.g., by one or more of hydrogen-bonds, van der Waals' forces, ionic interactions and covalent bonds) to each other (e.g., by an optionally substituted, variably unsaturated C1-C10 alkyl or alkenyl). In certain aspects, the head-group or moiety is hydrophilic (e.g., a hydrophilic head-group comprising an optionally-substituted alkyl amino). As used herein, the term "hydrophilic" is used to indicate in qualitative terms that a functional group is water-preferring, and water-soluble. As used herein, the term "hydrophobic" is used to indicate in qualitative terms that a functional group is water-avoiding, and typically such groups are not water soluble.

The phrase "pharmaceutically acceptable" is used herein to refer to those compounds, materials, compositions, and/or dosage forms which are, reasonably suitable for use in contact with the tissues of human beings and animals without excessive toxicity, irritation, allergic response, or other problem or complication.

The phrase "pharmaceutically acceptable excipient," as used herein, refers to any ingredient other than the compounds described herein and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

"Pharmaceutically acceptable compositions" may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; such as, nonaqueous media like ether, ethyl acetate, ethanol, isopropanol, or acetonitrile. Lists of suitable salts are found in Remington's Pharmaceutical Sciences, $17^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA, such as modified mRNA, circular mRNA, and self-amplifying mRNA), transfer RNA (tRNA), small interference RNA (siRNA), small activating RNA (saRNA), asymmetrical interfering RNA (aiRNA), microRNA (miRNA), Dicer-substrate RNA (dsRNA), small hairpin RNA (shRNA)). Translation of an mRNA encoding a particular polypeptide, for example, in vivo translation of an mRNA inside a mammalian cell, may produce the encoded polypeptide or regulatory structure. RNAs may be selected from the non-limiting group consisting of small interfering RNA (siRNA), asymmetrical interfering RNA (aiRNA), microRNA (miRNA), Dicer-substrate RNA (dsRNA), small hairpin RNA (shRNA), small activating RNA (saRNA), transfer RNA (tRNA), mRNA (modified mRNA, circular mRNA, and self-amplifying mRNA), and mixtures thereof.

As used herein, "size" or "mean size" in the context of nanoparticle compositions refers to the mean diameter of a nanoparticle composition.

The term "biologically active agent" refers to any agent that, when administered to a subject, has a therapeutic, diagnostic, and/or prophylactic effect and/or elicits a desired biological and/or pharmacological effect. Therapeutic agents are also referred to as "actives" or "active agents." Such agents include, but are not limited to, cytotoxins, radioactive ions, chemotherapeutic agents, small molecule drugs, proteins, and nucleic acids.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Nanoparticle Compositions

The disclosure also features nanoparticle compositions comprising a lipid component comprising a compound according to Formula (I), (II), (III), (IV), (V), (VI), and (VII) as described herein.

In one aspect, the present disclosure provides compounds of Formula (I):

(I)

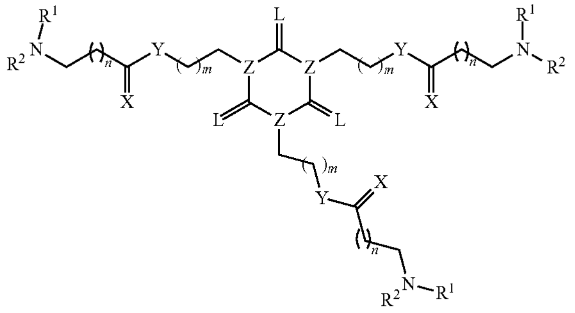

or a salt or isomer thereof, wherein each m and n are independently an integer from 0-10, e.g., 0, 1, 2, 3, 4, 5, 6, 7, 8, 9, or 10, or any subrange selected from within the range of 0-10, e.g., 2-9, 3-8, 4-7, 1-5, 1-4, 5-9, etc.;

each $R^1$ and $R^2$ are independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

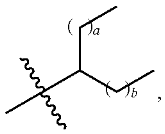 , 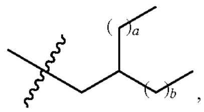 ,

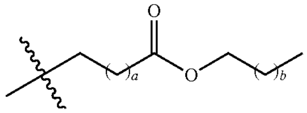 ,

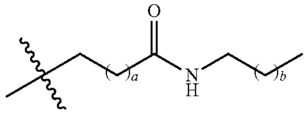 ,

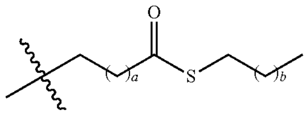 ,

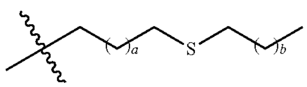 ,

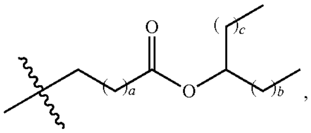 ,

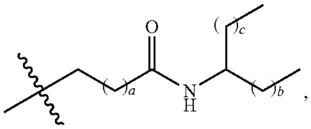 ,

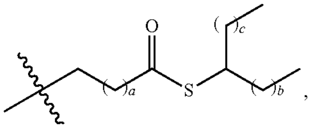 ,

-continued

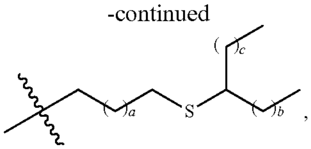,

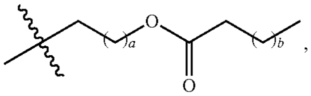,

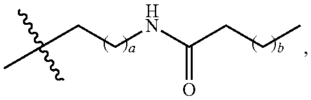,

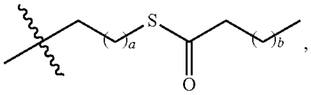,

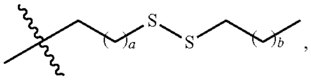,

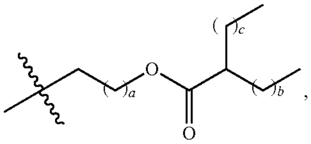,

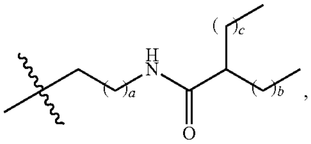,

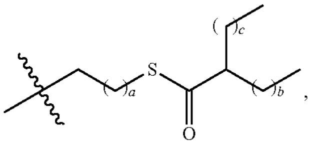,

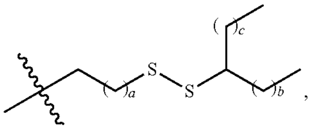, 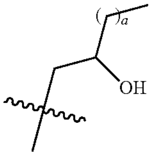,

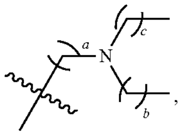, 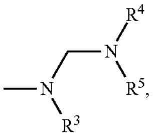

each a, b and c are independently an integer selected from 0-24, e.g., 0, 1, 2, 3, 4, 5, 6, 7, 8, 9, 10, 11, 12, 13, 14, 15, 16, 17, 18, 19, 20, 21, 22, 23, or any subrange selected from within the range of 0-24;

each $R^3$, $R^4$ and $R^5$ are independently selected from C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

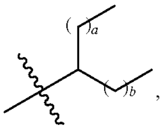, 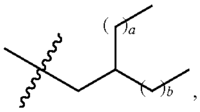,

-continued

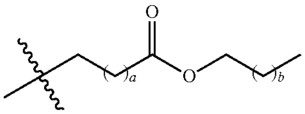,

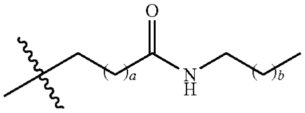,

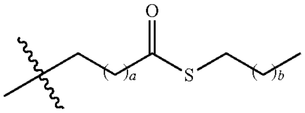,

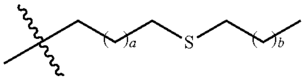,

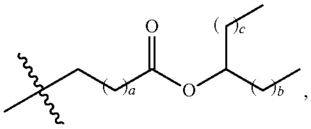,

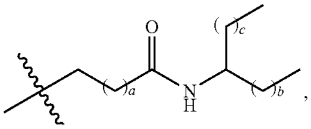,

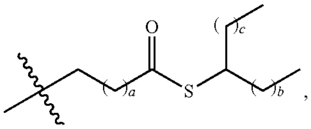,

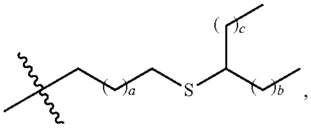,

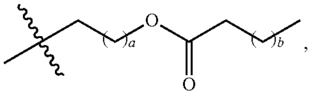,

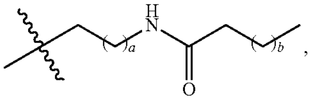,

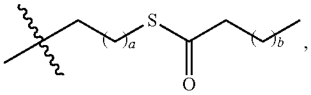,

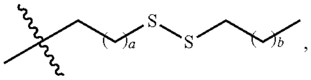,

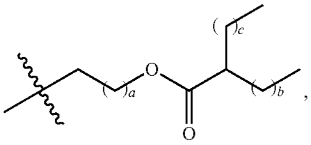,

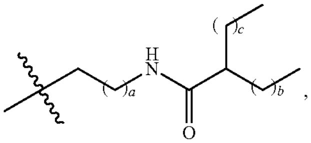,

-continued

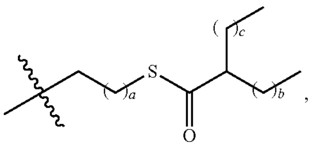
,

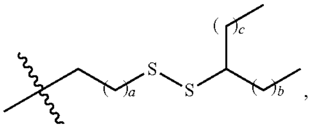
,
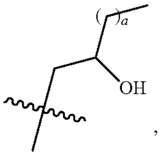
,

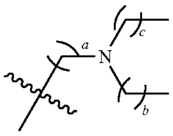

a, b and c are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24;

each X is independently selected from $CH_2$, NH, O, or S;

each Y is independently selected from $CH_2$, NH, O, or S;

each Z is independently selected from CH or N; and each L is independently selected from $CH_2$, NH, O, or S.

Synthesis Scheme 1.

General synthesis routes for the synthesis of compounds of Formula I.

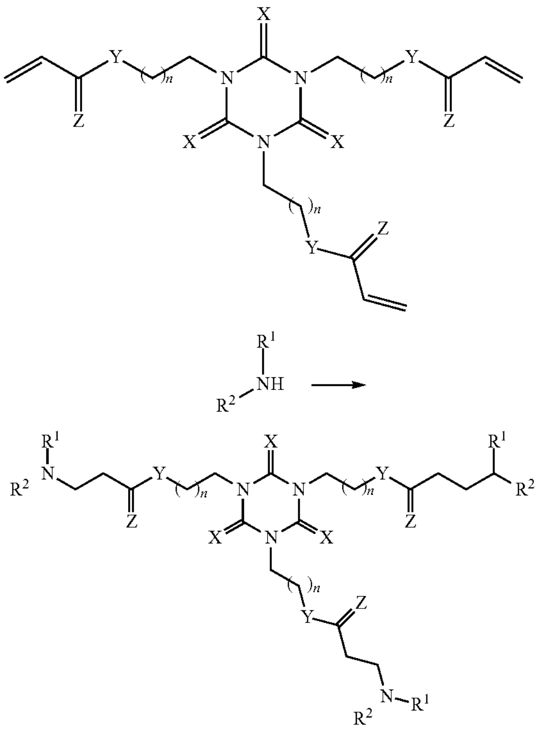
or

-continued

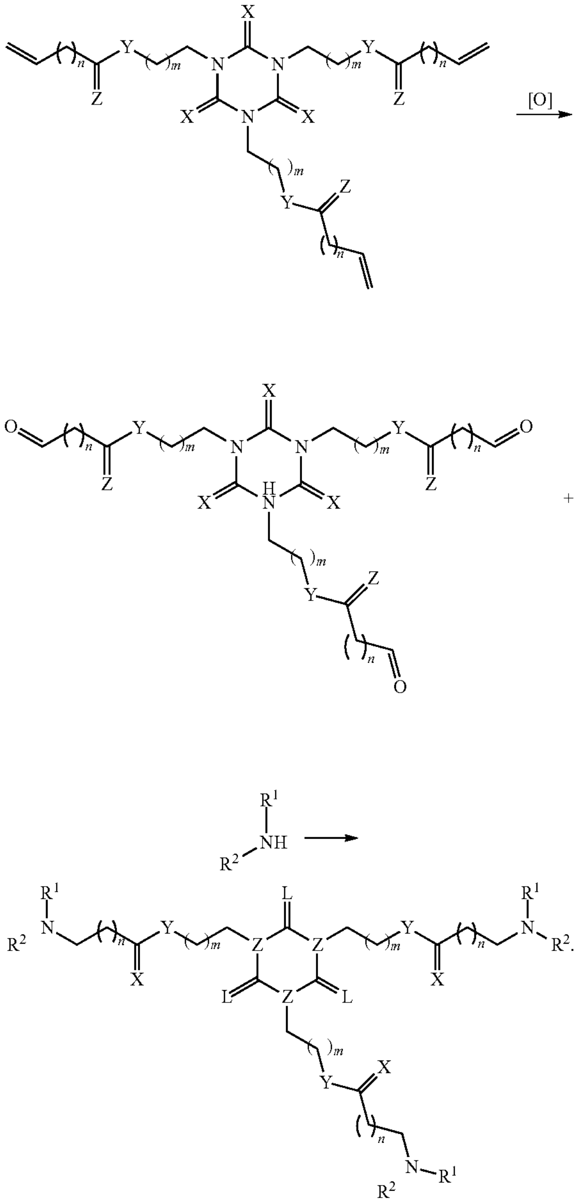

As an example, the α,β-unsaturated Michael Acceptor may be

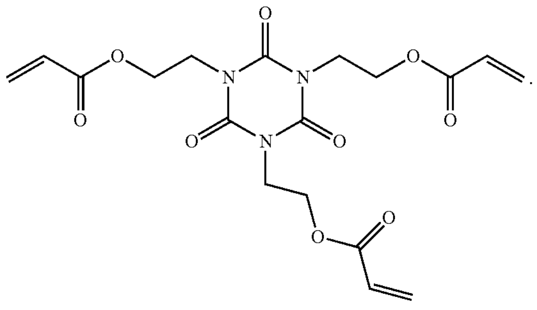

TAa

As an example, the amine may be selected from
DA8
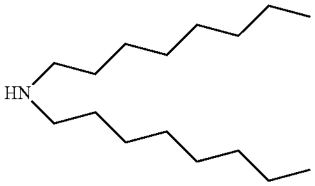
DA9
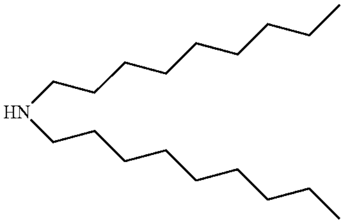
DA10
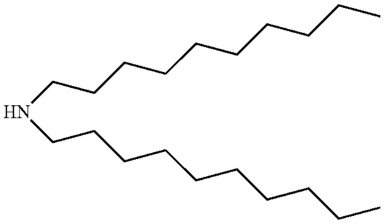
DA11
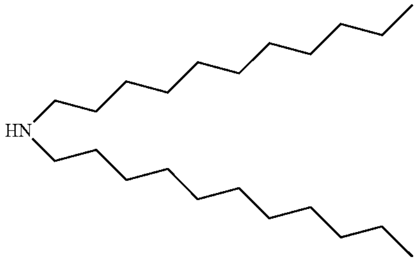
DA12
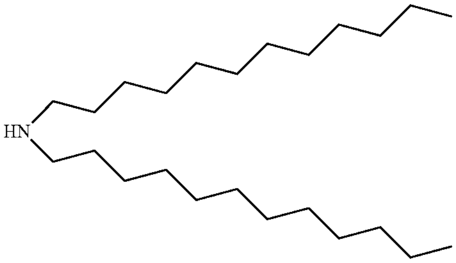
-continued
DA13
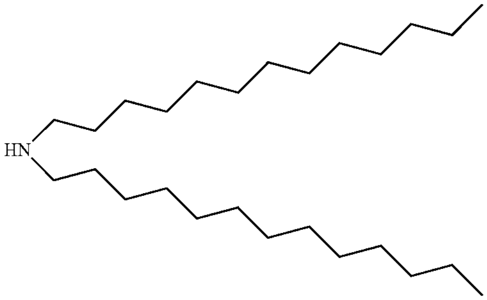
DA14
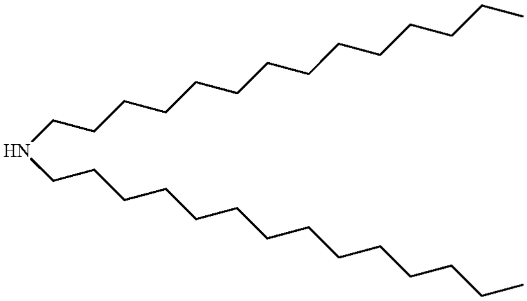
DA18
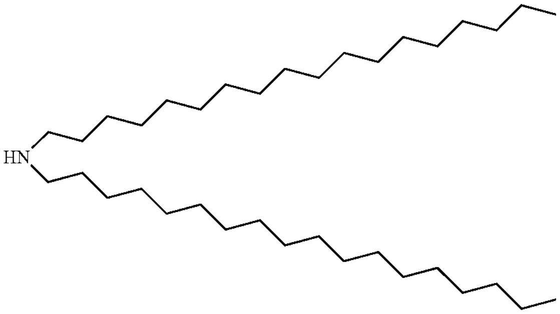
AP1
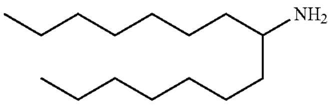
AP2
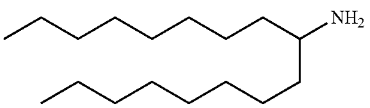

-continued

AP3

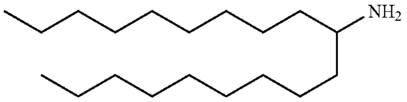

AP4

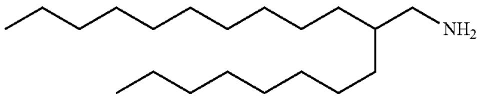

AP5

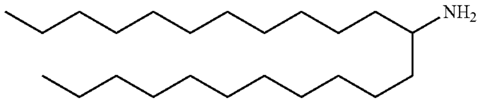

AP6

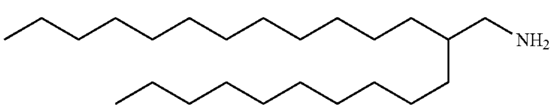

AP7

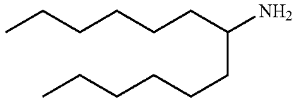

AP8

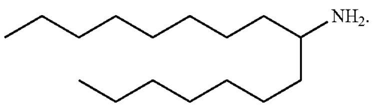

In certain aspects, compounds of Formula I may comprise, for example, the following formula:

I-1

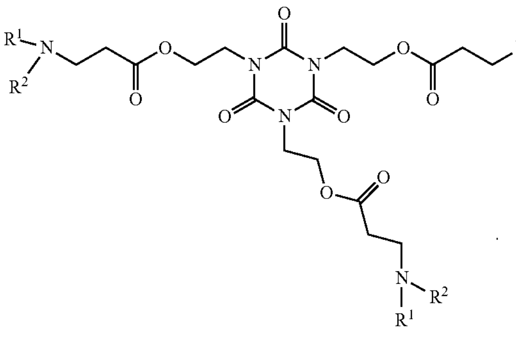

or a salt or isomer thereof, wherein each $R^1$ and $R^2$ are as defined above.

General synthesis route for the synthesis of compounds of Formula I-1:

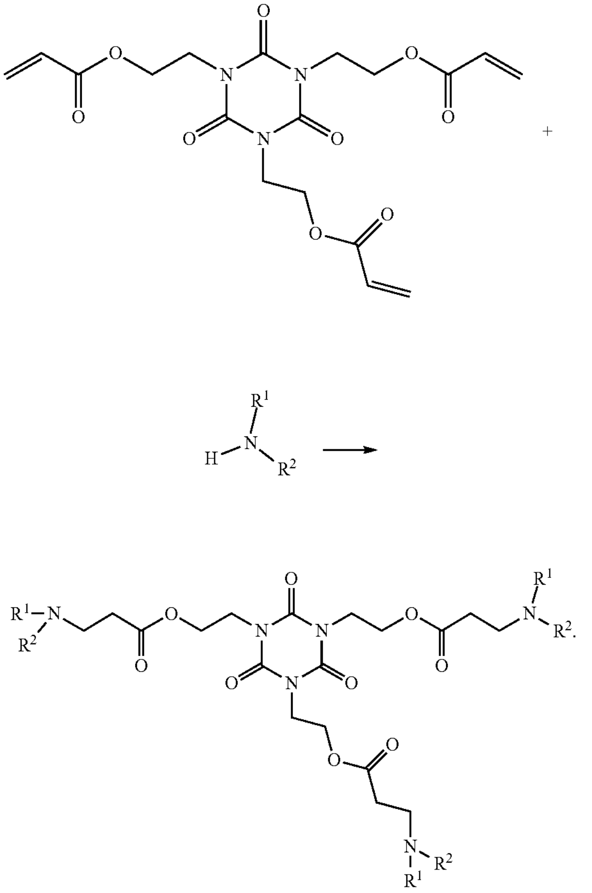

In one example, compounds of Formula I-1 were synthesized as follows:

Tris(2-acryloyloxyethyl) Isocyanurate (0.2 mmol) is mixed with amines (0.66 mmol) in 10 mL toluene/ACN (5/1) at 1 to 3.3 molar ratio and the mixture was stirred in glass screw-top vials in oil bath at 95° C. for two days. The solvent can be removed using methods known in the art, such as rotary evaporator. The product can be purified using methods known in the art, such as column chromatography by gradient elution of Hexane/ethyl acetate. Structures were confirmed using techniques known in the art, for example, nuclear magnetic resonance spectra of 1H and LC-Mass spectrometry.

(2,4,6-trioxo-1,3,5-triazinane-1,3,5-triyl)tris(ethane-2,1-diyl)tris(3-(ditetradecylamino)propanoate) (C7): yield (20%). $^1$H-NMR (400 MHz, CDCl3, δ) 4.29 (t, J=8 Hz, 3H), 4.16 (t, J=8 Hz, 3H), 2.75 (t, J=8 Hz, 3H), 2.60 (t, J=8 Hz, 3H), 2.42-2.34 (m, 12H), 1.50-1.26 (m, 84H), 0.87 (t, J=8 Hz, 18H). MS (APCI) m/z 1148.3 $[M+H]^+$.

(2,4,6-trioxo-1,3,5-triazinane-1,3,5-triyl)tris(ethane-2,1-diyl)tris(3-(dioctylamino)propanoate) (D7): yield (23%). $^1$H-NMR (400 MHz, CDCl3, δ) 4.29 (t, J=8 Hz, 3H), 4.17 (t, J=8 Hz, 3H), 2.75 (t, J=8 Hz, 3H), 2.60 (t, J=8 Hz, 3H), 2.39-2.34 (m, 12H), 1.50-1.26 (m, 156H), 0.89 (t, J=8 Hz, 18H). MS (APCI) m/z 1653.5 $[M+H]^+$.

In certain aspects, compounds of Formula I may include, for example, the following compounds:
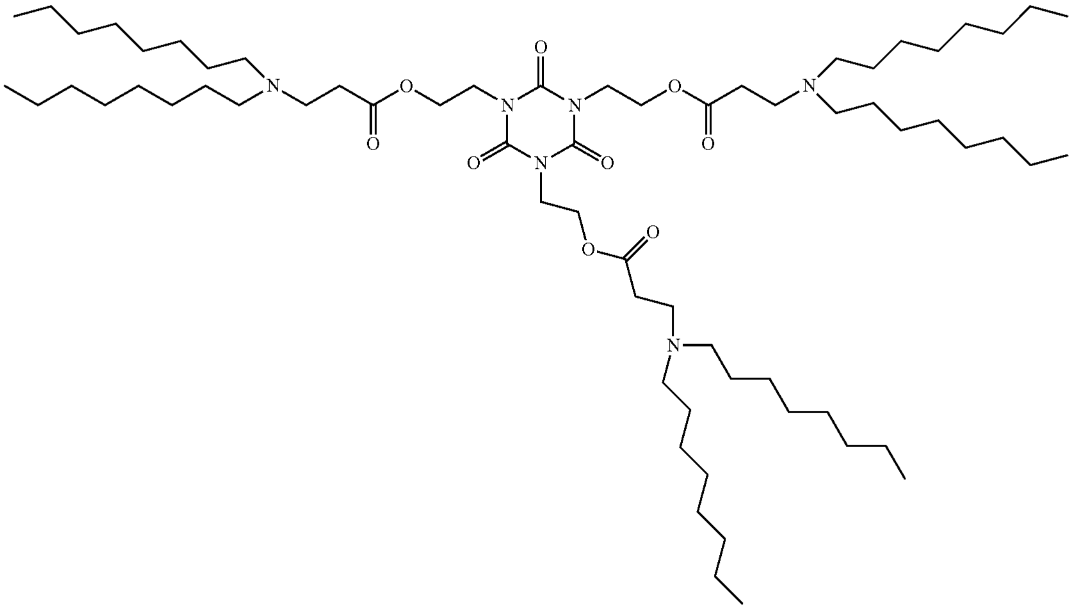
(Ia)
also referred to as C7;
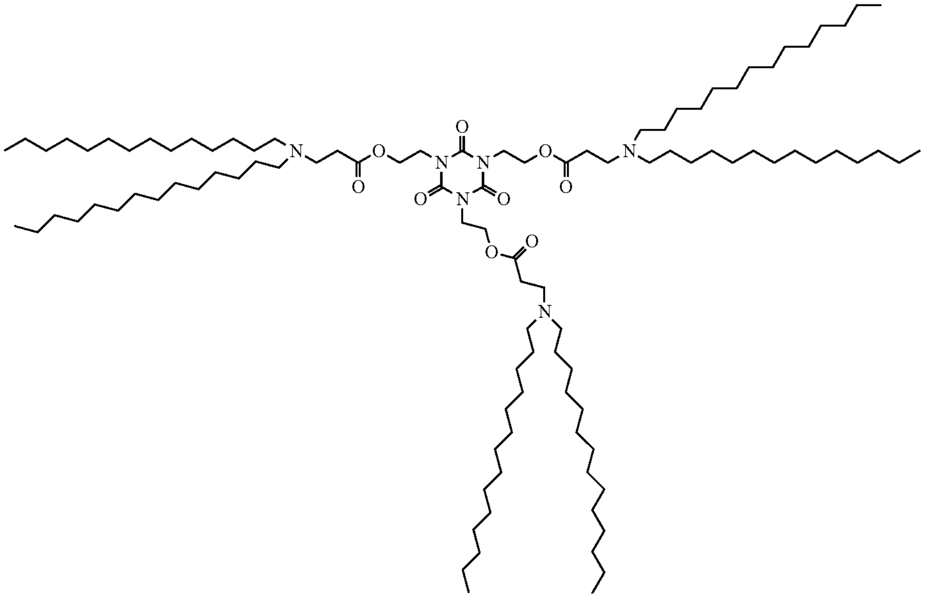
(Ib)
(Ib) also referred to as D7.

In another aspect, the present disclosure provides compounds of Formula (II):

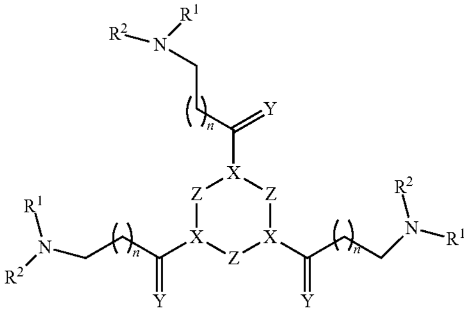

(II)

or a salt or isomer thereof, wherein each n is independently an integer from 0-10, e.g., 0, 1, 2, 3, 4, 5, 6, 7, 8, 9, or 10, or any subrange selected from within the range of 0-10, e.g., 2-9, 3-8, 4-7, 1-5, 1-4, 5-9, etc.;

each $R^1$ and $R^2$ are independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

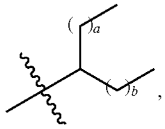
,
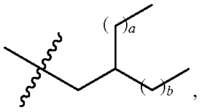
,

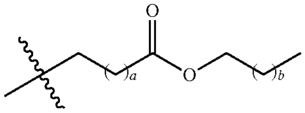
,

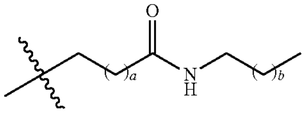
,

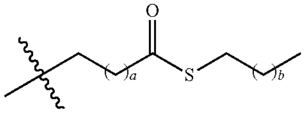
,

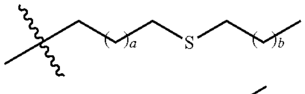
,

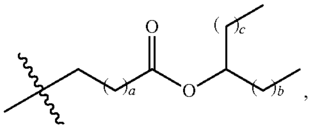
,

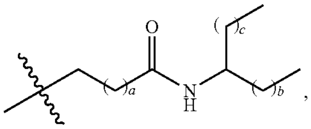
,

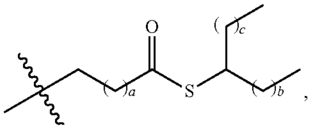
,

-continued

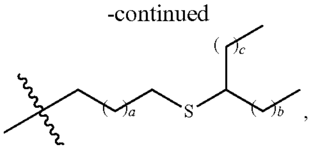
,

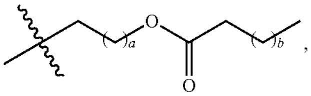
,

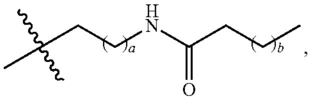
,

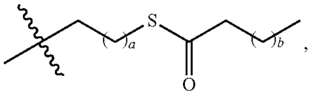
,

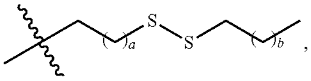
,

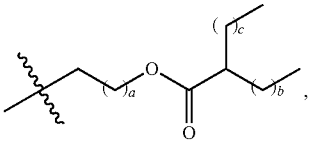
,

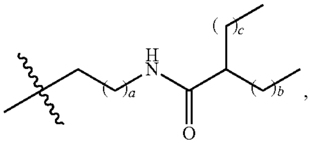
,

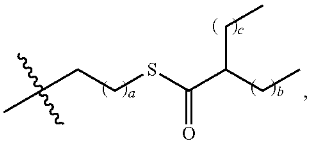
,

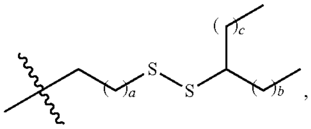
,
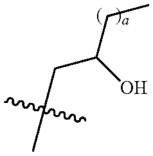
,

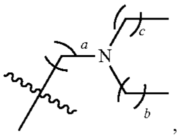
,
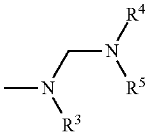

a, b and c are each independently an integer from 0-24;

each $R^3$, $R^4$ and $R^5$ are independently selected from C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

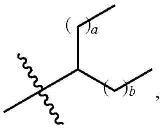
,
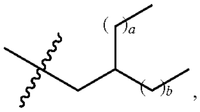
,

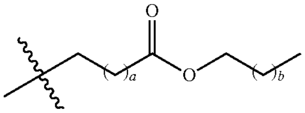
,

-continued
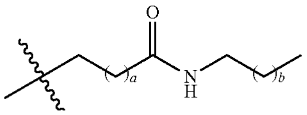
,
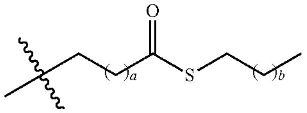
,
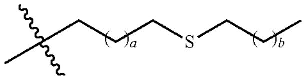
,
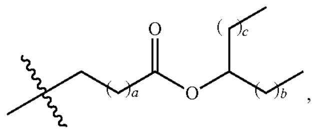
,
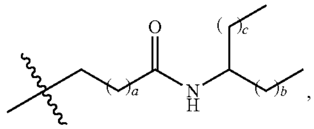
,
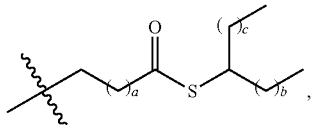
,
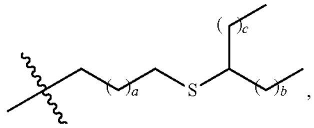
,
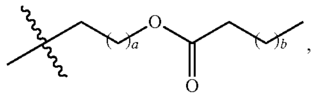
,
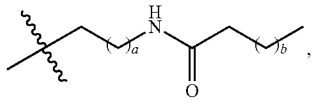
,
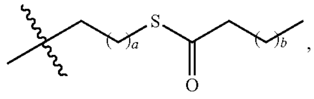
,
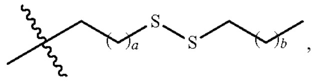
,
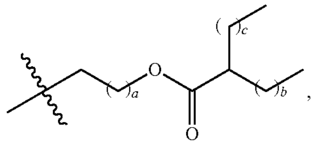
,
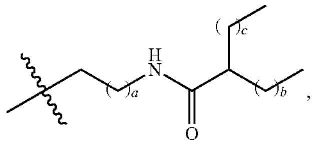
,
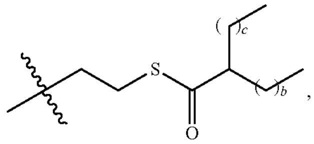
,
-continued
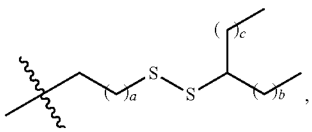
,
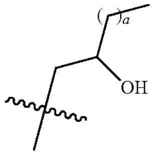
,
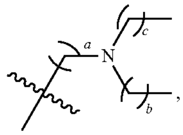
,
a, b and c are each independently an integer from 0-24, e.g., 1, 2, 3, 4, 5, 6, 7, 8, 9, 10, 11, 12, 13, 14, 15, 16, 17, 19, 20, 21, 22, 23, or any subrange selected from within the range of 0-24;
each X is independently selected from CH, or N;
each Y is independently selected from $CH_2$, NH, O, or 5; and
each Z is independently selected from $CH_2$, NH, O, or S.
Synthesis Scheme 2.
General synthetic routes for the synthesis of compounds of Formula II.
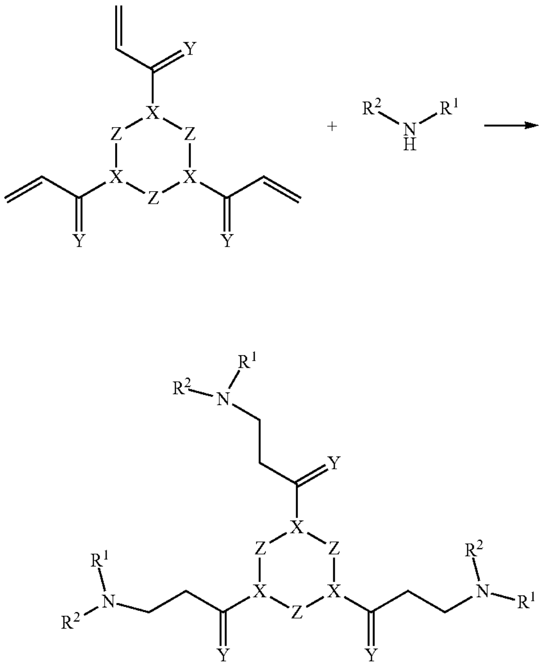
or
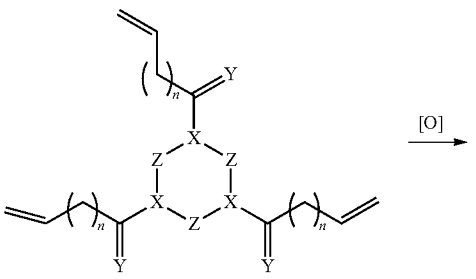

-continued

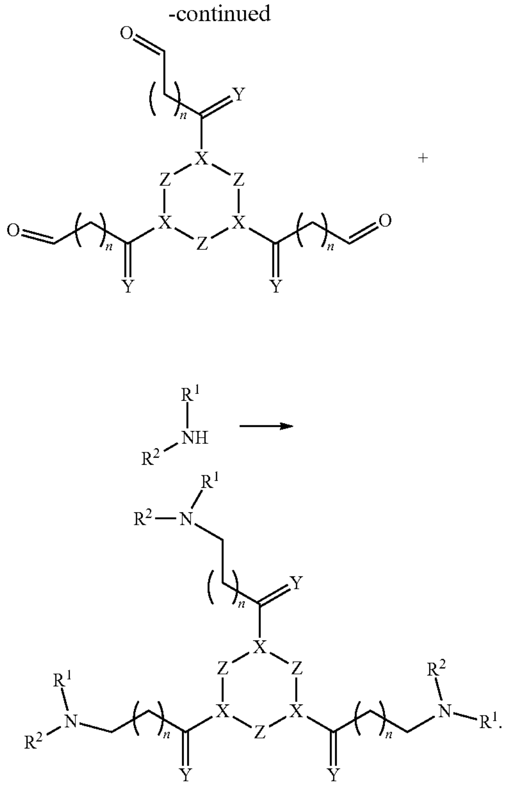

As an example, the α,β-unsaturated Michael Acceptor may be

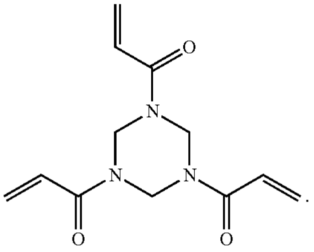 [SMILES: C=CC(=O)N1CN(C(=O)C=C)CN(C(=O)C=C)C1]

As an example, the amine may be, for example, selected from DA8-DA14, DA18, AP1-AP8, as shown above.

In certain aspects, compounds of Formula II may comprise, for example, the following formula:

II-1

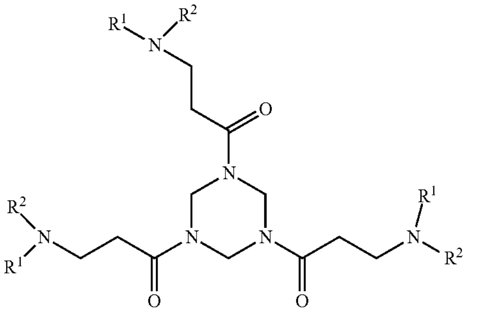

or a salt or isomer thereof, wherein each $R^1$ and $R^2$ are as defined above.

General synthesis route for the synthesis of compounds of Formula II-1:

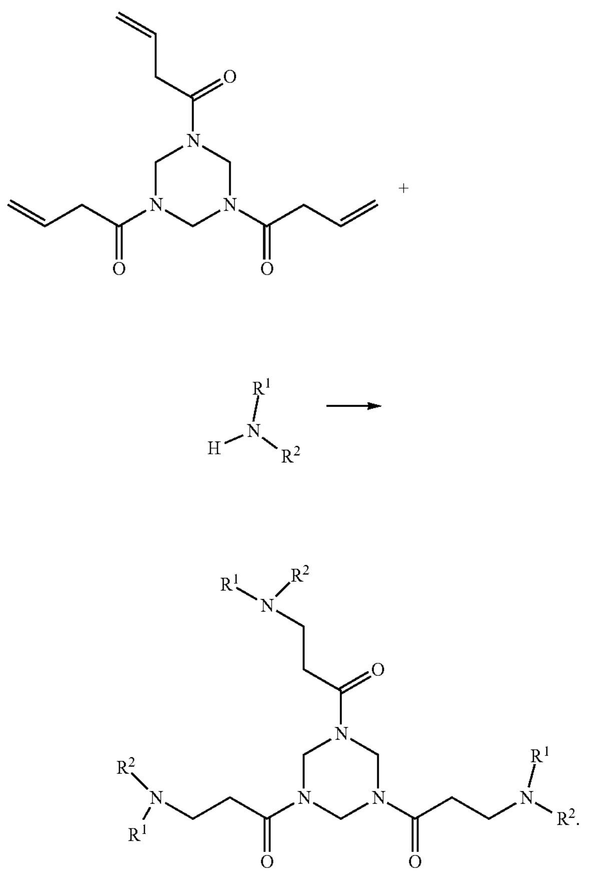

In some examples, compounds of Formula I-1 were synthesized as follows:

1,3,5-Triacryloylhexahydro-1,3,5-triazine (0.2 mmol) is mixed with amines (0.66 mmol) in 10 mL toluene/ACN (5/1) at 1 to 3.3 molar ratio and the mixture was stirred in glass screw-top vials in oil bath at 95° C. for two days. The solvent can be removed using techniques known in the art, such as rotary evaporator and the product can be purified using, for example, column chromatography. Structure can be confirmed using techniques known in the art, for example, nuclear magnetic resonance spectra of 1H and LC-Mass spectrometry.

1,1',1"-(1,3,5-triazinane-1,3,5-triyl)tris(3-(dinonylamino)propan-1-one) (E2): yield (25%). 1H-NMR (400 MHz, CDCl3, δ) 5.26 (s, 6H), 2.79 (t, J=8 Hz, 6H), 2.65 (t, J=8 Hz, 6H), 2.41 (t, J=8 Hz, 12H), 1.42-1.26 (m, 84H), 0.88 (t, J=8 Hz, 18H). MS (ESI) m/z 529.6 $[M+2H]^{2+}$.

1,1',1"-(1,3,5-triazinane-1,3,5-triyl)tris(3-(dinonylamino)propan-1-one) (E6): yield (22%). 1H-NMR (400 MHz, CDCl3, δ) 5.26 (s, 6H), 2.81 (t, J=8 Hz, 6H), 2.67 (t, J=8 Hz, 6H), 2.43 (t, J=8 Hz, 12H), 1.44-1.23 (m, 132H), 0.88 (t, J=8 Hz, 18H). MS (ESI) m/z 697.9 $[M+2H]^{2+}$.

In certain aspects, compounds of Formula II may include, for example, the following compounds:
(IIa)
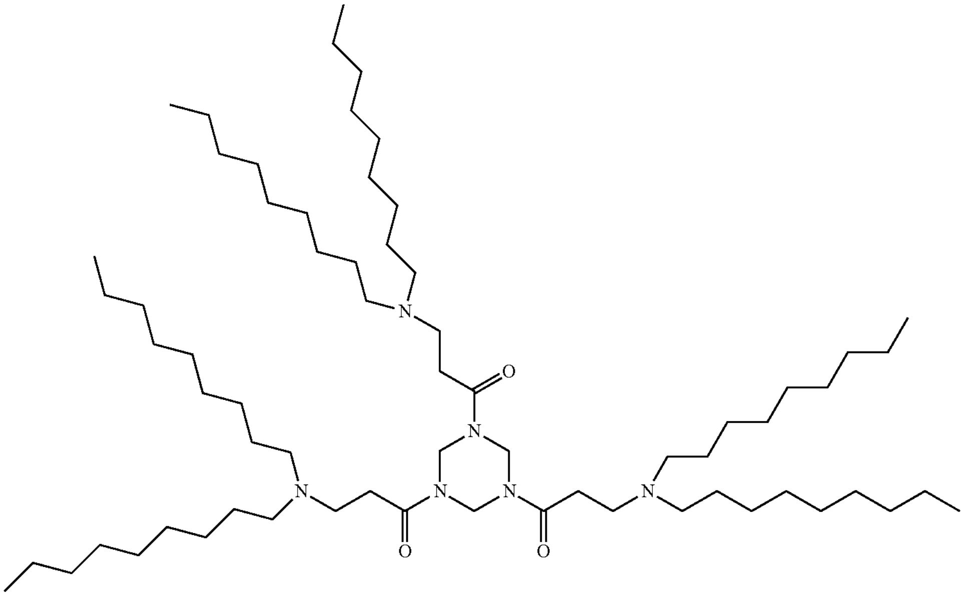
;
referred to as TAb-9, E2 or (II)-A;
(IIb)
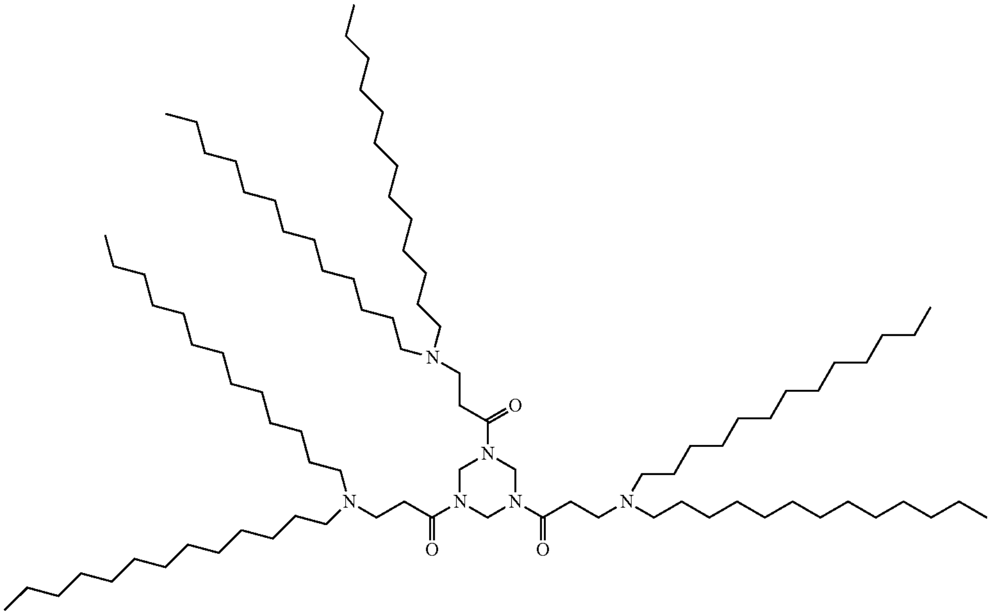
,
also referred to as TAb-13, E6 or (II)-B;
or a salt or isomer thereof.

In another aspect, the present disclosure provides compounds of Formula (III):

(III)

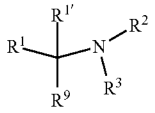

or a salt or isomer thereof, wherein each $R^1$, $R^{1'}$, $R^2$ and $R^3$ are independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

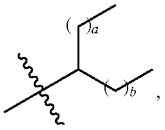,
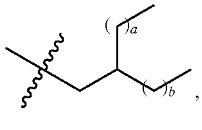,
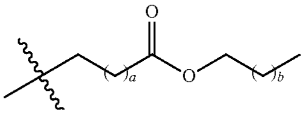,
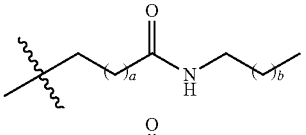,
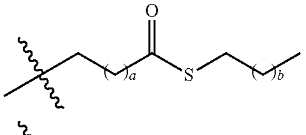,
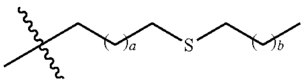,
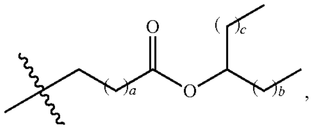,
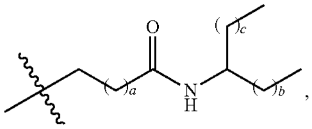,
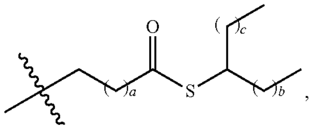,
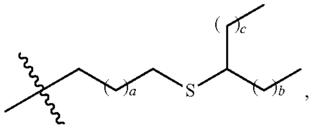,
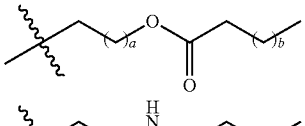,
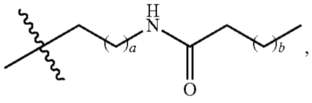, -continued

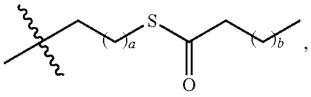,
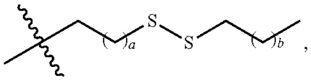,
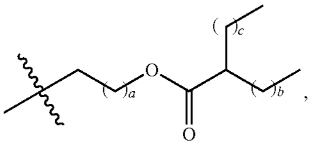,
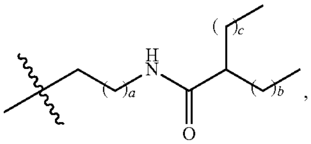,
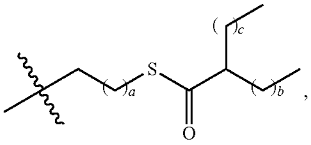,
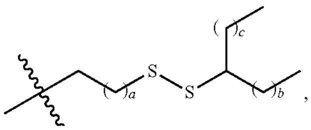,
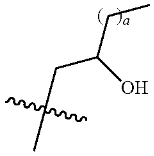,
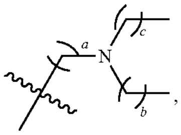,
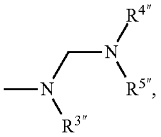

a, b and c are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24;

each $R^9$ is independently selected from

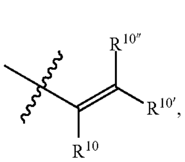
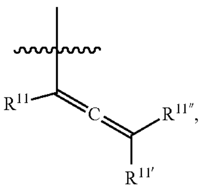 or
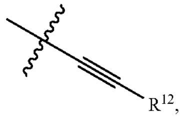

wherein each $R^{10}$, $R^{10'}$, $R^{10''}$, $R^{11}$, $R^{11'}$, $R^{11''}$, and $R^{12}$ are independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

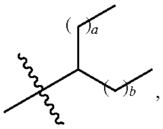, 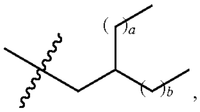,

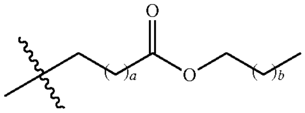,

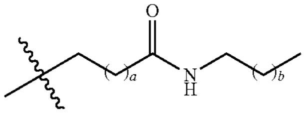,

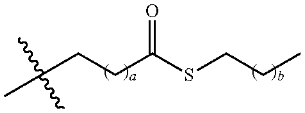,

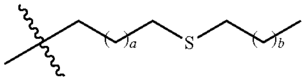,

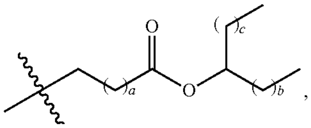,

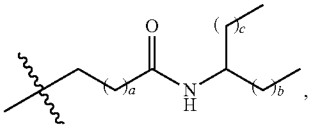,

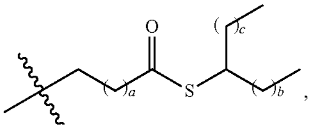,

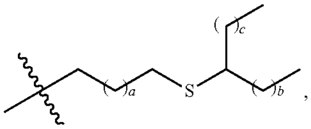,

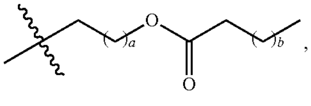,

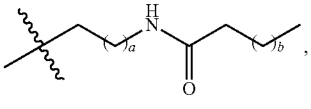,

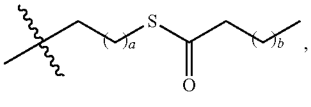,

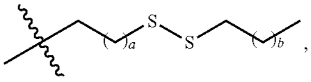,

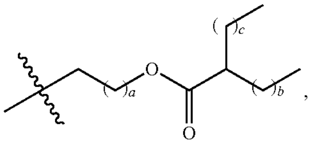,

-continued

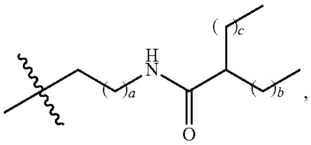,

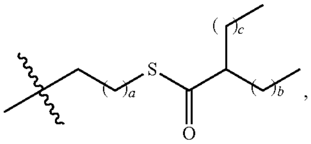,

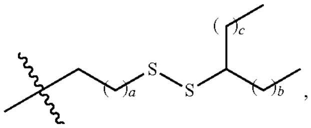, 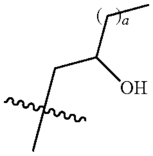,

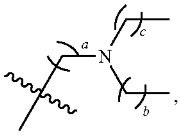, 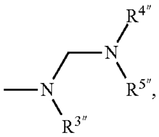, a, b and c are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24;

$R^{3''}$, $R^{4''}$, and $R^{5''}$ are independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

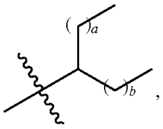, 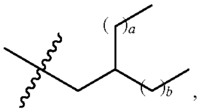,

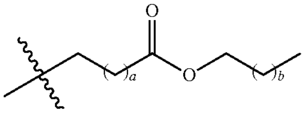,

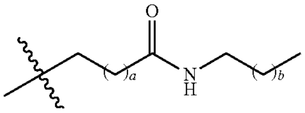,

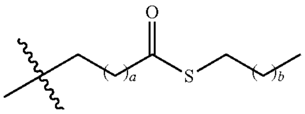,

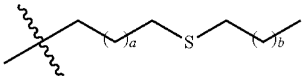,

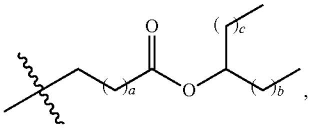,

-continued
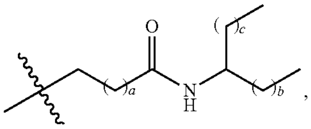
,
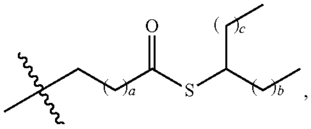
,
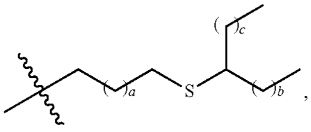
,
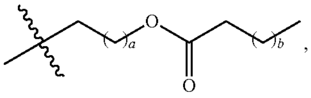
,
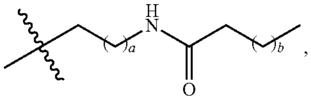
,
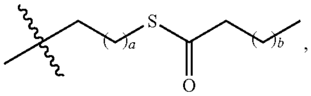
,
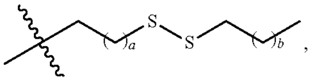
,
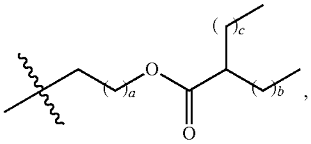
,
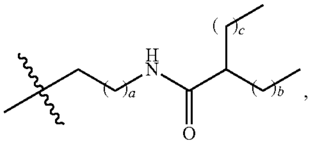
,
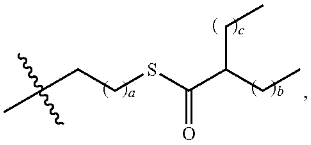
,
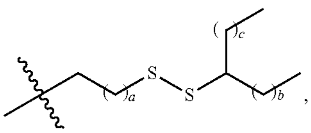
,
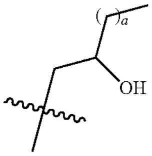
,
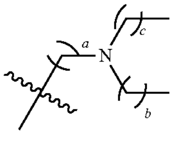
a, b and c are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24;
Synthesis Scheme 3.
General synthetic route for the synthesis of compounds of Formula III.
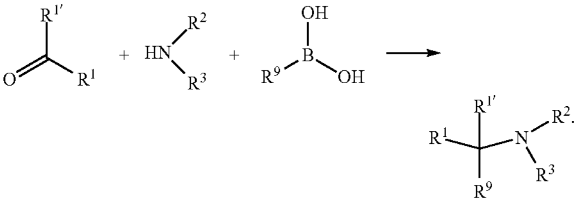
As examples, the boric acid may be selected from:
B1
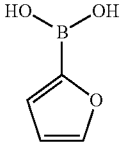
B2
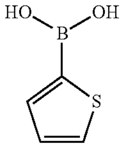
B3
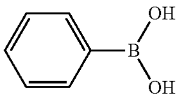
B4
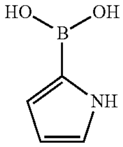
B5
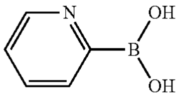
B6
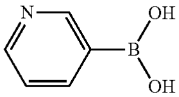
B7
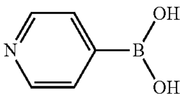
B8
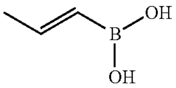
B9
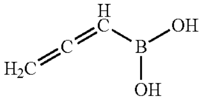
B10
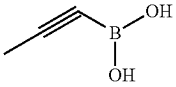

-continued
B11
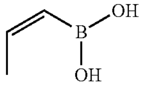
B12
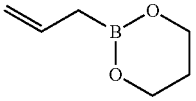
B13
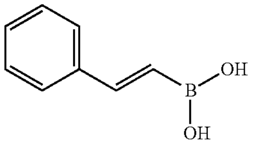
BA1
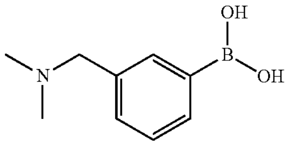
BA2
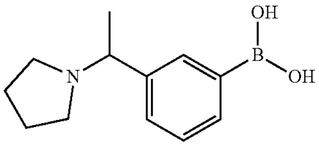
BA3
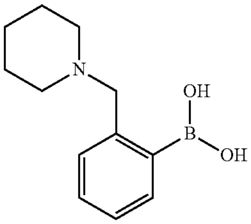
BA4
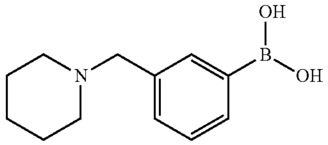
BA5
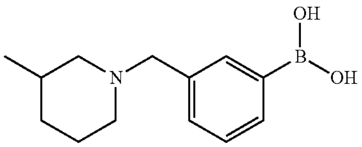
BA6
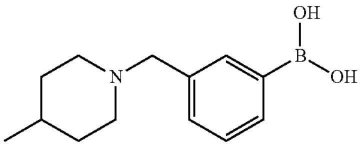
DB1
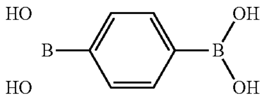
DB2
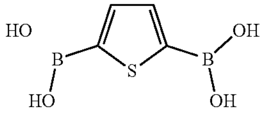
-continued
DB3
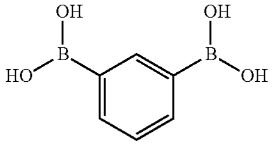
TB
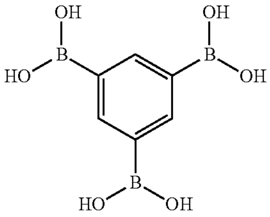
BLC12
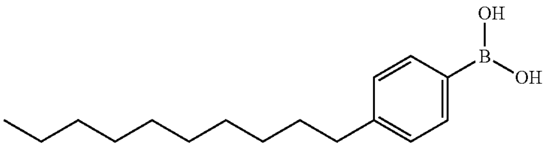
BsC12
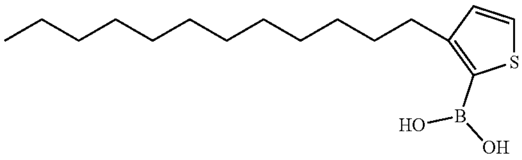
DBDC8
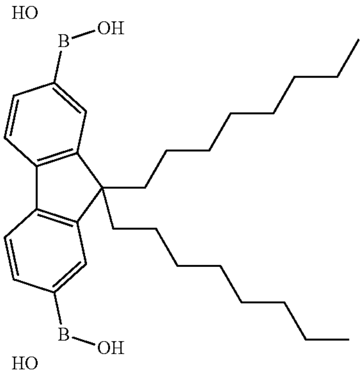
DBDC12
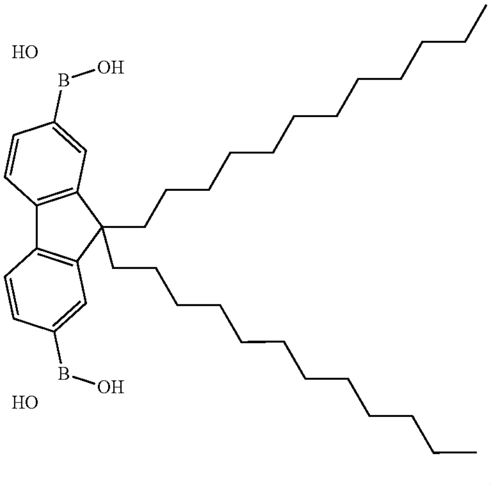
.

As examples, the amine may be, for example, selected from DA8-DA14, DA18, AP1-AP8, as shown above.

As examples, the aldehyde or ketone may be selected from:

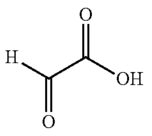
GA

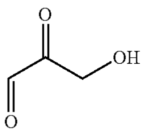
HOA

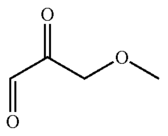
MOA

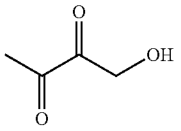
HBK

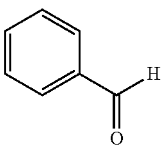
PA

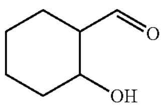
cHA-OH

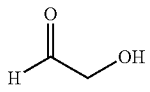
HA

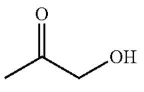
HK

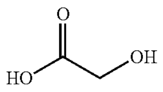
HAA

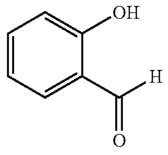
HPA

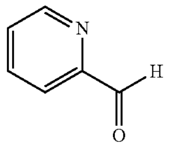
PiA

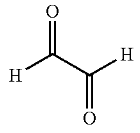
OA

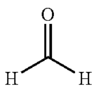
FA

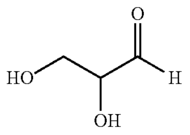
dHA

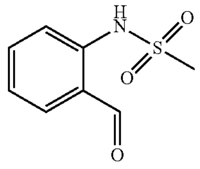
SNPA

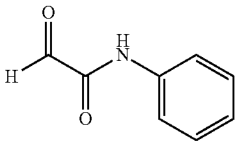
PNA

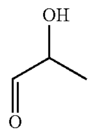
MHA

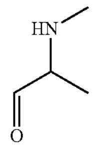
MNA

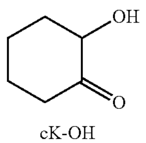
cK-OH

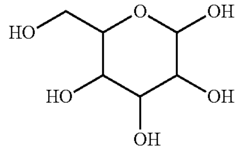
Hose

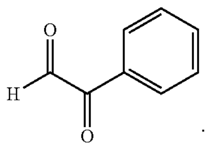
.

PKA

In some examples, the compounds of Formula III were synthesized as follows:

The ionizable lipid were synthesized with a molar ratio of boric acid/amine/aldehyde at 1:1:1 carried out on 96-well plates with glass insert. Structures were confirmed using techniques known in the art, for example, nuclear magnetic resonance spectra of 1H and LC-Mass spectrometry.

2,2'-(1,4-phenylenebis((dioctylamino)methylene))diphenol (TP1A11): yield (17%). 1H-NMR (400 MHz, CDCl3, δ) 7.37 (s, 4H), 7.10-7.14 (t, J=8 Hz, 2H), 6.83-6.85 (d, J=8 Hz, 2H), 6.77-6.80 (m, 2H), 6.64-6.69 (t, J=12 Hz, 2H), 4.88 (d, J=8 Hz, 2H), 2.42-2.65 (m, 8H), 1.21-1.25 (m, 40H), 0.84-0.89 (m, 12H). MS (APCI) m/z 769.7 $[M+H]^+$.

2-((ditetradecylamino)(thiophen-2-yl)methyl)phenol (TP4G11): yield 23%. HNMR (400 MHz, CDCl3, δ) 7.39 (d, J=8 Hz, 1H), 7.08-7.14 (m, 2H), 7.02-7.05 (m, 1H), 6.86-6.89 (d, J=12 Hz, 1H), 6.75-6.78 (m, 1H), 6.66-6.72 (m, 1H), 5.44 (s, 1H), 2.45-2.69 (m, 4H), 1.29 (m, 48H), 0.84-0.90 (t, 6H). MS (APCI) m/z 769.7 $[M+H]^+$.

2-((ditridecylamino)(4-dodecylphenyl)methyl)phenol (TP3F11): yield 25%. HNMR (400 MHz, CDCl3, δ) 7.30 (d, J=12 Hz, 2H), 7.14 (d, J=12 Hz, 3H), 6.85 (t, J=12 Hz, 2H), 6.69 (t, J=12 Hz, 1H), 4.92 (s, 1H), 2.60-2.55 (m, 4H), 2.39-2.44 (m, 2H), 1.59-1.51 (m, 6H), 1.25 (m, 60H), 0.88 (t, J=12 Hz, 9H). MS (APCI) m/z 732.7 $[M+H]^+$.

2-((ditetradecylamino)(4-dodecylphenyl)methyl)phenol (TP3G11): yield 26%. HNMR (400 MHz, CDCl3, δ) 7.30 (d, J=12 Hz, 2H), 7.14 (d, J=12 Hz, 3H), 6.82 (t, J=12 Hz, 2H), 6.66 (t, J=12 Hz, 1H), 4.92 (s, 1H), 2.60-2.55 (m, 4H), 2.39-2.44 (m, 2H), 1.59-1.51 (m, 6H), 1.25 (m, 64H), 0.88 (t, J=12 Hz, 9H). MS (APCI) m/z 732.7 $[M+H]^+$.

In certain aspects, compounds of Formula III may comprise, for example, the following formula:

(III-1)

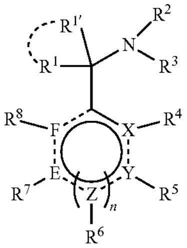

or a salt or isomer thereof, wherein each $R^1$, $R^{1'}$, $R^2$, $R^3$, $R^4$, $R^5$, $R^6$, $R^7$ and $R^8$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

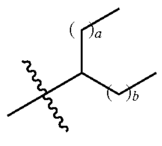
,
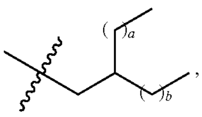
,
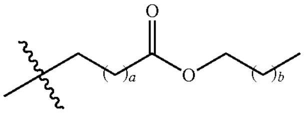
,

-continued
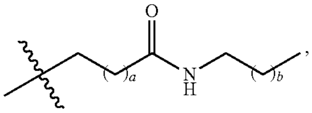
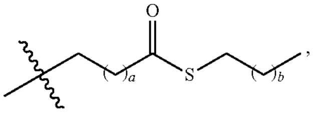
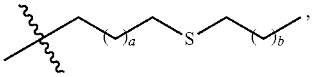
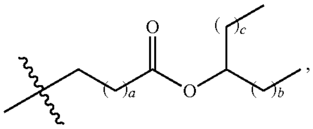
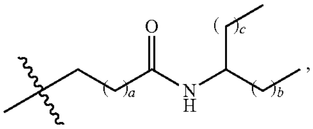
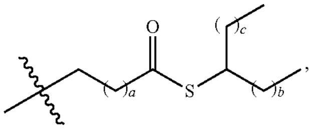
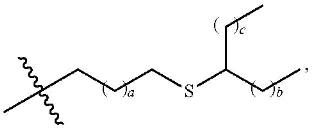
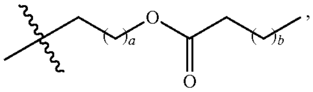
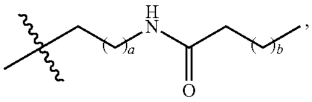
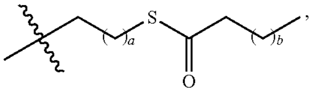
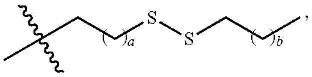
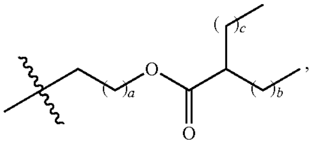
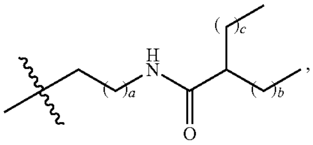
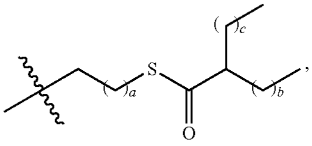
-continued
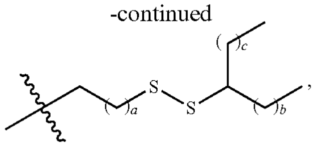
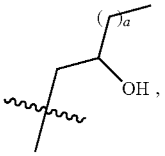 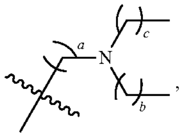 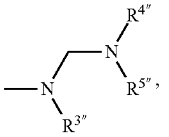
a, b and c are each independently an integer from 0-24; $R^{3''}$, $R^{4''}$, and $R^{5''}$ are independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,
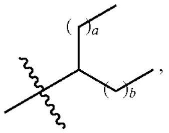 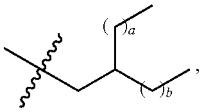
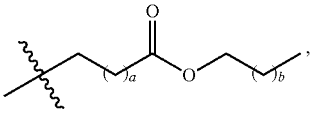
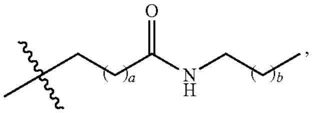
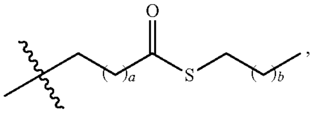
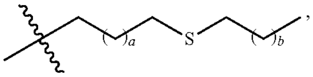
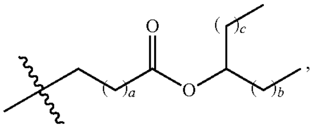
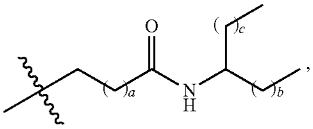
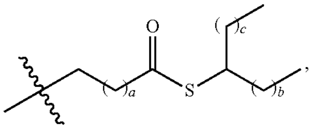
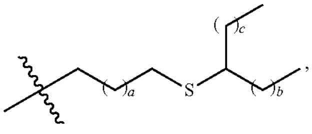
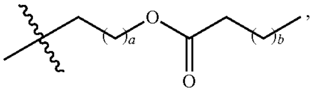

-continued

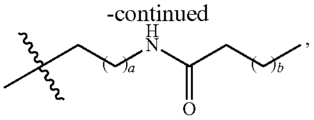,

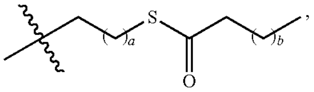,

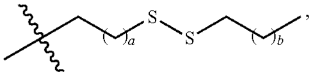,

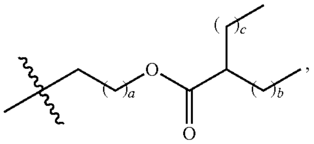,

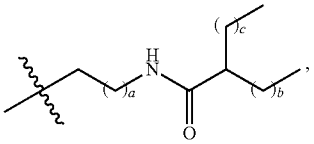,

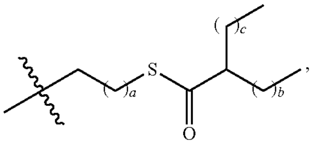,

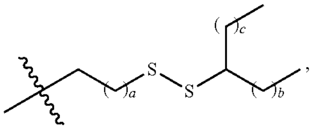,

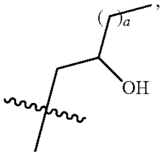, 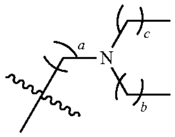

a, b and c are each independently an integer from 0-24; or wherein each $R^4$, $R^5$, $R^6$, $R^7$ and $R^8$ is independently:

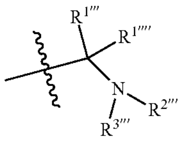

wherein $R^{1'''}$, $R^{1''''}$, $R^{2'''}$ and $R^{3'''}$ are independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

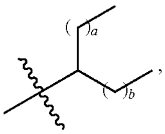, 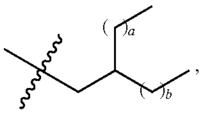,

-continued

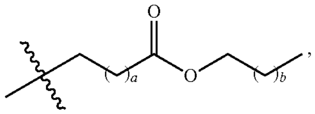,

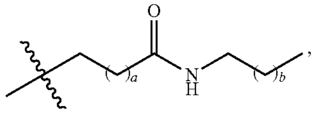,

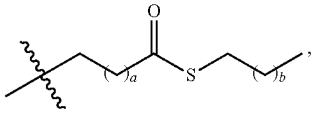,

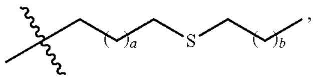,

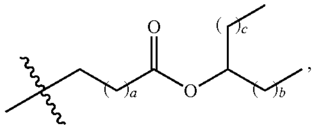,

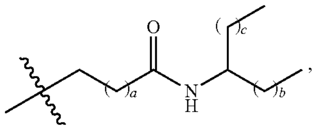,

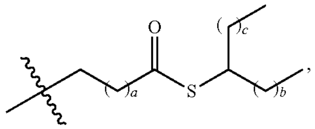,

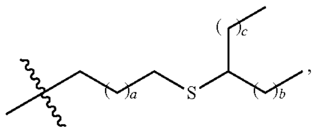,

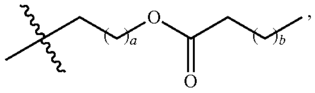,

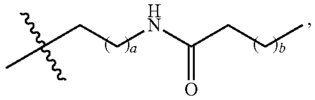,

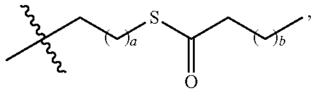,

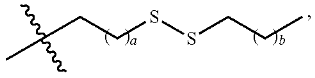,

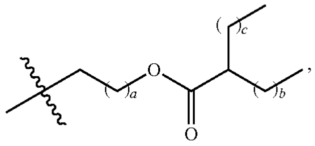,

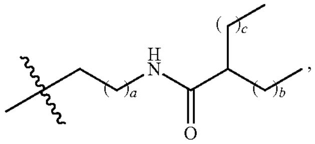,

-continued

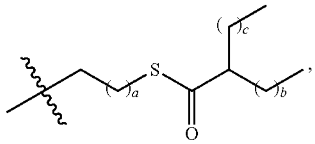

,

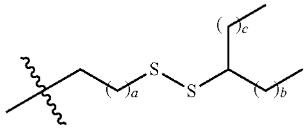

, each a, b, and c is independently an integer selected from 0-24;

each X is independently CH, N, O or S;

each Y is independently CH, N, O or S each Z is independently CH, N, O or S each F is independently CH, N, O or S and each E is independently CH, N, O or S.

General synthesis route for the synthesis of compounds of Formula III-1:

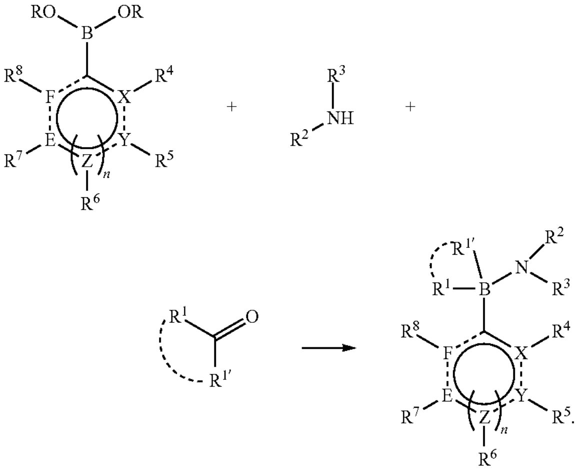

In certain aspects, compounds of Formula III may include, for example, the following compounds:

(IIIa)

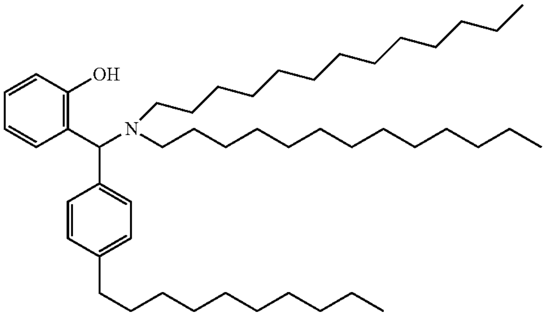

-continued (IIIb)

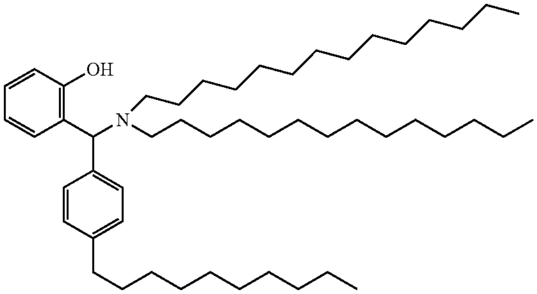

;

(IIIc)

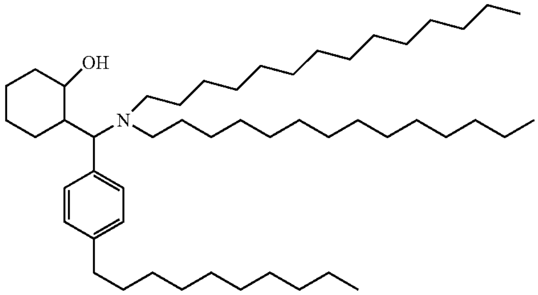

;

(IIIe)

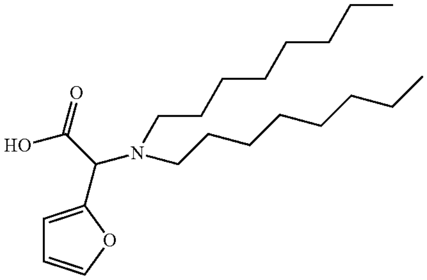

;

(IIId)

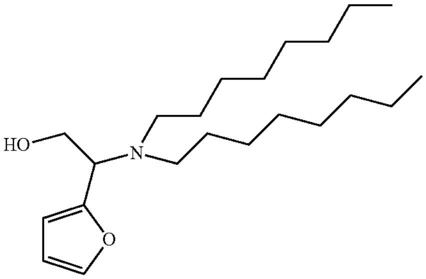

;

(IIIf)

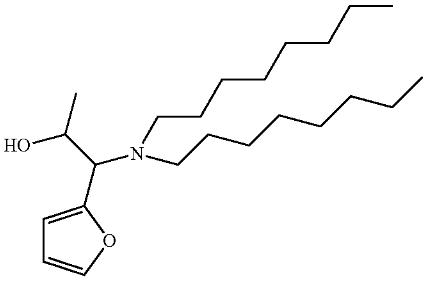

;

-continued
(IIIg)
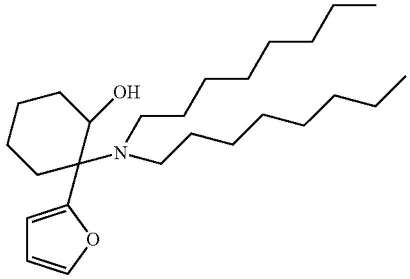
;
(IIIh)
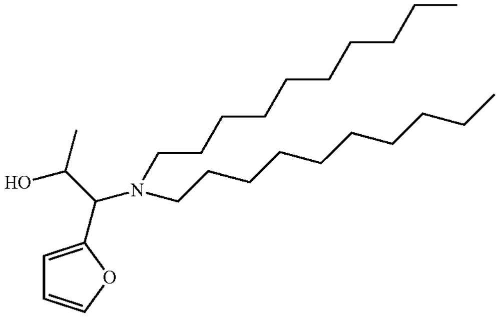
;
(IIIi)
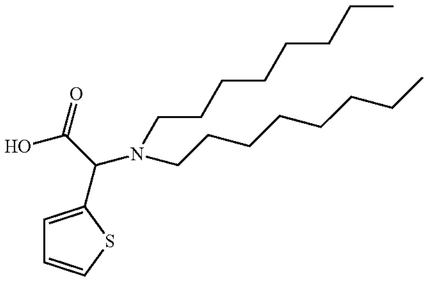
;
(IIIj)
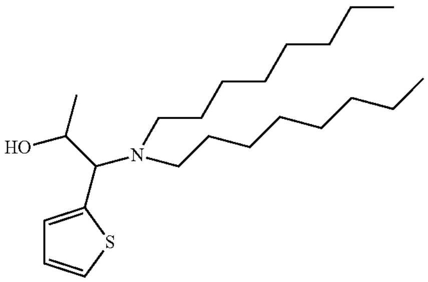
;
(IIIk)
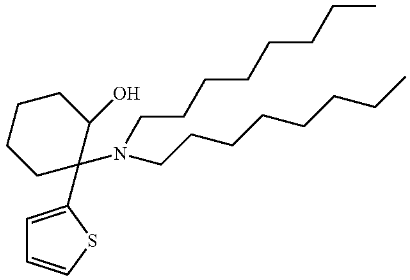
;
-continued
(IIIl)
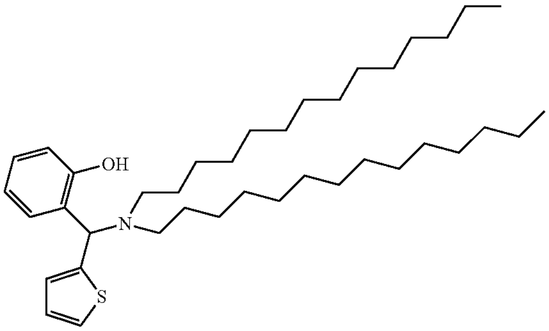
also referred to as TP4G11;
(IIIm)
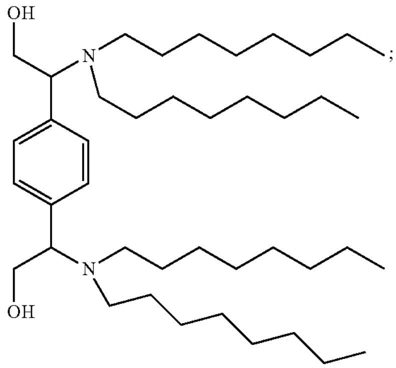
;
(IIIn)
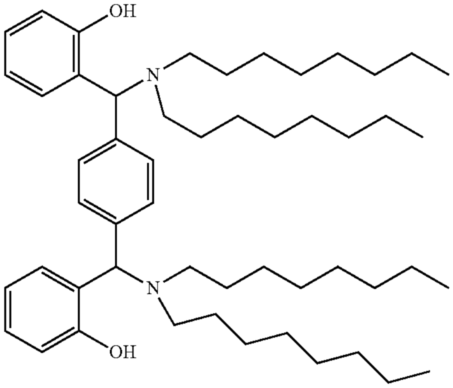

also referred to as TP1A11;
(IIIo)
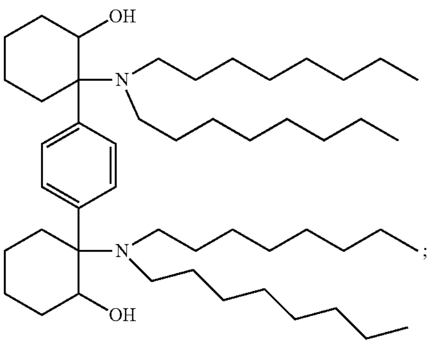
(IIIp)
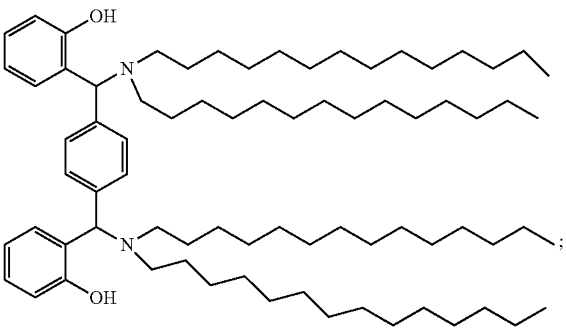
(IIIq)
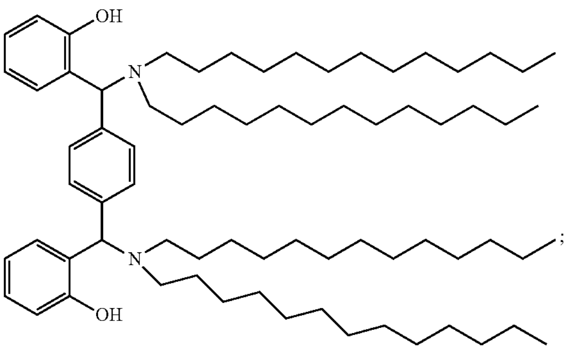
(IIIr)
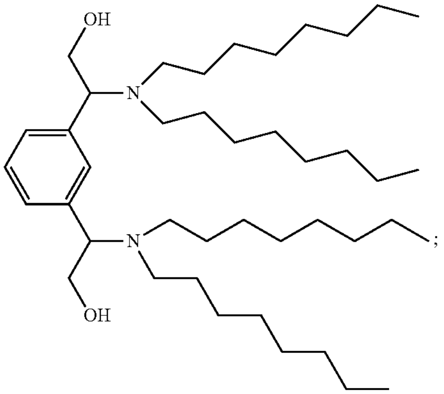
(IIIs)
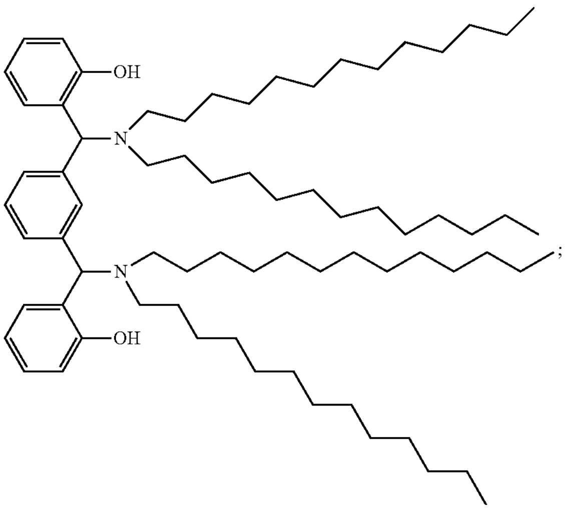
(IIIt)
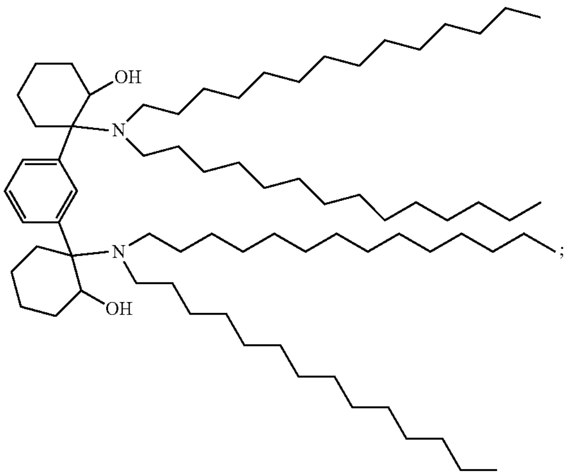

-continued
(IIIu)
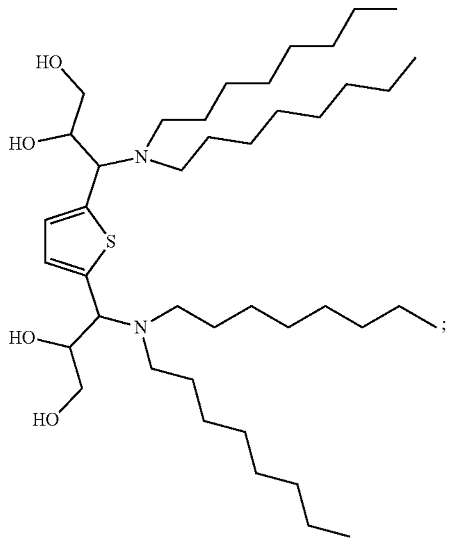
(IIIv)
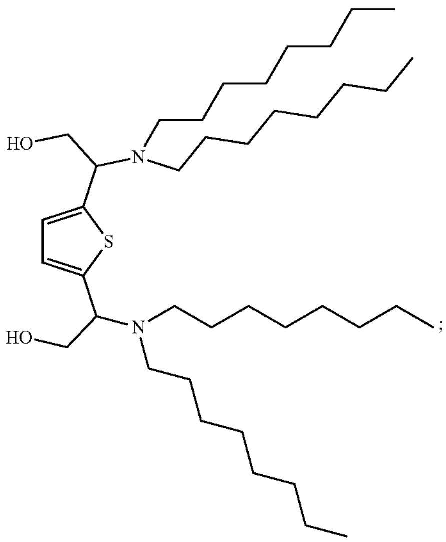
(IIIw)
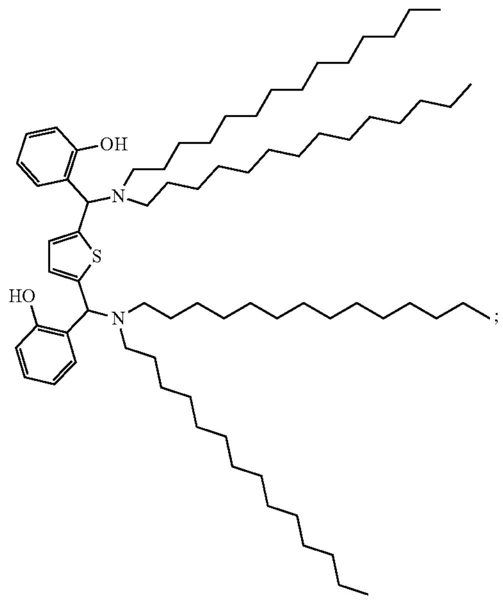

-continued
(IIIx)
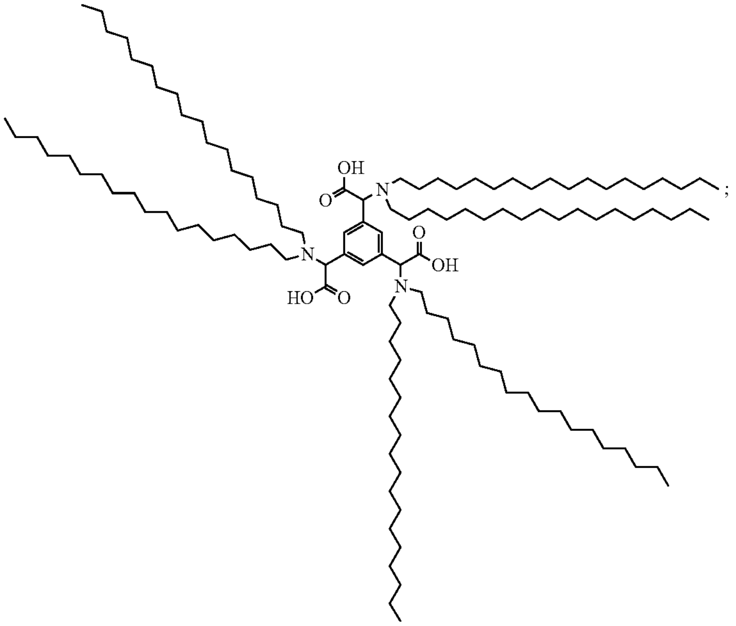
(IIIy)
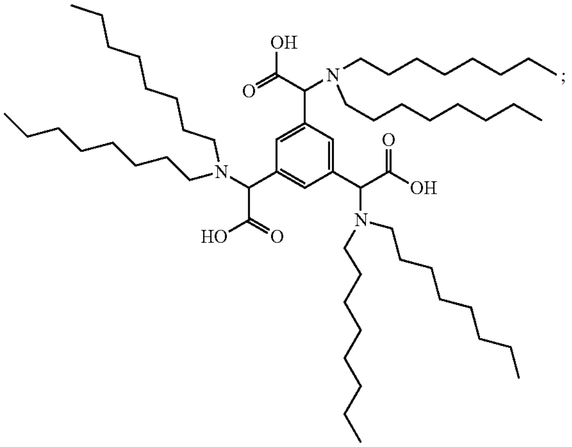
(IIIz)
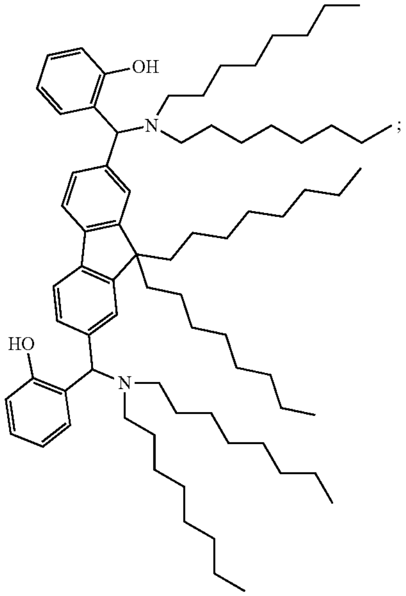
(III-2)
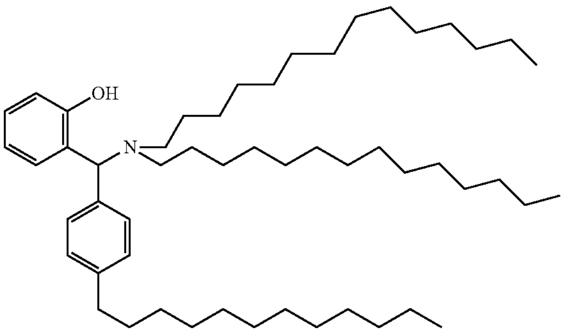

also referred to as TP3G11;

(III-3)

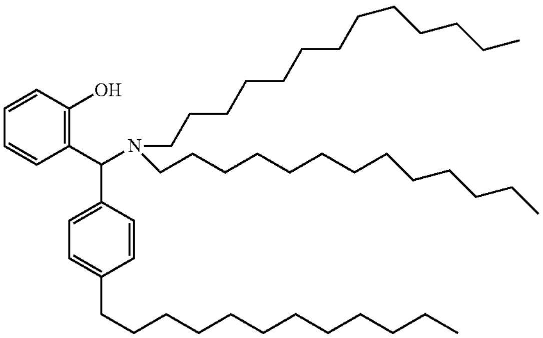

also referred to as TP3F11;

(III-4)

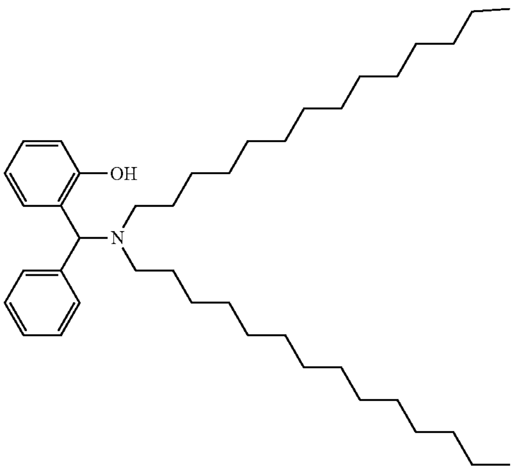

also referred to as TP5A1;

or a salt or isomer thereof.

In another aspect, the present disclosure provides compounds of Formula (IV):

(IV)

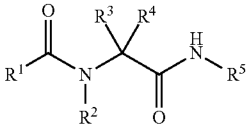

or a salt or isomer thereof, wherein each $R^1$, $R^2$, $R^3$, $R^4$ and $R^5$ is independently selected from H, C1-C24 alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

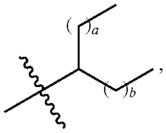,
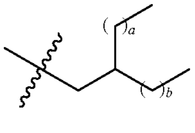,

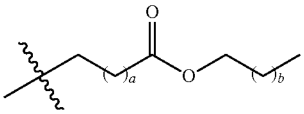,

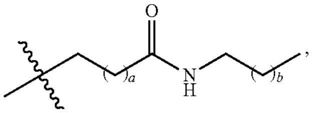,

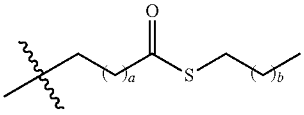,

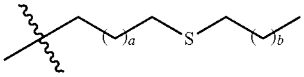,

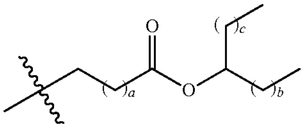,

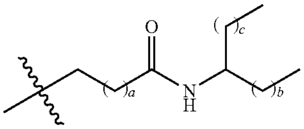,

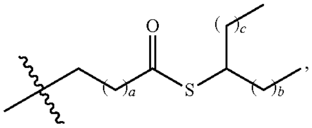,

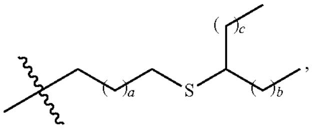,

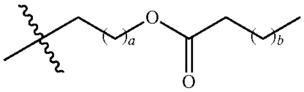,

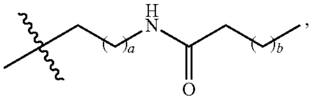,

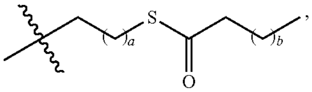,

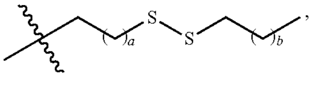,

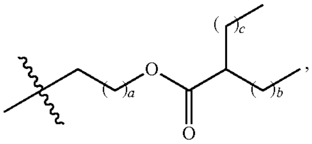,

-continued

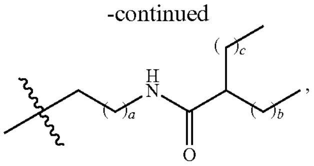

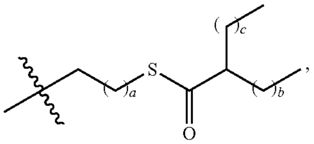

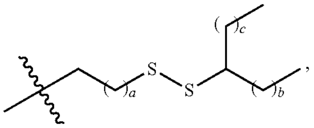

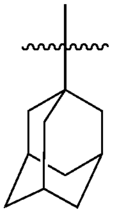
,
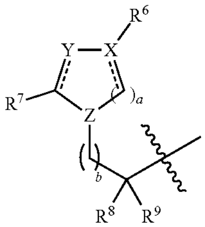
,
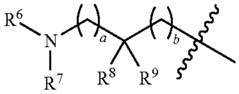

a, b and c are each independently an integer from 0-24;

each $R^6$, $R^7$, $R^8$ and $R^9$ are independently selected from H, C1-C24 alkyl, C1-C24 alkenyl, C1-C24 alkynyl, substituted alkyl, substituted alkenyl, substituted alkynyl, substituted acyl, substituted carbocyclyl, substituted heterocyclyl, substituted aryl, substituted heteroaryl,

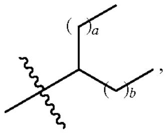

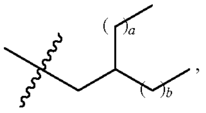

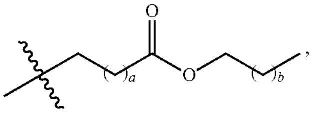

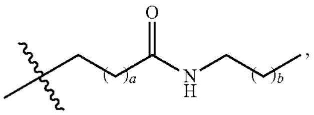

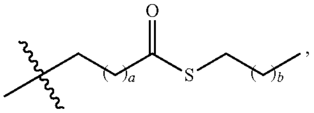

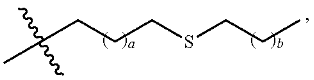

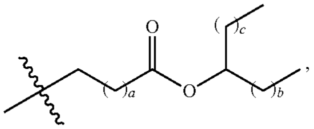

-continued

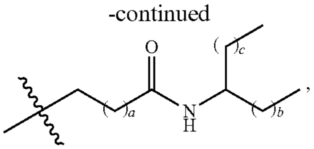

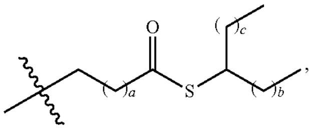

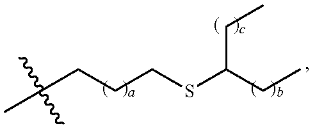

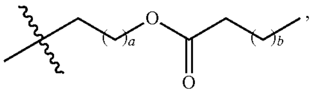

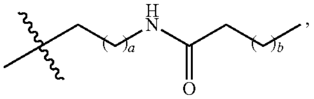

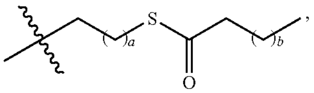

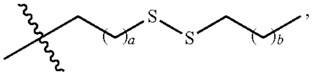

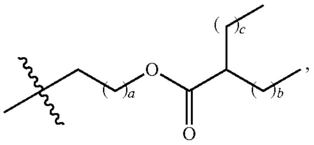

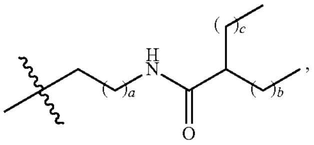

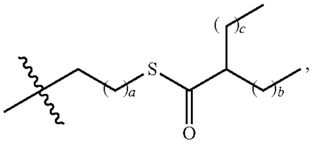

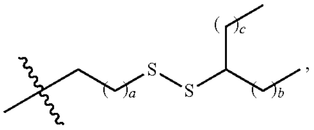

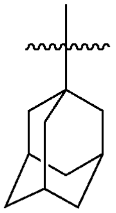
, a, b and c are each independently an integer from 0-24;

each X is independently selected from CH, N;

each Y is independently selected from $CH_2$, NH, O, or S;

each Z is independently selected from CH or N.

Synthesis Scheme 4.
General synthetic route for the synthesis of compounds of Formula IV.
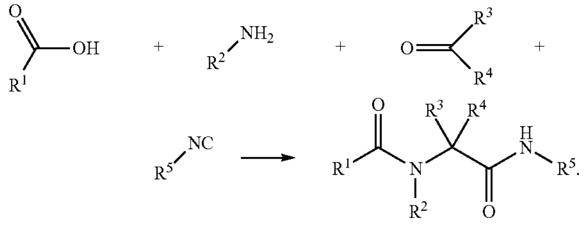
As an example, the aldehyde or ketone may be selected from:
ALA1
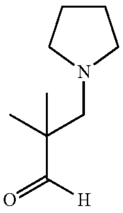
ALA2
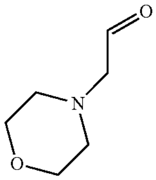
ALA3
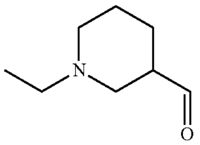
ALA4
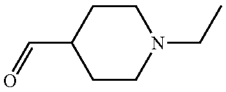
ALA5
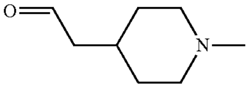
ALA6
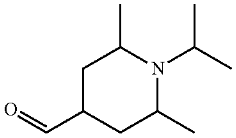
ALA7
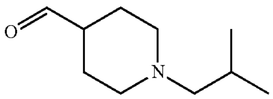
ALA8
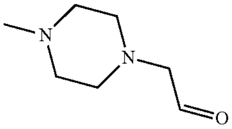
-continued
ALA9
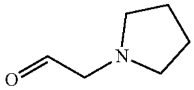
ALA10
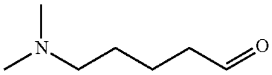
ALA11
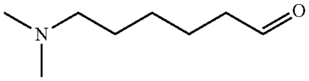
ALA12
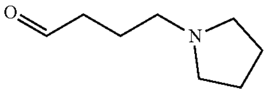
ALA13
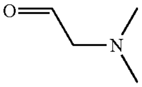
ALA14
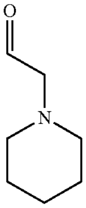
ALA15
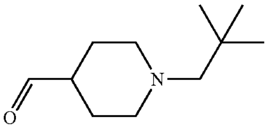
ALA16
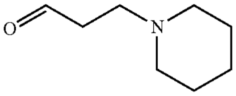
ALA17
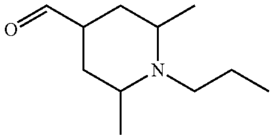
AL8
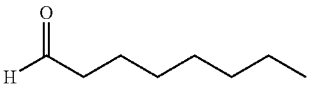
AL9
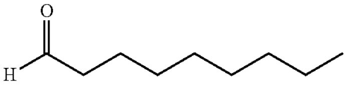
AL10
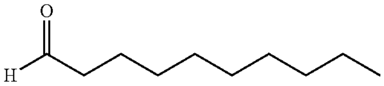
AL11
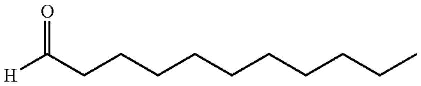
AL12
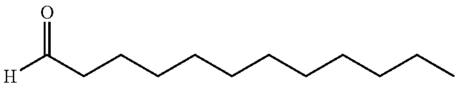

-continued
AL13
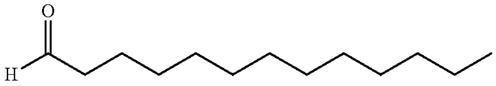
AL15
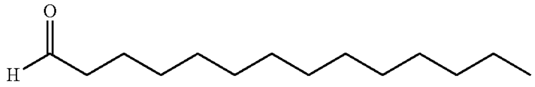
AL16
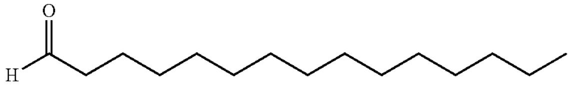
AL16e
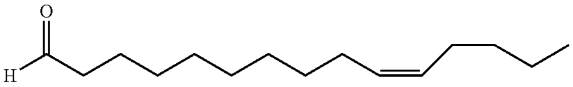
AL10P
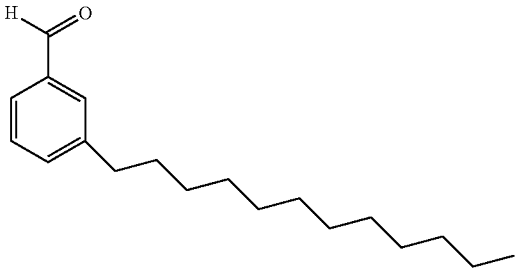
AL14e
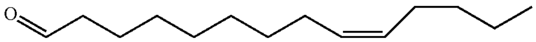
AL18e
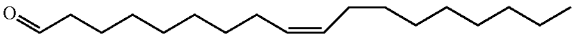
ALd1
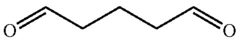
ALd2
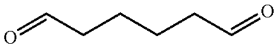
DK1
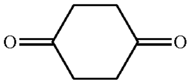
K9
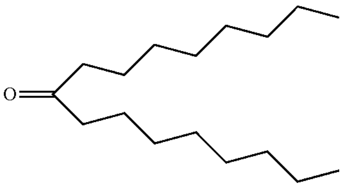
K10
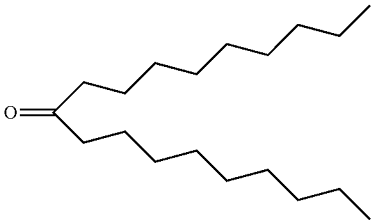
-continued
K11
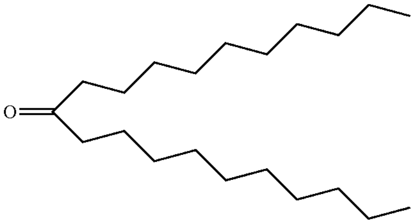
K12
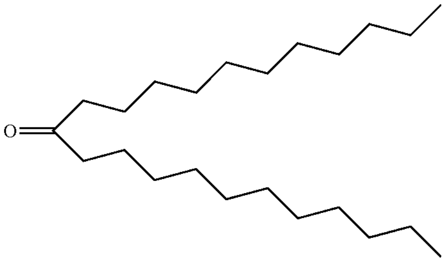
K14
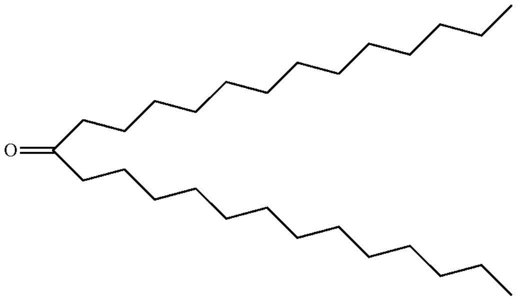
K16
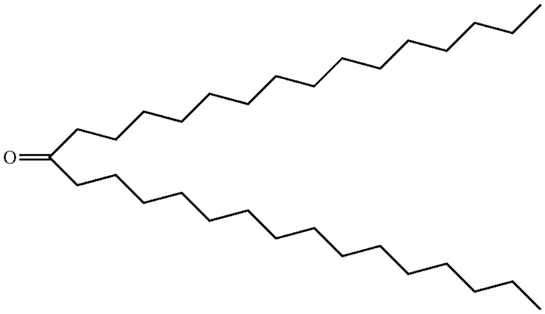
K18e
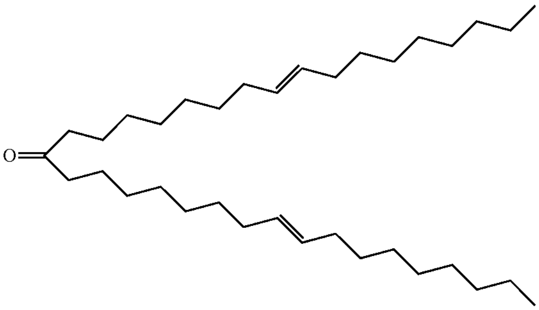
.

As examples, the amine may be selected from:
AP1
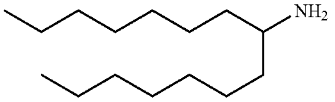
AP2
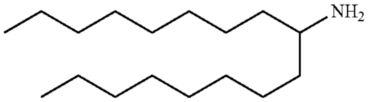
AP3
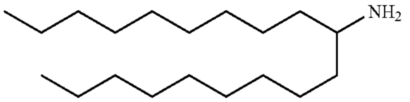
AP4
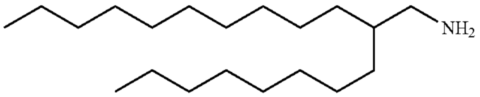
AP5
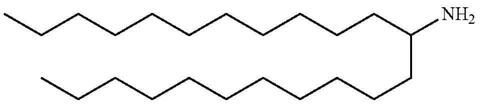
AP6
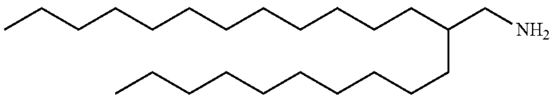
AP7
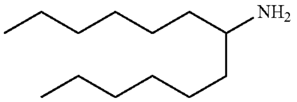
AP8
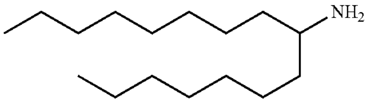
A1
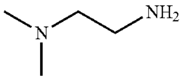
A3
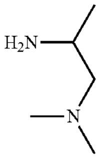
A2
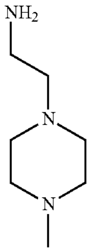
-continued
A4
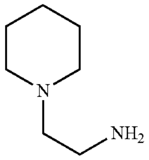
A5
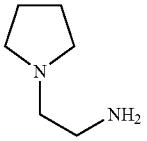
A21
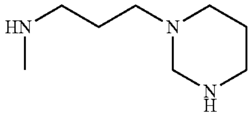
A6
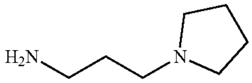
A7
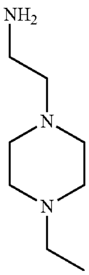
A8
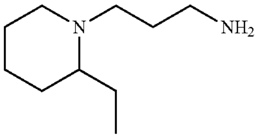
A9
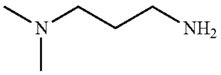
A10
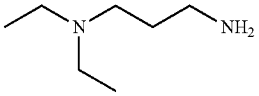
A22
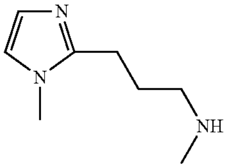
A11
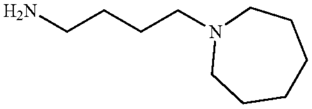

-continued
A12
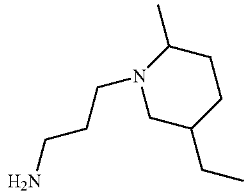
A13
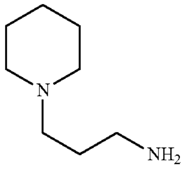
A14
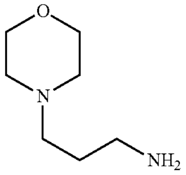
A15
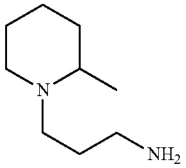
A16
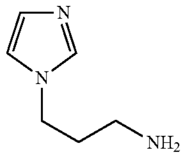
A17
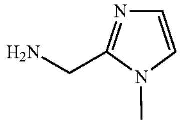
A18
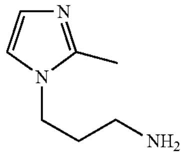
A19
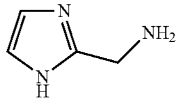
A20
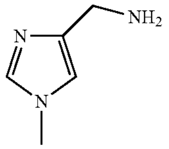
A21
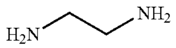
A22
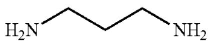
-continued
A23
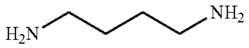
A24
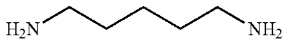
A25
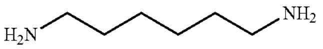
A26
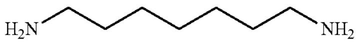
A27
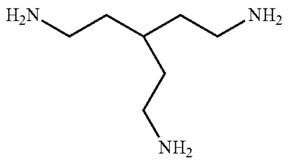
SA6
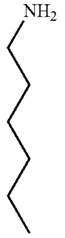
SA7
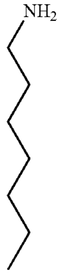
SA8
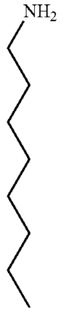
SA9
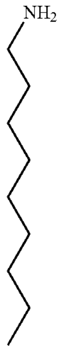

-continued
SA10
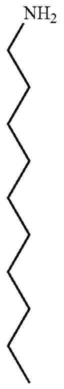
SA11
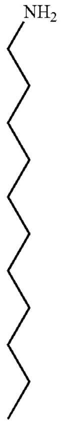
SA12
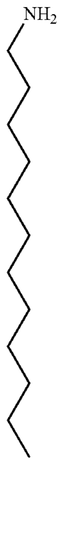
-continued
SA13
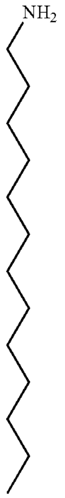
SA14
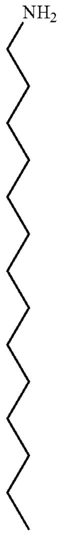
SA15
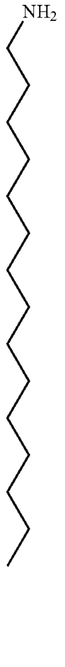

-continued
SA16
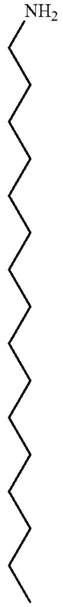
SA17
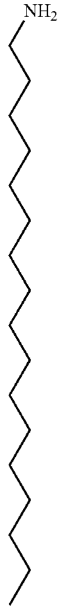
SA18
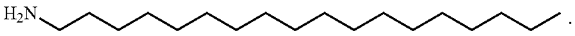
As examples, the acid may be selected from:
AAC1
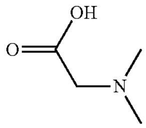
-continued
AAC2
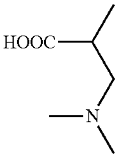
AAC3
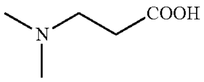
AAC4
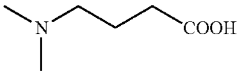
AAC5
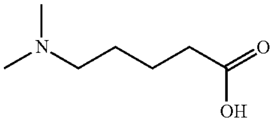
AAC6
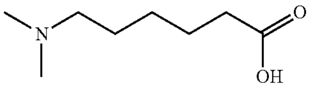
AAC7
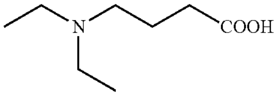
AAC8
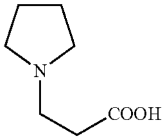
AAC9
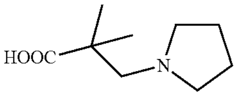
AAC10
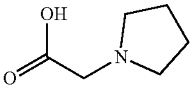
AAC11
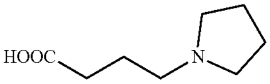
AAC12
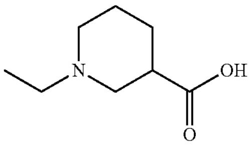
AAC13
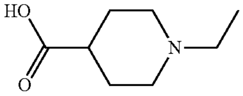
AAC14
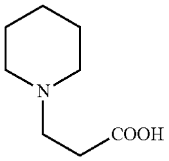

-continued
AAC15
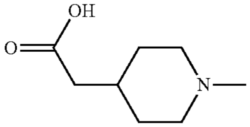
AAC16
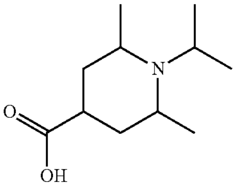
AAC17
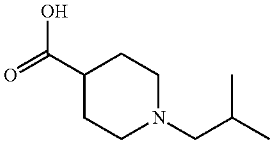
AAC18
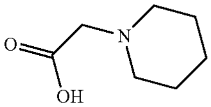
AAC19
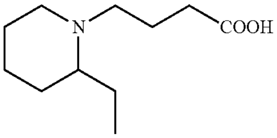
AAC20
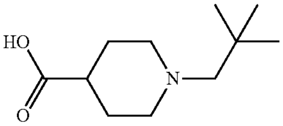
AAC21
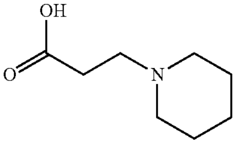
AAC22
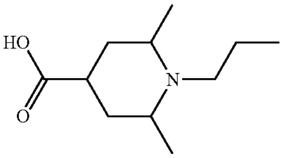
AAC23
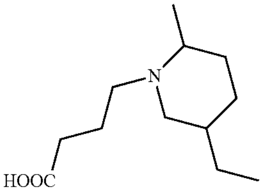
AAC24
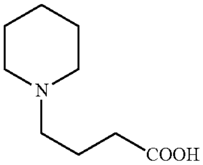
-continued
AAC25
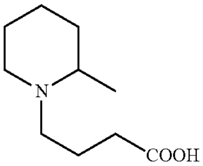
AAC26
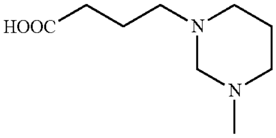
AAC27
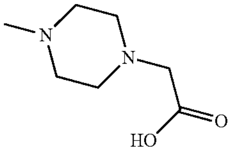
AAC28
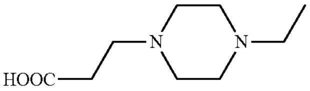
AAC29
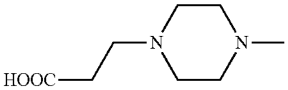
AAC30
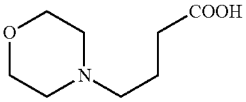
AAC31
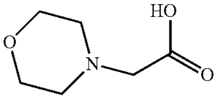
AAC32
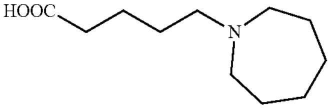
AAC33
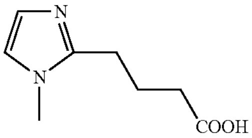
AAC34
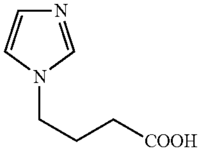
AAC35
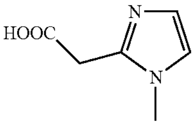

-continued
AAC36
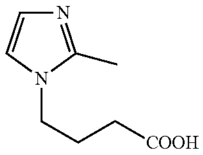
AAC37
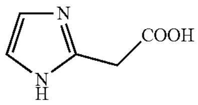
AAC38
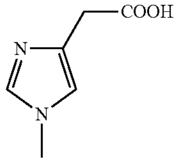
AC18
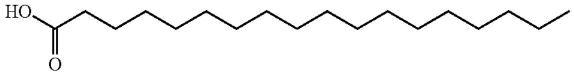
ACe18
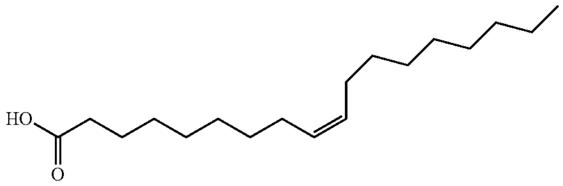
ACd13
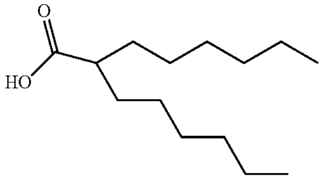
ACd11
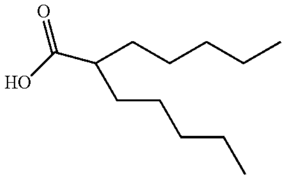
ACd15
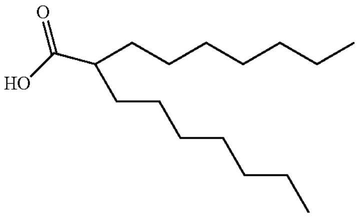
ACe16
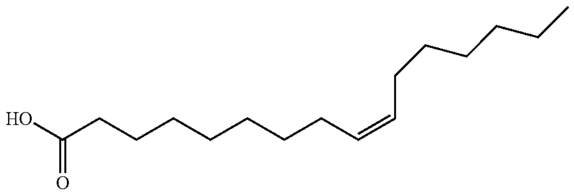
-continued
ACd19
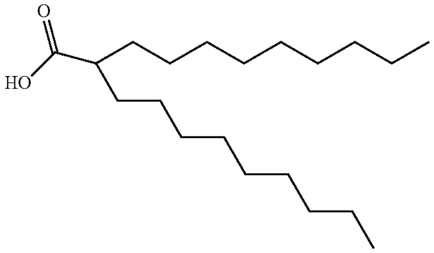
ACe17
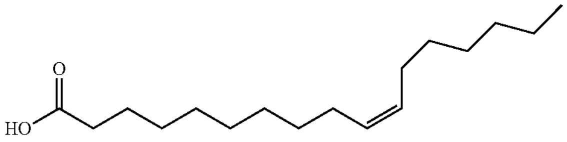
ACd17
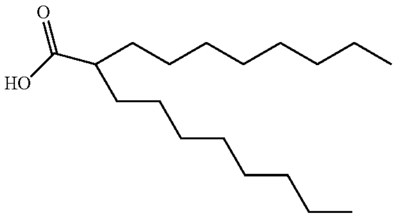
ACe15
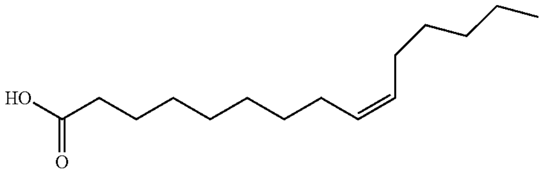
ACd21
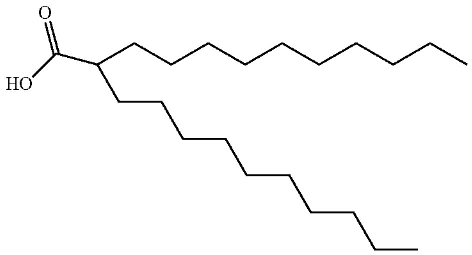
AC6
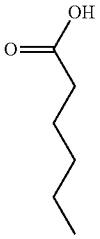

-continued
AC7
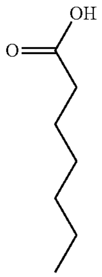
AC8
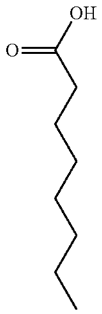
AC9
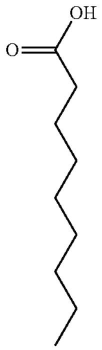
AC10
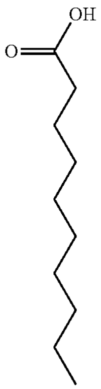
-continued
AC11
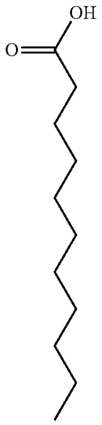
AC12
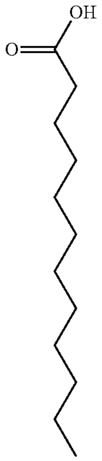
AC13
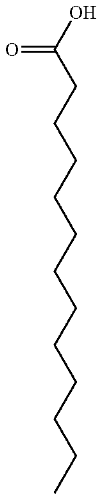

-continued
AC14
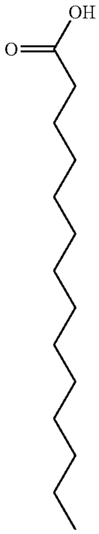
AC15
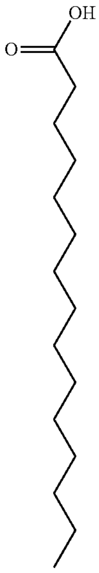
-continued
AC16
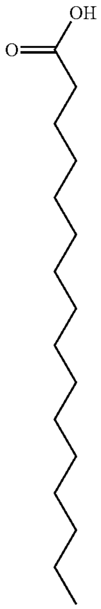
AC17
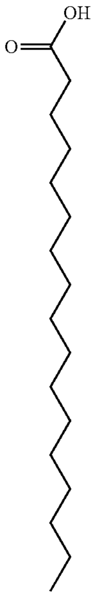
ACe13
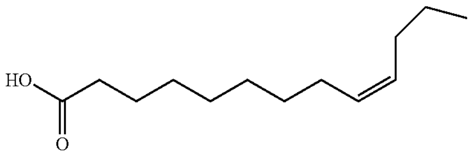
ACe12
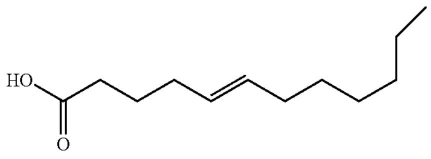

-continued
ACe14
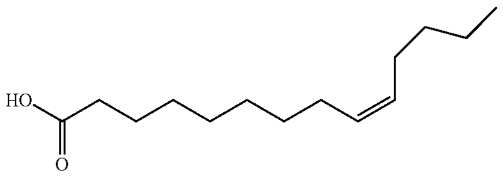
VAC1
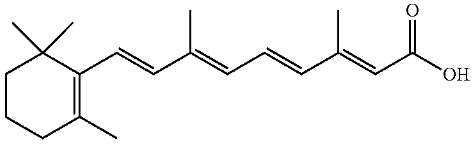
VAC2
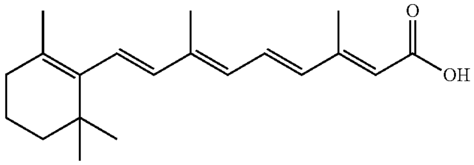
ACh1
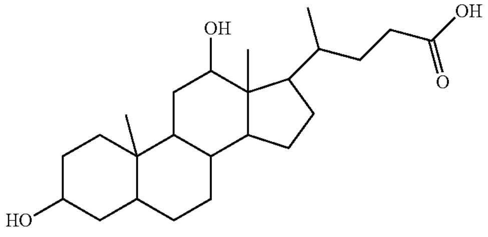
ACh2
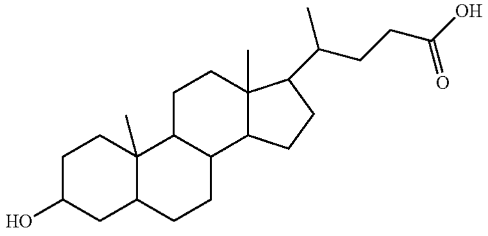
ACh3
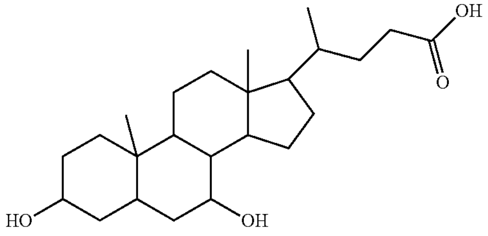
ACh4
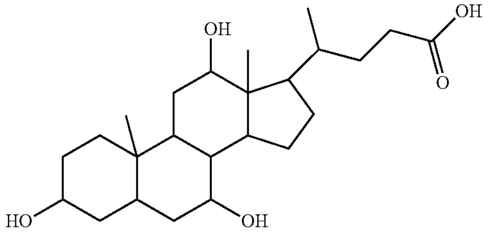
-continued
ACh5
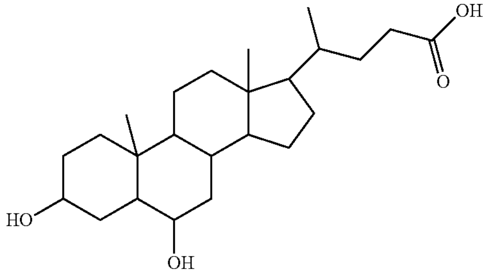
ACh6
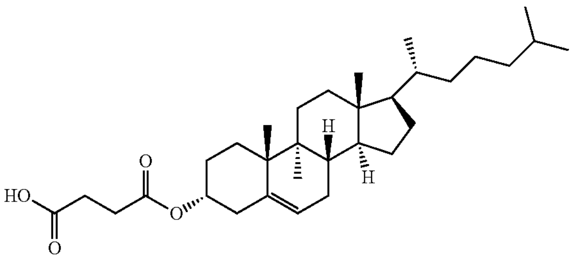
DAC1
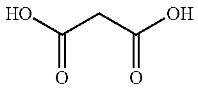
DAC2
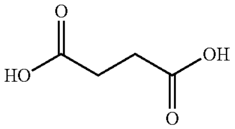
DAC3
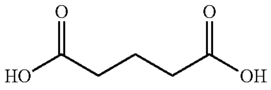
DAC4
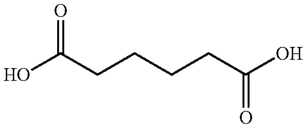
DAC5
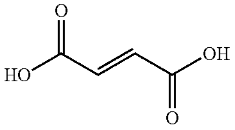
As examples, the isocyanide may be selected from:
Iso1
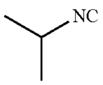
Iso2
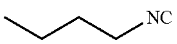
Iso3
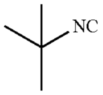
Iso4
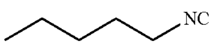

-continued

Iso5

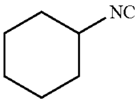

Iso6

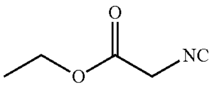

Iso7

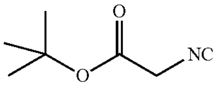

Iso8

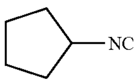

Iso9

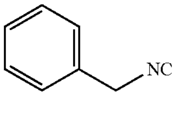

Iso10

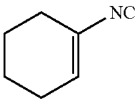

Iso11

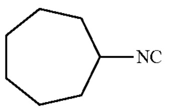

Iso12

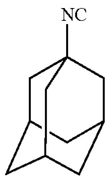

Iso13

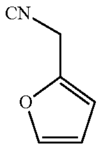

Iso 14

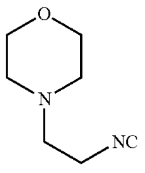

Iso15

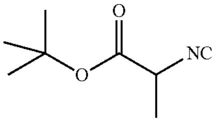

Iso16

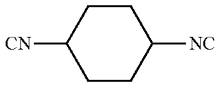

Iso17

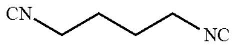

Iso18

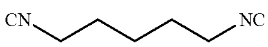

-continued

Iso19

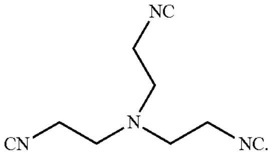

In some examples, the compounds of Formula IV were synthesized as follows: The ionizable lipid was synthesized by two-step/one-pot reaction with a molar ratio of acid/amine/aldehyde/isocyanide at 1:1:1:1.

Aldehyde (1 mmol) and amine (1 mmol) were mixed in 3 mL MeOH at room temperature and stirred for one hour, then isocyanide (1 mmol) and acid (1 mmol) were added. The resulting mixture was stirred further overnight. Removed the solvent with Rotary evaporator. Ethyl acetate (100 mL) was added and washed with brine (2×50 mL), dried over $MgSO_4$. Removed Ethyl acetate and the residue was purified by column chromatography using a Combi-Flash Rf system with a silica column (Redisep Gold Resolution, Teledyne, Isco) by gradient elution of $CH_2Cl_2$/methanol (0%-40% methanol). Structure was confirmed using techniques known in the art, for example, nuclear magnetic resonance spectra of 1H and LC-Mass spectrometry.

Ethyl (2-(1-ethylpiperidin-4-yl)-2-(N-(pentadecan-8-yl)tridecanamido)acetyl)glycinate (P1C1): yield (16%). 1H-NMR (400 MHz, Me-OD, 6) 4.34 (d, J=8 Hz, 1H), 4.21-4.14 (m, 4H), 3.41 (t, J=8 Hz, 1H), 3.01 (q, J=8 Hz, 2H), 2.47-2.40 (m, 5H), 2.01-1.83 (t, J=12 Hz, 2H), 1.65-1.56 (m, 6H), 1.29-1.17 (m, 42H), 1.17-1.10 (m, 6H), 0.93-0.89 (m, 9H). MS (APCI) m/z 678.7 [M+H]+.

N-(2-(cyclohex-1-en-1-ylamino)-1-(1-ethylpiperidin-4-yl)-2-oxoethyl)-N-(heptadecan-9-yl)palmitamide (P6A2): yield (45%). 1H-NMR (400 MHz, Me-OD, δ) 6.05 (t, J=8 Hz, 1H), 4.26 (s, 1H), 3.26-3.17 (m, 3H), 2.49-2.42 (m, 5H), 2.19-2.01 (m, 6H), 1.67-1.57 (m, 14H), 1.31-1.16 (m, 48H), 0.92-0.87 (m, 12H). MS (APCI) m/z 742.7 [M+H]+.

N-(2-(cyclohexylamino)-1-(1-ethylpiperidin-4-yl)-2-oxoethyl)-N-(pentadecan-8-yl)palmitamide (P30A1): yield (58%). 1H-NMR (400 MHz, CDCl3, δ) 8.41 (d, J=8 Hz, 1H), 3.70-3.63 (m, 1H), 3.57 (t, J=8 Hz, 1H), 3.18-3.09 (m, 3H), 2.80-2.24 (m, 3H), 2.44-2.24 (m, 4H), 1.79-1.20 (m, 67H), 0.89-0.85 (m, 9H). MS (APCI) m/z 716.8 [M+H]+.

N-(2-(((1s,3s)-adamantan-1-yl)amino)-1-(1-ethylpiperidin-4-yl)-2-oxoethyl)-N-(2-decyltetradecyl)undecanamide (P54B6): yield (48%). MS (APCI) m/z 824.8 [M+H]+.

N-(2-(cycloheptylamino)-1-(1-ethylpiperidin-4-yl)-2-oxoethyl)-N-(pentadecan-8-yl)tetradecanamide (P38D1): yield (56%). MS (APCI) m/z 702.7 [M+H]+.

N-(2-(((1s,3s)-adamantan-1-yl)amino)-1-(1-ethylpiperidin-4-yl)-2-oxoethyl)-N-(pentadecan-8-yl)palmitamide (P56A1): yield (53%). MS (APCI) m/z 768.7 [M+H]+.

N-(2-(((1s,3s)-adamantan-1-yl)amino)-1-(1-ethylpiperidin-4-yl)-2-oxoethyl)-N-(pentadecan-8-yl)heptadecanamide (P56B1): yield (59%). MS (APCI) m/z 782.8 [M+H]+.

N-(2-(butylamino)-1-(1-ethylpiperidin-4-yl)-2-oxoethyl)-N-(heptadecan-9-yl)octanamide (P14A2): yield (40%). MS (APCI) m/z 606.6 [M+H]+.

N-(2-(butylamino)-1-(1-ethylpiperidin-4-yl)-2-oxoethyl)-N-(pentadecan-8-yl)undecanamide (P16B1): yield (43%). MS (APCI) m/z 620.6 [M+H]+.

N-(2-(cyclohexylamino)-1-(1-ethylpiperidin-4-yl)-2-oxo-ethyl)-N-(2-octyldodecyl) tetradecanamide (P26D4): yield (23%). MS (APCI) m/z 758.8 [M+H]+. Ethyl (2-(1-ethylpiperidin-4-yl)-2-(N-(2-octyldodecyl)tetra-decanamido)acetyl)glycinate (P1D4): yield (30%). MS (APCI) m/z 762.8 [M+H]+.

N-(1-(cyclohexylamino)-3-(1-methylpiperidin-4-yl)-1-oxopropan-2-yl)-N-(pentadecan-8-yl)heptadecanamide (P30B7): yield (56%). MS (APCI) m/z 730.8 [M+H]+.

N-(1-(cyclohexylamino)-3-(1-methylpiperidin-4-yl)-1-oxopropan-2-yl)-N-(pentadecan-8-yl)stearamide (P30C7): yield (53%). MS (APCI) m/z 744.8 [M+H]+.

N-(1-(cycloheptylamino)-3-(1-methylpiperidin-4-yl)-1-oxopropan-2-yl)-N-(pentadecan-8-yl)tetradecanamide (P38D7): yield (45%). MS (APCI) m/z 702.7 [M+H]+.

N-(1-(cycloheptylamino)-3-(1-methylpiperidin-4-yl)-1-oxopropan-2-yl)-N-(heptadecan-9-yl)tetradecanamide (P38D8): yield (52%). MS (APCI) m/z 730.7 [M+H]+.

N-(1-(cycloheptylamino)-3-(1-methylpiperidin-4-yl)-1-oxopropan-2-yl)-N-(2-octyldodecyl)undecanamide (P40B10): yield (42%). MS (APCI) m/z 730.7 [M+H]+.

N-(1-(cycloheptylamino)-3-(1-methylpiperidin-4-yl)-1-oxopropan-2-yl)-N-(tricosan-12-yl)dodecanamide (P40C11): yield (57%). MS (APCI) m/z 786.8 [M+H]+.

N-(1-(cycloheptylamino)-3-(1-methylpiperidin-4-yl)-1-oxopropan-2-yl)-N-(2-octyldodecyl)dodecanamide (P40C10): yield (70%). MS (APCI) m/z 744.8 [M+H]+.

N-(1-(tert-butylamino)-3-(1-methylpiperidin-4-yl)-1-oxopropan-2-yl)-N-(2-decyltetradecyl)tridecanamide (P51C12): yield (70%). MS (APCI) m/z 774.8 [M+H]+.

N-(1-(cycloheptylamino)-3-(1-methylpiperidin-4-yl)-1-oxopropan-2-yl)-N-(pentadecan-8-yl)pentadecanamide (P40D7): yield (61%). MS (APCI) m/z 716.7 [M+H]+.

N-(2-(tert-butylamino)-1-(1-ethylpiperidin-4-yl)-2-oxo-ethyl)-N-(tricosan-12-yl)decanamide (P53A5): yield (61%). MS (APCI) m/z 718.7 [M+H]+.

N-(2-(tert-butylamino)-1-(1-ethylpiperidin-4-yl)-2-oxo-ethyl)-N-(2-decyltetradecyl)decanamide (P53A6): yield (61%). MS (APCI) m/z 732.7 [M+H]+

N-(2-(cycloheptylamino)-1-(1-ethylpiperidin-4-yl)-2-oxoethyl)-N-(2-decyltetradecyl)tetradecanamide (P38D4): yield (51%). MS (APCI) m/z 828.7 [M+H]+

N-(2-(((1s,3s)-adamantan-1-yl)amino)-1-(1-ethylpiperidin-4-yl)-2-oxoethyl)-N-(heptadecan-9-yl)palmitamide (P56A2): yield (46%). MS (APCI) m/z 796.7 [M+H]+

N-(2-(cycloheptylamino)-1-(1-ethylpiperidin-4-yl)-2-oxoethyl)-N-(heptadecan-9-yl)oleamide (P149A2): yield (42%). MS (APCI) m/z 784.8 [M+H]+ dodecyl 4-((2-(cycloheptylamino)-1-(1-ethylpiperidin-3-yl)-2-oxoethyl)(2-octyldodecyl)amino)-4-oxobutanoate (P159C10): yield (43%). MS (APCI) m/z 830.8 [M+H]+

N-(1-(((1s,3s)-adamantan-1-yl)amino)-3-(1-methylpiperidin-4-yl)-1-oxopropan-2-yl)-4-(3,6-dihydroxy-10,13-dimethylhexadecahydro-1H-cyclopenta[a]phenanthren-17-yl)-N-(2-octyldodecyl)pentanamide (P161F10): yield (53%). MS (APCI) m/z 974.9 [M+H]+.

In certain aspects, compounds of Formula IV may include, for example, the following compounds:

(IVa)

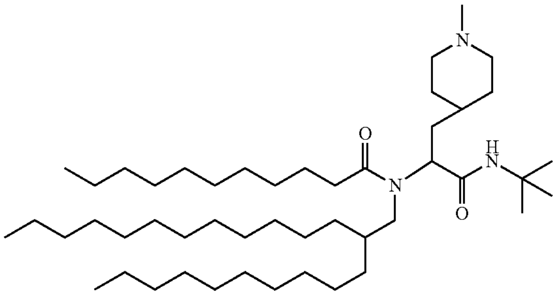

also referred to as P53F12;

(IVb)

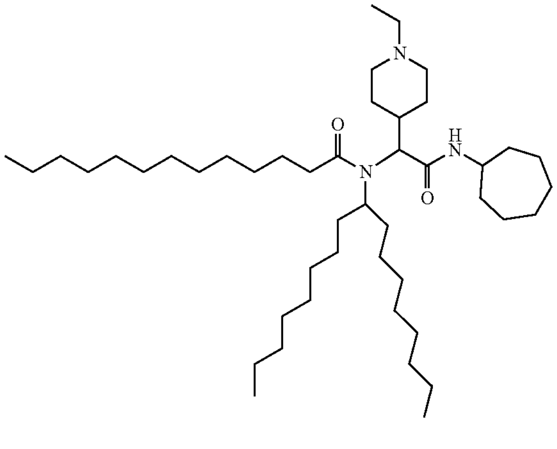

also referred to as P38C2;

IVc)

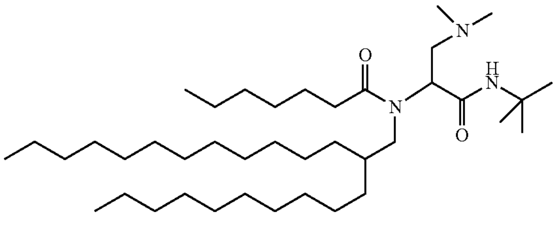

also referred to as P55H12;
(IVd)
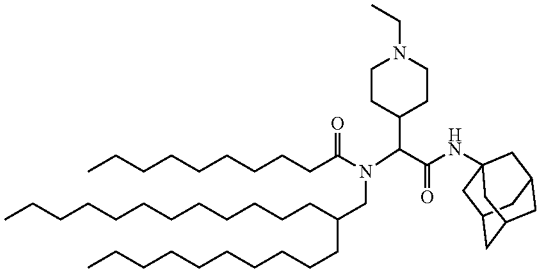
also referred to as P54A6;
(IVe)
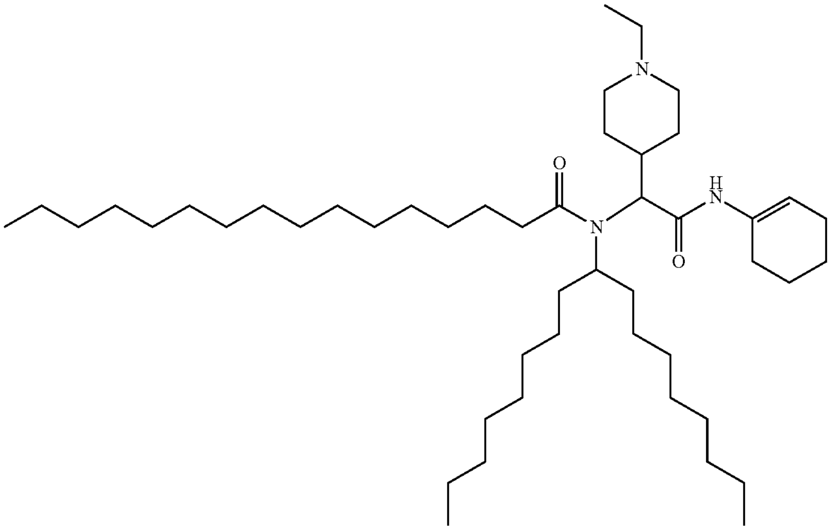
also referred to as P6A2;
(IVf)
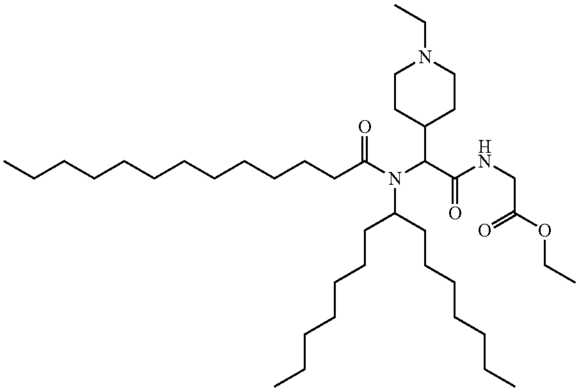

also referred to as P1C1;
(IVg)
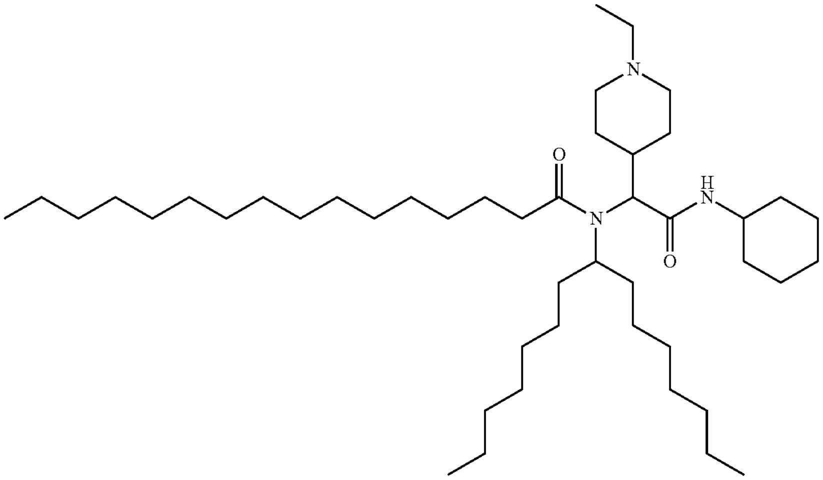
also referred to as P30A1;
(IVh)
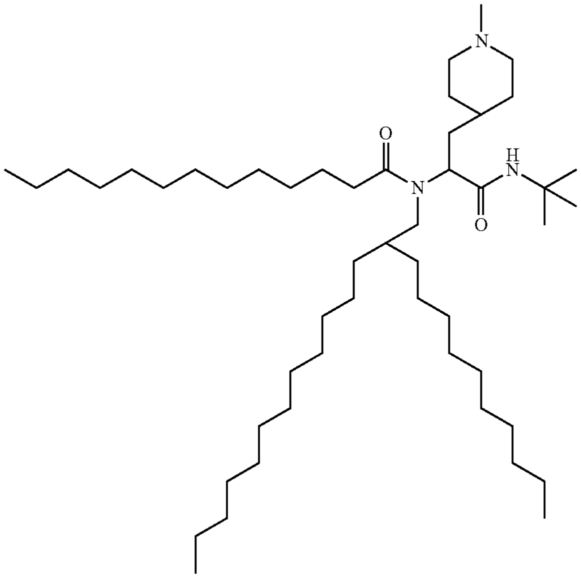
also referred to as P51C12;
(IVi)
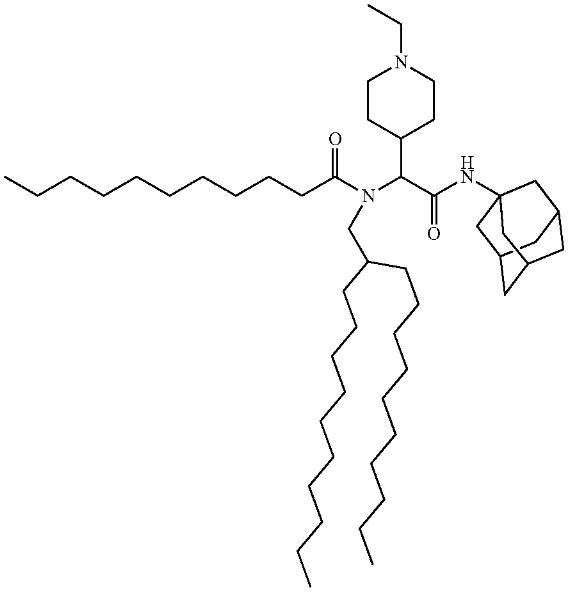

also referred to as P54B1;
(IVj)
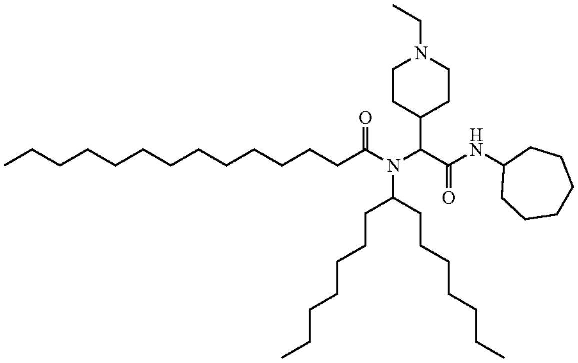
also referred to as P38D1;
(IVk)
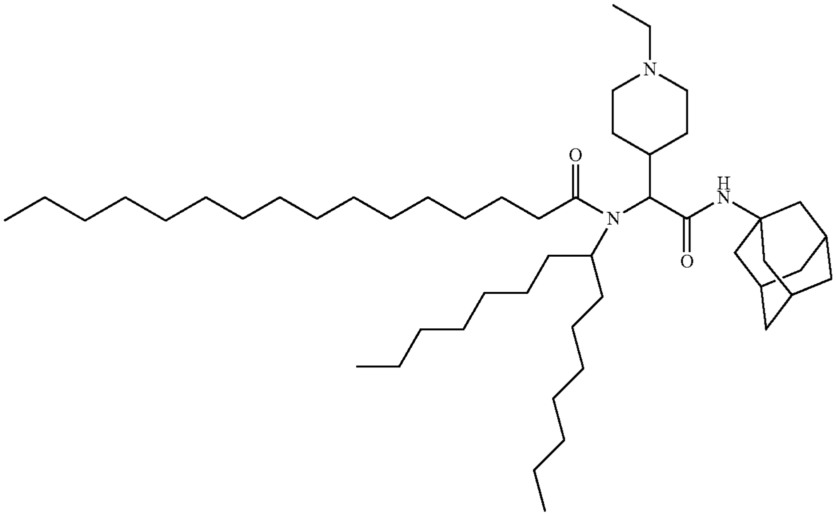

also referred to as P56A1;
(IV1)
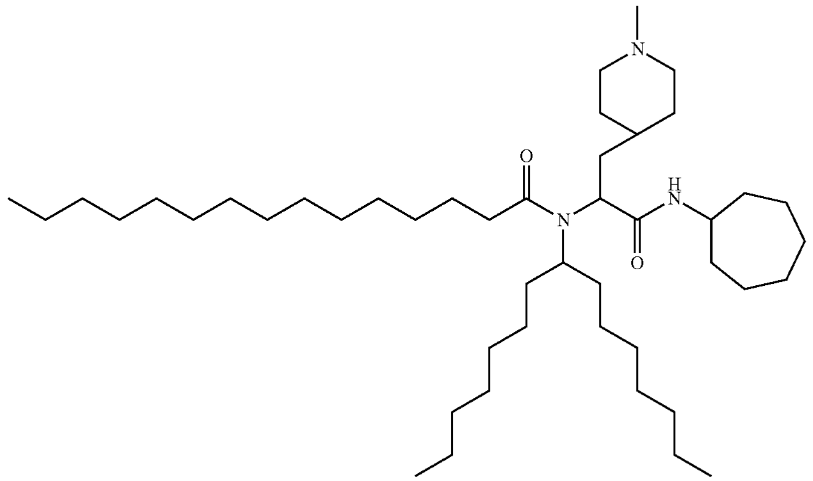
also referred to as P40D7;
(IVm)
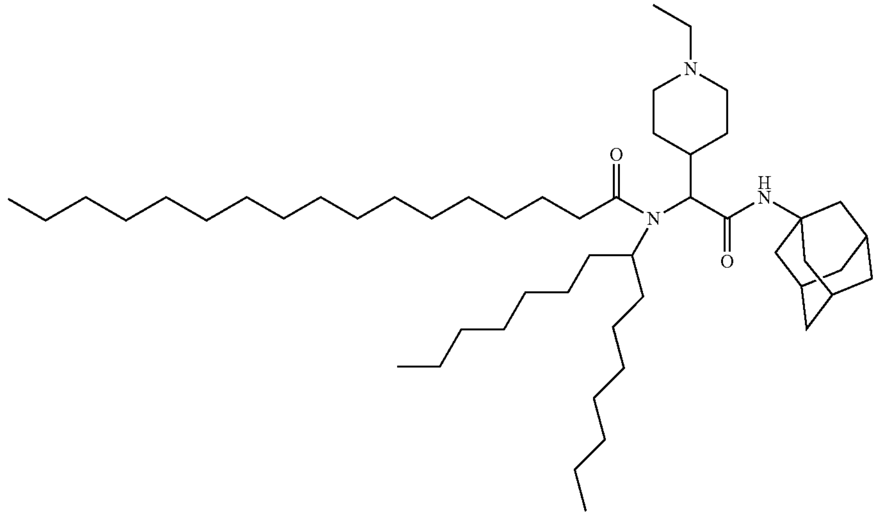

also referred to as P56B1;
(IVn)
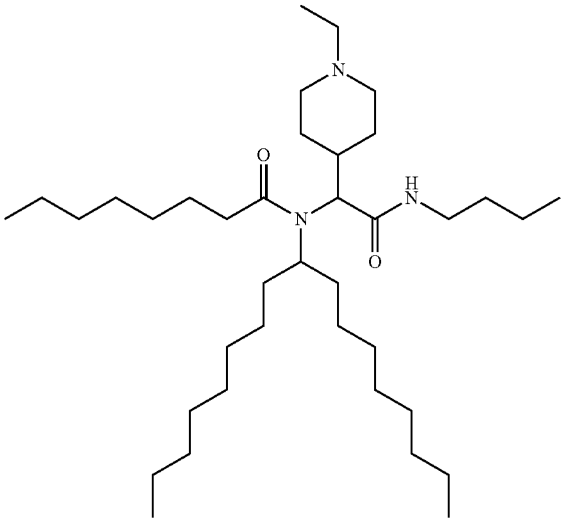
also referred to as P14A2;
(IVo)
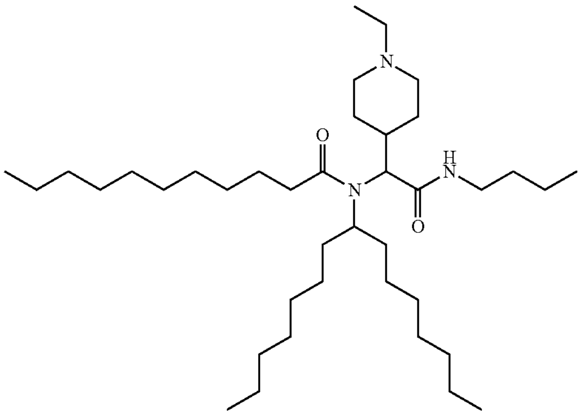
also referred to as P16B1;
(IVp)
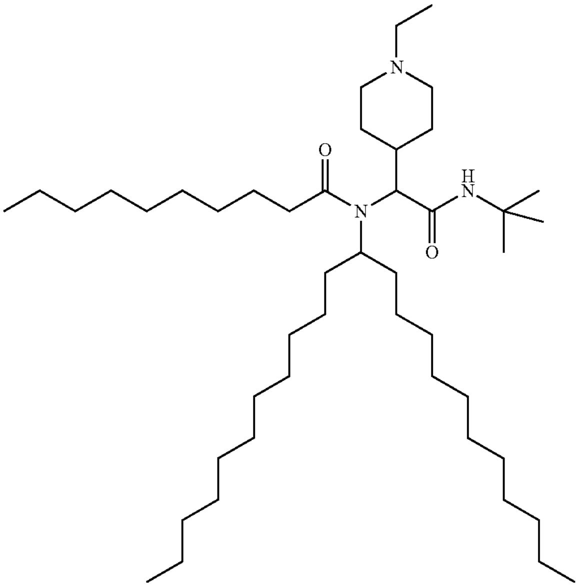
also referred to as P53A5;
(IVq)
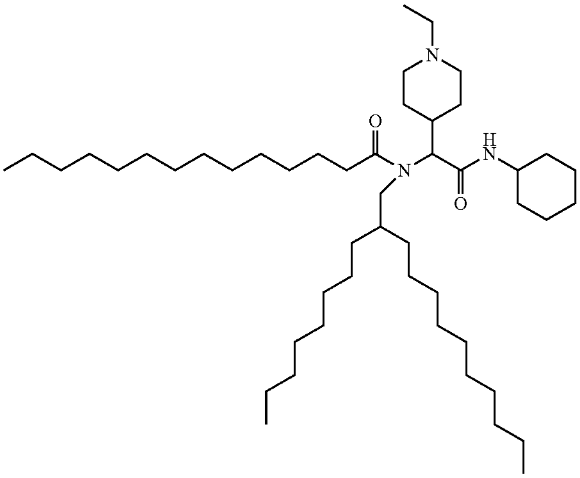

also referred to as P26D4;
(IVr)
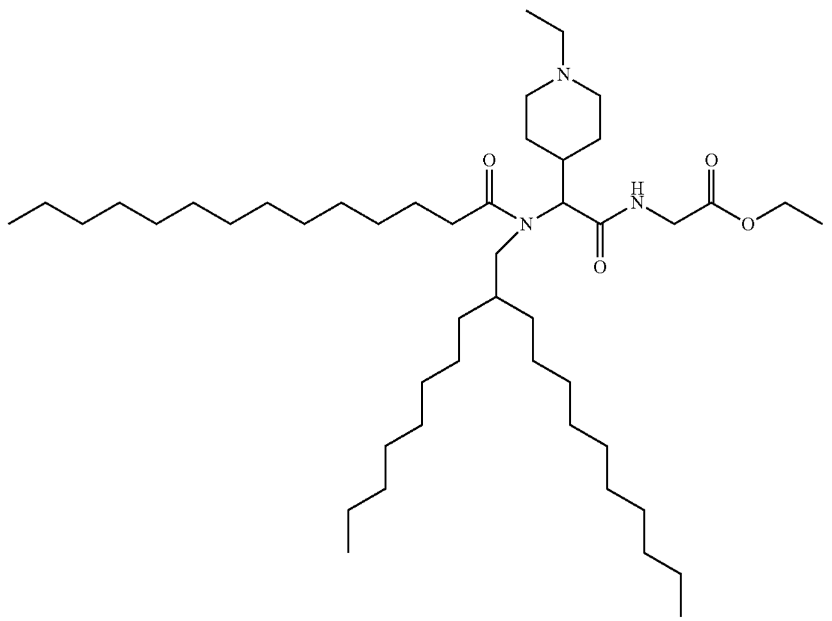
also referred to as P1D4;
(IVs)
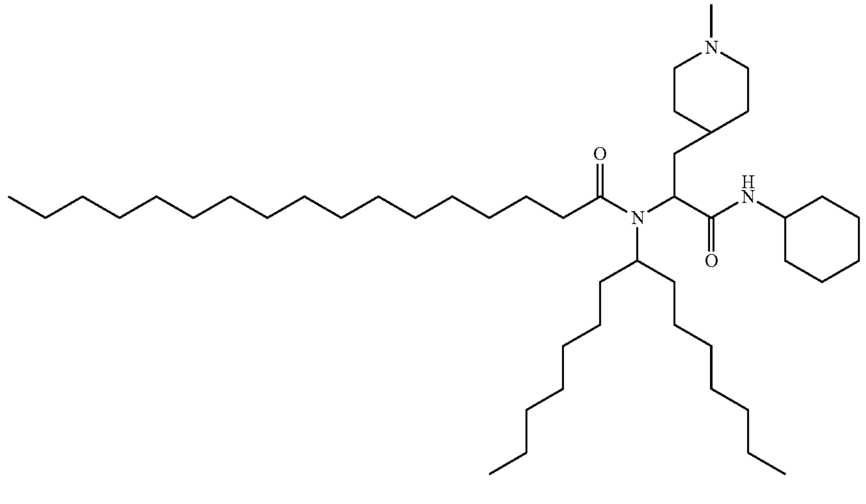

also referred to as P30B7;
(IVt)
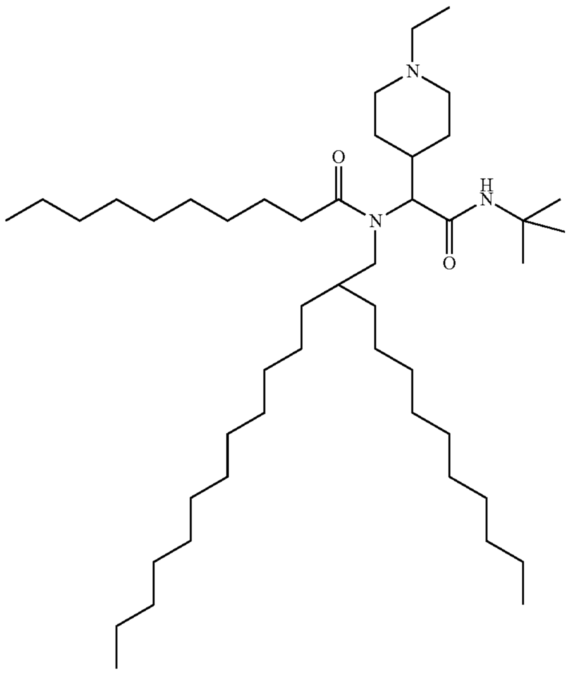
also referred to as P53A6;
(IVu)
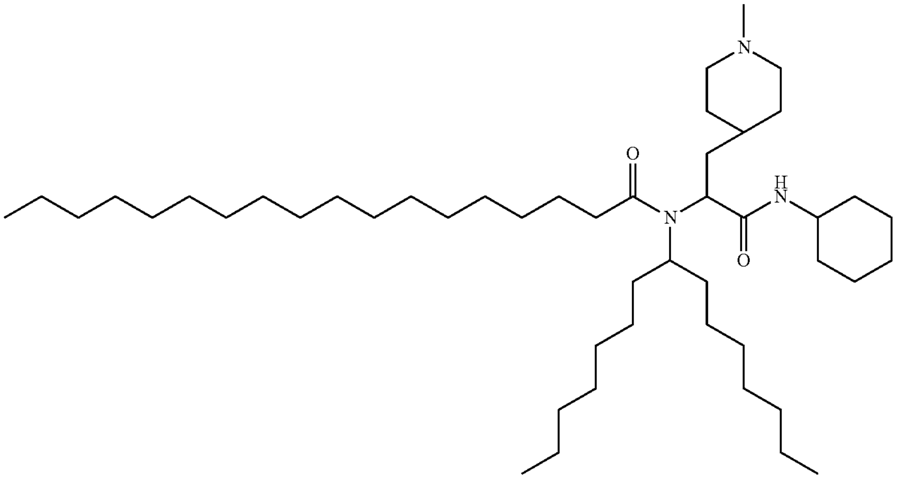

also referred to as P30C7;
(IVv)
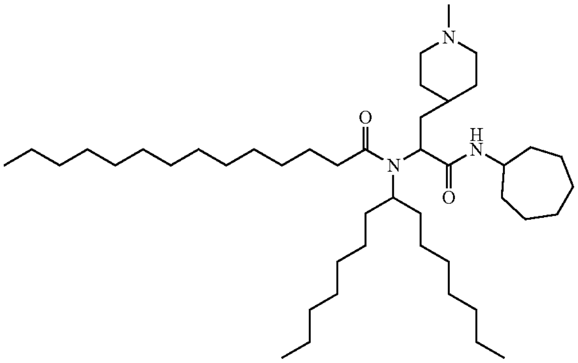
also referred to as P38D7;
(IVw)
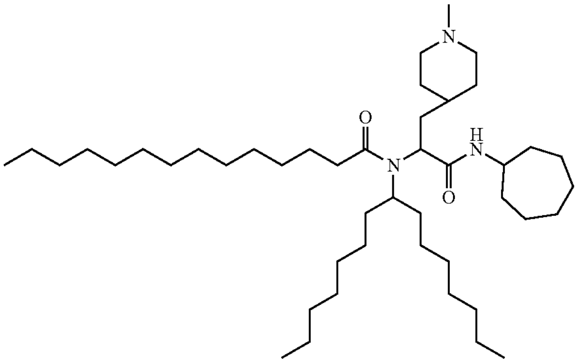
also referred to as P38D8;
(IVx)
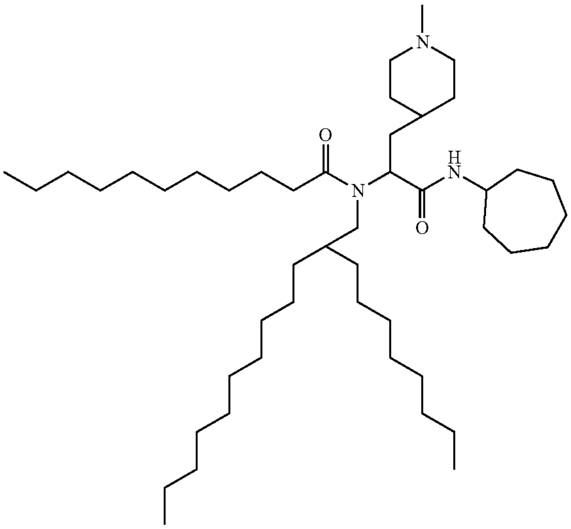
also referred to as P40B10;
(IVy)
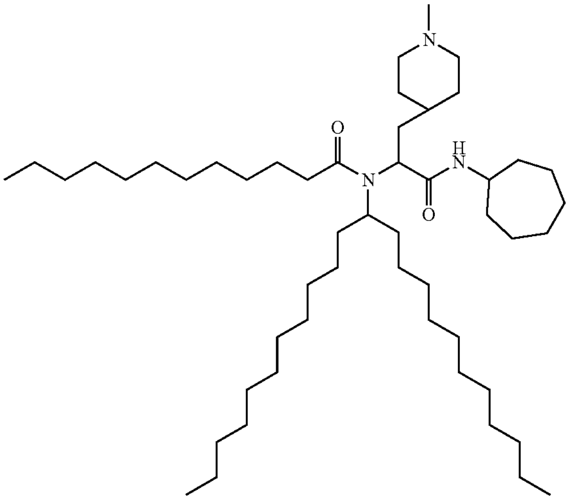
also referred to as P40C11;
(IVz)
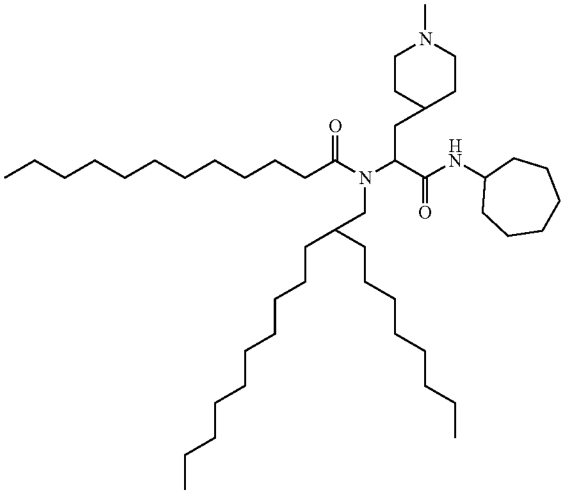

also referred to as P40C10;
(IVaa)
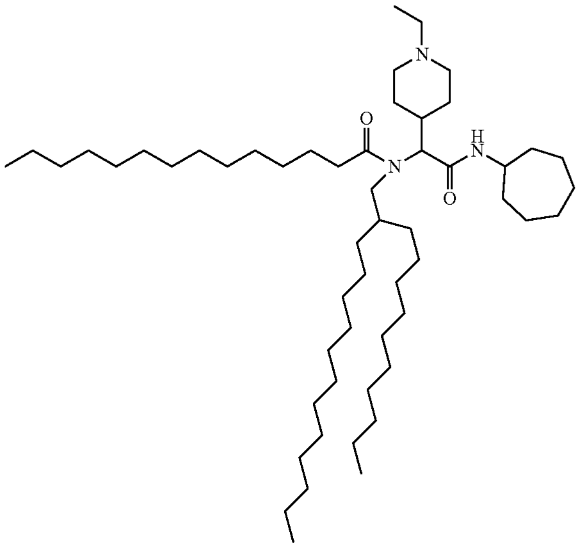
also referred to as P38D4;
(IVab)
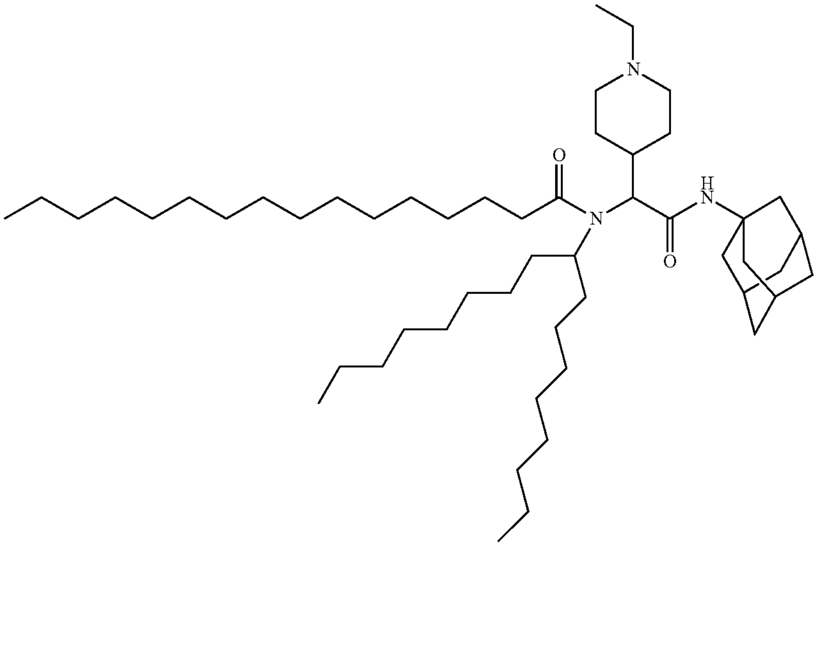
also referred to as P56A2;
(IVac)
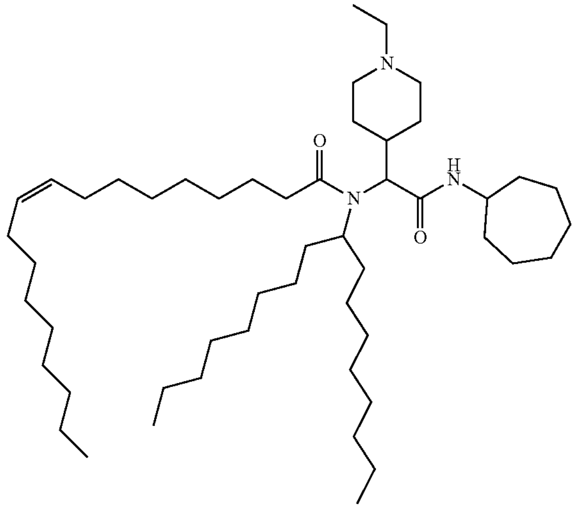

also referred to as P149A2;

(IVad)

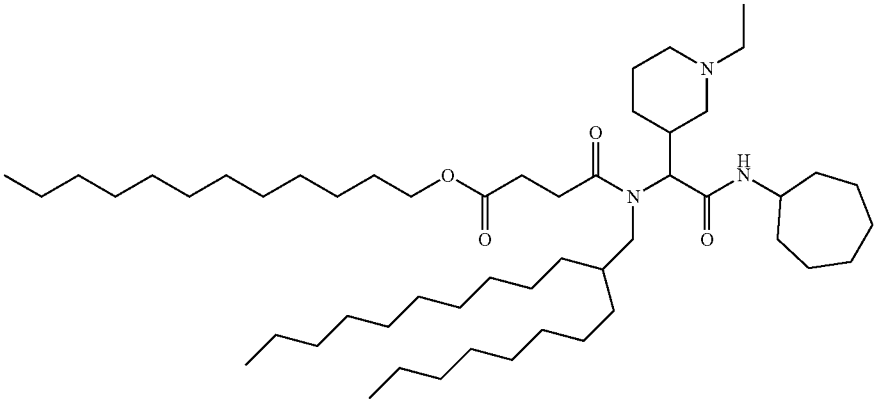

also referred to as P159C10;

(IVae)

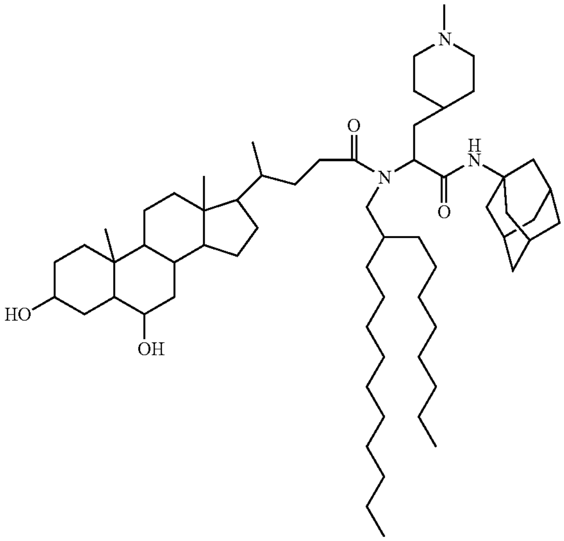

also referred to as P161F10;

or a salt or isomer thereof.

In another aspect, the present disclosure provides compounds of Formula (V):

(V)

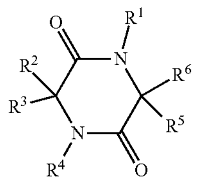

or a salt or isomer thereof, wherein each $R^1$, $R^2$, $R^3$, $R^4$, $R^5$ and $R^6$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

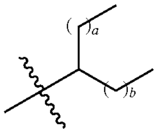,
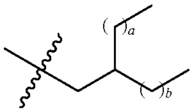,

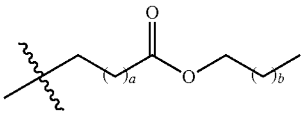,

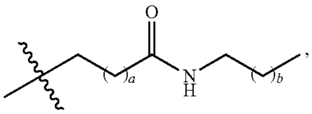,

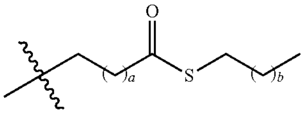,

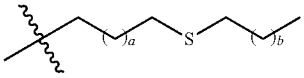,

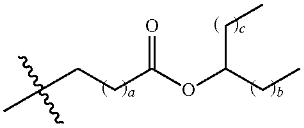,

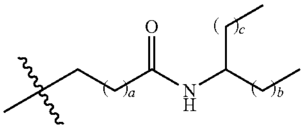,

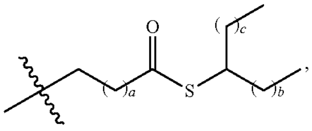,

-continued
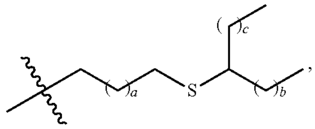
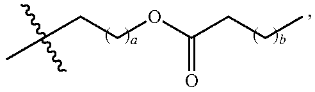
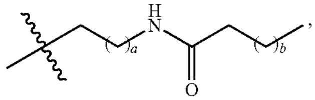
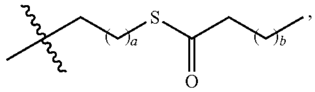
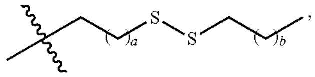
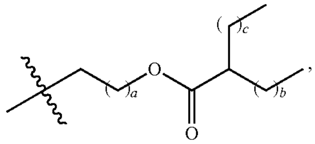
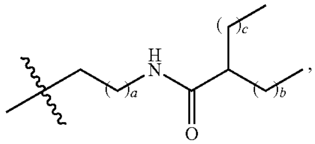
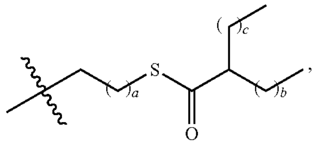
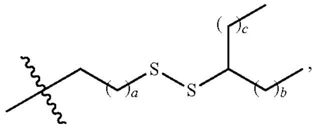
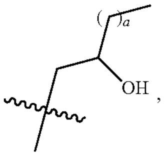
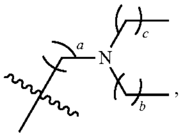
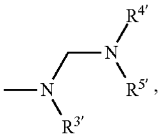
a, b and c are each independently an integer from 0-24;
each $R^{3'}$, $R^{4'}$ and $R^{5'}$ is independently selected from H, $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,
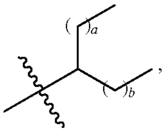
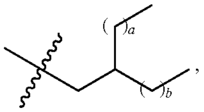
-continued
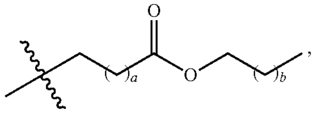
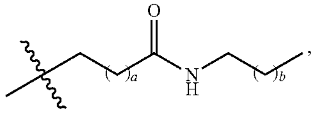
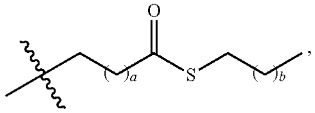
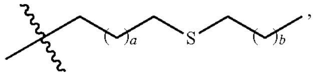
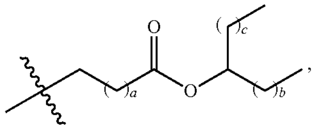
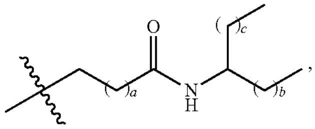
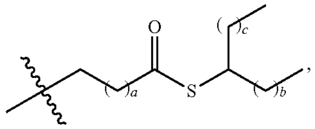
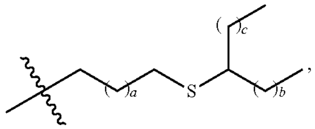
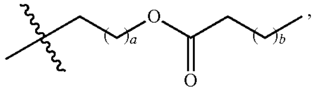
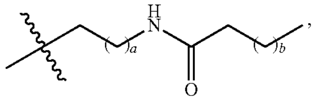
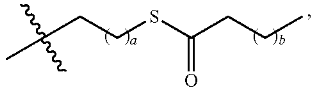
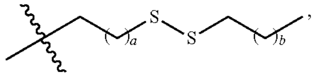
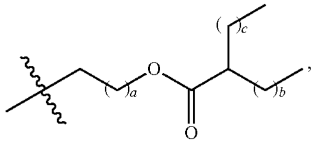
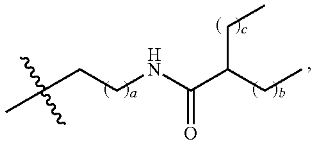

-continued
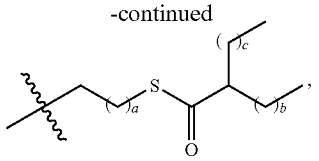
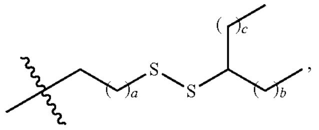
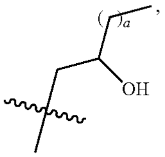
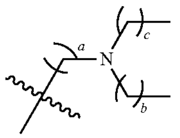
a, b and c are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24.
Synthesis Scheme 5.
General synthetic route for the synthesis of compounds of Formula V.
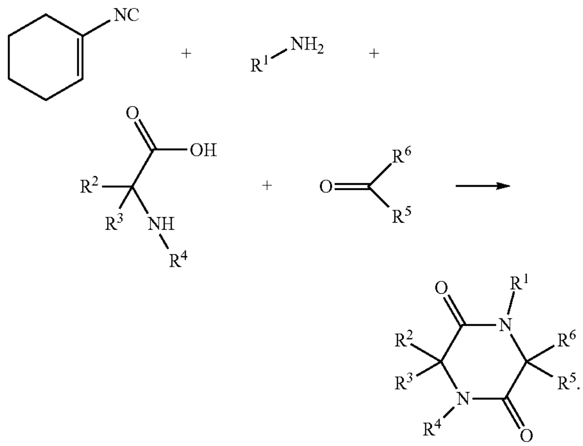
As an example, the aldehyde or ketone may be selected from:
ALA1
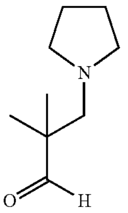
ALA2
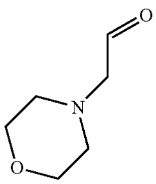
-continued
ALA3
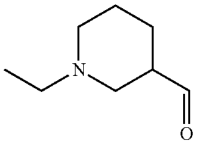
ALA4
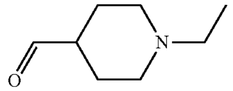
ALA5
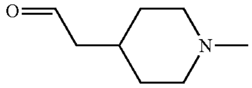
ALA6
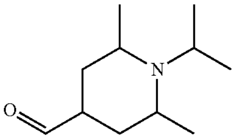
ALA7
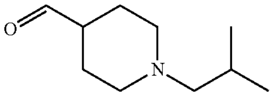
ALA8
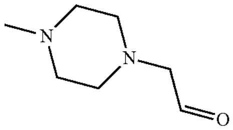
ALA9
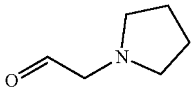
ALA10
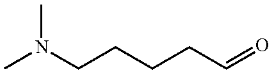
ALA11
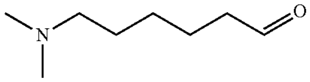
ALA12
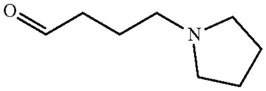
ALA13
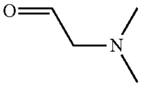
ALA14
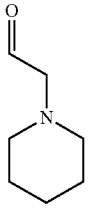
ALA15
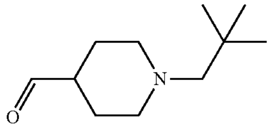

-continued
ALA16
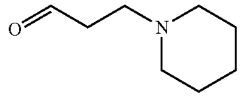
ALA17
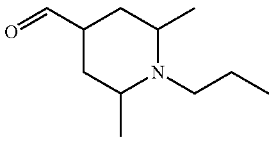
AL8
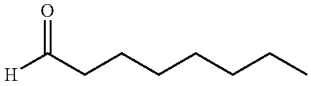
AL9
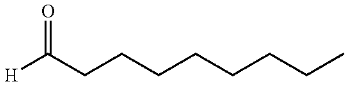
AL10
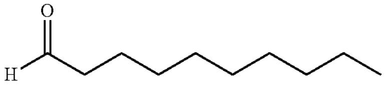
AL11
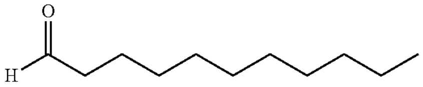
AL12
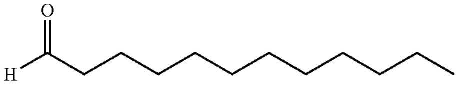
AL13
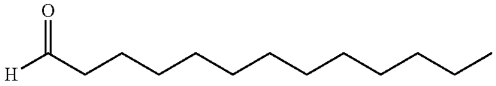
AL15
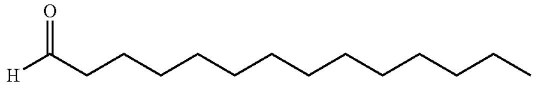
AL16
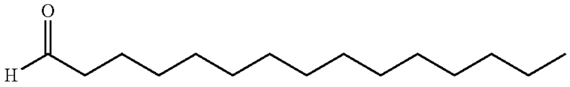
AL16e
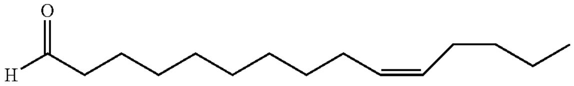
AL10P
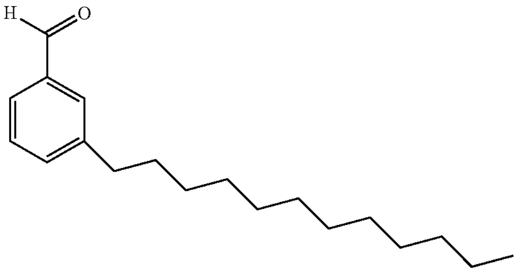
AL14e
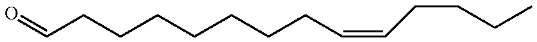
-continued
AL18e
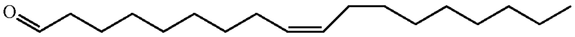
K9
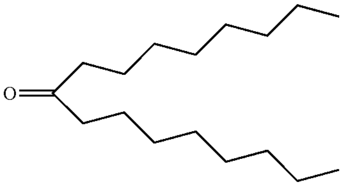
K10
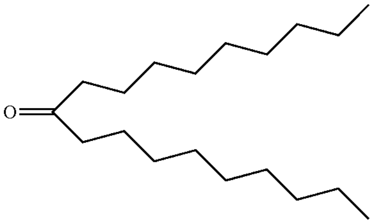
K11
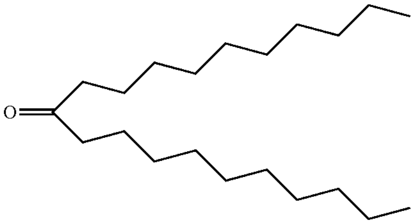
K12
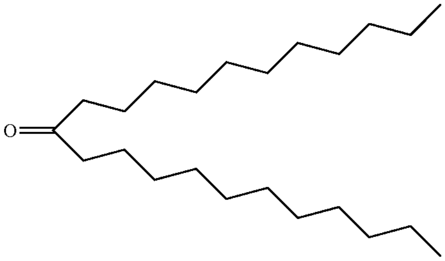
K14
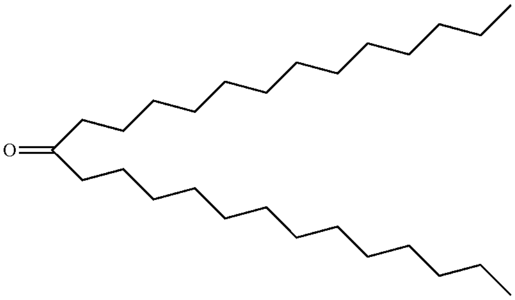

-continued
K16
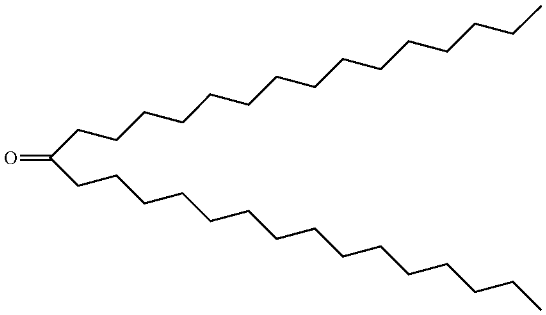
K18e
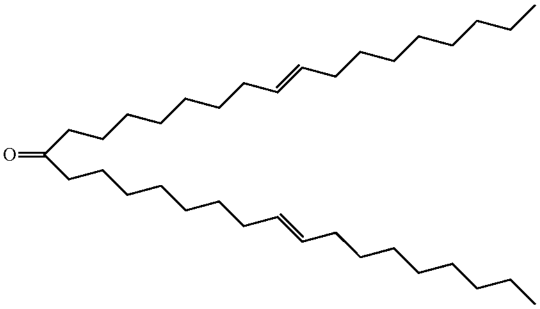
As examples, the amine may be selected from:
AP1
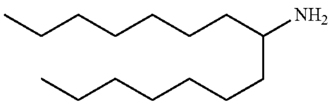
AP2
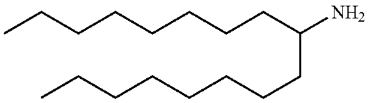
AP3
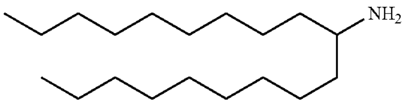
AP4
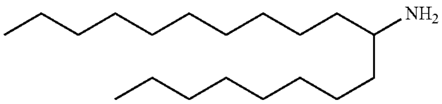
AP5
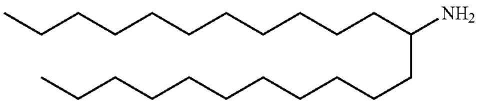
AP6
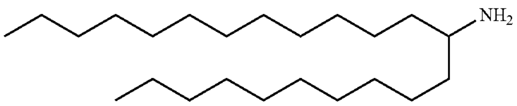
AP7
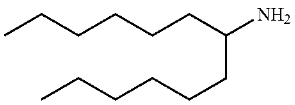
-continued
AP8
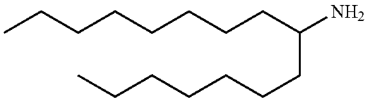
A1
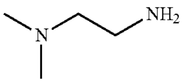
A3
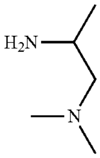
A2
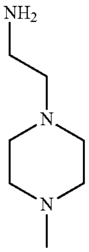
A4
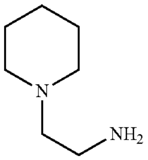
A5
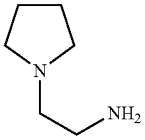
A21
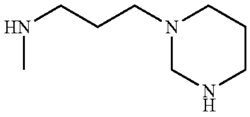
A6
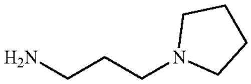
A7
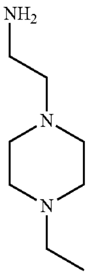
A8
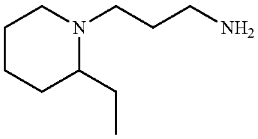

-continued
A9
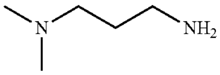
A10
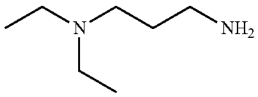
A22
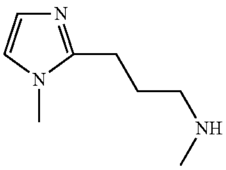
A11
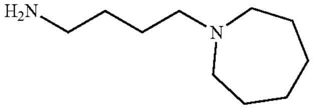
A12
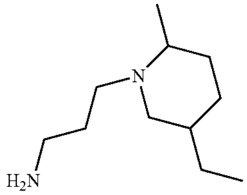
A13
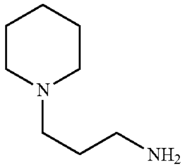
A14
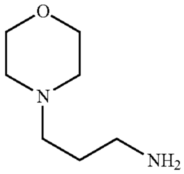
A15
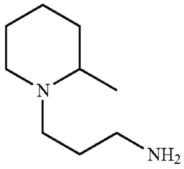
A16
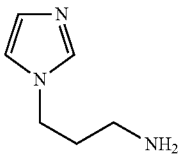
A17
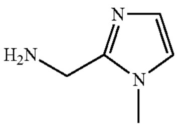
-continued
A18
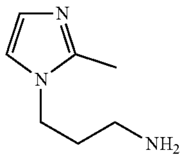
A19
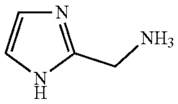
A20
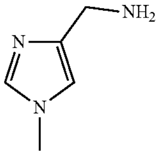
SA6
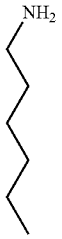
SA7
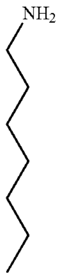
SA8
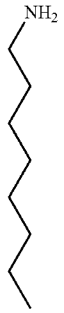
SA9
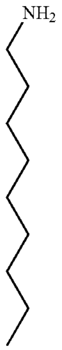

-continued
SA10
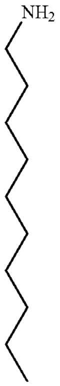
SA11
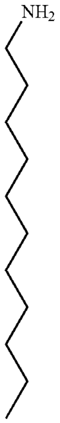
SA12
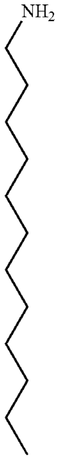
-continued
SA13
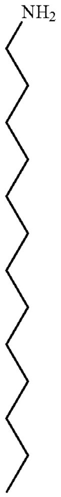
SA14
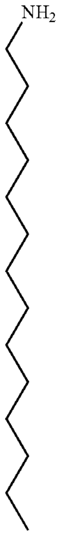
SA15
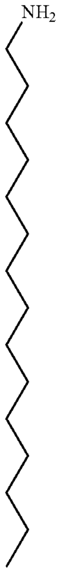

-continued
SA16
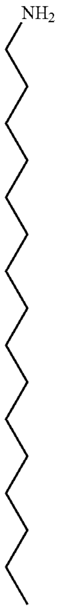
SA17
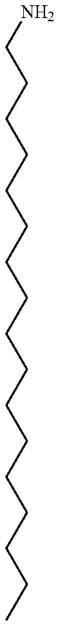
SA18
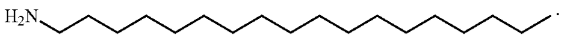
As examples, the boc amino acid may be selected from:
NA1
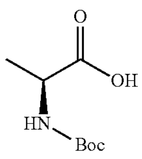
-continued
NA2
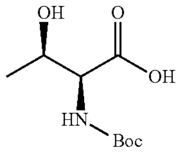
NA3
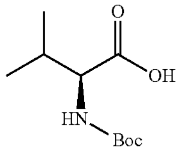
NA4
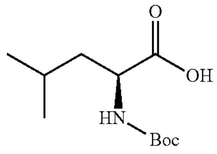
NA5
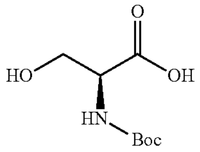
NA6
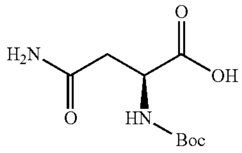
NA7
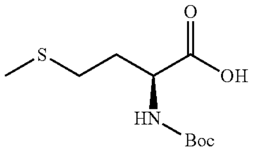
NA8
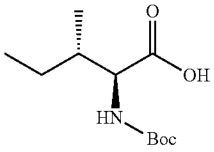
NA9
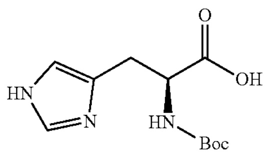
NA10
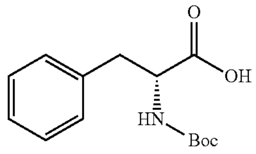
NA11
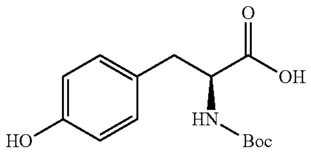

-continued
NA12
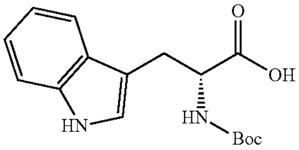
NA13
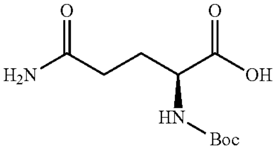
NA14
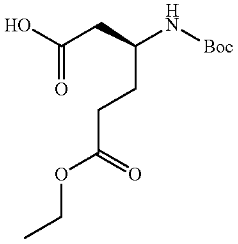
NA15
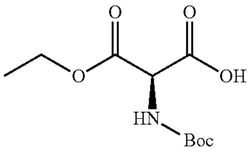
-continued
NA16
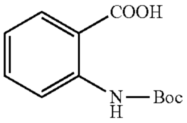
NAC8
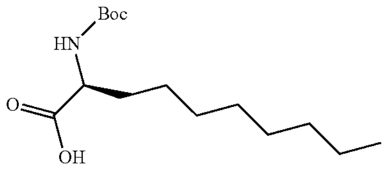
NA-12
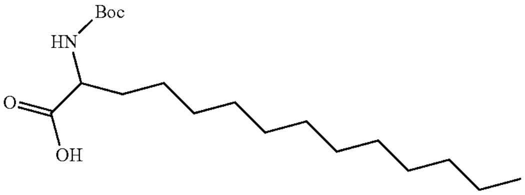
.
In certain aspects, compounds of Formula V may include, for example, the following compounds:
(Va)
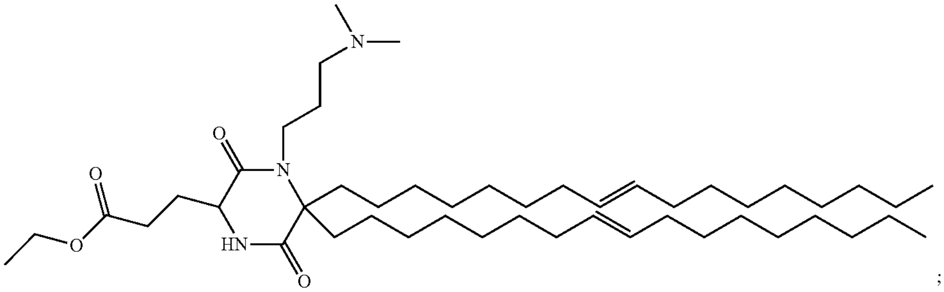
;
(Vb)
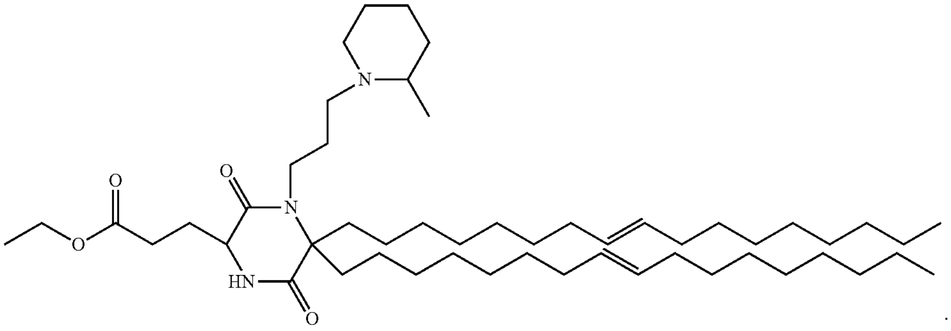
.
or a salt or isomer thereof.

In another aspect, the present disclosure provides compounds of Formula (VI):

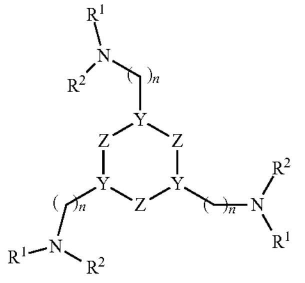

(VI)

or a salt or isomer thereof, wherein each n is independently an integer from 0-10, e.g., 1, 2, 3, 4, 5, 6, 7, 8, 9, or 10, or any subrange selected from the range of 0-10, e.g., 2-9, 3-8, 4-7, 1-5, 1-4, 5-9, etc.;

each $R^1$ and $R^2$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

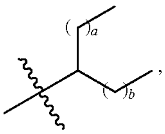,

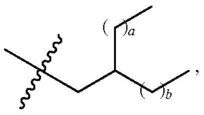,

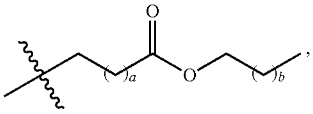,

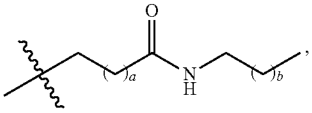,

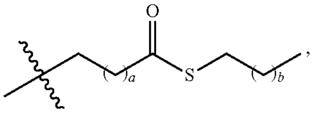,

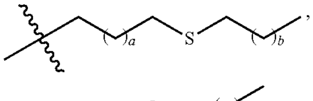,

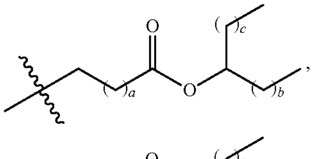,

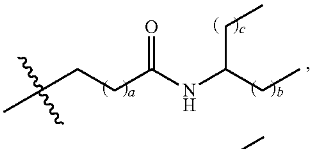,

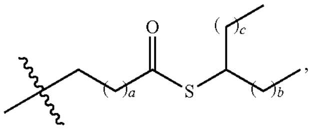,

-continued

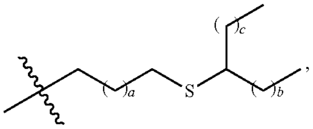,

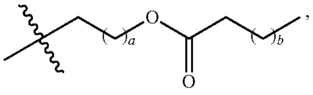,

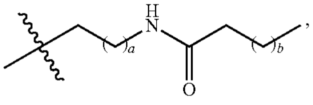,

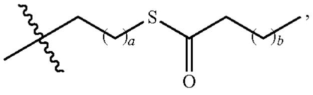,

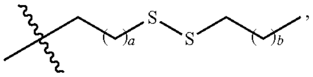,

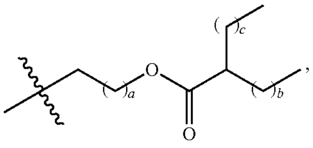,

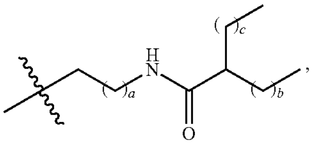,

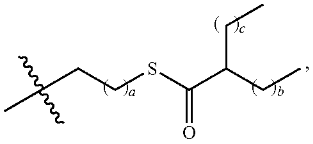,

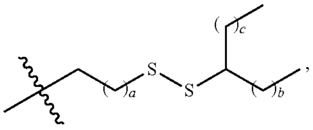,

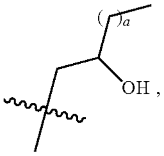,

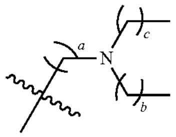,

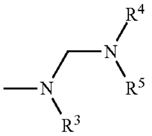

a, b and c are each independently an integer from 0-24;

each $R^3$, $R^4$ and $R^5$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

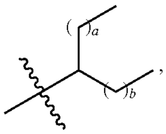,

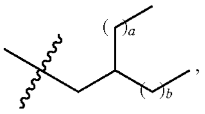,

-continued
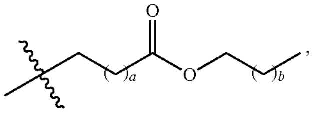,
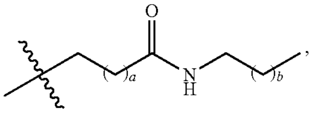,
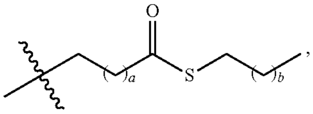,
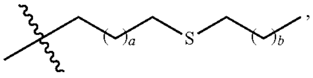,
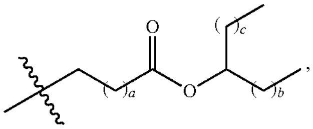,
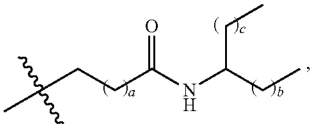,
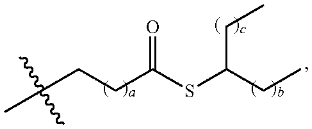,
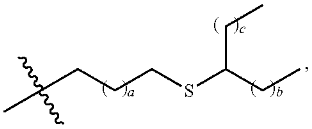,
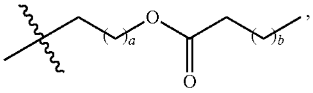,
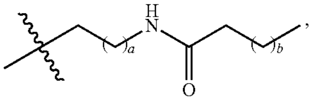,
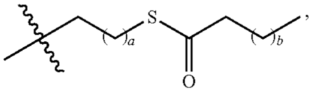,
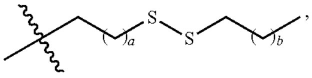,
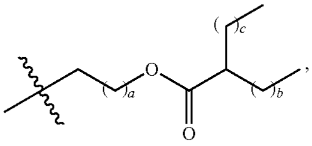,
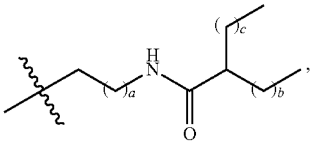,
-continued
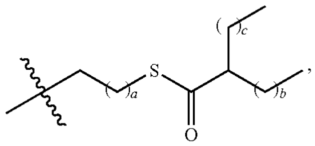,
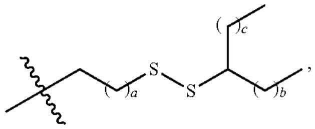,
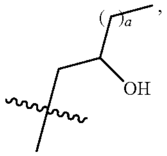,
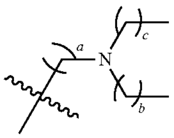
a, b and c are each independently an integer from 0-24, e.g., 1, 2, 3, 4, 5, 6, 7, 8, 9, 10, 11, 12, 13, 14, 15, 16, 17, 18, 19, 20, 21, 22, 23, or any subrange selected from within the range of 0-24;
each Y is independently selected from CH or N;
each Z is independently selected from $CH_2$, NH, O, or S.
Synthesis Scheme 6.
General synthetic route for the synthesis of compounds of Formula VI.
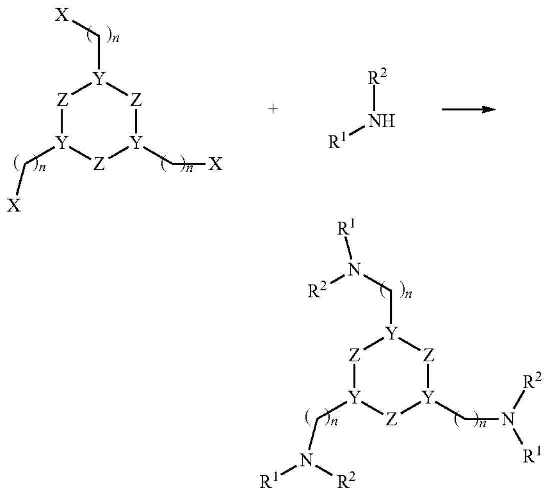
or,
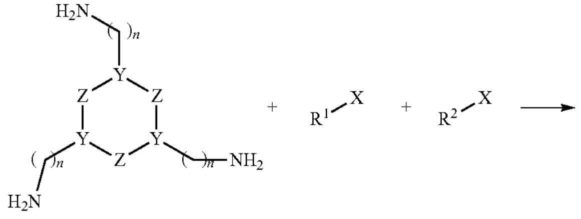

-continued

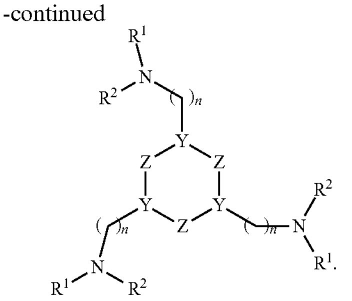

wherein X is independently selected from F, Cl, Br, Ts,

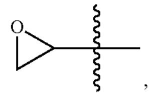, 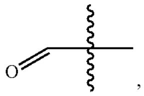, 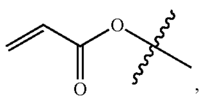, and wherein each n is independently an integer from 0-10, e.g., 0, 1, 2, 3, 4, 5, 6, 7, 8, 9, or 10, or any subrange selected from the range of 0-10, e.g., 2-9, 3-8, 4-7, 1-5, 1-4, 5-9, etc.

As an example, the amine may be, for example, selected from DA8-DA14, DA18, AP1-AP8, as shown above.

In certain aspects, compounds of Formula VI may comprise, for example, the following formula:

VI-1

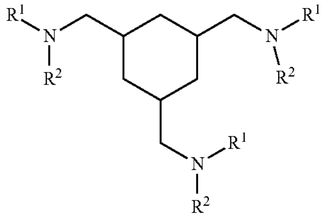

or a salt or isomer thereof, wherein each $R^1$ and $R^2$ are as defined above.

General synthesis route for the synthesis of compounds of Formula VI-1:

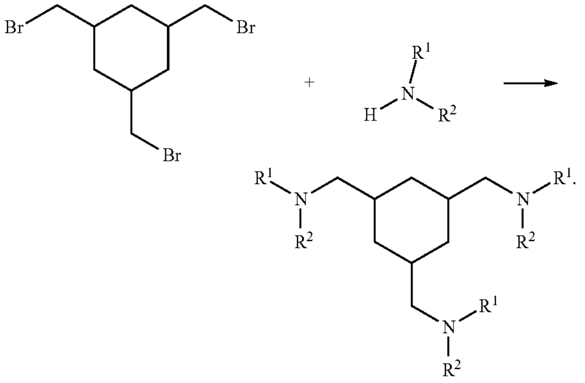

In certain aspects, compounds of Formula VI may include, for example, the following compounds:

(VIa)

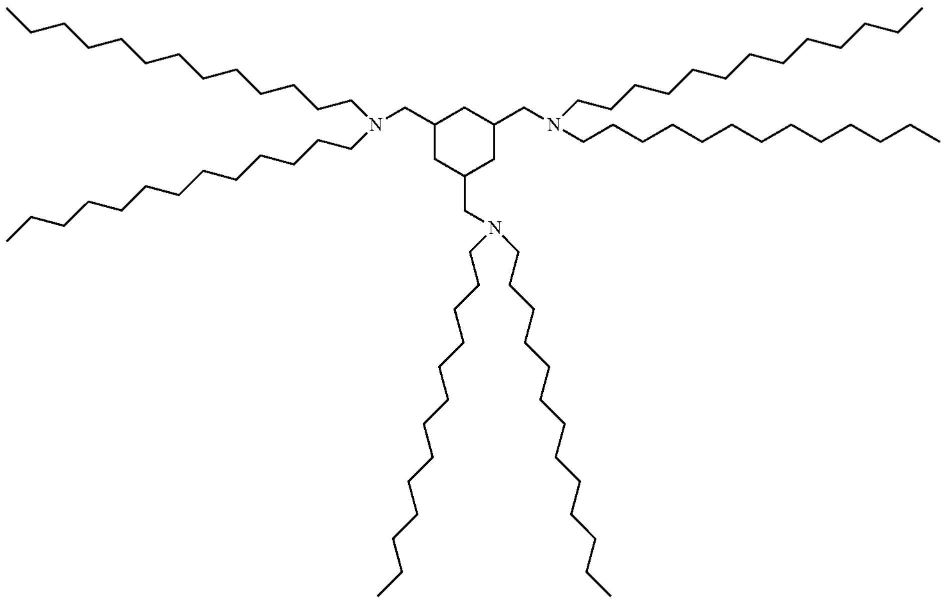

-continued
(VIb)
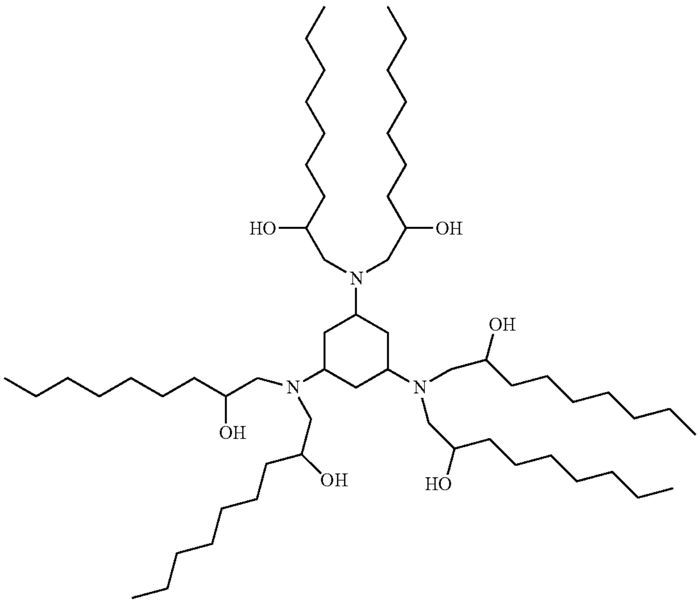
(VIc)
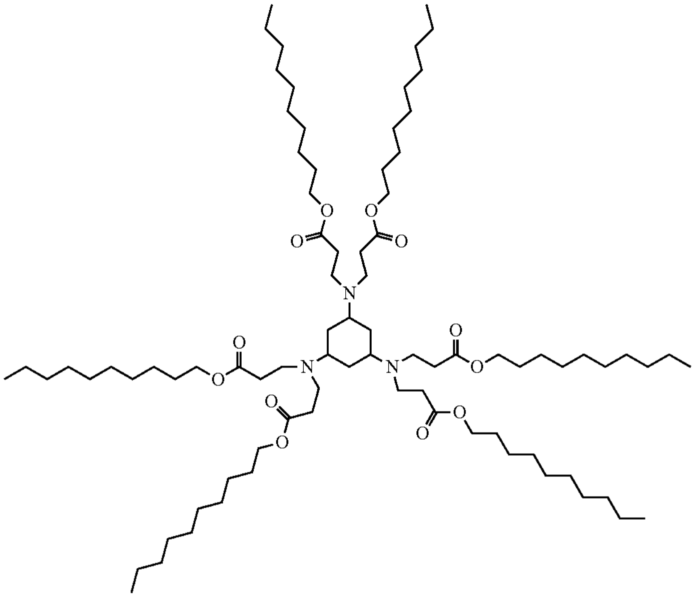
;
or a salt or isomer thereof.

In another aspect, the present disclosure provides compounds of Formula (VII):

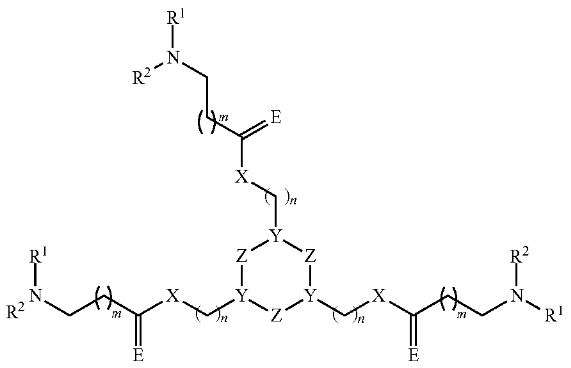

or a salt or isomer thereof, wherein each n and m are independently an integer from 0-10, e.g., 1, 2, 3, 4, 5, 6, 7, 8, 9, or 10, or any subrange selected from the range of 0-10, e.g., 2-9, 3-8, 4-7, 1-5, 1-4, 5-9, etc.;

each $R^1$ and $R^2$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl,

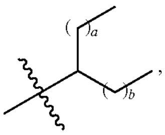

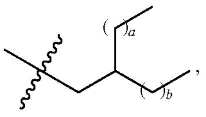

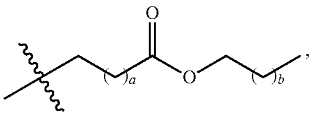

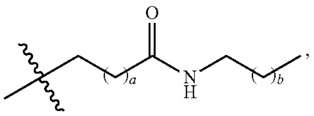

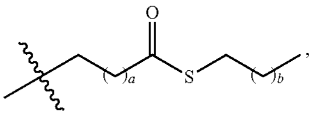

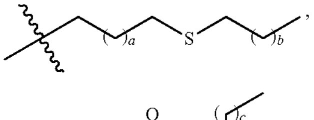

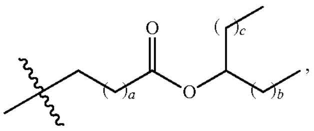

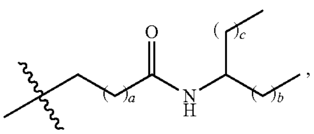

-continued

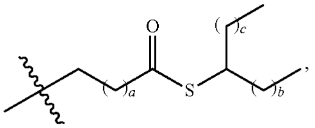

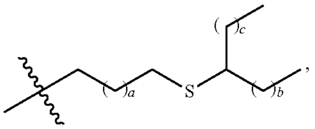

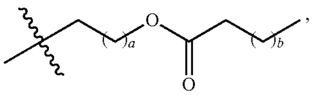

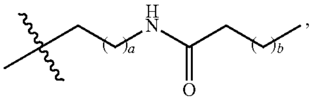

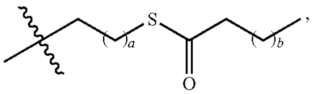

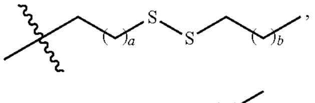

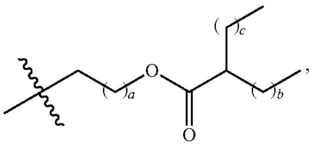

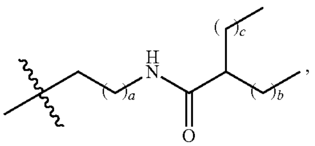

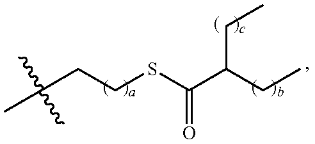

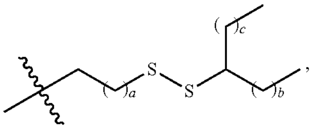

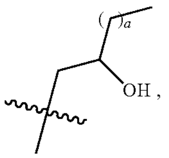

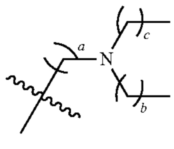

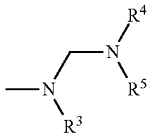

a, b and c are each independently an integer from 0-24;

each $R^3$, $R^4$ and $R^5$ is independently selected from $C_1$-$C_{24}$ alkyl, $C_1$-$C_{24}$ alkenyl, $C_1$-$C_{24}$ alkynyl, substituted alkyl, substituted alkenyl, substituted alkynyl, substituted acyl, substituted carbocyclyl, substituted heterocyclyl, substituted aryl, substituted heteroaryl, -continued
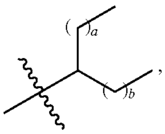
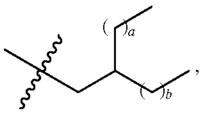
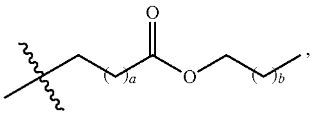
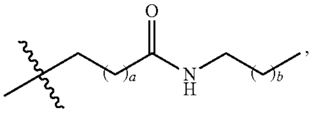
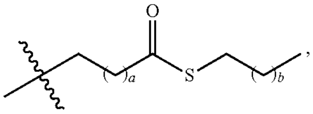
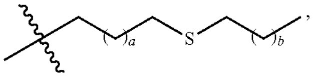
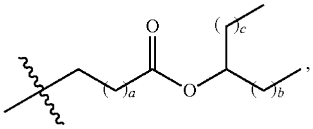
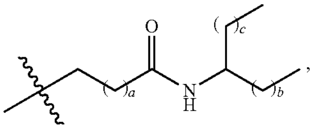
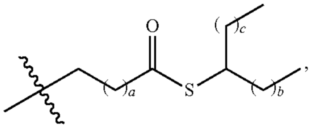
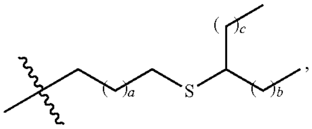
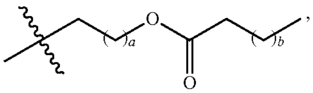
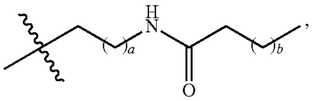
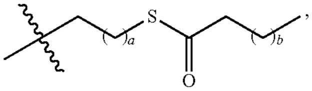
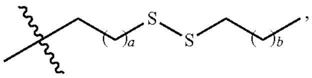
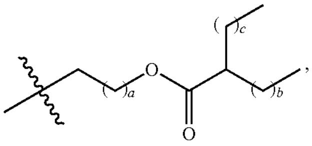
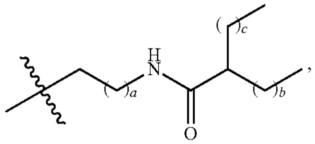
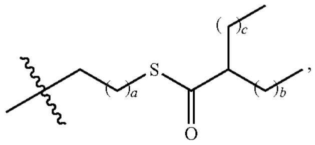
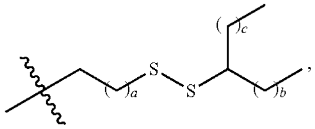
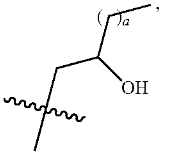
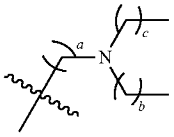
a, b and c are each independently an integer from 0-24;
each X is independently selected from $CH_2$, NH, O, or S;
each Y is independently selected from CH, N;
each Z is independently selected from $CH_2$, NH, O, or S; and
each E is independently selected from $CH_2$, NH, O, or S.
Synthesis Scheme 7.
General synthetic route for the synthesis of compounds of Formula VII.
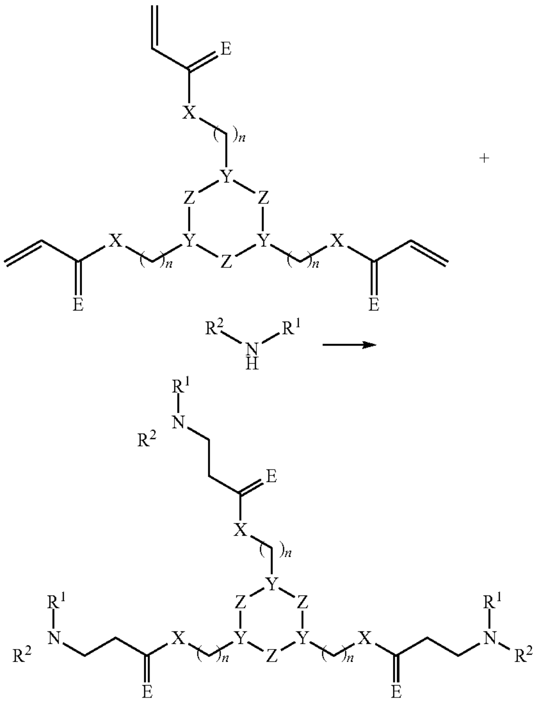
or -continued

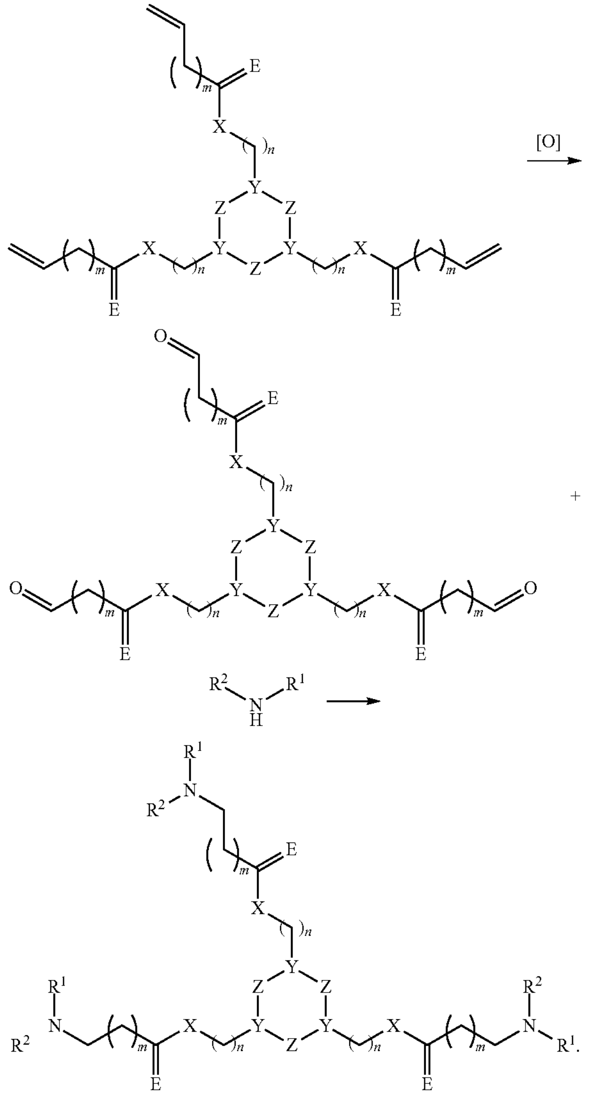

In certain aspects, compounds of Formula VII may comprise, for example, the following formula:

VII-1

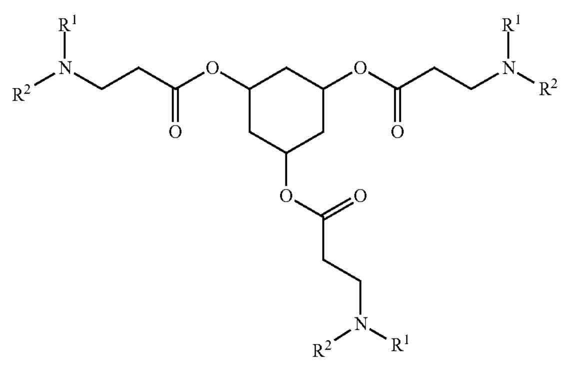

or a salt or isomer thereof, wherein each $R^1$ and $R^2$ are as defined above.

General synthesis route for the synthesis of compounds of Formula VII-1:

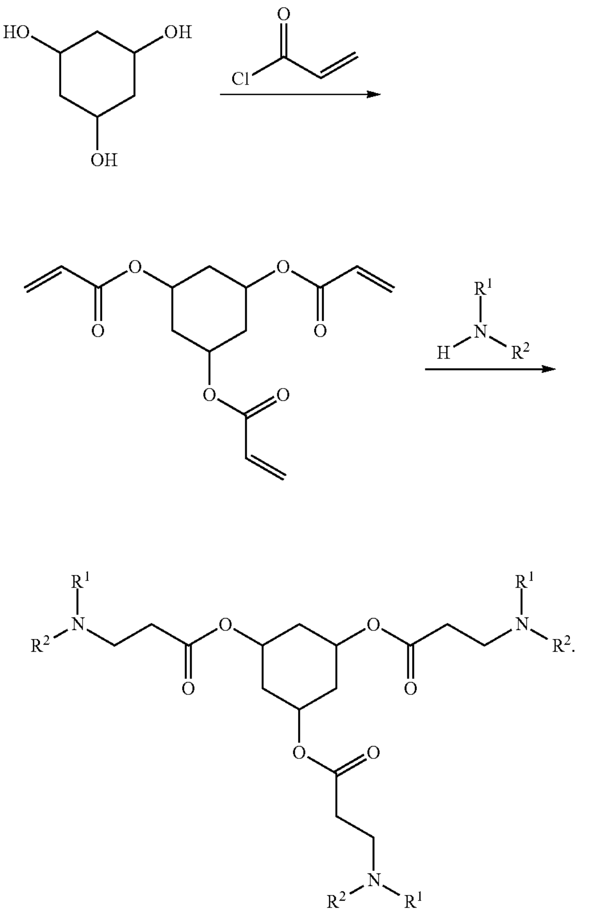

In some aspects, the compounds of Formula VII-1 can be synthesized as follows:

A solution of acryloyl chloride (56 mmol) in dry $CH_2$C12 (50 mL) is added dropwise to a mixture of cyclohexane-1,3,5-triol (14 mmol) and Et3N (84 mmol) in dry CH2C12 (60 mL) at 0° C. under N2. Around 1 hour later, the mixture is brought to room temperature and reacted for 4 hours. Then the mixture is treated with saturated sodium bicarbonate solution (150 mL) and brine (150 mL) and extracted with CH2C12 (150 mL×3). The combined organic layers are dried using, for example anhydrous magnesium sulfate, and the solvent is removed. The crude product is purified by column chromatography using Hexane/ethyl acetate to afford the compound cyclohexane-1,3,5-triyl triacrylate as a white solid. 1H-NMR (400 MHz, Me-OD, δ) 6.40 (dd, J=16, 4 Hz, 3H), 6.08 (dd, J=20, 8 Hz, 3H), 5.83 (dd, J=16, 4 Hz, 3H), 4.98-4.87 (m, 3H), 1.24 (s, 6H). MS (ESI) m/z 317.1 $[M+Na]^+$.

Cyclohexane-1,3,5-triyl triacrylate (0.1 mmol) is mixed with amines in 5 mL ethanol at 1 to 3.3 molar ratio and the mixture was stirred in glass screw-top vials in oil bath at 50° C. for two days. The solvent was removed by rotary evaporator and the product can be purified by column chromatography. Structure can be confirmed using techniques known in the art, for example, nuclear magnetic resonance spectra of 1H and LC-Mass spectrometry.

In certain aspects, compounds of Formula VII may include, for example, the following compounds:
(VIIa)
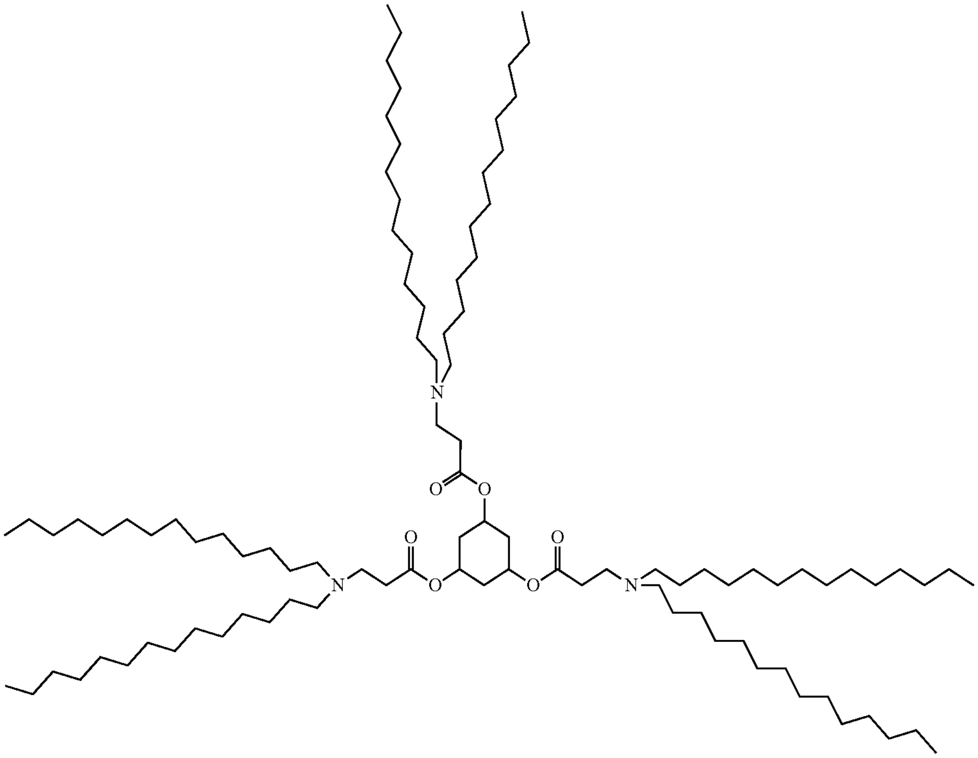
referred to as T7;
(VIIb)
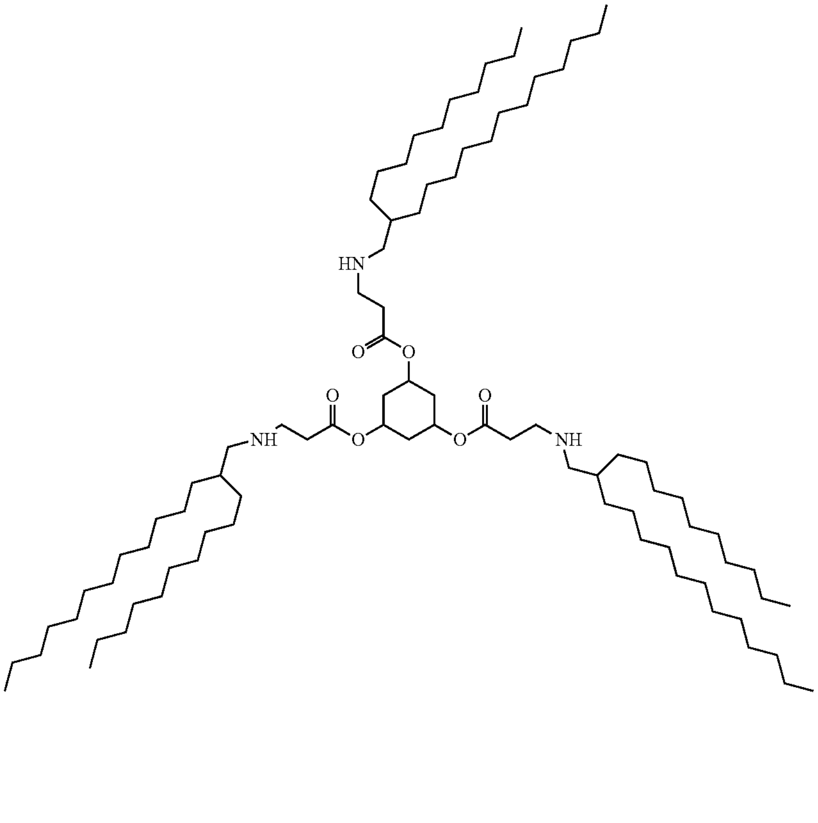

also referred to as P7;

or a salt or isomer thereof.

Lipid Nanoparticle

In some aspects, the dimension of a nanoparticle composition is 1 m or shorter (e.g., 1 m, 900 nm, 800 nm, 700 nm, 600 nm, 500 nm, 400 nm, 300 nm, 200 nm, 175 nm, 150 nm, 125 nm, 100 nm, 75 nm, 50 nm, or shorter) encapsulating mRNA sizes ranging from 1,000 to 20,000 nucleotides, e.g., when measured by dynamic light scattering (DLS), transmission electron microscopy, scanning electron microscopy, or another method. In some aspects, the encapsulated mRNA has a size of 1,000, 1,500, 1,700, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, or 20,000 nucleotides, and any number of nucleotides within the disclosed range is included in this description as if specifically stated herein. Nanoparticle compositions include, for example, lipid nanoparticles (LNPs), liposomes, lipid vesicles, and lipoplexes. In some aspects, nanoparticle compositions are vesicles including one or more lipid bilayers. In certain aspects, a nanoparticle composition includes two or more concentric bilayers separated by aqueous compartments. Lipid bilayers may be functionalized and/or crosslinked to one another. Lipid bilayers may include one or more ligands, proteins, or channels.

Nanoparticle compositions comprise a lipid component including at least one compound according to Formulae (I), (II), (III), (IV), (V), (VI), and (VII). For example, the lipid component of a nanoparticle composition may include one or more of Compounds Ia-VIIb. Nanoparticle compositions may also include a variety of other components. For example, the lipid component of a nanoparticle composition may include one or more other lipids in addition to a lipid according to Formula (I), (II), (III), (IV), (V), (VI), and (VII).

Ionizable Lipids

The lipid component of a nanoparticle composition may include one or more ionizable lipids. A nanoparticle composition may include one or more ionizable lipids in addition to a lipid according to Formulae (I), (II), (III), (IV), (V), (VI), and (VII). As used herein, the term "Ionizable lipids of the present disclosure" include lipid compounds according to Formulae (I), (II), (III), (IV), (V), (VI), and (VII), such as, but not limited to, Compounds Ia-VIIb. The ionizable lipids of the present disclosure can be synthesized in one step.

PEG Lipids

The lipid component of a nanoparticle composition may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

Structural Lipids

The lipid component of a nanoparticle composition may include one or more structural lipids. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, and mixtures thereof. In some aspects, the structural lipid is cholesterol. In some aspects, the structural lipid includes cholesterol and a corticosteroid (such as prednisolone, dexamethasone, prednisone, and hydrocortisone), or a combination thereof.

Phospholipids

The lipid component of a nanoparticle composition may include one or more phospholipids, such as one or more (poly)unsaturated lipids. Phospholipids may assemble into one or more lipid bilayers. In general, phospholipids may include a phospholipid moiety and one or more fatty acid moieties.

Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some aspects, a nanoparticle composition includes DSPC. In certain aspects, a nanoparticle composition includes DOPE. In some aspects, a nanoparticle composition includes both DSPC and DOPE.

Adjuvants

In some aspects, a nanoparticle composition that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Biologically Active Agents

Nanoparticle compositions may include one or more biologically active agents. The disclosure features methods of delivering a biologically active agent to a mammalian cell or organ, producing a polypeptide of interest in a mammalian cell, and treating a disease or disorder in a mammal in need thereof comprising administering to a mammal and/or contacting a mammalian cell with a nanoparticle composition including a biologically active agent.

Biologically active agents may be a substance that, once delivered to a cell or organ, brings about a desirable change in the cell, organ, or other bodily tissue or system. Such species may be useful in the treatment of one or more diseases, disorders, or conditions.

In some aspects, a biologically active agent is a small molecule drug useful in the treatment of a particular disease, disorder, or condition. Examples of drugs useful in the nanoparticle compositions include, but are not limited to, antineoplastic agents (e.g., vincristine, doxorubicin, mitoxantrone, camptothecin, cisplatin, bleomycin, cyclophosphamide, methotrexate, and streptozotocin); antitumor agents (e.g., actinomycin D, vincristine, vinblastine, cystine arabinoside, anthracyclines, alkylative agents, platinum compounds, antimetabolites, and nucleoside analogs, such as methotrexate and purine and pyrimidine analogs); anti-infective agents; local anesthetics (e.g., dibucaine and chlorpromazine); beta-adrenergic blockers (e.g., propranolol, timolol, and labetolol), antihypertensive agents (e.g., clonidine and hydralazine); anti-depressants (e.g., imipramine, amitriptyline, and doxepim); anti-conversants (e.g., phenytoin); antihistamines (e.g., diphenhydramine, chlorphenirimine, and promethazine); antibiotic/antibacterial agents (e.g., gentamycin, ciprofloxacin, and cefoxitin); antifungal agents (e.g., miconazole, terconazole, econazole, isoconazole, butaconazole, clotrimazole, itraconazole, nystatin, naftifine, and amphotericin B); antiparasitic agents; hormones; hormone antagonists; immunomodulators; neurotransmitter antagonists; antiglaucoma agents; vitamins; narcotics; and imaging agents.

In some aspects, a biologically active agent is a polynucleotide or nucleic acid (e.g., ribonucleic acid or deoxyribonucleic acid). The term "nucleic acid," in its broadest sense, includes any compound and/or substance that is or can be incorporated into an oligonucleotide chain. Exemplary nucleic acids for use in accordance with the present disclosure include, but are not limited to, one or more of deoxyribonucleic acid (DNA), ribonucleic acid (RNA) including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In some aspects, a therapeutic and/or prophylactic is an RNA. RNAs useful in the compositions and methods described herein can be selected from the group consisting of, but are not limited to, shortmers, antagomirs, antisense, ribozymes, small interfering RNA (siRNA), asymmetrical interfering RNA (aiRNA), small activating mRNA (saRNA), microRNA (miRNA), Dicer-substrate RNA (dsRNA), small hairpin RNA (shRNA), transfer RNA (tRNA), messenger RNA (mRNA), and mixtures thereof. In certain aspects, the RNA is an mRNA.

In certain aspects, a biologically active agent is an mRNA. An mRNA may encode any polypeptide or regulatory structure of interest, including any naturally or non-naturally occurring or otherwise modified polypeptide. A polypeptide encoded by an mRNA may be of any size and may have any secondary structure or activity. In some aspects, a regulatory structure or polypeptide encoded by an mRNA may have a therapeutic effect when expressed in a cell.

In one aspects, a biologically active agent is an self-amplifying mRNA. A self-amplifying mRNA may be derived from a modified alphavirus species, including, but not limited to, a Venezuelan equine encephalitis virus (VEEV). A self-amplifying mRNA may encode both a polypeptide or regulatory structure of interest, including any naturally or non-naturally occurring or otherwise modified polypeptide and an RNA dependent RNA polymerase which can replicate the entire self-amplifying mRNA or a polypeptide or regulatory structure of interest after delivery inside the targeted cell. A self-amplifying mRNA may be produced inside a target cell upon delivery of an appropriate construct to the nucleus. Self-amplifying mRNA can generate a larger number of mRNA templates and thereby enhanced expression at lower doses compared to a non-self-amplifying RNA.

In other aspects, a biologically active agent is an siRNA. An siRNA may be capable of selectively knocking down or down regulating expression of a gene of interest. For example, an siRNA could be selected to silence a gene associated with a particular disease, disorder, or condition upon administration to a subject in need thereof of a nanoparticle composition including the siRNA. An siRNA may comprise a sequence that is complementary to an mRNA sequence that encodes a gene or protein of interest. In some aspects, the siRNA may be an immunomodulatory siRNA.

In some aspects, a biologically active agent is an shRNA or a vector or plasmid encoding the same. An shRNA may be produced inside a target cell upon delivery of an appropriate construct to the nucleus. Constructs and mechanisms relating to shRNA are well known in the relevant arts.

Nucleic acids and polynucleotides useful in the disclosure may include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some aspects, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some aspects, a polynucleotide or nucleic acid (e.g., an mRNA) may include a 5' cap structure, a chain terminating nucleotide, a stem loop, a polyA sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine or 1-ethyl-pseudouridine), and/or a 5-substituted cytidine (e.g., 5-methyl-cytidine).

Formulations

Nanoparticle compositions may include a lipid component and one or more additional components, such as a biologically active agent. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to Formulae (I), (II), (III), (IV), (V), (VI), and (VII), a phospholipid (such as an unsaturated lipid, e.g., DOPE or DSPC), a PEG lipid, and a structural lipid. The elements of the lipid component may be provided in specific fractions.

The amount of a therapeutic and/or prophylactic in a nanoparticle composition may depend on the size, composition, desired target and/or application, or other properties of the nanoparticle composition as well as on the properties of the therapeutic and/or prophylactic. For example, the amount of an RNA useful in a nanoparticle composition may depend on the size, sequence, and other characteristics of the RNA. The relative amounts of a therapeutic and/or prophylactic and other elements (e.g., lipids) in a nanoparticle composition may also vary. In some aspects, the wt/wt ratio of the lipid component to a biologically active agent in a nanoparticle composition may be from about 1:1 to about 60:1, such as 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic may be from about 10:1 to about 40:1. In certain aspects, the wt/wt ratio is about 20:1. The amount of a therapeutic diagnostic and/or prophylactic in a nanoparticle composition may, for example, be measured using absorption spectroscopy (e.g., ultraviolet-visible spectroscopy).

Nanoparticle compositions may be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy,* $21^{st}$ Edition, A. R. Gennaro; Lippincott, Williams & Wilkins, Baltimore, Md., 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a nanoparticle composition if its combination with the component may result in any undesirable biological effect or otherwise deleterious effect.

In some aspects, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some aspects, a pharmaceutically acceptable excipient is at least 95%, at least 96%, at least 97%, at least 98%, at least 99%, or 100% pure. In some aspects, an excipient is approved for use in humans and for veterinary use. In some aspects, an excipient is approved by United States Food and Drug Administration. In some aspects, an excipient is pharmaceutical grade. In some aspects, an excipient meets the standards of the United States Pharmacopoeia (USP), the European Pharmacopoeia (EP), the British Pharmacopoeia, and/or the International Pharmacopoeia.

Relative amounts of the one or more nanoparticle compositions, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered.

In certain aspects, the nanoparticle compositions and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. For example, the pharmaceutical composition comprising a compound of any of Formula (I), (II), (III), (IV), (V), (VI), and (VII) is a solution that is refrigerated for storage and/or shipment at, for example, about −20° C., −30° C., −40° C., −50° C., −60° C., −70° C., or −80° C. In certain aspects, the disclosure also relates to a method of increasing stability of the nanoparticle compositions and/or pharmaceutical compositions comprising a compound of any of Formulae (I), (II), (III), (IV), (V), (VI), and (VII) by storing the nanoparticle compositions and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the nanoparticle compositions and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In one aspect, the formulation is stabilized for at least 4 weeks at about 4° C. In certain aspects, the pharmaceutical composition of the disclosure comprises a nanoparticle composition disclosed herein and a pharmaceutically acceptable carrier selected from one or more of Tris, an acetate (e.g., sodium acetate), an citrate (e.g., sodium citrate), saline, PBS, and sucrose. In certain aspects, the pharmaceutical composition of the disclosure has a pH value between about 5 and 8 (e.g., 5, 5.5, 6, 6.5, 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a nanoparticle composition disclosed herein, Tris, saline and sucrose, and has a pH of about 7.5-8, which is suitable for storage and/or shipment at, for example, about −20° C. For example, a pharmaceutical composition of the disclosure comprises a nanoparticle composition disclosed herein and PBS and has a pH of about 7-7.8, suitable for storage and/or shipment at, for example, about 4° C. or lower. "Stability," "stabilized," and "stable" in the context of the present disclosure refers to the resistance of nanoparticle compositions and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

Nanoparticle compositions and/or pharmaceutical compositions including one or more nanoparticle compositions may be administered to any patient or subject, including those patients or subjects that may benefit from a therapeutic effect provided by the delivery of a therapeutic and/or prophylactic to one or more particular cells, tissues, organs, or systems or groups thereof, such as the renal system. Although the descriptions provided herein of nanoparticle compositions and pharmaceutical compositions including nanoparticle compositions are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, horses, sheep, cats, dogs, mice, and/or rats.

A pharmaceutical composition including one or more nanoparticle compositions may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

The present disclosure provides methods of producing a polypeptide or regulatory structure of interest in a mammalian cell. Methods of producing polypeptides involve contacting a cell with a nanoparticle composition including an mRNA encoding the polypeptide or regulatory structure of interest. Upon contacting the cell with the nanoparticle composition, the mRNA may be taken up and translated in the cell to produce the polypeptide of interest.

In general, the step of contacting a mammalian cell with a nanoparticle composition including an mRNA encoding a polypeptide or regulatory structure of interest may be performed in vivo, ex vivo, in culture, or in vitro. The amount of nanoparticle composition contacted with a cell, and/or the amount of mRNA therein, may depend on the type of cell or tissue being contacted, the means of administration, the physiochemical characteristics of the nanoparticle composition and the mRNA (e.g., size, charge, and chemical composition) therein, and other factors. In general, an effective amount of the nanoparticle composition will allow for efficient polypeptide production in the cell. Metrics for efficiency may include polypeptide translation (indicated by polypeptide expression), level of mRNA degradation, and immune response indicators.

The step of contacting a nanoparticle composition including an mRNA with a cell may involve or cause transfection. A phospholipid including in the lipid component of a nanoparticle composition may facilitate transfection and/or increase transfection efficiency, for example, by interacting and/or fusing with a cellular or intracellular membrane. Transfection may allow for the translation of the mRNA within the cell.

The present disclosure provides methods of delivering a biologically active agent to a mammalian cell or organ. Delivery of a biologically active agent to a cell involves administering a nanoparticle composition including the biologically active agent to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some aspects, a nanoparticle composition may target a particular type or class of cells (e.g., cells of a particular organ or system thereof). For example, a nanoparticle composition including a biologically active agent of interest may be specifically delivered to a mammalian liver, kidney, spleen, femur, or lung. Specific delivery to a particular class of cells, an organ, or a system or group thereof implies that a higher proportion of nanoparticle compositions including a therapeutic and/or prophylactic are delivered to the destination (e.g., tissue) of interest relative to other destinations, e.g., upon administration of a nanoparticle composition to a mammal. In some aspects, specific delivery may result in a greater than 2 fold, 5 fold, 10 fold, 15 fold, or 20 fold increase in the amount of therapeutic and/or prophylactic per 1 g of tissue of the targeted destination (e.g., tissue of interest, such as a liver) as compared to another destination (e.g., the spleen). In some aspects, the tissue of interest is selected from the group consisting of a liver, kidney, a lung, a spleen, a femur, an ocular tissue (e.g., via intraocular, subretinal, or intravitreal injection), vascular endothelium in vessels (e.g., intra-coronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in a nanoparticle composition. An mRNA may additionally or instead be used to direct the synthesis and extracellular localization of lipids, carbohydrates, or other biological moieties. Alternatively, other biologically active agents or elements (e.g., lipids or ligands) of a nanoparticle composition may be selected based on their affinity for particular receptors (e.g., low density lipoprotein receptors) such that a nanoparticle composition may more readily interact with a target cell population including the receptors. For example, ligands may include, but are not limited to, members of a specific binding pair, antibodies, monoclonal antibodies, Fv fragments, single chain Fv (scFv) fragments, Fab' fragments, $F(ab')_2$ fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some aspects, a ligand may be a surface-bound antibody, which can permit tuning of cell targeting specificity. This is especially useful since highly specific antibodies can be raised against an epitope of interest for the desired targeting site. In one aspect, multiple antibodies are expressed on the surface of a cell, and each antibody can have a different specificity for a desired target. Such approaches can increase the avidity and specificity of targeting interactions.

In certain aspects, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic (e.g., an mRNA) in a given dose, where a dose of 1 mg/kg (mpk) provides 1 mg of a therapeutic and/or prophylactic per 1 kg of subject body weight. In some aspects, a dose of about 0.001 mg/kg to about 10 mg/kg of a therapeutic and/or prophylactic (e.g., mRNA) of a nanoparticle composition may be administered. In other aspects, a dose of about 0.005 mg/kg to about 2.5 mg/kg of a therapeutic and/or prophylactic may be administered. In certain aspects, a dose of about 0.1 mg/kg to about 1 mg/kg may be administered. In other aspects, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect.

The desired dosage may be delivered, for example, three times a day, two times a day, once a day, every other day, every third day, every week, every two weeks, every three weeks, or every four weeks. In certain aspects, the desired dosage may be delivered using multiple administrations (e.g., two, three, four, five, six, seven, eight, nine, ten, eleven, twelve, thirteen, fourteen, or more administrations). In some aspects, a single dose may be administered, for example, prior to or after a surgical procedure or in the instance of an acute disease, disorder, or condition.

Nanoparticle compositions including one or more therapeutic and/or prophylactics may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more nanoparticle compositions including one or more different therapeutic and/or prophylactics may be administered in combination. Compositions can be administered concurrently with, prior to, or subsequent to, one or more other desired therapeutics or medical procedures. In general, each agent will be administered at a dose and/or on a time schedule determined for that agent. In some aspects, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some aspects, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

EXAMPLES

The following examples are provided to assist in further understanding the invention and not to limit of the reasonable scope of the invention thereof.

Example 1: One-Step Synthesis Schemes

Currently, synthesis of ionizable lipids generally comprise multiple steps, which is both time efficient and cost effective. Ionizable lipids of the present disclosure, Formulae (I-VI), were designed to be synthesized using a one-step synthesis scheme, which enabled synthesis of the ionizable lipids in a high throughput manner. The same formulae can be synthesized using a multi-step synthesis scheme. For example, a two-component reaction can be used to synthesize compounds of Formula I, II and VI; a three-component reaction for synthesis of Formula III; and a four-component reaction for synthesis of Formulae IV and V. 16,824ionizable lipids were synthesized using Formulas I, II, III, and IV, however, Formulae I-VI could be used as a basis to synthesize limitless ionizable lipids.

Figure 9:
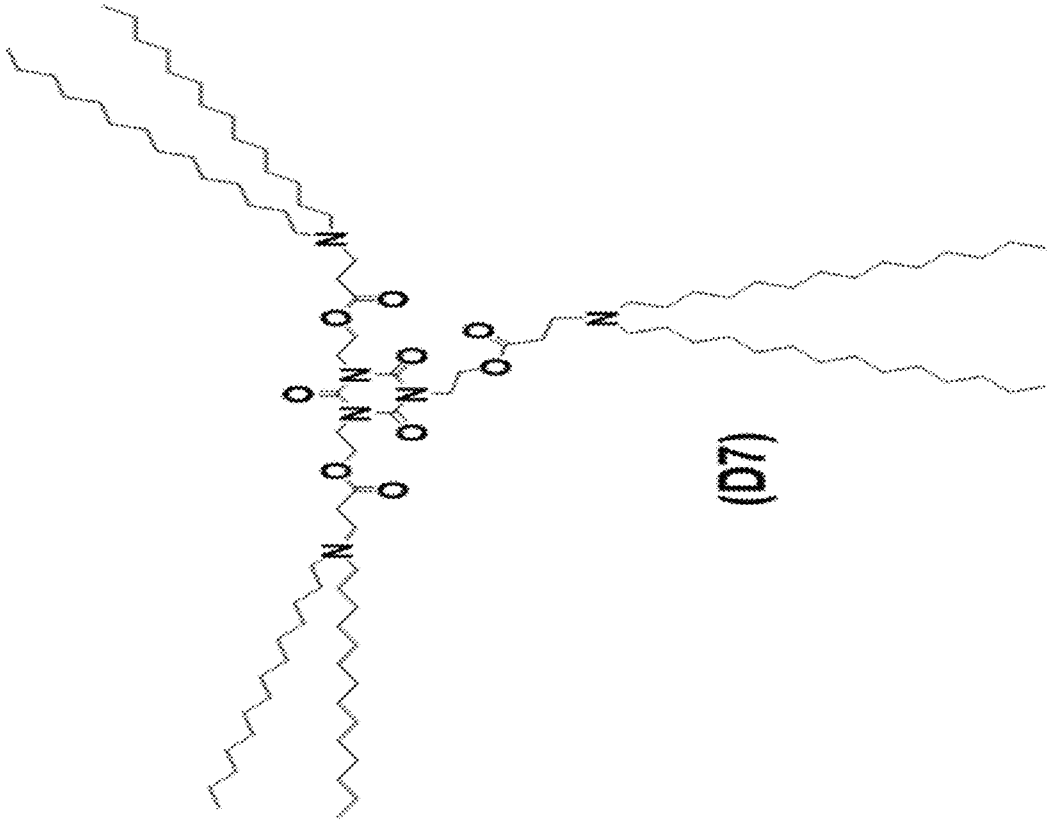
FIG. 9 shows FACS of (C7 and D7) ionizable lipid formulated LNPs and control LNPs encapsulated with self-amplifying mRNA encoding with GFP, which transfect and express GFP-mRNA in C2C12 cells. The GFP positive live cells are as indicated in Q3.
Figure 9:
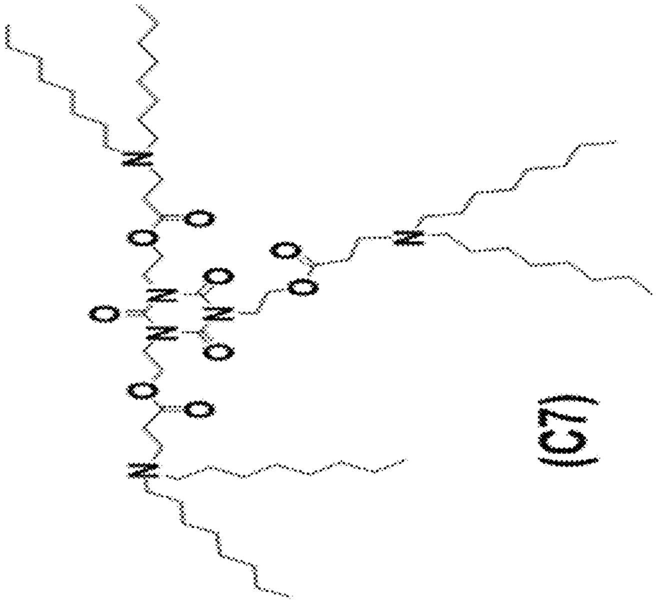
Figure 9:
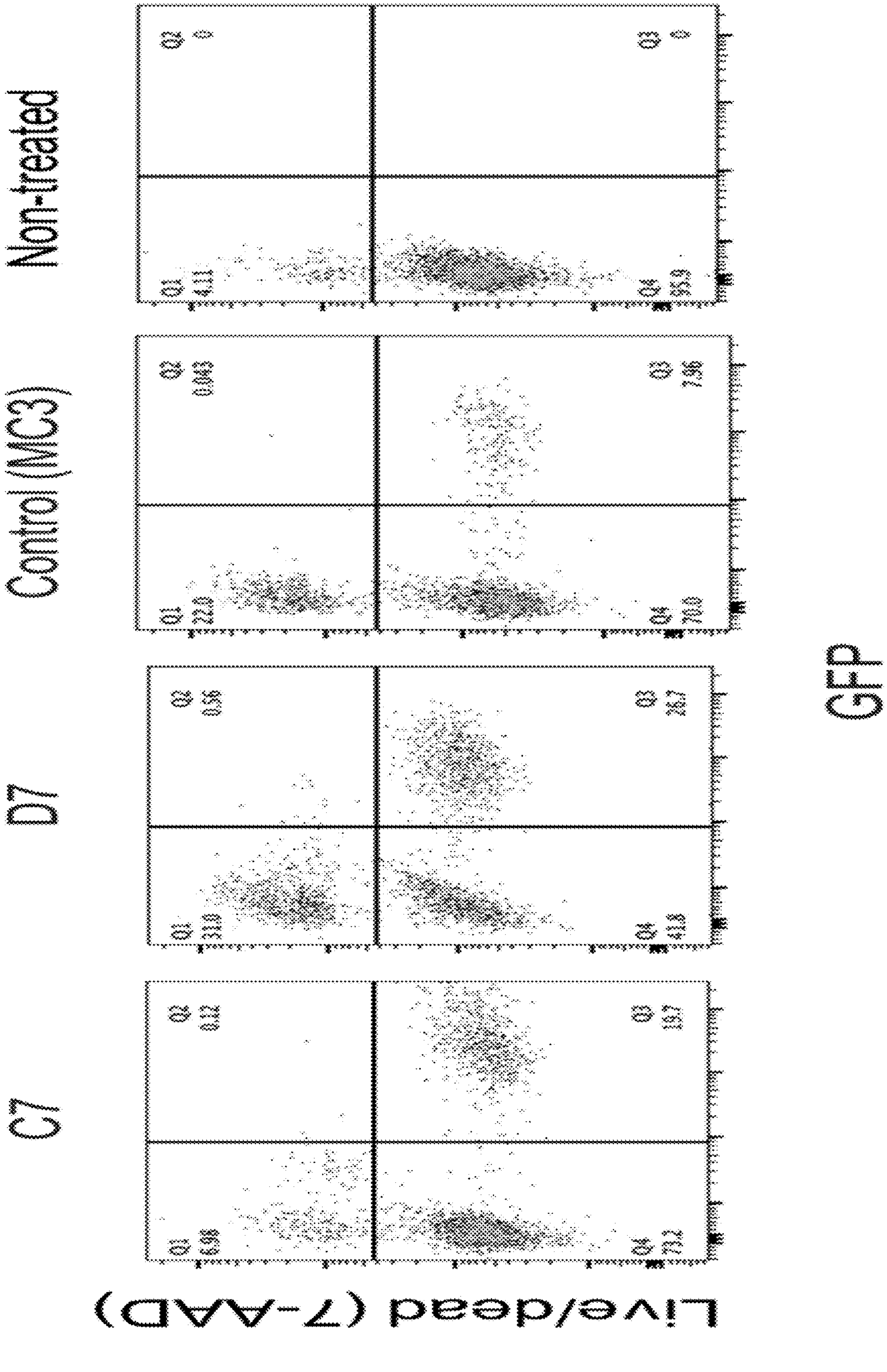

Synthesis of the ionizable lipids of Formula I, such as C7 (2,4,6-trioxo-1,3,5-triazinane-1,3,5-triyl)tris(ethane-2,1-diyl) tris(3-(ditetradecylamino)propanoate) (FIG. 9), can be prepared via the two-component reaction as follows:

Tris(2-acryloyloxyethyl) Isocyanurate (0.2 mmol) was mixed with dioctylamine (0.66 mmol) in 10 mL toluene/acetonitrile (v/v=5/1) was stirred in capped glass vials at 95°

C. for two days. The mixture was purified by flash column chromatography to obtain compound C7.

Synthesis of the ionizable lipids of Formula II, such as TAa-9 (2,4,6-trioxo-1,3,5-triazinane-1,3,5-triyl)tris(ethane-2,1-diyl) tris(3-(dinonylamino)propanoate) (FIG. 1), can be prepared via the two-component reaction as follows:

1,3,5-Triacryloylhexahydro-1,3,5-triazine (0.2 mmol) was mixed with dinonylamine (0.66 mmol) in 10 mL toluene/acetonitrile (v/v=5/1) was stirred in capped glass vials at 95° C. for three days. The mixture was purified by flash column chromatography to obtain compound TAa-9.

Figure 5:
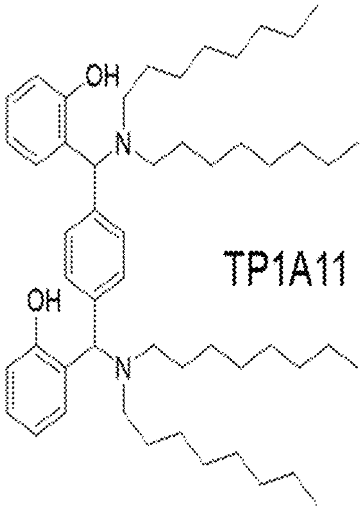
FIG. 5 shows the molecular structures of 4 individual ionizable lipids that were synthesized by three-component reactions. The formulated LNPs showed better or comparable transfection efficacies than control ionizable lipid used in LNPs approved by FDA.
Figure 5:
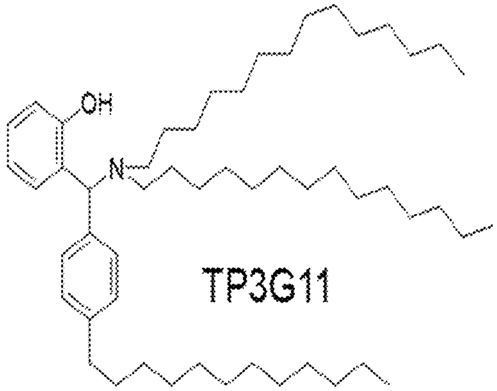
Figure 5:
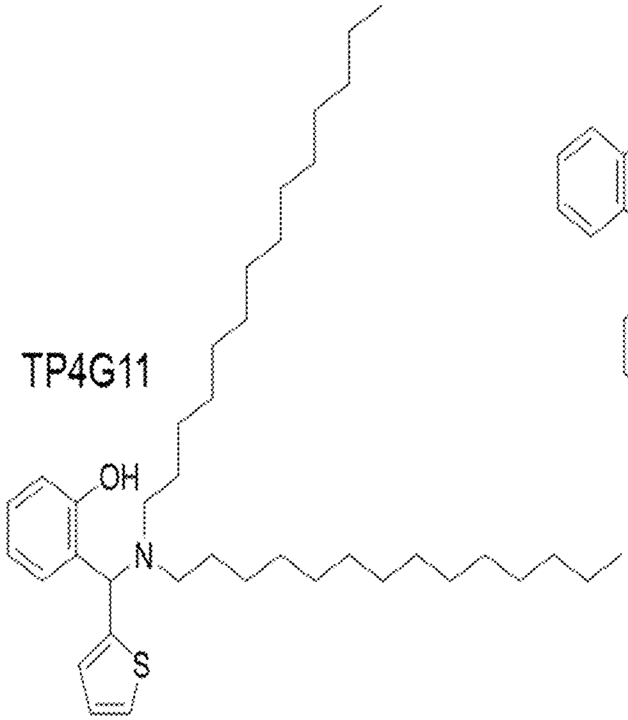
Figure 5:
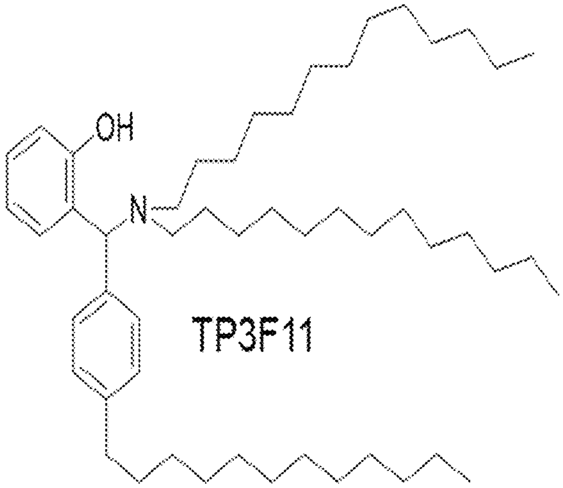

Synthesis of the ionizable lipids of Formula III, such as TP3G11 (2-((ditetradecylamino)(4-dodecylphenyl)methyl) phenol) (FIG. 5), can be prepared via the three-component reaction as follows:

Ditetradecylamine (0.11 mmol, in 2.5 mL of MeOH) was added to a solution of 2-hydroxybenzaldehyde (0.11 mmol, in 2.5 mL Toluene), then (4-dodecylphenyl)boronic acid (0.1 mmol) was added to the same mixture. This reaction mixture was stirred at 95° C. for three days. The mixture was purified by flash column chromatography to obtain compound TP3G11.

Synthesis of the ionizable lipids of Formula IV, such as IVe (N-(2-(cyclohex-1-en-1-ylamino)-1-(1-ethylpiperidin-4-yl)-2-oxoethyl)-N-(heptadecan-9-yl)palmitamide, was prepared via a four-component reaction as follows:

1-ethylpiperidine-4-carbaldehyde (0.1 mmol) was added to a solution of heptadecan-9-amine (0.1 mmol, in 2 mL MeOH) at room temperature. After 2 hours palmitic acid (0.1 mmol) and 1-isocyanocyclohex-1-ene (0.1 mmol) was added to this reaction mixture and the mixture was stirred at room temperature overnight. The mixture was purified by flash column chromatography to obtain compound IVe.

Synthesis of the ionizable lipids of Formula V, such as Va (ethyl 4-(3-(dimethylamino)propyl)-5,5-di((E)-heptadec-8-en-1-yl)-3,6-dioxopiperazine-2-carboxylate), was prepared via a four-component reaction as follows:

Pentatriaconta-9,26-dien-18-one (0.1 mmol) was added to a solution of N',N'-dimethylpropane-1,3-diamine (0.1 mmol, in 2 mL $CH_2Cl_2$) at room temperature. After two hours, 2-((tert-butoxycarbonyl)amino)-3-ethoxy-3-oxopropanoic acid (0.1 mmol) and 1-isocyanocyclohex-1-ene (0.1 mmol) was added to this reaction mixture and the mixture was stirred at room temperature overnight. Then, 0.1 mL of HCl (1M) was added to the reaction mixture and stirred at room temperature overnight. The mixture was purified by flash column chromatography to obtain compound Va.

Synthesis of the ionizable lipids of Formula VI, such as VIa N,N',N''-(cyclohexane-1,3,5-triyltris(methylene))tris(N-tridecyltridecan-1-amine), can be prepared via the two-component reaction as follows:

1,3,5-tris(bromomethyl)cyclohexane (0.2 mmol) was mixed with ditridecylamine (0.66 mmol) in 10 mL MeOH/DMF (v/v=5/1) was stirred in capped glass vials at room temperature for four days. The mixture was purified by flash column chromatography to obtain compound VIa.

Example 2: Multi-Step Synthesis Schemes

Synthesis of the ionizable lipids of Formula VII. The ionizable lipid was synthesized in two steps as follows:

A solution of acryloyl chloride (56 mmol) in dry CH2Cl2 (50 mL) was added dropwise to a mixture of cyclohexane-1,3,5-triol (14 mmol) and Et3N (84 mmol) in dry CH2Cl2 (60 mL) at 0° C. under N2. Around 1 hour later, the mixture was allowed to raise to room temperature and reacted for 4 hours. Then the mixture was treated with saturated sodium bicarbonate solution (150 mL) and brine (150 mL) and extracted with CH2Cl2 (150 mL×3). The combined organic layers were dried over anhydrous magnesium sulfate and the solvent was removed by rotary evaporator. The crude product was purified by column chromatography using a CombiFlash Rf system with a silica column (Redisep Gold Resolution, Teledyne, Isco) by Hexane/ethyl acetate (5%-100% ethyl acetate) to afford the compound cyclohexane-1,3,5-triyl triacrylate as a white solid (0.92 g, 22.4%). 1H-NMR (400 MHz, Me-OD, δ) 6.40 (dd, J=16, 4 Hz, 3H), 6.08 (dd, J=20, 8 Hz, 3H), 5.83 (dd, J=16, 4 Hz, 3H), 4.98-4.87 (m, 3H), 1.24 (s, 6H). MS (ESI) m/z 317.1 [M+Na]+.

Cyclohexane-1,3,5-triyl triacrylate (0.1 mmol) was mixed with amines (0.33 mmol) in 5 mL ethanol at 1 to 3.3 molar ratio and the mixture was stirred in glass screw-top vials in oil bath at 50° C. for two days. The solvent was removed by rotary evaporator and the product was purified by column chromatography using a CombiFlash Rf system with a silica column (Redisep Gold Resolution, Teledyne, Isco) by Hexane/ethyl acetate (5%-100% ethyl acetate). Structure was confirmed by nuclear magnetic resonance spectra of 1H (Bruker AVANCE-400 NMR, Custom NMR Services, Inc.) and LC-Mass spectra (Agilent 1100 & 1200 HPLC/MS, Organix, Inc).

Synthesis of the ionizable lipids of Formula I. The ionizable lipid was synthesized in one step as follows:

Tris(2-acryloyloxyethyl) Isocyanurate (0.2 mmol) was mixed with amines (0.66 mmol) in 10 mL toluene/ACN (5/1) at 1 to 3.3 molar ratio and the mixture was stirred in glass screw-top vials in oil bath at 95° C. for two days. The solvent was removed by rotary evaporator and the product was purified by column chromatography using a CombiFlash Rf system with a silica column (Redisep Gold Resolution, Teledyne, Isco) by gradient elution of Hexane/ethyl acetate (5%-100% ethyl acetate). Structure was confirmed by nuclear magnetic resonance spectra of 1H (Bruker AVANCE-400 NMR, Custom NMR Services, Inc.) and LC-Mass spectra (Agilent 1100 & 1200 HPLC/MS, Organix, Inc).

(2,4,6-trioxo-1,3,5-triazinane-1,3,5-triyl)tris(ethane-2,1-diyl) tris(3-(ditetradecylamino)propanoate) (C7): yield (20%). 1H-NMR (400 MHz, CDCl3, δ) 4.29 (t, J=8 Hz, 3H), 4.16 (t, J=8 Hz, 3H), 2.75 (t, J=8 Hz, 3H), 2.60 (t, J=8 Hz, 3H), 2.42-2.34 (m, 12H), 1.50-1.26 (m, 84H), 0.87 (t, J=8 Hz, 18H). MS (APCI) m/z 1148.3 [M+H]+.

(2,4,6-trioxo-1,3,5-triazinane-1,3,5-triyl)tris(ethane-2,1-diyl) tris(3-(dioctylamino)propanoate) (D7): yield (23%). 1H-NMR (400 MHz, CDCl3, δ) 4.29 (t, J=8 Hz, 3H), 4.17 (t, J=8 Hz, 3H), 2.75 (t, J=8 Hz, 3H), 2.60 (t, J=8 Hz, 3H), 2.39-2.34 (m, 12H), 1.50-1.26 (m, 156H), 0.89 (t, J=8 Hz, 18H). MS (APCI) m/z 1653.5 [M+H]+.

Synthesis of the ionizable lipids of Formula II. The ionizable lipid was synthesized in one step as follows:

1,3,5-Triacryloylhexahydro-1,3,5-triazine (0.2 mmol) was mixed with amines (0.66 mmol) in 10 mL toluene/ACN (5/1) at 1 to 3.3 molar ratio and the mixture was stirred in glass screw-top vials in oil bath at 95° C. for two days. The solvent was removed by rotary evaporator and the product was purified by column chromatography using a CombiFlash Rf system with a silica column (Redisep Gold Resolution, Teledyne, Isco) by gradient elution of CH2Cl2/methanol (0%-40% methanol). Structure was confirmed by nuclear magnetic resonance spectra of 1H (Bruker AVANCE-400 NMR, Custom NMR Services, Inc.) and LC-Mass spectra (Agilent 1100 & 1200 HPLC/MS, Organix, Inc).

1,1',1"-(1,3,5-triazinane-1,3,5-triyl)tris(3-(dinonylamino) propan-1-one) (E2): yield (25%). 1H-NMR (400 MHz, CDCl3, δ) 5.26 (s, 6H), 2.79 (t, J=8 Hz, 6H), 2.65 (t, J=8 Hz, 6H), 2.41 (t, J=8 Hz, 12H), 1.42-1.26 (m, 84H), 0.88 (t, J=8 Hz, 18H). MS (ESI) m/z 529.6 [M+2H]2+.

1,1',1"-(1,3,5-triazinane-1,3,5-triyl)tris(3-(dinonylamino) propan-1-one) (E6): yield (25%). 1H-NMR (400 MHz, CDCl3, δ) 5.26 (s, 6H), 2.81 (t, J=8 Hz, 6H), 2.67 (t, J=8 Hz, 6H), 2.43 (t, J=8 Hz, 12H), 1.44-1.23 (m, 132H), 0.88 (t, J=8 Hz, 18H). MS (ESI) m/z 697.9 [M+2H]2+.

Synthesis of the ionizable lipids of Formula III. The ionizable lipid was synthesized in one step as follows:

The ionizable lipid was synthesized with a molar ratio of boric acid/amine/aldehyde at 1:1:1. The library reactions were carried out on 96-well plates with glass insert (Analytical Sales and Services). The reaction was taken placed in toluene/methanol (10/1) at 95° C. overnight. The product mixtures were directly used for in vitro high throughput screening. Otherwise, the ionizable lipids were purified by column chromatography using a CombiFlash Rf system with a silica column (Redisep Gold Resolution, Teledyne, Isco) by gradient elution of CH2Cl2/methanol (0%-40% methanol). Structure was confirmed by nuclear magnetic resonance spectra of 1H (Bruker AVANCE-400 NMR, Custom NMR Services, Inc.) and LC-Mass spectra (Agilent 1100 & 1200 HPLC/MS, Organix, Inc).

2,2'-(1,4-phenylenebis((dioctylamino)methylene))diphenol (TP1A11): yield (17%). 1H-NMR (400 MHz, CDCl3, δ) 7.37 (s, 4H), 7.10-7.14 (t, J=8 Hz, 2H), 6.83-6.85 (d, J=8 Hz, 2H), 6.77-6.80 (m, 2H), 6.64-6.69 (t, J=12 Hz, 2H), 4.88 (d, J=8 Hz, 2H), 2.42-2.65 (m, 8H), 1.21-1.25 (m, 40H), 0.84-0.89 (m, 12H). MS (APCI) m/z 769.7 [M+H]+.

2-((ditetradecylamino)(thiophen-2-yl)methyl)phenol (TP4G11): yield 23%. HNMR (400 MHz, CDCl3, δ) 7.39 (d, J=8 Hz, 1H), 7.08-7.14 (m, 2H), 7.02-7.05 (m, 1H), 6.86-6.89 (d, J=12 Hz, 1H), 6.75-6.78 (m, 1H), 6.66-6.72 (m, 1H), 5.44 (s, 1H), 2.45-2.69 (m, 4H), 1.29 (m, 48H), 0.84-0.90 (t, 6H). MS (APCI) m/z 769.7 [M+H]+.

2-((ditridecylamino)(4-dodecylphenyl)methyl)phenol (TP3F11): yield 25%. HNMR (400 MHz, CDCl3, δ) 7.30 (d, J=12 Hz, 2H), 7.14 (d, J=12 Hz, 3H), 6.85 (t, J=12 Hz, 2H), 6.69 (t, J=12 Hz, 1H), 4.92 (s, 1H), 2.60-2.55 (m, 4H), 2.39-2.44 (m, 2H), 1.59-1.51 (m, 6H), 1.25 (m, 60H), 0.88 (t, J=12 Hz, 9H). MS (APCI) m/z 732.7 [M+H]+.

2-((ditetradecylamino)(4-dodecylphenyl)methyl)phenol (TP3G11): yield 26%. HNMR (400 MHz, CDCl3, δ) 7.30 (d, J=12 Hz, 2H), 7.14 (d, J=12 Hz, 3H), 6.82 (t, J=12 Hz, 2H), 6.66 (t, J=12 Hz, 1H), 4.92 (s, 1H), 2.60-2.55 (m, 4H), 2.39-2.44 (m, 2H), 1.59-1.51 (m, 6H), 1.25 (m, 64H), 0.88 (t, J=12 Hz, 9H). MS (APCI) m/z 732.7 [M+H]+.

Synthesis of the ionizable lipids of Formula IV. The ionizable lipid was synthesized in one-pot as follows:

The ionizable lipid was synthesized by four-component reaction with a molar ratio of acid/amine/aldehyde/isocyanide at 1:1:1:1. The library reactions were carried out on 96-well plates with glass insert (Analytical Sales and Services). Amine and aldehyde were first mixed and stirred at room temperature (r.t.), then added acid and isocyanide. The reaction was stirred at r.t. overnight.

Synthesis of exemplary ionizable lipids. Aaldehyde (1 mmol) and amine (1 mmol) were mixed in 3 mL MeOH at room temperature and stirred for one hour, then isocyanide (1 mmol) and acid (1 mmol) were added. The resulting mixture was stirred further overnight. Remove the solvent with Rotary evaporator. Ethyl acetate (100 mL) was added and washed with brine (2×50 mL), dried over MgSO4. Remove Ethyl acetate and the residue was purified by column chromatography using a CombiFlash Rf system with a silica column (Redisep Gold Resolution, Teledyne, Isco) by gradient elution of CH2Cl2/methanol (0%-40% methanol). Structure was confirmed by nuclear magnetic resonance spectra of 1H (Bruker AVANCE-400 NMR, Custom NMR Services, Inc.) and/or LC-Mass spectra (Agilent 1100 & 1200 HPLC/MS, Organix, Inc).

Ethyl (2-(1-ethylpiperidin-4-yl)-2-(N-(pentadecan-8-yl) tridecanamido)acetyl)glycinate (P1C1): yield (16%). 1H-NMR (400 MHz, Me-OD, δ) 4.34 (d, J=8 Hz, 1H), 4.21-4.14 (m, 4H), 3.41 (t, J=8 Hz, 1H), 3.01 (q, J=8 Hz, 2H), 2.47-2.40 (m, 5H), 2.01-1.83 (t, J=12 Hz, 2H), 1.65-1.56 (m, 6H), 1.29-1.17 (m, 42H), 1.17-1.10 (m, 6H), 0.93-0.89 (m, 9H). MS (APCI) m/z 678.7 [M+H]+.

N-(2-(cyclohex-1-en-1-ylamino)-1-(1-ethylpiperidin-4-yl)-2-oxoethyl)-N-(heptadecan-9-yl)palmitamide (P6A2): yield (45%). 1H-NMR (400 MHz, Me-OD, δ) 6.05 (t, J=8 Hz, 1H), 4.26 (s, 1H), 3.26-3.17 (m, 3H), 2.49-2.42 (m, 5H), 2.19-2.01 (m, 6H), 1.67-1.57 (m, 14H), 1.31-1.16 (m, 48H), 0.92-0.87 (m, 12H). MS (APCI) m/z 742.7 [M+H]+.

N-(2-(cyclohexylamino)-1-(1-ethylpiperidin-4-yl)-2-oxoethyl)-N-(pentadecan-8-yl)palmitamide (P30A1): yield (58%). 1H-NMR (400 MHz, CDCl3, δ) 8.41 (d, J=8 Hz, 1H), 3.70-3.63 (m, 1H), 3.57 (t, J=8 Hz, 1H), 3.18-3.09 (m, 3H), 2.80-2.24 (m, 3H), 2.44-2.24 (m, 4H), 1.79-1.20 (m, 67H), 0.89-0.85 (m, 9H). MS (APCI) m/z 716.8 [M+H]+.

N-(2-(((1s,3s)-adamantan-1-yl)amino)-1-(1-ethylpiperidin-4-yl)-2-oxoethyl)-N-(2-decyltetradecyl)undecanamide (P54B6): yield (48%). MS (APCI) m/z 824.8 [M+H]+.

N-(2-(cycloheptylamino)-1-(1-ethylpiperidin-4-yl)-2-oxoethyl)-N-(pentadecan-8-yl)tetradecanamide (P38D1): yield (56%). MS (APCI) m/z 702.7 [M+H]+.

N-(2-(((1s,3s)-adamantan-1-yl)amino)-1-(1-ethylpiperidin-4-yl)-2-oxoethyl)-N-(pentadecan-8-yl)palmitamide (P56A1): yield (53%). MS (APCI) m/z 768.7 [M+H]+.

N-(2-(((1s,3s)-adamantan-1-yl)amino)-1-(1-ethylpiperidin-4-yl)-2-oxoethyl)-N-(pentadecan-8-yl)heptadecanamide (P56B1): yield (59%). MS (APCI) m/z 782.8 [M+H]+.

N-(2-(butylamino)-1-(1-ethylpiperidin-4-yl)-2-oxoethyl)-N-(heptadecan-9-yl)octanamide (P14A2): yield (40%). MS (APCI) m/z 606.6 [M+H]+.

N-(2-(butylamino)-1-(1-ethylpiperidin-4-yl)-2-oxoethyl)-N-(pentadecan-8-yl)undecanamide (P16B1): yield (43%). MS (APCI) m/z 620.6 [M+H]+.

N-(2-(cyclohexylamino)-1-(1-ethylpiperidin-4-yl)-2-oxoethyl)-N-(2-octyldodecyl) tetradecanamide (P26D4): yield (23%). MS (APCI) m/z 758.8 [M+H]+. Ethyl (2-(1-ethylpiperidin-4-yl)-2-(N-(2-octyldodecyl)tetradecanamido)acetyl)glycinate (P1D4): yield (30%). MS (APCI) m/z 762.8 [M+H]+.

N-(1-(cyclohexylamino)-3-(1-methylpiperidin-4-yl)-1-oxopropan-2-yl)-N-(pentadecan-8-yl)heptadecanamide (P30B7): yield (56%). MS (APCI) m/z 730.8 [M+H]+.

N-(1-(cyclohexylamino)-3-(1-methylpiperidin-4-yl)-1-oxopropan-2-yl)-N-(pentadecan-8-yl)stearamide (P30C7): yield (53%). MS (APCI) m/z 744.8 [M+H]+.

N-(1-(cycloheptylamino)-3-(1-methylpiperidin-4-yl)-1-oxopropan-2-yl)-N-(pentadecan-8-yl)tetradecanamide (P38D7): yield (45%). MS (APCI) m/z 702.7 [M+H]+.

N-(1-(cycloheptylamino)-3-(1-methylpiperidin-4-yl)-1-oxopropan-2-yl)-N-(heptadecan-9-yl)tetradecanamide (P38D8): yield (52%). MS (APCI) m/z 730.7 [M+H]+.

N-(1-(cycloheptylamino)-3-(1-methylpiperidin-4-yl)-1-oxopropan-2-yl)-N-(2-octyldodecyl)undecanamide (P40B10): yield (42%). MS (APCI) m/z 730.7 [M+H]+.

N-(1-(cycloheptylamino)-3-(1-methylpiperidin-4-yl)-1-oxopropan-2-yl)-N-(tricosan-12-yl)dodecanamide (P40C11): yield (57%). MS (APCI) m/z 786.8 [M+H]+.

N-(1-(cycloheptylamino)-3-(1-methylpiperidin-4-yl)-1-oxopropan-2-yl)-N-(2-octyldodecyl)dodecanamide (P40C10): yield (70%). MS (APCI) m/z 744.8 [M+H]+.

N-(1-(tert-butylamino)-3-(1-methylpiperidin-4-yl)-1-oxopropan-2-yl)-N-(2-decyltetradecyl)tridecanamide (P51C12): yield (70%). MS (APCI) m/z 774.8 [M+H]+.

N-(1-(cycloheptylamino)-3-(1-methylpiperidin-4-yl)-1-oxopropan-2-yl)-N-(pentadecan-8-yl)pentadecanamide (P40D7): yield (61%). MS (APCI) m/z 716.7 [M+H]+.

N-(2-(tert-butylamino)-1-(1-ethylpiperidin-4-yl)-2-oxoethyl)-N-(tricosan-12-yl)decanamide (P53A5): yield (61%). MS (APCI) m/z 718.7 [M+H]+.

N-(2-(tert-butylamino)-1-(1-ethylpiperidin-4-yl)-2-oxoethyl)-N-(2-decyltetradecyl)decanamide (P53A6): yield (61%). MS (APCI) m/z 732.7 [M+H]+

N-(2-(cycloheptylamino)-1-(1-ethylpiperidin-4-yl)-2-oxoethyl)-N-(2-decyltetradecyl)tetradecanamide (P38D4): yield (51%). MS (APCI) m/z 828.7 [M+H]+

N-(2-(((1s,3s)-adamantan-1-yl)amino)-1-(1-ethylpiperidin-4-yl)-2-oxoethyl)-N-(heptadecan-9-yl)palmitamide (P56A2): yield (46%). MS (APCI) m/z 796.7 [M+H]+

N-(2-(cycloheptylamino)-1-(1-ethylpiperidin-4-yl)-2-oxoethyl)-N-(heptadecan-9-yl)oleamide (P149A2): yield (42%). MS (APCI) m/z 784.8 [M+H]+ dodecyl 4-((2-(cycloheptylamino)-1-(1-ethylpiperidin-3-yl)-2-oxoethyl)(2-octyldodecyl)amino)-4-oxobutanoate (P159C10): yield (43%). MS (APCI) m/z 830.8 [M+H]+

N-(1-(((1s,3s)-adamantan-1-yl)amino)-3-(1-methylpiperidin-4-yl)-1-oxopropan-2-yl)-4-(3,6-dihydroxy-10,13-dimethylhexadecahydro-1H-cyclopenta[a]phenanthren-17-yl)-N-(2-octyldodecyl)pentanamide (P161F10): yield (53%). MS (APCI) m/z 974.9 [M+H]+.

Example 3: LNP Synthesis

Self-amplifying mRNAs (samRNAs) encoding with Firefly luciferase (SamRNA-LUC) and GFP (SamRNA-GFP) were prepared by SunVax mRNA Therapeutics. Fetal bovine serum (FBS) and Ribogreen reagents were purchased from Fisher Scientific. 1-palmitoyl-2-oleoyl-sn-glycero-3-phosphoethanolamine (DOPE), 1,2-dimyristoyl-rac-glycero-3-methoxypolyethylene glycol-2000 (DMG-PEG2000), and Cholesterol were purchased from Avanti Polar Lipids. The chemical reagents were purchased from Sigma-Aldrich, Millipore Sigma, Fisher Scientific, TCI America, Ambeed, CaymanChem, A2B Chem, BLD pharm, Aaron Chemicals, AAblocks, 1clickchemistry, Enamine, Aurum, Achemblock, BroadPharm, ChemShuttle, Biopharma PEG.

The ionizable lipids of the present disclosure were synthesized and formulated into LNPs with DOPE, cholesterol and DMG-PEG2000.

Figure 4:
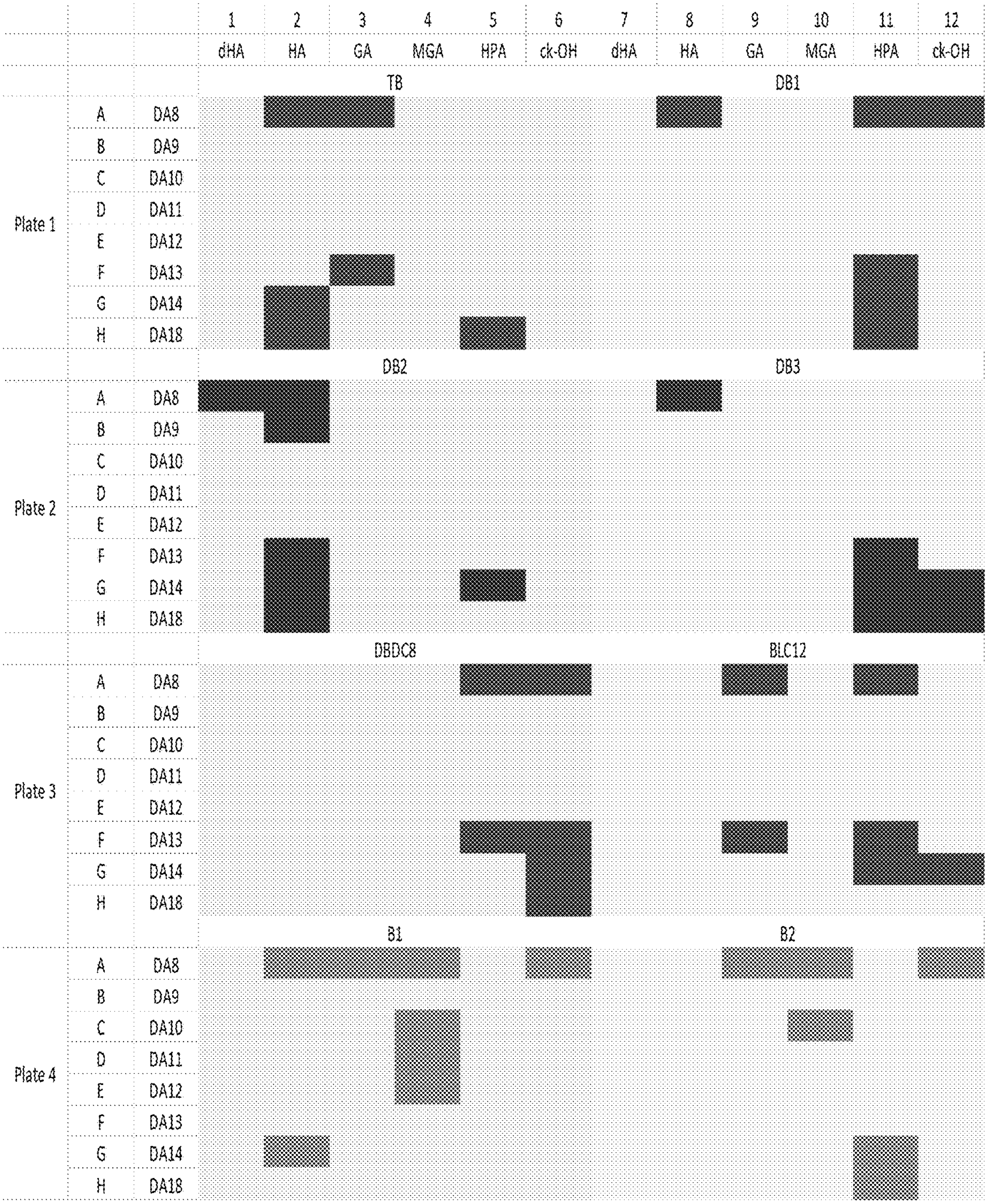
FIG. 4 shows high-throughput screening of ionizable lipids synthesized by three-component reaction that were used to formulate LNP encapsulated with self-amplifying mRNA encoding with GFP, which transfect GFP-mRNA into C2C12, 293T and MC38 cells in 96-well plate map. The formulated LNP with more than 2% of GFP expression in the above cells were highlighted.
Figure 6:
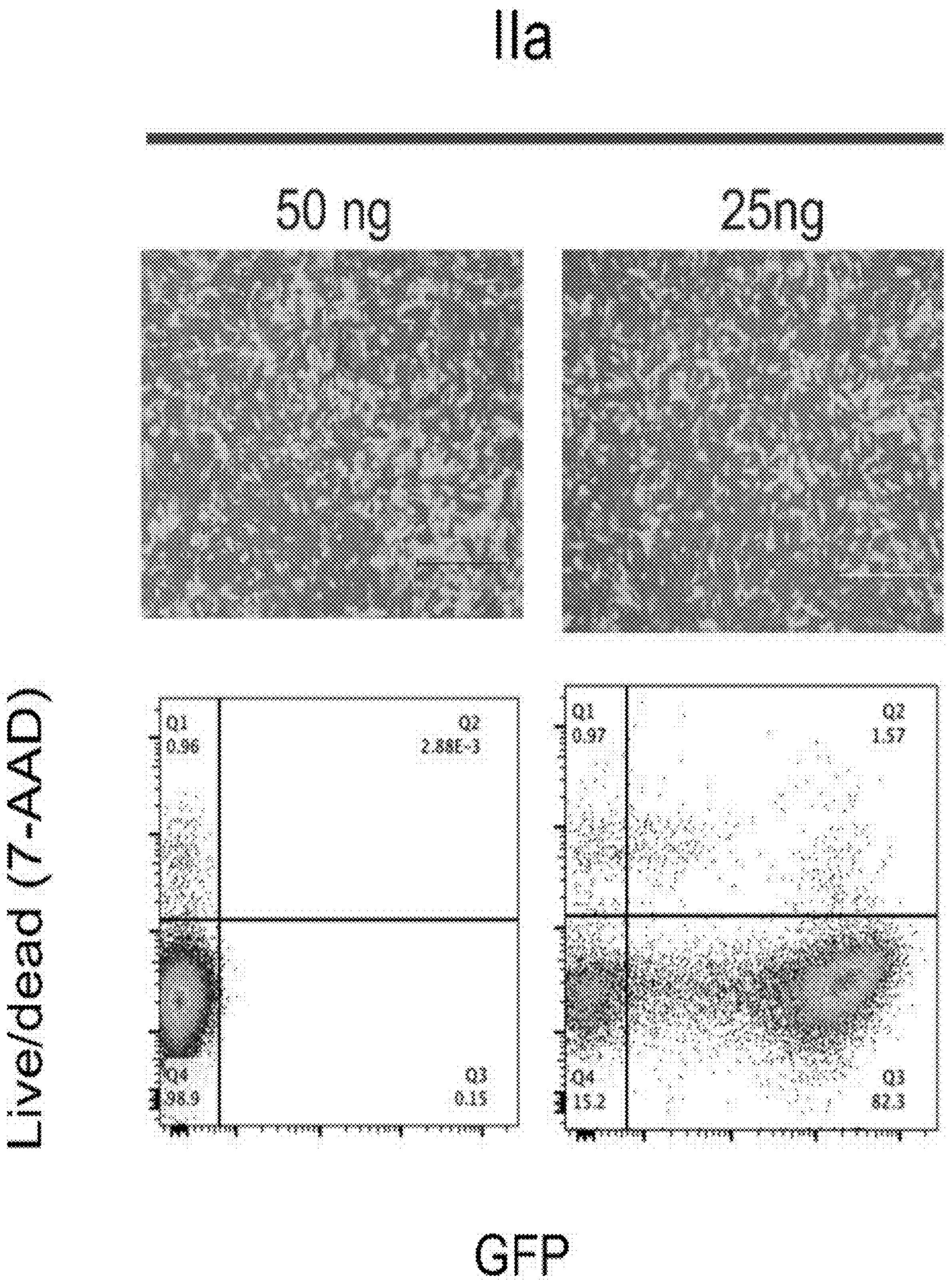
FIG. 6 shows FACS of TAb-9 (IIa) formulated ionizable lipid formulated LNPs and control LNPs encapsulated with self-amplifying mRNA encoding with GFP, which transfect and express GFP-mRNA in C2C12 cells. The bottom is plots of GFP (X-axis) versus live/dead (7-AAD, Y-axis). The GFP positive live cells are as indicated in Q3.
Figure 6:
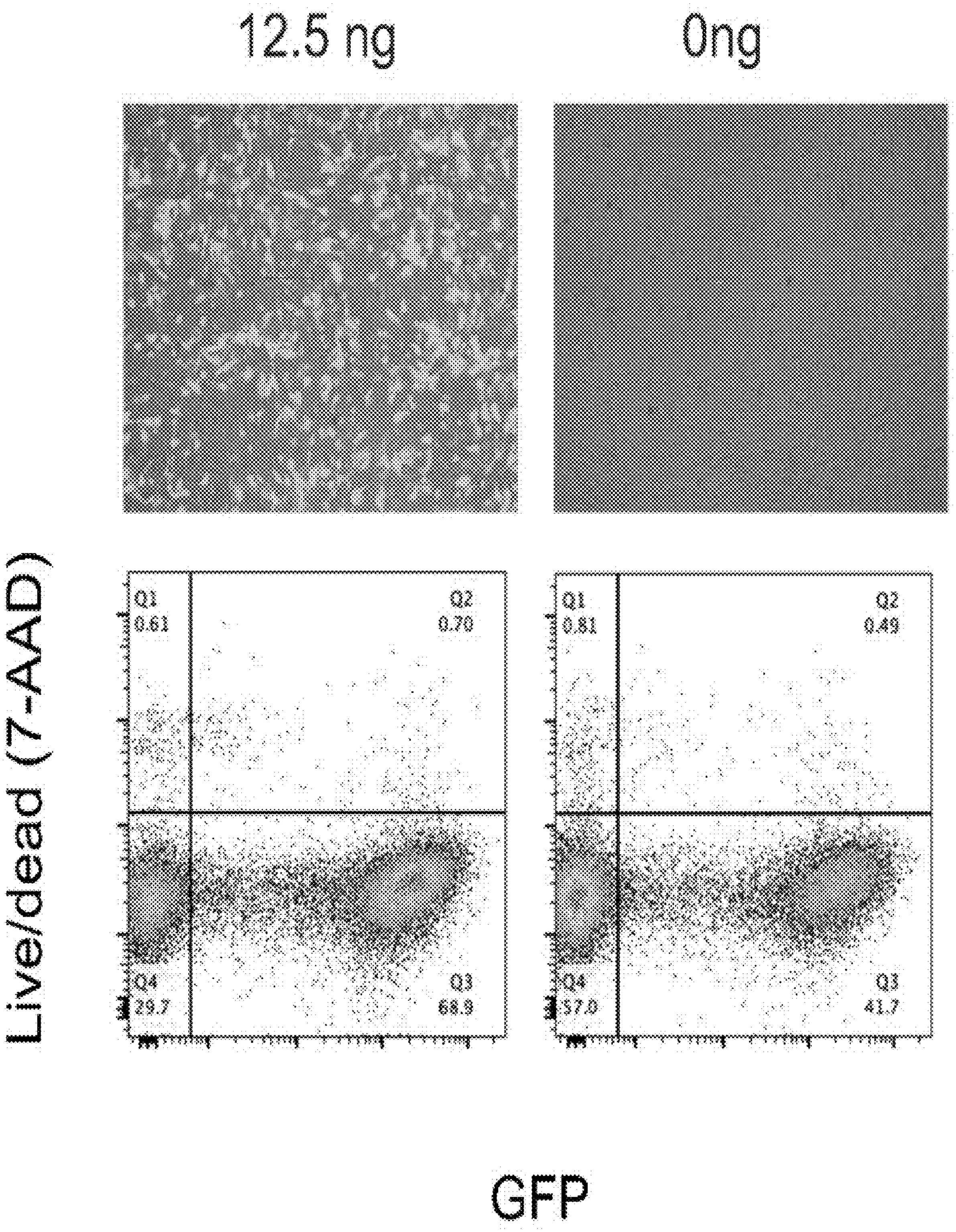
Figure 6:
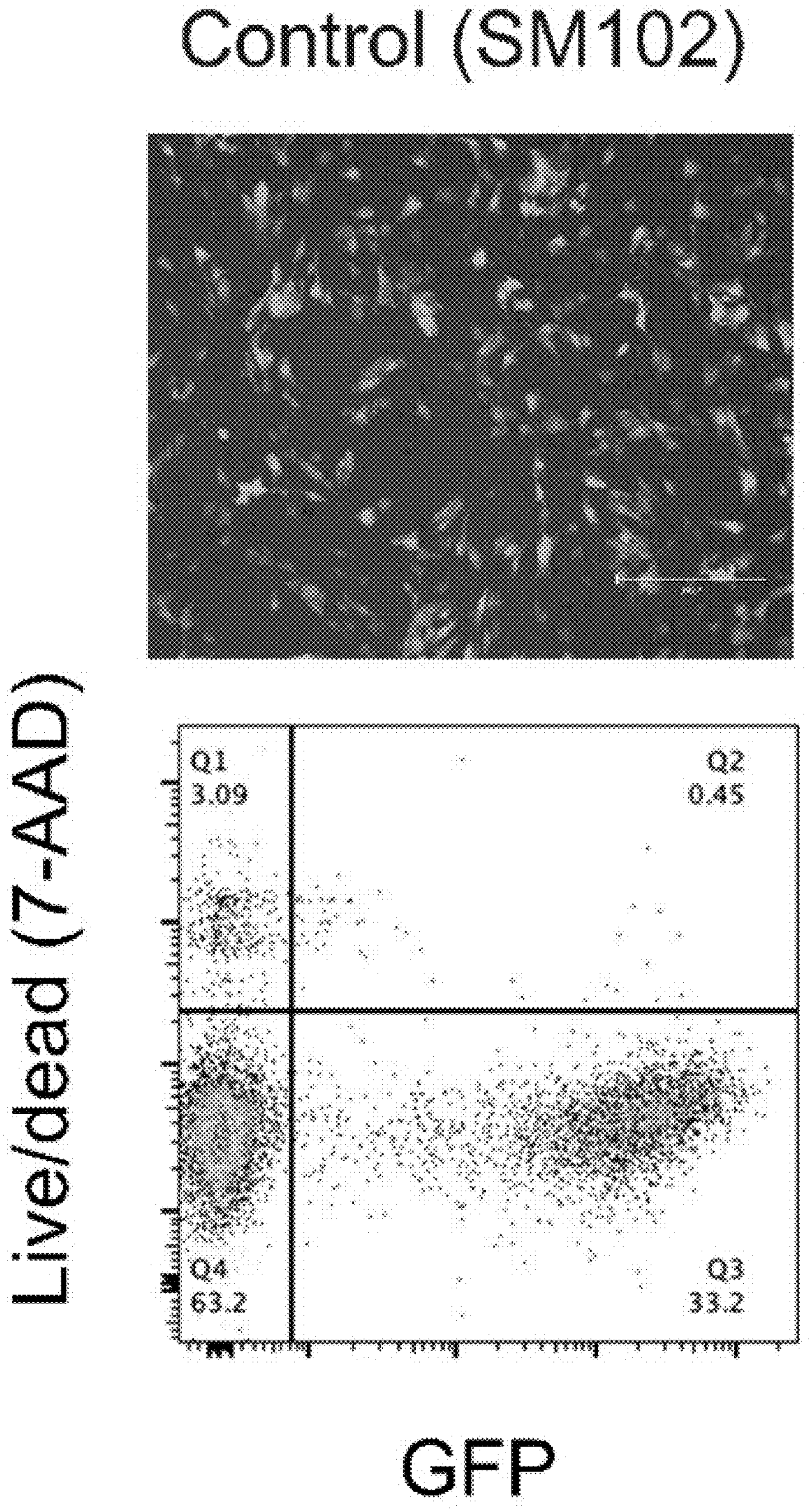
Figure 7:
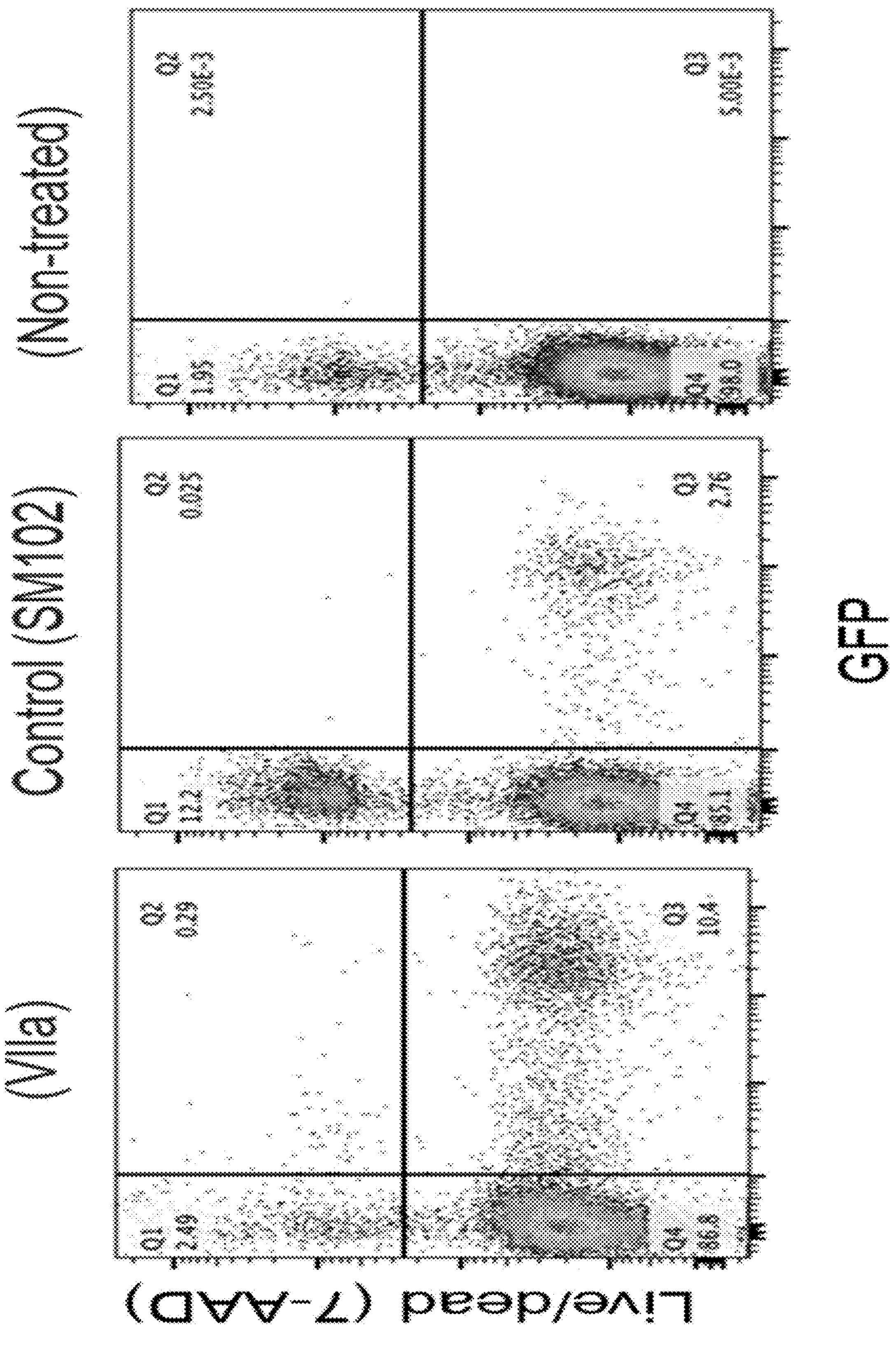
FIG. 7 shows FACS of (VIIa) ionizable lipid formulated LNPs and control LNPs encapsulated with self-amplifying mRNA encoding with GFP, which transfect and express GFP-mRNA in 293T cells at day 1 post transfection. The GFP positive live cells are as indicated in Q3.
Figure 8:
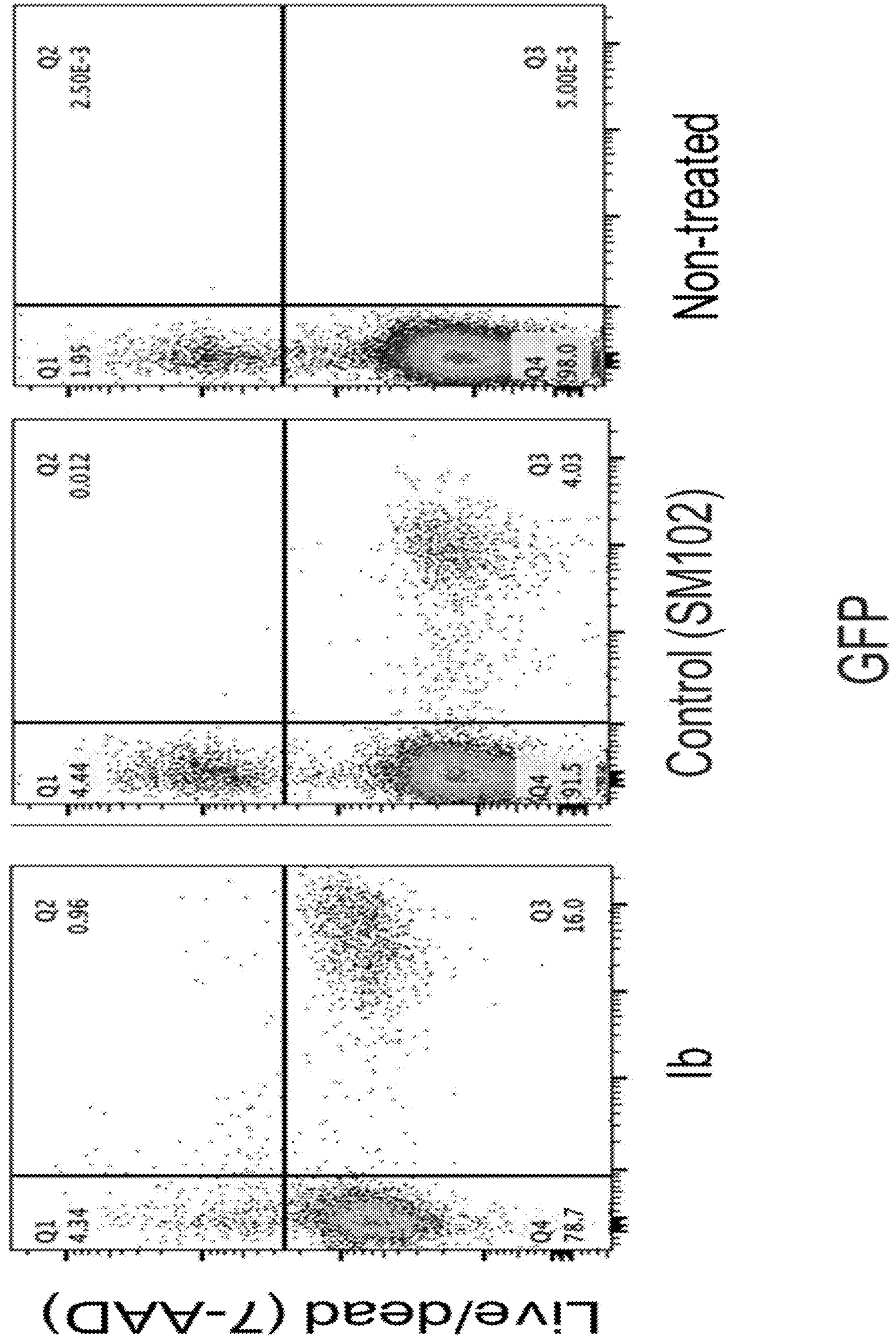
FIG. 8 shows FACS of (Ib) ionizable lipid formulated LNPs and control LNPs encapsulated with self-amplifying mRNA encoding with GFP, which transfect and express GFP-mRNA in 293T cells. The GFP positive live cells are as indicated in Q3.

More than 50 LNPs made using the lipids of the present disclosure showed effective transfection (FIG. 4). The results demonstrated four individual ionizable lipids (FIGS. 1-3, 9) synthesized by two-component reactions and twelve individual ionizable lipids (FIG. 5) synthesized by three-component reactions formulating LNPs encapsulated self-amplifying mRNA encoding with GFP-mRNA transfect, which showed better or comparable transfection efficacies than those LNPs approved by FDA. Additional examples of effective transfection with LNPs made using additional lipids of the present disclosure were shown in FIGS. 6-8. The LNPs of the present disclosure were found to effectively transfect C2C12, MC38, and 293T cells in vitro. The data demonstrated better or comparable transfection efficacies than LNPs currently approved by FDA.

The LNPs with ionizable lipids of the present disclosure were prepared by mixing the lipid-containing ethanol phase with a mRNA-containing aqueous phase using a pipette. The ethanol phase was prepared by mixing the ionizable lipids, 1,2-Dioleoyl-sn-glycero-3-phosphoethanolamine (DOPE, Avanti), cholesterol (Avanti) and 1,2-dimyristoyl-rac-glycero-3-methoxypolyethylene glycol-2000 (DMG-PEG2000, Broadpharm) at a predetermined molar ratio of 50:10:38.5:1.5 in ethanol. The aqueous phase was prepared in citrate buffer (10 mM, pH 3.0, MilliporeSigma) with GMP-mRNA. The aqueous and ethanol phases were mixed at 1:1 ratio with N:P at 6:1 ratio. The formulated LNP was dialyzed against PBS in a 20,000 MWCO cassette (Fisher) at 4° C. for 2 hours and stored at 4° C. before using. The size, polydispersity index and zeta potentials of the formulated LNP is measured using DLS, specifically (AnoPartica SZ-100-Z2, Horiba).

The size and polydispersity index (PDI) were measured by dynamic light scattering (SZ-100-Z2 (MTS), Horiba Scientific). Diameters are reported as the intensity mean peak average. The nucleic acid encapsulation efficiency was calculated by a modified Quant-iT RiboGreen RNA assay (Invitrogen).

Example 4: Biologically Active Agent Synthesis

The GFP-mRNA transfect, a self-amplifying mRNA encoding GFP, was synthesized de novo from Venezuelan equine encephalitis (VEE) virus strain TC-83. The sequences of GFP mRNA were encoded in the subgenomic region of VEE to replace the structural proteins. The self-amplifying mRNA were transcribed in vitro from the synthesized plasmids and capped by vaccinia capping system. The synthesized mRNAs were then purified for use in vitro or in vivo assays.

The delivery system used to deliver the GFP-mRNA transfect are LNPs formulated using 12 individual ionizable lipids synthesized by three-component reactions. To generate the LNP encapsulated self-amplifying mRNA, the ionizable lipids of the present disclosure were dissolved in ethanol and directly added into an ethanol solution containing DOPE, cholesterol and DMG-PEG2000 at predetermined molar ratio. Self-amplifying mRNA encoding GFP sequences aqueous solution was mixed and the LNP mixture (100 ng mRNA) was added to a 96-well plate pre-seeded with MC38, C2C12 or 293T cells. The cells were incubated at 5% CO2 and 37° C. overnight. The GFP mRNA transfection efficiency was measured by flow cytometry.

Example 5: Transfection Efficiency

The ionizable lipids of the present disclosure were formulated with DOPE, Cholesterol, and DMG-PEG2000 to encapsulate the large size self-amplifying mRNA, which encodes reporter genes such as green fluorescent protein (GFP) or Luciferase (LUC). The ionizable lipids of the disclosure could form LNPs and encapsulate larger size nucleic acids, such as self-amplifying mRNA, the current LNP mainly developed for small size mRNA, such as mRNA encoding a portion of the COVID spike protein. Ionizable lipids of the disclosure, DOPE, Cholesterol, and DMG-PEG2000 were formulated into LNPs and tested for transfection efficiency.

Figure 10:
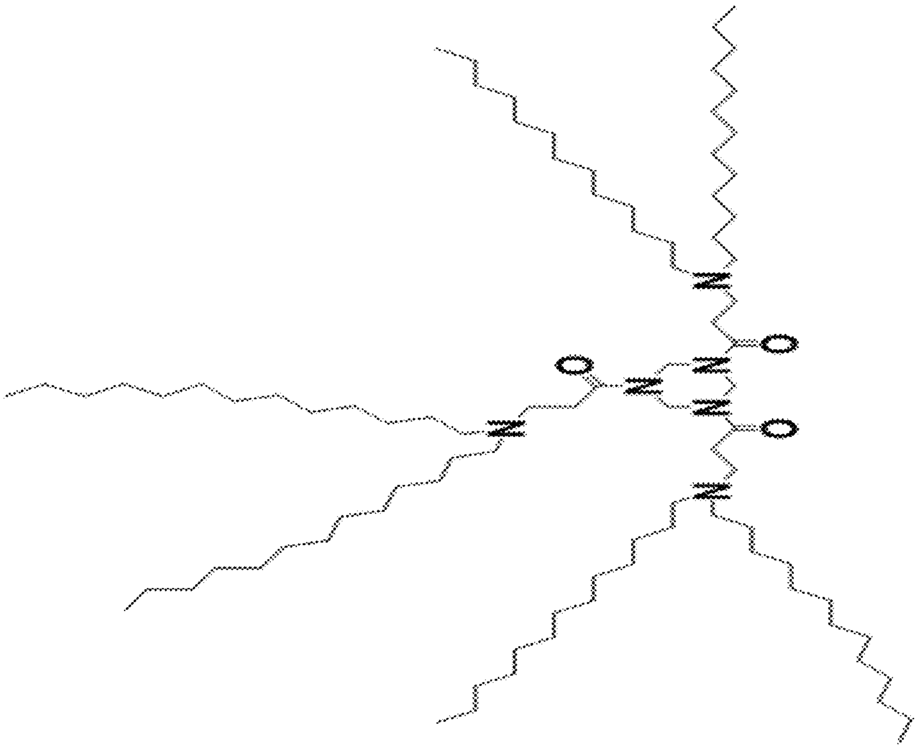
FIG. 10 shows FACS of (E2 and E6) ionizable lipid formulated LNPs and control LNPs encapsulated with self-amplifying mRNA encoding with GFP, which transfect and express GFP-mRNA in 293T cells. The GFP positive live cells are as indicated in Q3.
Figure 10:
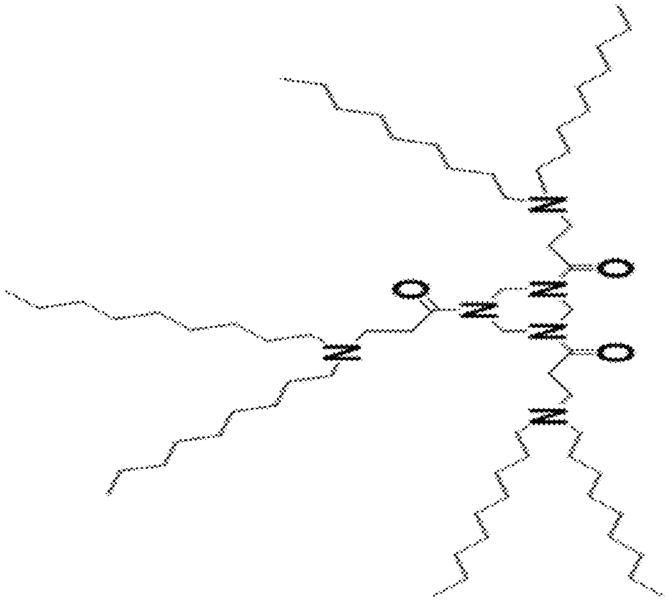
Figure 10:
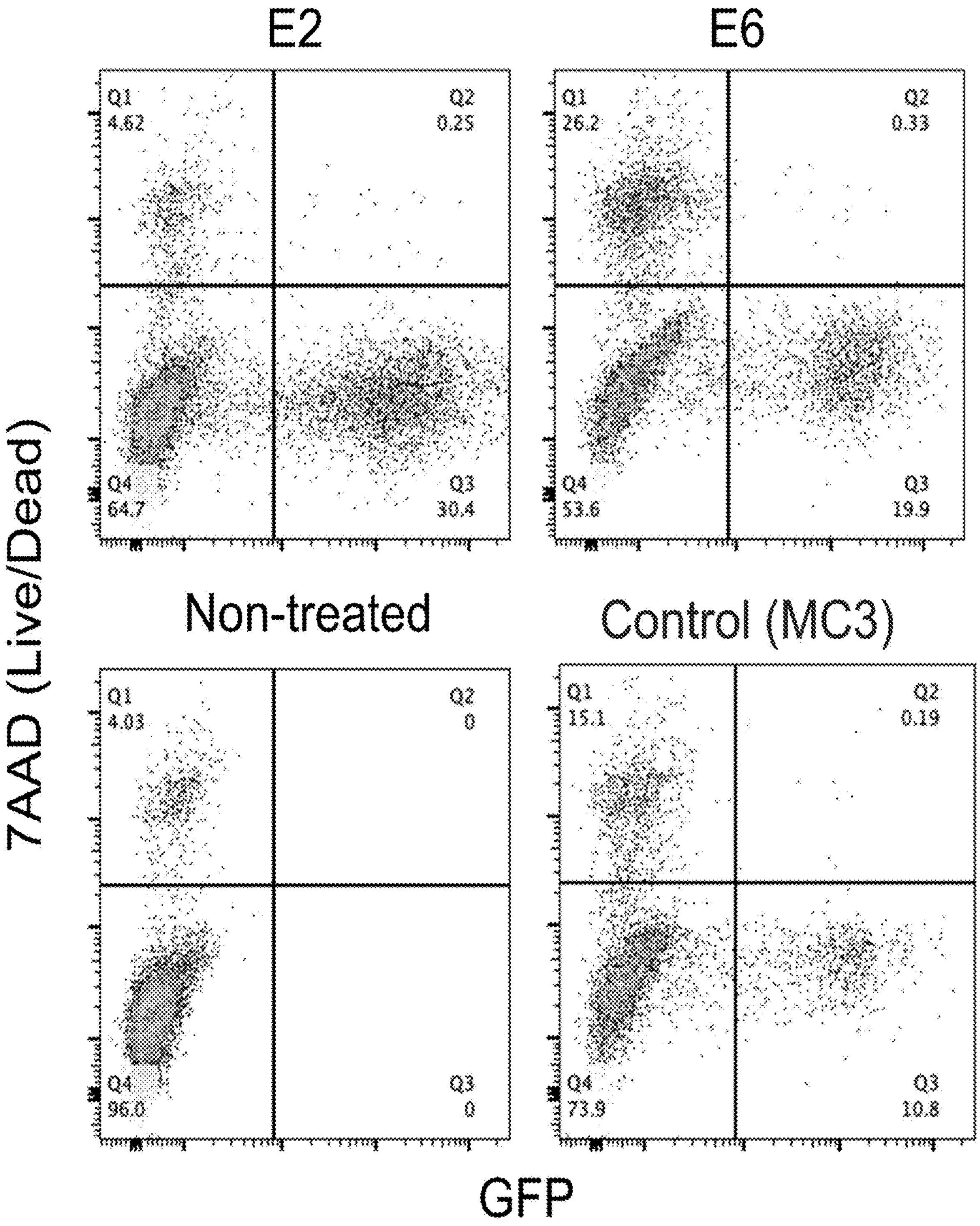
Figure 23:
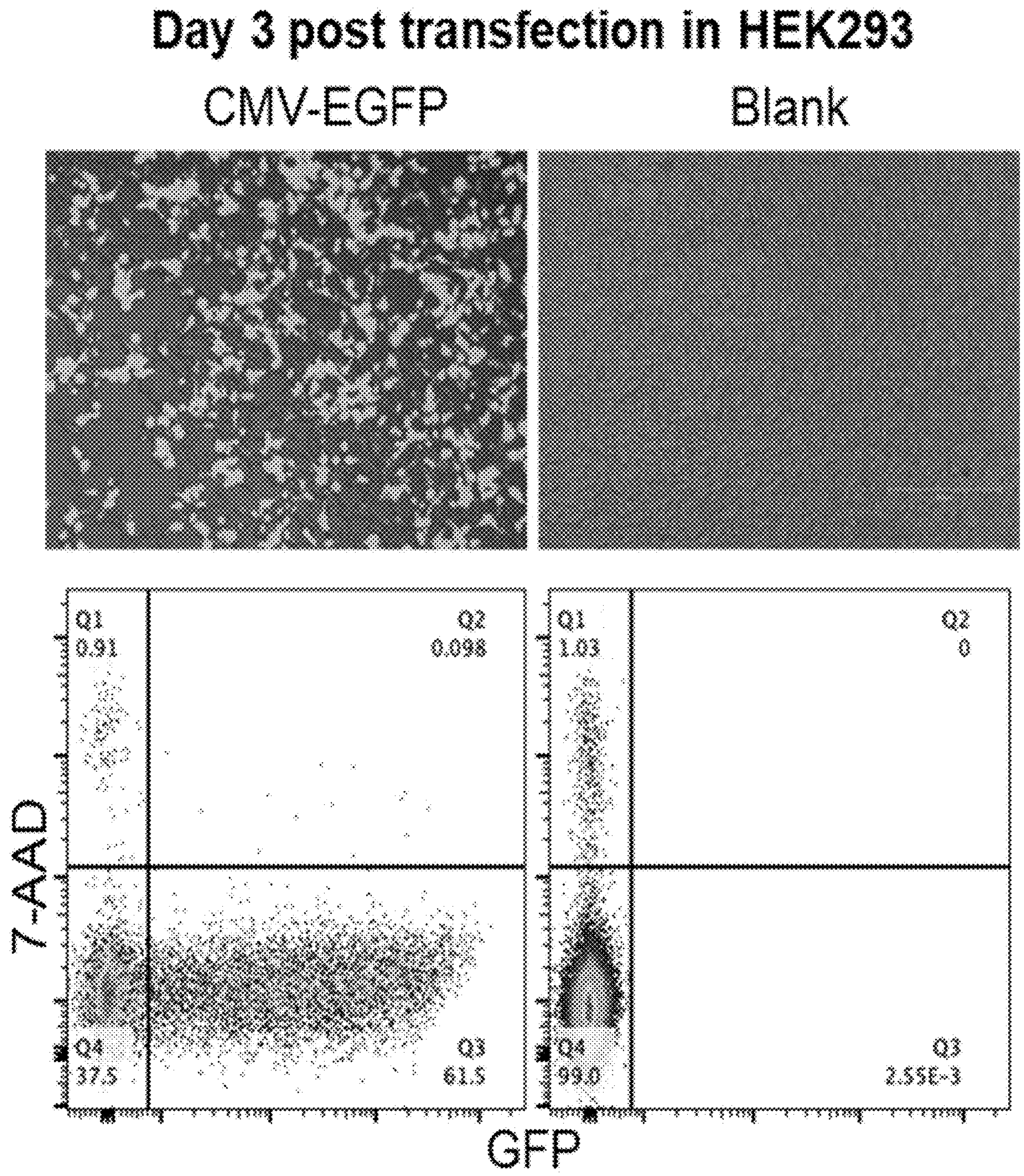
FIG. 23 shows FACS of (E6) ionizable lipid formulated LNPs encapsulated with DNA encoding with CMV-EGFP, which transfect and express GFP in HEK293 cells. The bottom shows plots of GFP (X-axis) versus live/dead (7-AAD, Y-axis). The GFP positive live cells are as indicated in Q3.

E6, an ionizable lipid of the disclosure, was formulated into LNPs with 1,2-Dioleoyl-sn-glycero-3-phosphoethanolamine (DOPE), cholesterol (Chol), methoxypolyethylene glycol (DMG-$PEG_{2000}$) with a mole ratio of 50/10/38.5/1.5 (ionizable lipid/DOPE/Chol/DMG-$PEG_{2000}$) encapsulated self-amplifying mRNA or DNA encoding with reporter genes either green fluorescent protein (samRNA-GFP or DNA-CMV-EGFP) or firefly Luciferase (samRNA-LUC). Formulations containing 100 ng of self-amplifying mRNA were incubated to a well of 96-well plate with 60-70% confluent of HEK293, or C2C12, or MC38 cells (FIGS. 10, 23). The transfection efficiency was determined by flow cytometry for detection of GFP, or plate reader for detection of luciferase. LNP formulated using FDA approved ionizable lipid MC3 was used as a control (FIG. 10).

The LNPs containing SamRNA-GFP (or SamRNA-LUC, 100 ng/well) were added into 96-well plate which was pre-seeded with 293T, C2C12 or MC38 cells. After 24 hours incubation at 37° C. and 5% CO2, the luciferase SamRNA transfection efficiency was measured by plate reader (Perkin Elmer Envision 2104). The GFP SamRNA transfection efficiency was measured by flow cytometry (BD FACSymphony™ A5 SE Cell Analyzer).

Figure 11:
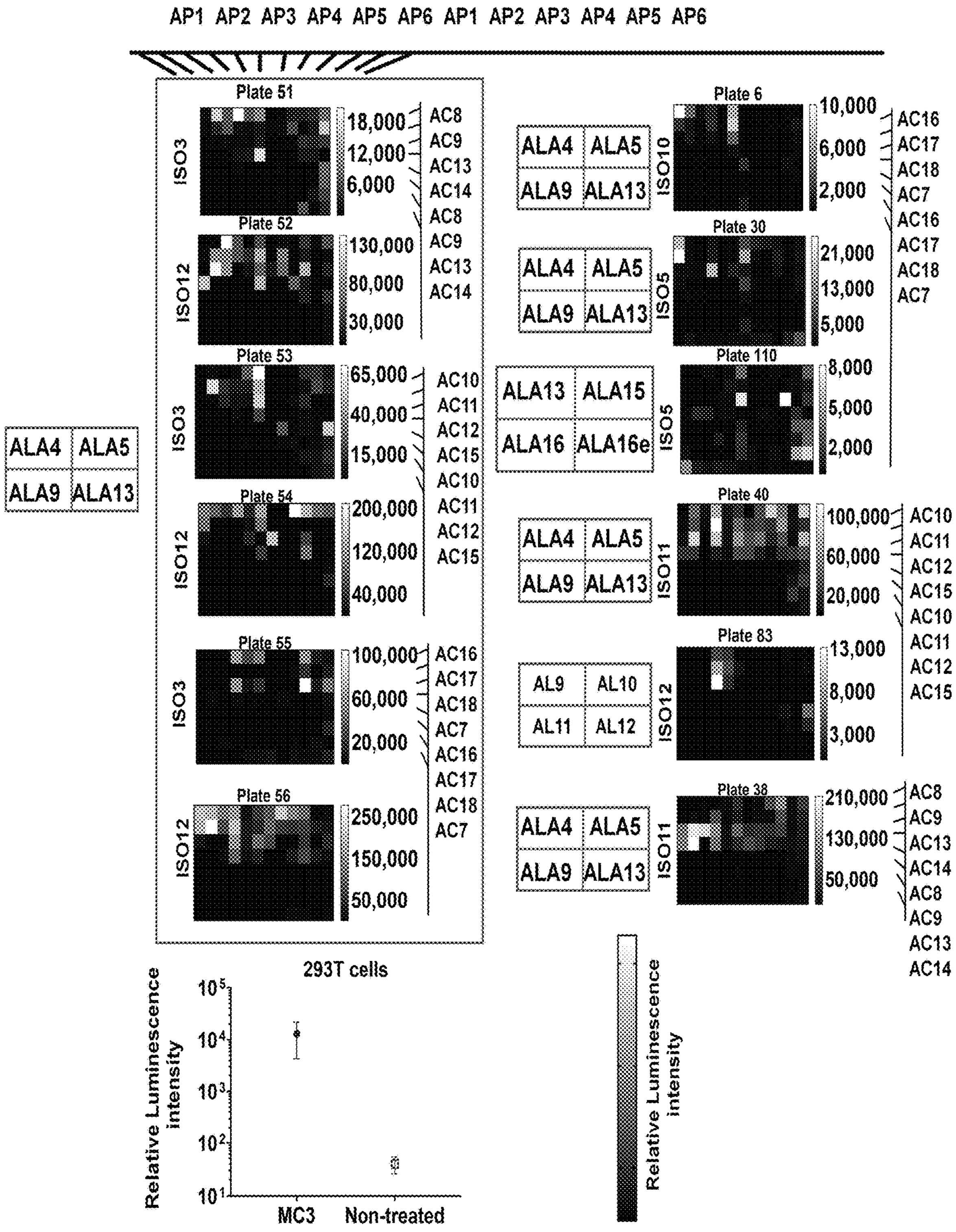
FIG. 11 shows heat maps showing relative luminescence intensity of high throughput synthesized ionizable lipids using four-component reactions of the present disclosure formulated into LNPs encapsulating self-amplifying mRNA encoding LUC, which were transfected into 293T cells and incubated overnight. Data are triplicated and represented as the mean±SD.
Figure 12:
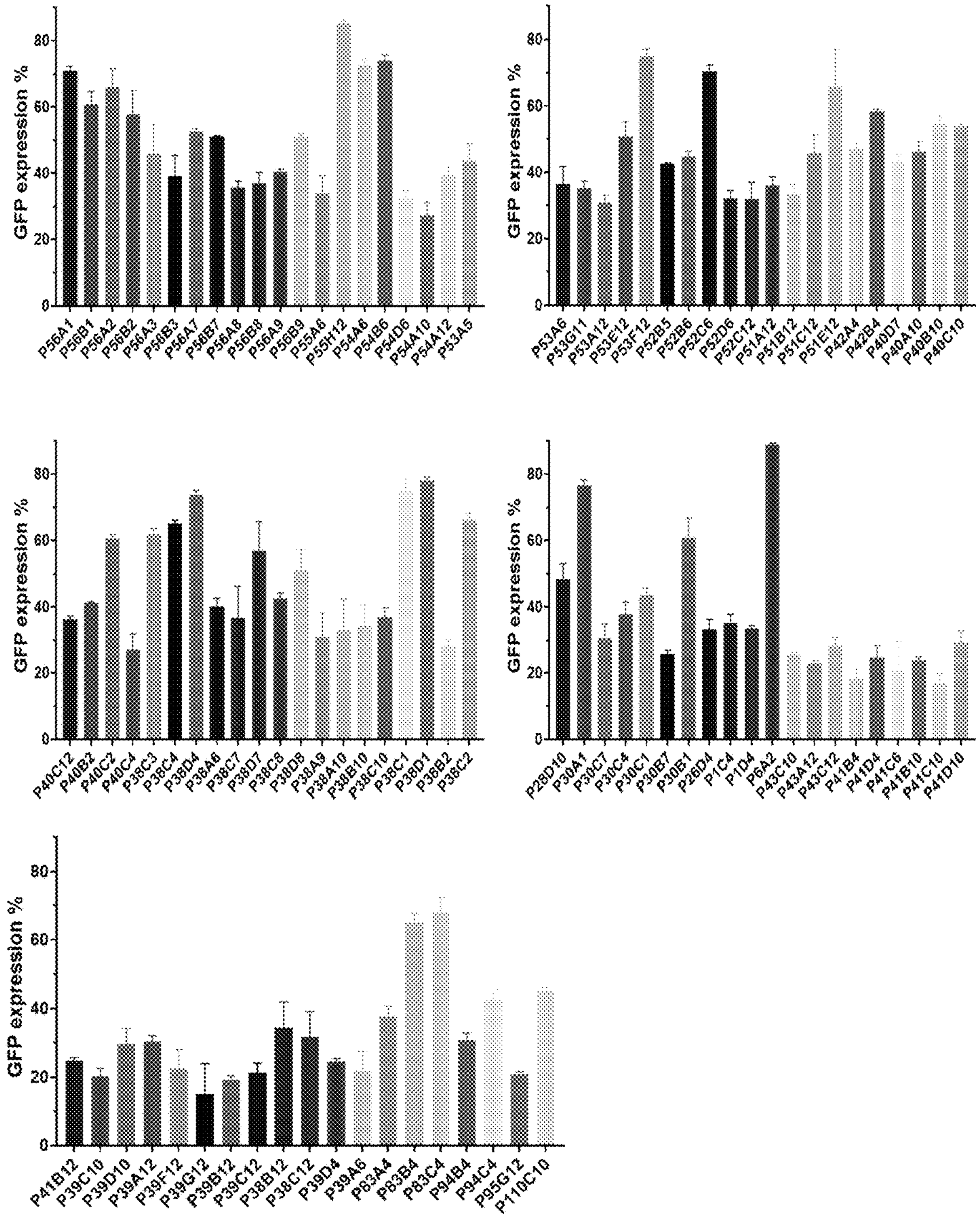
FIG. 12 shows GFP expression percentage in 293T cells that were treated by LNPs formulated with ionizable lipids of the present disclosure encapsulating self-amplifying mRNA encoding GFP for 24 hours. Data are triplicated and represented as the mean±standard deviation (SD).

The LNP-SamRNA-GFPs formulated with synthesized C7 and D7 (FIGS. 8-9) of Formula I; E2 and E6 (FIGS. 6 and 10) LNPs of Formula II; and TP1A2, TP1H5, TP3A5, TP3G11, TP3G12, TP4G4, TP4G11, TP1A11, TP3F11 of Formula III could more effectively deliver mRNA-GFP (FIGS. 4-5) than FDA approved ionizable lipid MC3. LNP-SamRNA-Lucs formulated with P1C1, P6A2, P30A1, P54B6, P38D1, P56A1, P56B1, P14A2, P16B1, P26D4, P1D4, P30B7, P30C7, P38D7, P38D8, P40B10, P40C11, P40C10, P51C12, P40D7, P53A5, and P53A6 of Formula IV, showed stronger bioluminescence signals than MC3-LNP-SamRNA-Luc (FIG. 11). Other lead ionizable lipids showed very high samRNA-GFP delivery efficiency in 239T cells which is shown in FIG. 12. High throughput synthesis of ionizable lipids by three-component are shown in FIG. 4 and part of four-component reactions are shown in FIG. 11.

Of the tested ionizable lipids, 117 ionizable lipids showed high transfection efficacies, shown in percentages of GFP positive cells or luminescence by Luciferase after transfection (FIGS. 11-12). Orthogonal experiments formulated using 22 ionizable lipids of the disclosure were conducted to find better ratios among ionizable lipids, DOPE, Cholesterol, and DMG-PEG2000 for compensation optimizations of LNP. The LNPs were applied in mice, 15 of the LNPs formulated using the tested ionizable lipids of the disclosure showed higher in vivo delivery efficiency than FDA approved ionizable lipid D-Lin-MC3-DMA (MC3).

Example 6: Characterization of Ionizable Lipids

Ionizable lipids C7, D7, E2, E6, TP1A11, TP3G11, TP4G11, TP3F11, TP5A1, P4G11, P1C1, P6A2, P30A1, P54B6, P38D1, P56A1, P56B1, P14A2, P16B1, P26D4, P1D4, P30B7, P30C7, P38D7, P38D8, P40B10, P40C11, P40C10, P51C12, P40D7, P53A5, P53A6, P56A2, and P38D4 were purified, and the structures were confirmed by 1H-NMR spectroscopy, mass spectrometry, or both.

Figure 13:
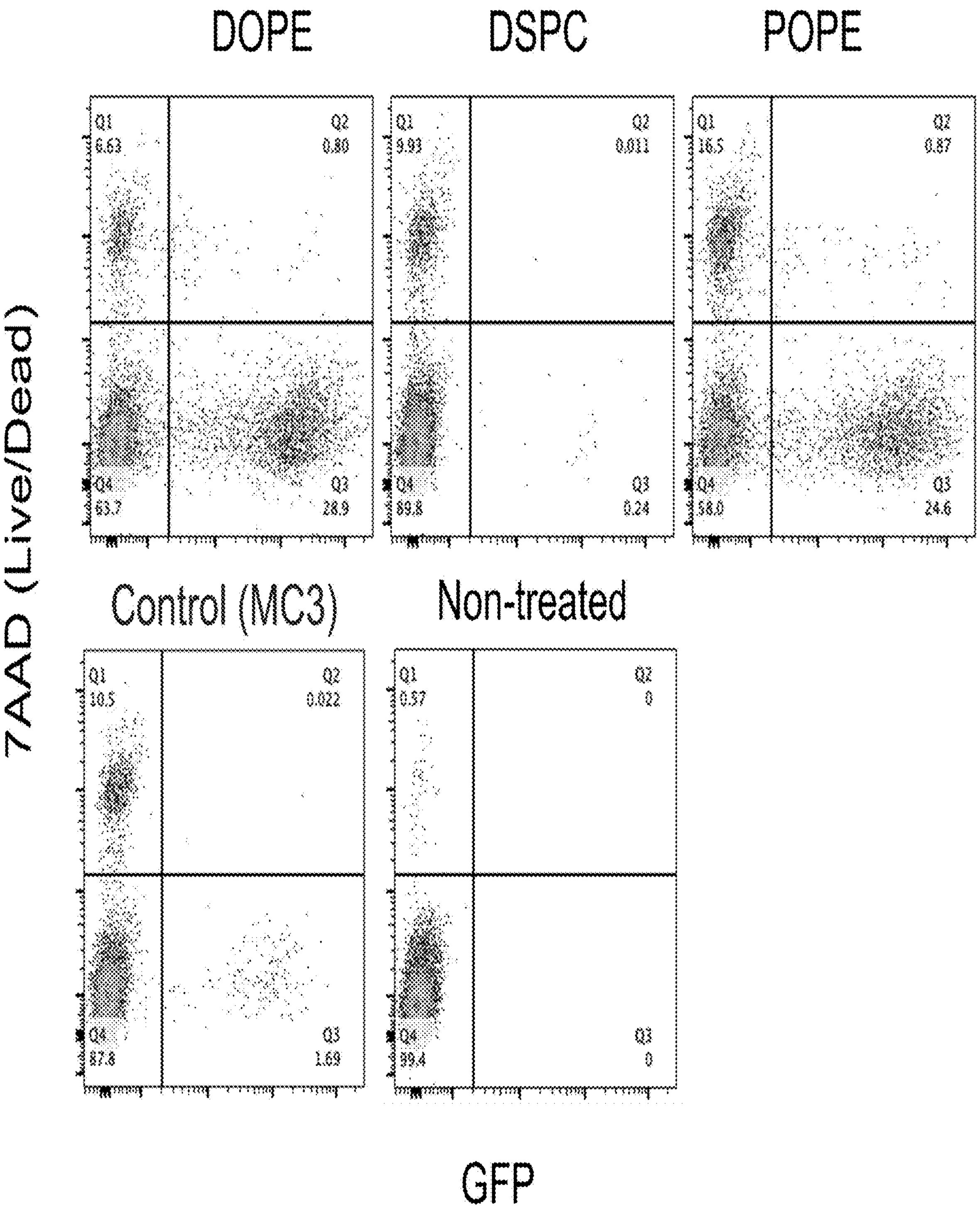
FIG. 13 shows FACS LNPs formulated with E2 ionizable lipid and DOPE, DSPC or POPE phospholipids and control LNPs, which transfect and express GFP-mRNA in 293T cells. The GFP positive live cells are as indicated in Q3.

LNPs formulated with E6; Chol; DMG-PEG2000; and either DOPC, DSPC or DOPE. The delivery efficiency of LNPs formulated with DOPE is higher than DSPC and POPE (FIG. 13) in 293T cells. DOPE was used for further studies.

An orthogonal experimental design was applied to optimize the formulation of synthesized ionizable lipids, DOPE, Chol and DMG-PEG2000 that encapsulated samRNA-GFP. Library A contained 16 formulations with four factors and four levels.

TABLE 2

Orthogonal array for combination optimization of P6A2-LNPs

| | formulation components (mole ratio) | | | |
|---|---|---|---|---|
| LNPs | P6A2 | DOPE | Chol | DMG-PEG2000 |
| A-1 | 30 | 2.5 | 38.5 | 3 |
| A-2 | 40 | 10 | 18.5 | 1.5 |
| A-3 | 50 | 10 | 38.5 | 6 |
| A-4 | 60 | 2.5 | 18.5 | 0.75 |
| A-5 | 30 | 5 | 18.5 | 6 |
| A-6 | 40 | 1.25 | 38.5 | 0.75 |
| A-7 | 50 | 1.25 | 18.5 | 3 |
| A-8 | 60 | 5 | 38.5 | 1.5 |
| A-9 | 30 | 1.25 | 48.5 | 1.5 |
| A-10 | 40 | 5 | 28.5 | 3 |
| A-11 | 50 | 5 | 48.5 | 0.75 |
| A-12 | 60 | 1.25 | 28.5 | 6 |
| A-13 | 30 | 10 | 28.5 | 0.75 |
| A-14 | 40 | 2.5 | 48.5 | 6 |
| A-15 | 50 | 2.5 | 28.5 | 1.5 |
| A-16 | 60 | 10 | 48.5 | 3 |

Figure 14:
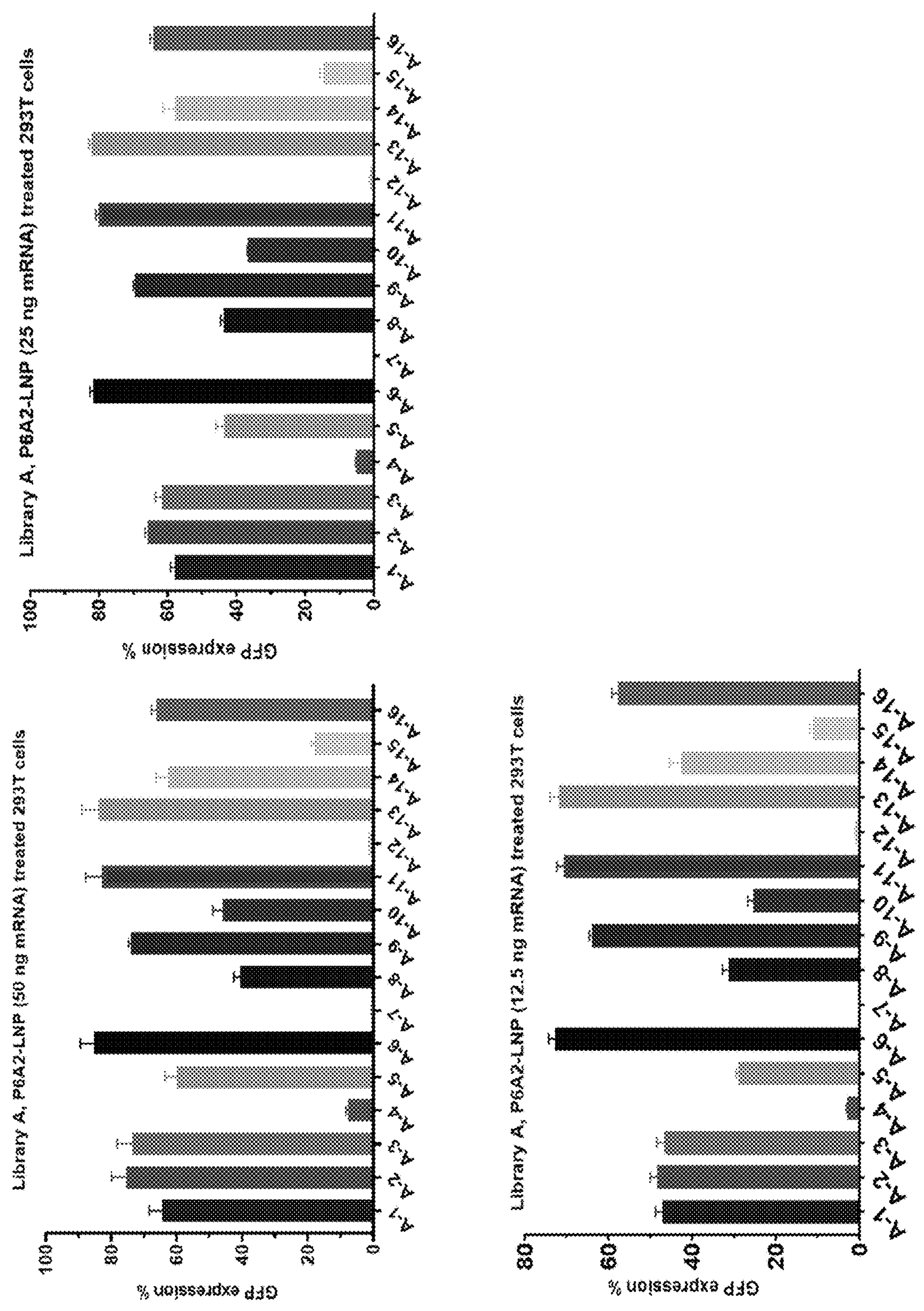
FIG. 14 shows GFP expression in 293T cells that were treated by sixteen combinations (A-1 to A-16) P6A2-LNPs for 24 hours. The cells were treated with 50, 25, or 12.5 ng of self-amplifying mRNA encoding GFP. Data are triplicated and represented as the mean±SD.
Figure 15:
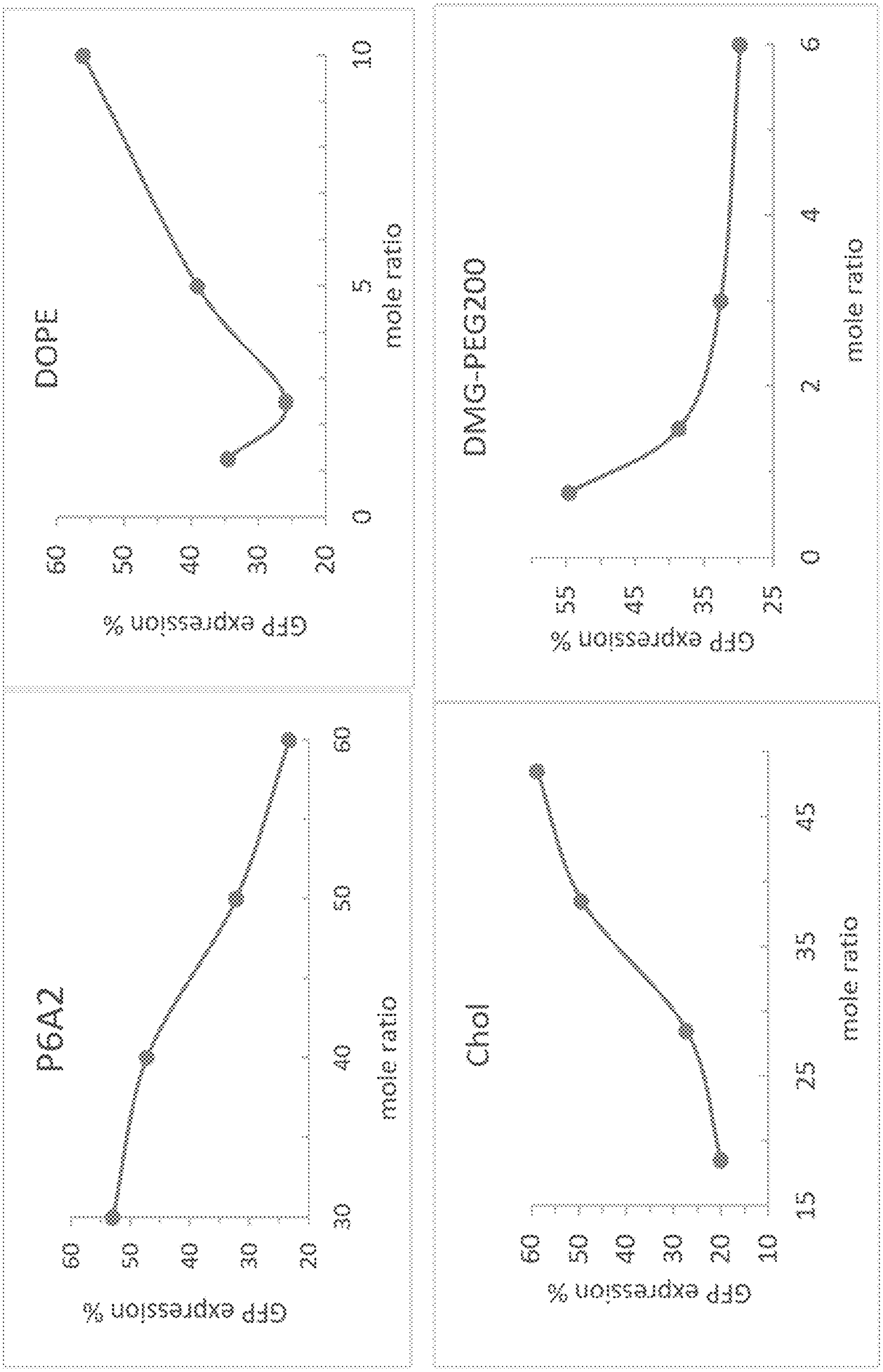
FIG. 15 shows average GFP expression of LNP formulations comprising varying molar ratios of cholesterol, DOPE, P6A2 and DMG-PEG2000 encompassing self-amplifying mRNA encoding GFP. GFP delivery efficiency increased with increased molar ratios of cholesterol and DOPE. Increased molar ratios of P6A2 and DMG-PEG2000 reduced GFP delivery efficiency. Data are triplicated and represented as the mean±SD.

In Library A, the 293T cells were treated in different amounts of LNPs (50, 25 and 2.5 ng of SamRNA-GFP). The delivery efficiency of LNPs-SamRNA-GFP of A-6, A-9, A-10, A-13 show more than 60% GFP expression when the 293T cells were transfected with 50, 25 and 12.5 ng of mRNA (FIG. 14). The samRNA-GFP delivery efficiency increased with the molar ratios of Chol and DOPE increase, while increased the molar ratios of P6A2 and DMG-PEG2000 reduced the samRNA-GFP delivery efficiency (FIG. 15).

Figure 16:
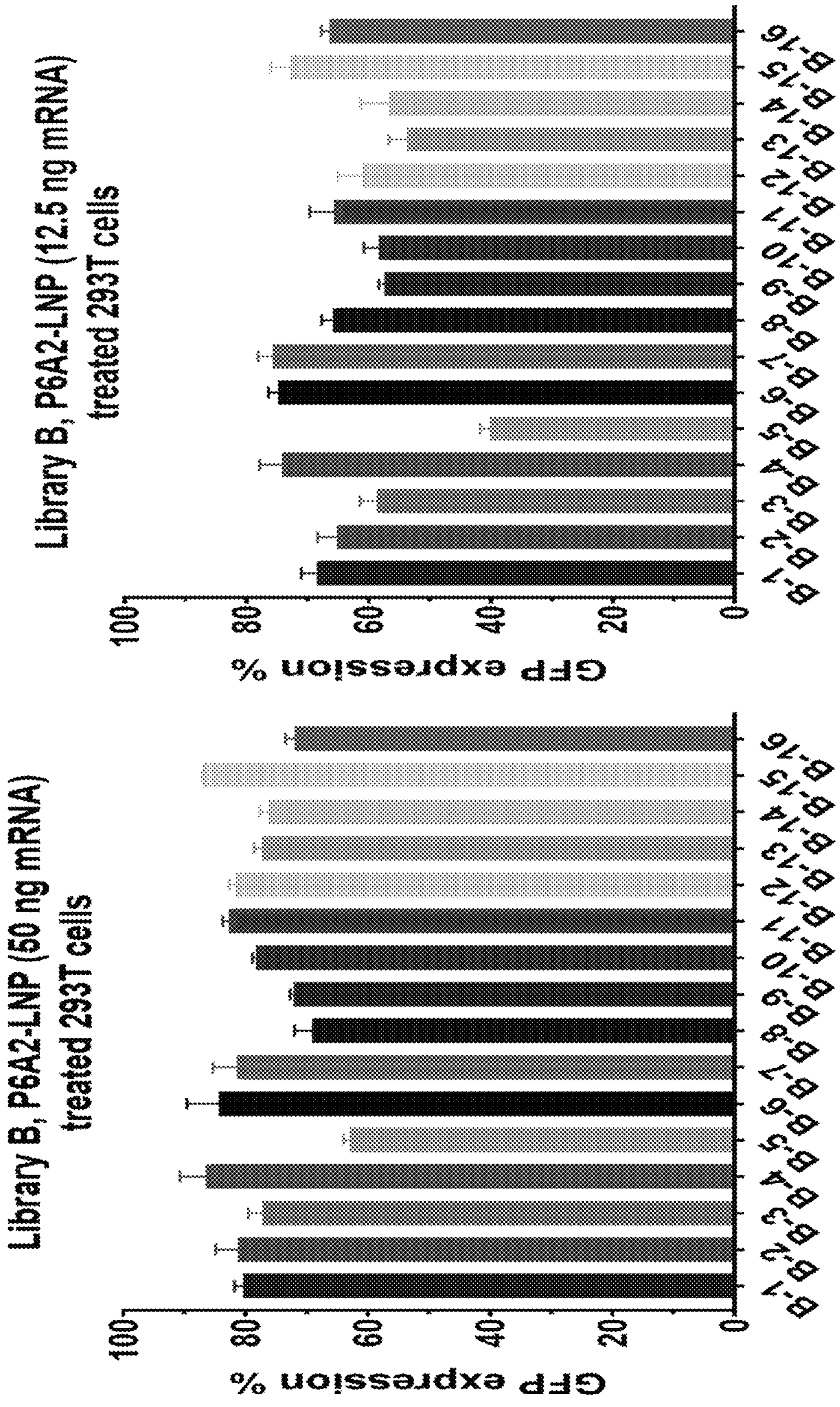
FIG. 16 shows GFP expression in 293T cells that were treated by sixteen combinations (B-1 to B-16) P6A2-LNPs for 24 hours. The cells were treated with 50 or 12.5 ng of self-amplifying mRNA encoding GFP. Data are triplicated and represented as the mean±SD.

A second orthogonal experimental design was applied to optimize the formulation of LNPs. In Library B, the 293T cells were treated with 50 or 12.5 ng of samRNA-GFP (FIG. 16).

TABLE 2

Orthogonal array table B for combination optimization of P6A2-LNPs

| | formulation components (mole ratio) | | | |
|---|---|---|---|---|
| LNPs | P6A2 | DOPE | Chol | DMG-PEG2000 |
| B-1 | 20 | 15 | 50 | 1.5 |
| B-2 | 25 | 25 | 40 | 1 |

TABLE 2-continued

| Orthogonal array table B for combination optimization of P6A2-LNPs | | | | |
|---|---|---|---|---|
| | formulation components (mole ratio) | | | |
| LNPs | P6A2 | DOPE | Chol | DMG-PEG2000 |
| B-3 | 30 | 25 | 50 | 2 |
| B-4 | 35 | 15 | 40 | 0.5 |
| B-5 | 20 | 20 | 40 | 2 |
| B-6 | 25 | 10 | 50 | 0.5 |

TABLE 2-continued

| Orthogonal array table B for combination optimization of P6A2-LNPs | | | | |
|---|---|---|---|---|
| | formulation components (mole ratio) | | | |
| LNPs | P6A2 | DOPE | Chol | DMG-PEG2000 |
| B-7 | 30 | 10 | 40 | 1.5 |
| B-8 | 35 | 20 | 50 | 1 |
| B-9 | 20 | 10 | 55 | 1 |
| B-10 | 25 | 20 | 45 | 1.5 |
| B-11 | 30 | 20 | 55 | 0.5 |
| B-12 | 35 | 10 | 45 | 2 |
| B-13 | 20 | 25 | 45 | 0.5 |
| B-14 | 25 | 15 | 55 | 2 |
| B-15 | 30 | 15 | 45 | 1 |
| B-16 | 35 | 25 | 55 | 1.5 |

Figure 17:
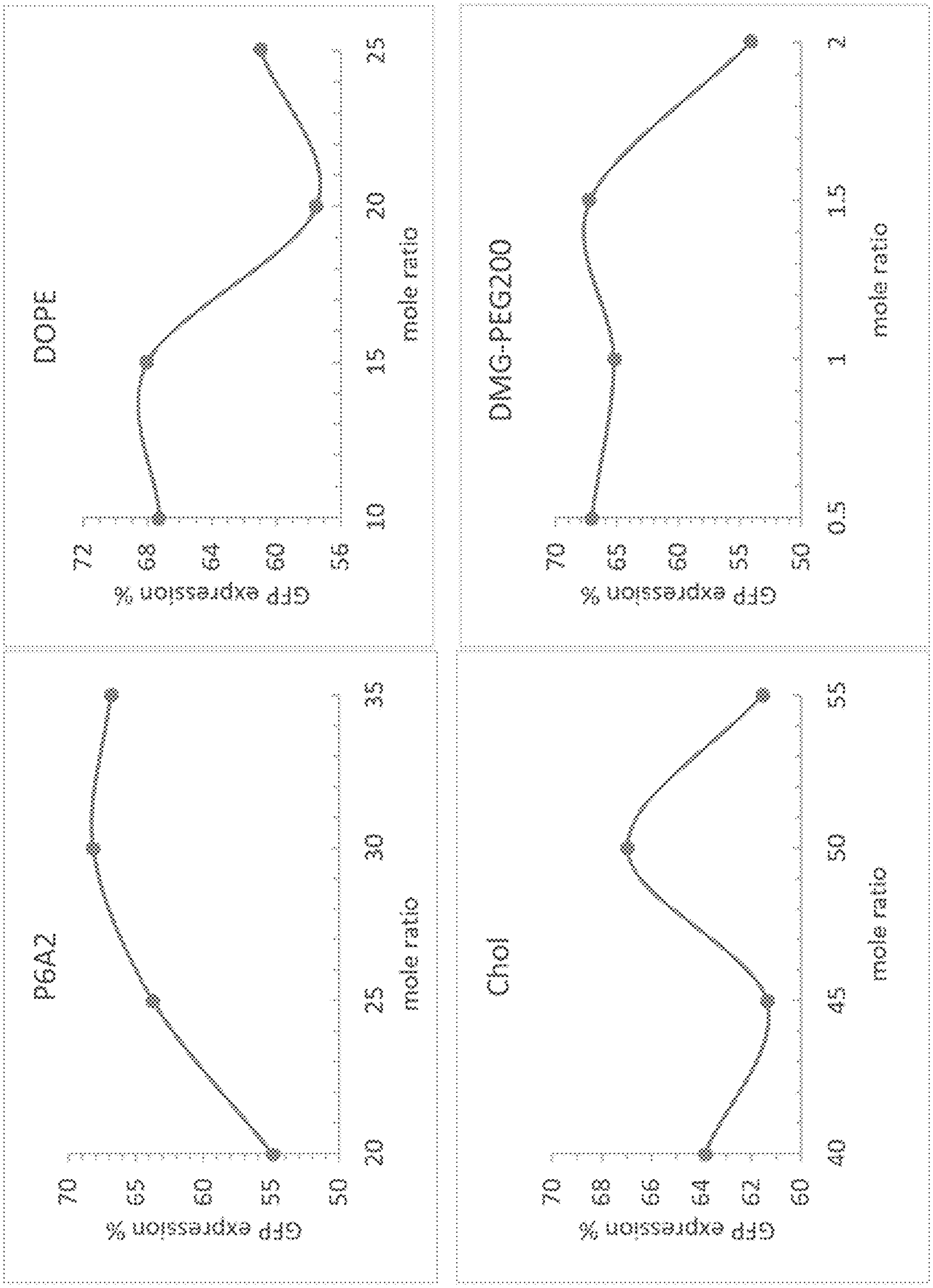
FIG. 17 shows average GFP expression of LNP formulations comprising varying molar ratios of cholesterol, DOPE, P6A2 and DMG-PEG2000 encompassing self-amplifying mRNA encoding GFP. A formulation combination of the present disclosure is P6A2/DOPE/Chol/DMG-PEG2000 30/15/50/1.5. Data are triplicated and represented as the mean±SD.
Figure 18:
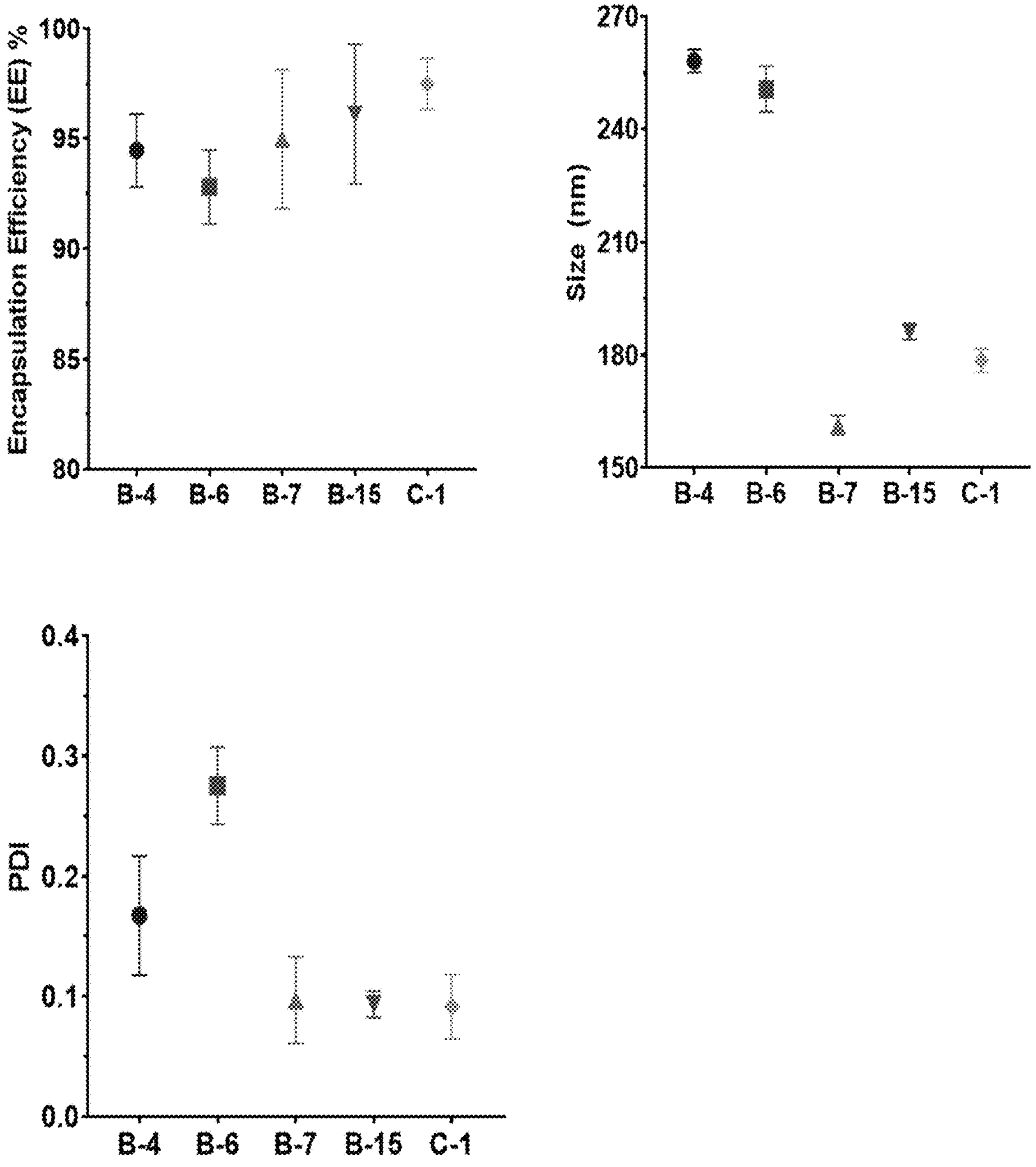
FIG. 18 shows encapsulation efficiency, nanoparticles size and polydispersity index (PDI) of P6A2 LNPs. Data are triplicated and represented as the mean±SD.
Figure 19:
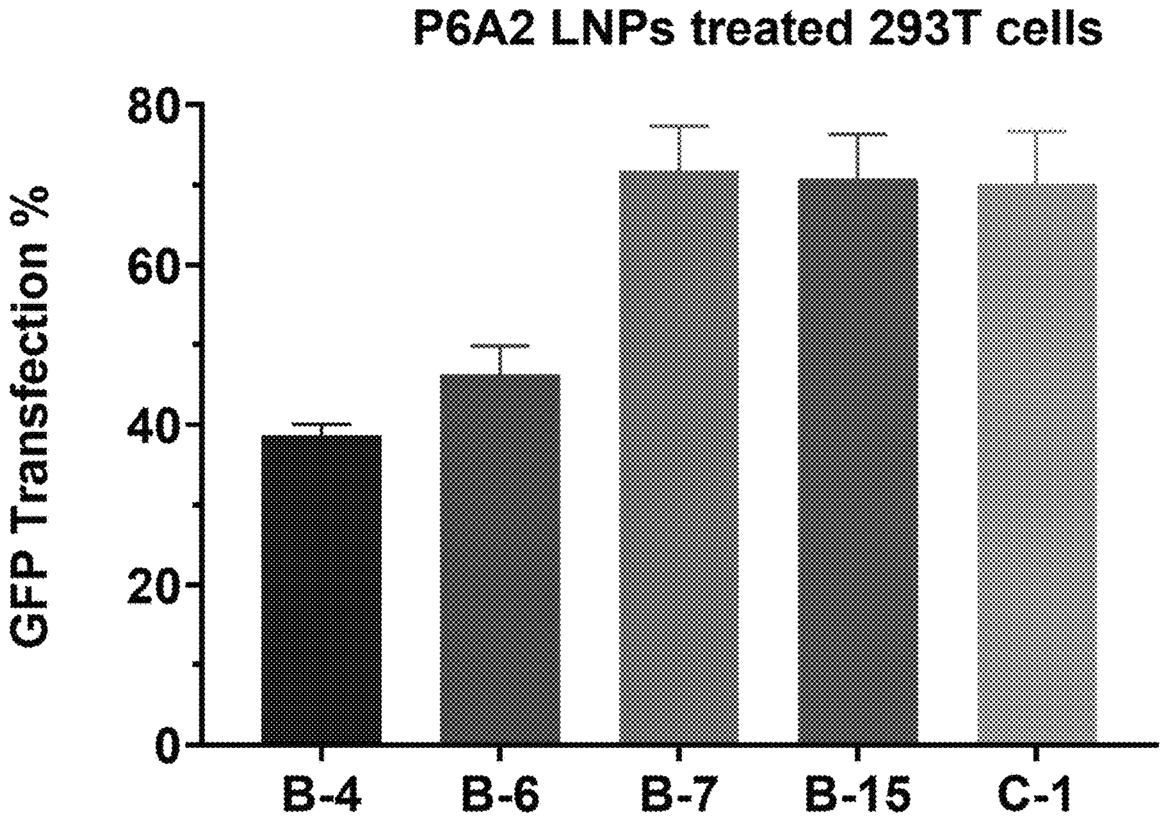
FIG. 19 shows GFP expression in 293T cells treated by LNPs formulated with ionizable lipid P6A2 for 24 hours. The cells were treated with 12.5 ng of self-amplifying mRNA-GFP. Data are triplicated and represented as the mean±SD.

The impact trend of P6A2, DOPE, Chol and DMG-PEG2000 was shown in FIG. 17. In Library B, the LNPs of B-4, B-6, B-7, and B-15 are the top-performing formulations in both 50 and 12.5 ng of mRNA treated groups. The predicted best formulation combination (C-1) is P6A2/DOPE/Chol/DMG-PEG2000=30/15/50/1.5. The particles size, PDI and encapsulation efficiency of P6A2-LNP formulation candidates were measured by a dynamic light-scattering instrument and a Ribogreen assay (FIG. 18). C-1 formulation of P6A2-LNP showed comparable delivery efficiency to B-7 and B-15, and higher than B-4 and B-6 (FIG. 19).

Ionizable lipid C7 in Formula I, E2 and E6 in Formula II, TP4G11 in Formula III were performed optimization of LNP formulation as the above methods. The nanoparticle size, PDI, and encapsulation efficiency of mRNA of the optimized C7, D7, E2, E6, TP4G11, P4G11, PD4, P6A2, P30B7, P30C7, P30A1, P54B6, P38D1, P38D7, P38D8, P4510, P40C11, P56A1, P56B1, P28D10, P53A5, P40C10, P51C12, P53A6, P40D7 LNPs were assayed by dispersed light scanner and by Ribogreen assay, respectively.

TABLE 3

| LNP characterization | | | | | | | |
|---|---|---|---|---|---|---|---|
| | | | Encapsulation | formulation components (mole ratio) | | | |
| LNP | Avg. Size (nm) | Avg. PDI (RLU) | Efficiency (EE) % | Ionizable lipid | DOPE | Chol | DMG-PEG2000 |
| C7 | 181 | 0.1 | 53.9 | 10 | 30 | 45 | 2.5 |
| E6 | 217 | 0.13 | 97.5 | 20 | 30 | 40 | 1.5 |
| E2 | 200 | 0.1 | 95.1 | 20 | 40 | 40 | 1.5 |
| TP4G11 | 230 | 0.09 | 74.5 | 30 | 20 | 40 | 2 |
| P6A2 | 190.7 | 0.12 | 90.4 | 30 | 15 | 50 | 1.5 |
| P38D7 | 236.3 | 0.21 | 94.8 | 30 | 15 | 50 | 1.5 |
| P38D8 | 186.9 | 0.18 | 95.4 | 30 | 15 | 50 | 1.5 |
| P40B10 | 189.9 | 0.14 | 95.8 | 30 | 15 | 50 | 1.5 |
| P40C11 | 189.3 | 0.14 | 96.6 | 30 | 15 | 50 | 1.5 |
| P56A1 | 186.3 | 0.12 | 89.1 | 30 | 15 | 50 | 1.5 |
| P56B1 | 173.2 | 0.10 | 90.6 | 30 | 15 | 50 | 1.5 |
| P28D10 | 188.0 | 0.10 | 95.5 | 30 | 15 | 50 | 1.5 |
| P1D4 | 170.4 | 0.17 | 92.7 | 30 | 15 | 50 | 1.5 |
| P30B7 | 151.6 | 0.10 | 91.0 | 30 | 15 | 50 | 1.5 |
| P30C7 | 166.8 | 0.11 | 93.9 | 30 | 15 | 50 | 1.5 |
| P30A1 | 176.6 | 0.11 | 97.8 | 30 | 15 | 50 | 1.5 |
| P54B6 | 181.2 | 0.10 | 93.4 | 30 | 15 | 50 | 1.5 |
| P38D1 | 179.1 | 0.12 | 97.4 | 30 | 15 | 50 | 1.5 |
| P40C10 | 192.9 | 0.25 | 99.1 | 30 | 15 | 50 | 1.5 |
| P40D7 | 149.2 | 0.18 | 98.2 | 30 | 15 | 50 | 1.5 |
| P53A5 | 173.8 | 0.10 | 97.9 | 30 | 15 | 50 | 1.5 |
| P53A6 | 175.6 | 0.16 | 98.3 | 30 | 15 | 50 | 1.5 |
| P51C12 | 186.5 | 0.26 | 98.1 | 30 | 15 | 50 | 1.5 |

Example 7: In Vivo Validation of Transfection Efficacy

Figure 20:
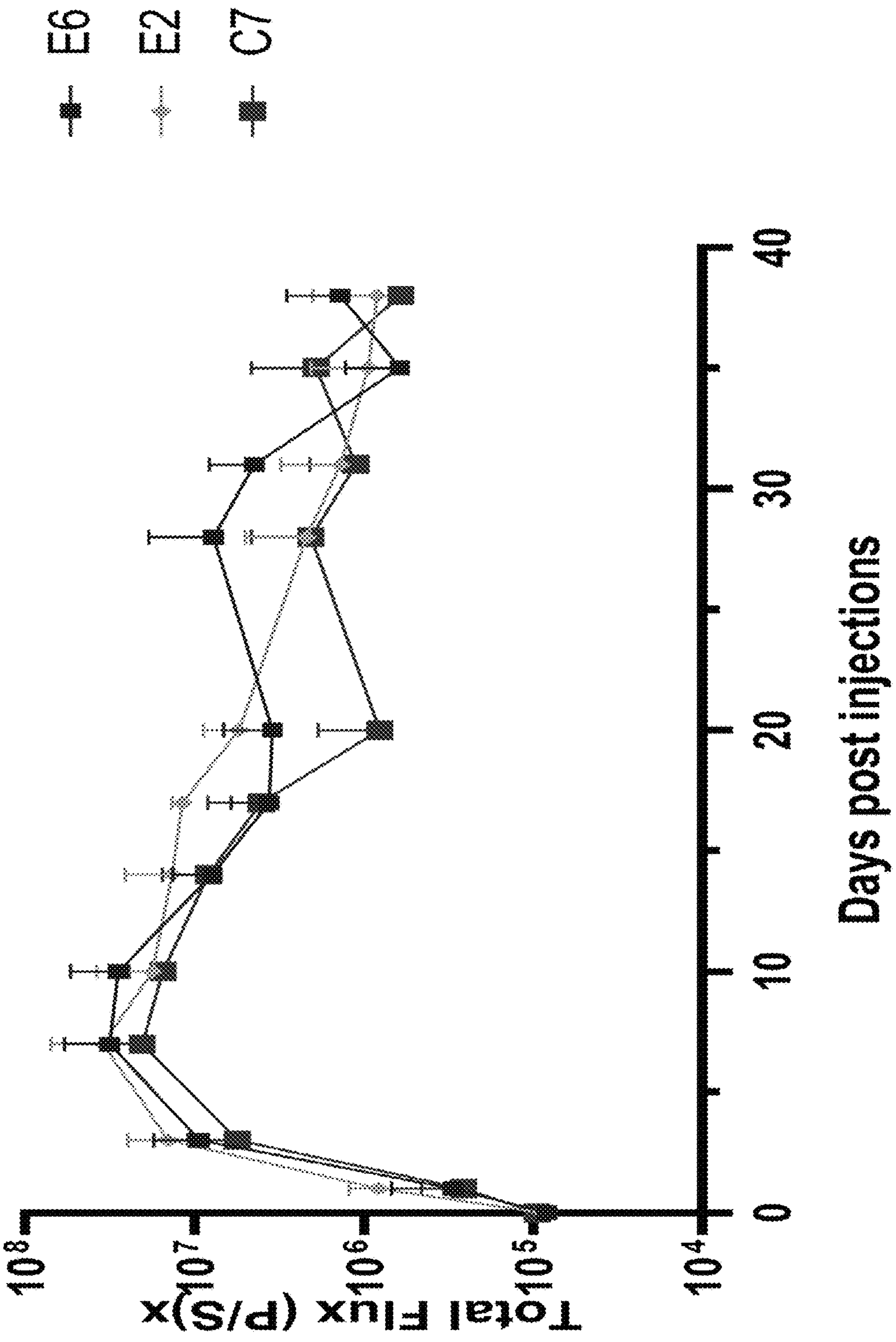
FIG. 20 shows in vivo bioluminescence intensity of metastatic sites in mice treated with LNPs formulated with ionizable lipids C7, E2 and E6 encapsulating SamRNA-LUC. Each mouse was treated with 1 μg of self-amplifying mRNA-LUC. Data represents mean±SD from 5 mice.
Figure 21:
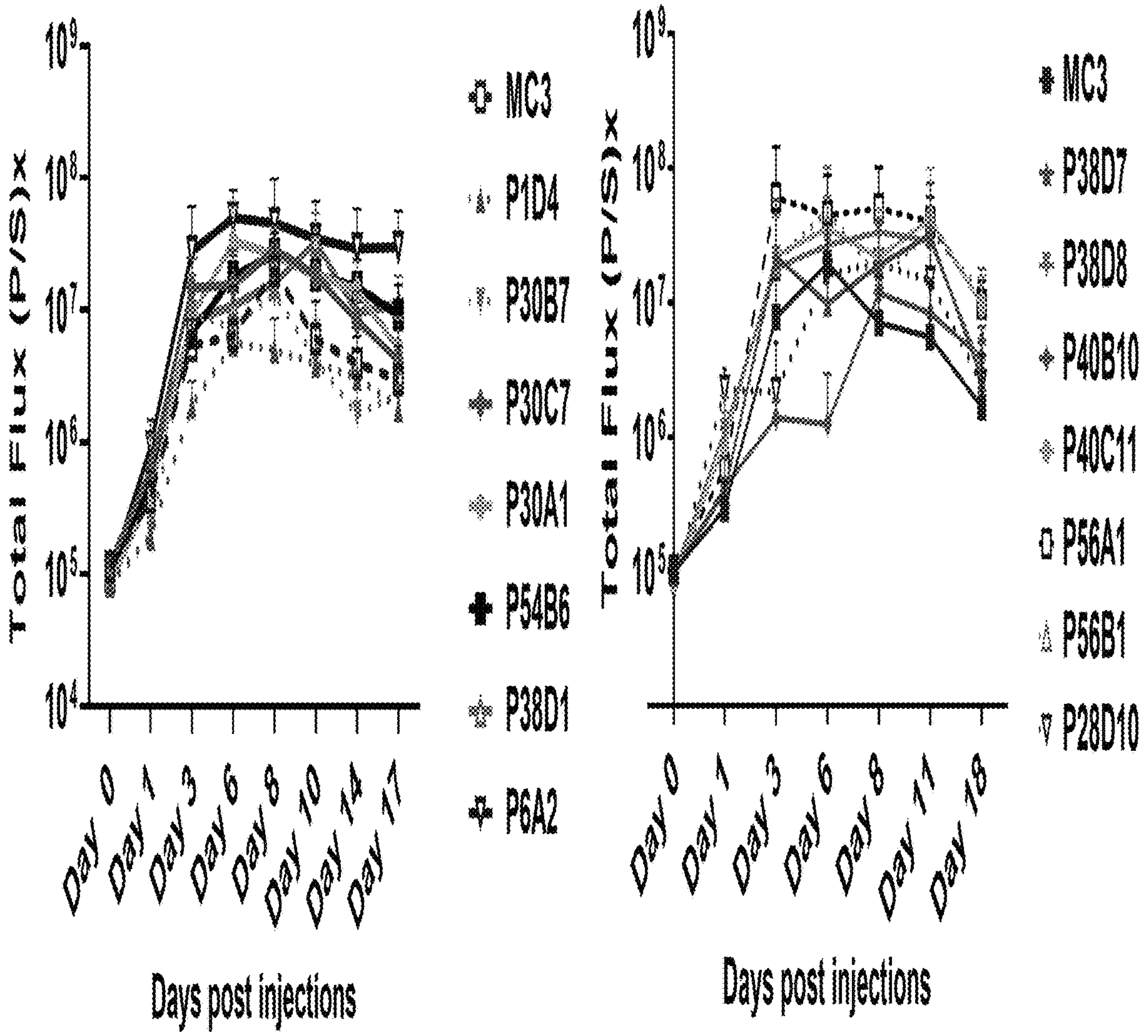
FIG. 21 shows in vivo bioluminescence intensity of metastatic sites in mice treated with P1D4-LNP, P30B7-LNP, P30C7-LNP, P30A1-LNP, P54B6-LNP, P38D1-LNP and P6A2-LNP (top left), P38D7-LNP, P38D8-LNP, P40B10-LNP, P40C11-LNP, P56A1-LNP, P56B1-LNP and P28D10 (top right), P40C10, P40D7, P53A6, P53A5 and P51C12 (bottom) encapsulating SamRNA-LUC, MC3-LNP was used as a control group. Each mouse was treated with 1 μg of SamRNA-LUC. Data represents mean±SD from 5 mice.
Figure 21:
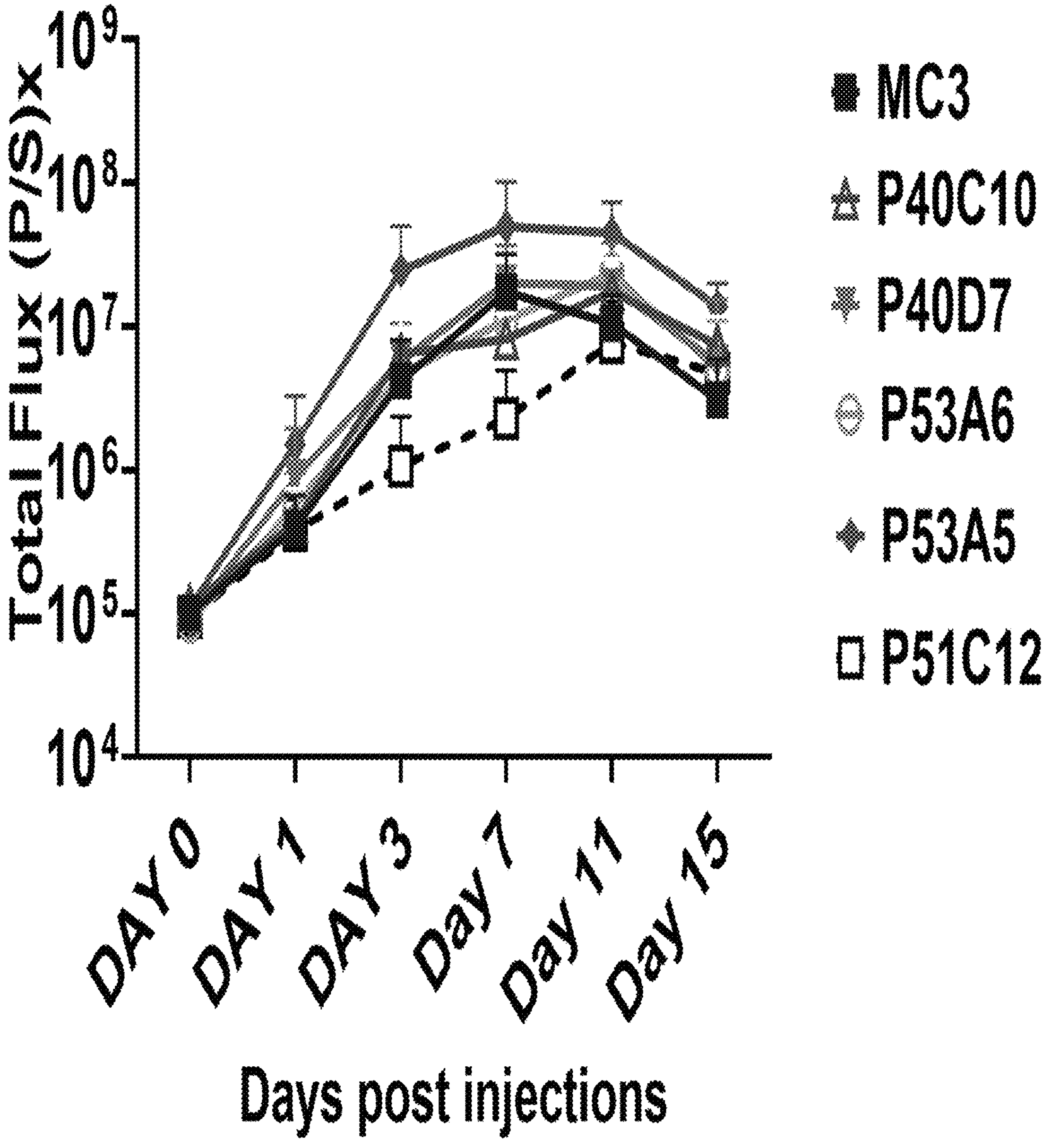

In vivo delivery efficiency of LNPs formulated using C7, E2, E6, P1D4, P30B7, P30C7, P30A1, P54B6, P38D1, P6A2, P38D7, P38D8, P40B10, P40C11, P56A1, P56B1, P28D10, P40C10, P40D7, P53A6, P51C12 and P53A5 encapsulating a self-amplify mRNA encoding with Luciferase were tested (FIGS. 20 and 21). The mice were injected intramuscularly with 1 μg of LNPs encapsulating samRNA-LUC, including control (MC3-LNP-samRNA-LUC), After intraperitoneal injection of Luciferin (Perkin Elmer, 6 mg/mouse), the expression of Luciferase (luminescence) was determined by In Vivo Imaging System (IVIS, Perkin Elmer). LNP formulated with 13 of the screened ionizable lipids showed better delivery efficacies than MC3-LNP-SamRNA-Luc. LNPs formulated with 9 of the screened ionizable lipids showed comparable delivery efficacies as the MC3-LNP (FIGS. 20 and 21).

All animals' procedures were performed with ethical compliance and approval by Institutional Animal Care and Use Committee (IACUC). Female Balb/c mice (6-8 weeks) were obtained from Charles River Laboratories Inc.

Example 8: Design and Synthesis of Formula VII

Figure 22:
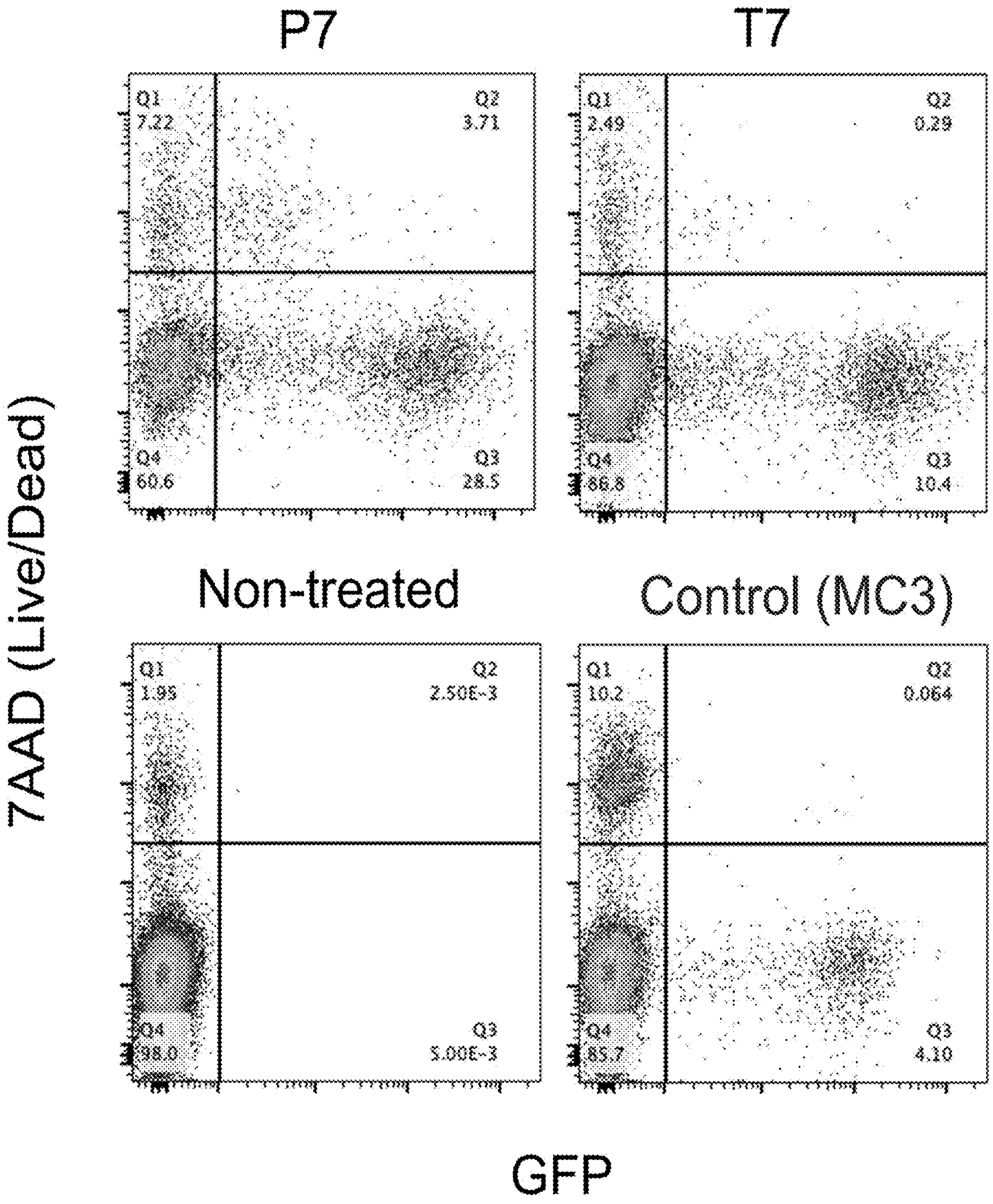
FIG. 22 shows FACS of (P7 and T7) ionizable lipid formulated LNPs and control LNPs encapsulated with self-amplifying mRNA encoding with GFP, which transfect and express GFP-mRNA in 293T cells. The GFP positive live cells are as indicated in Q3.

Formula VII was initially designed so that the compounds of Formula VII required a synthesis scheme using multiple steps. LNPs formulated with ionizable lipids of Formula VII (P7 and T7) showed better delivery efficacies than FDA approved ionizable lipid MC3 (FIG. 22). Therefore, the multi-step synthesis scheme of Formula VII was redesigned using the information gained from designing the one-step synthesis schemes of Formula I-VI to allow high-throughput production of compounds of Formula VII by creating a method of synthesizing compounds of Formula VII using a two-step synthesis scheme.

Therefore, the information generated in formula I-VII and Libraries A and B of the disclosure could be used as a database for manual redesign of known ionizable lipids, machine learning, or artificial intelligence. Furthermore, the database library could be used to design and synthesize ionizable lipids with better or comparable transfection efficacies compared to currently commercially available ionizable lipids.

It is to be understood that any particular embodiment of the present disclosure that falls within the prior art may be explicitly excluded from any one or more of the claims. Since such embodiments would be deemed to be known to one of ordinary skill in the art, they may be excluded even if the exclusion is not set forth explicitly herein.

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A compound, wherein the compound is:

(Ia)

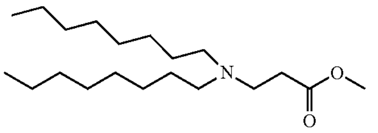

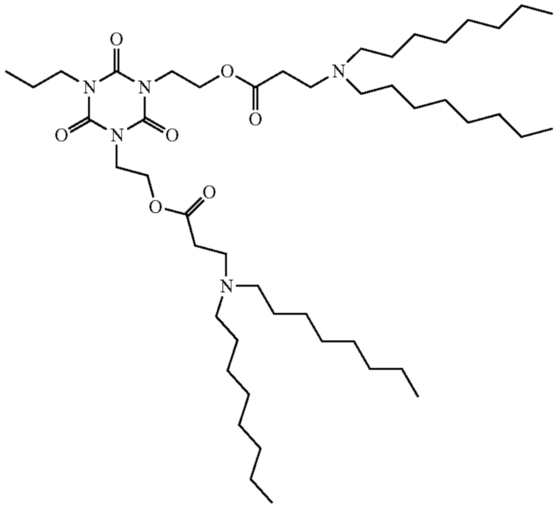

;

-continued (Ib)

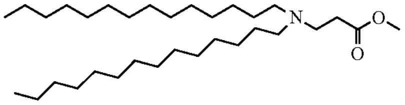

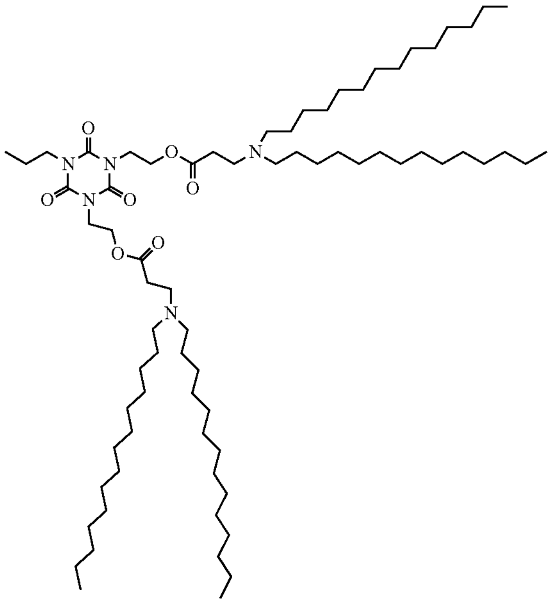

;

(IIa)

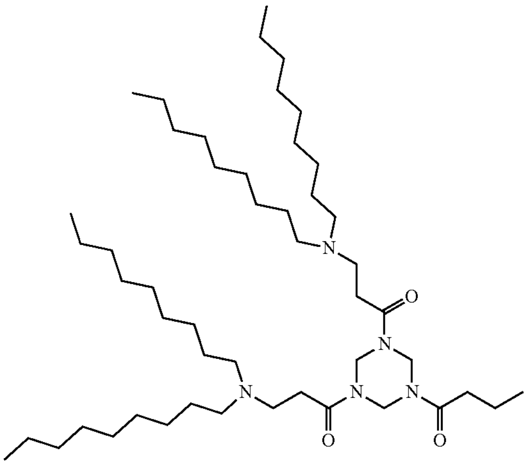

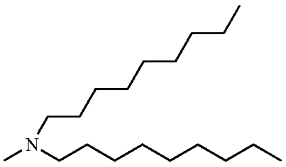

;

-continued
(Iib)
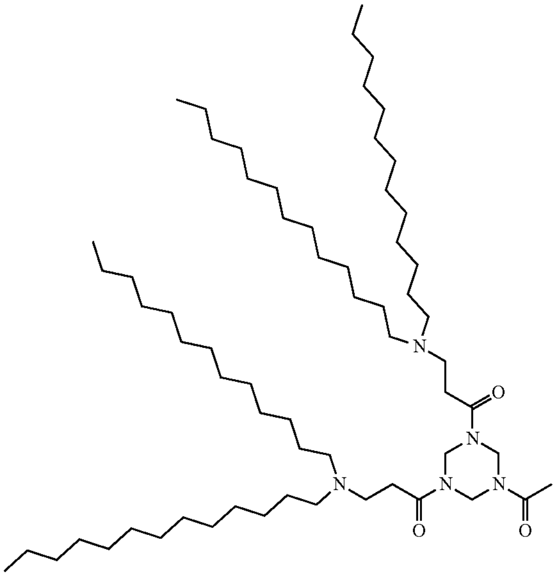
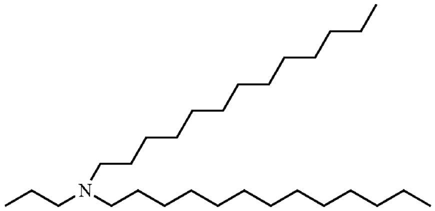
;
(IIIa)
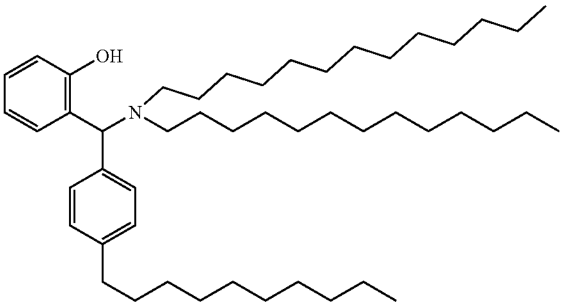
;
(IIIb)
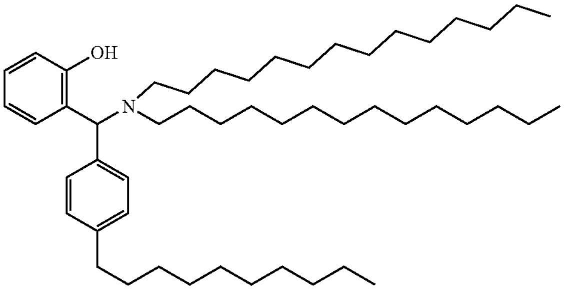
;
-continued
(IIIc)
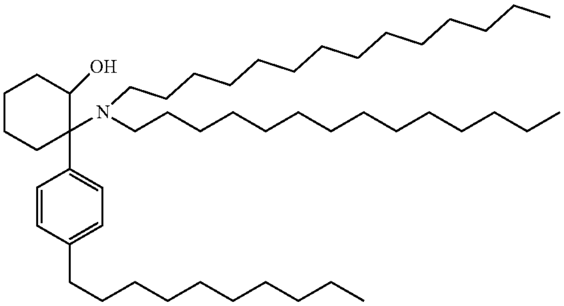
;
(IIId)
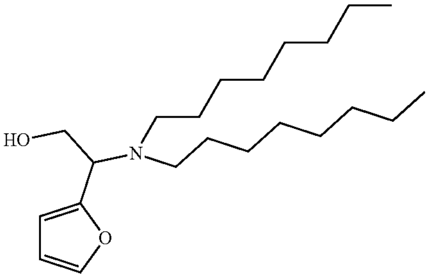
;
(IIIe)
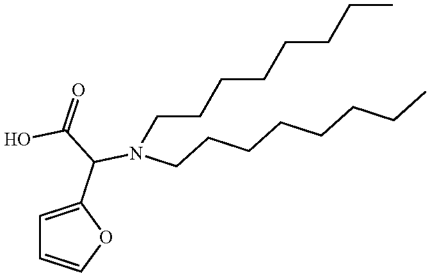
;
(IIIf)
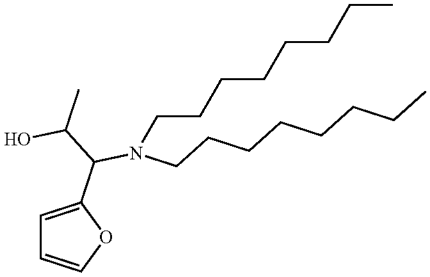
;
(IIIg)
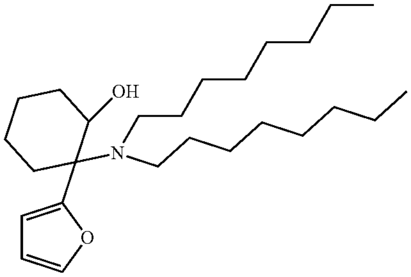
;

-continued
(IIIh)
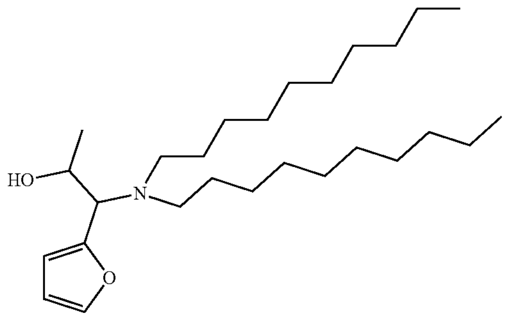
;
(IIIi)
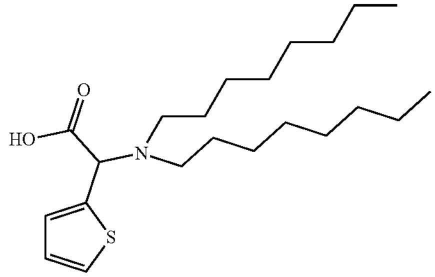
;
(IIIj)
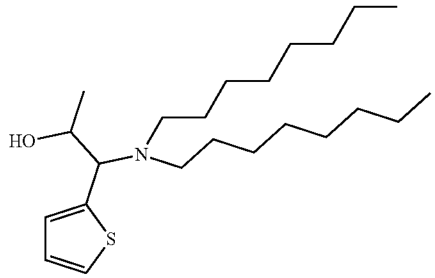
;
(IIIk)
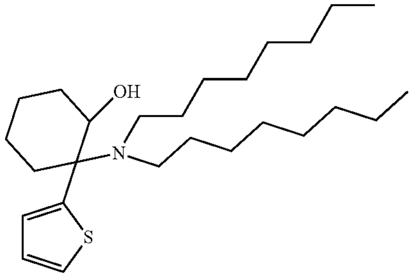
;
(IIIl)
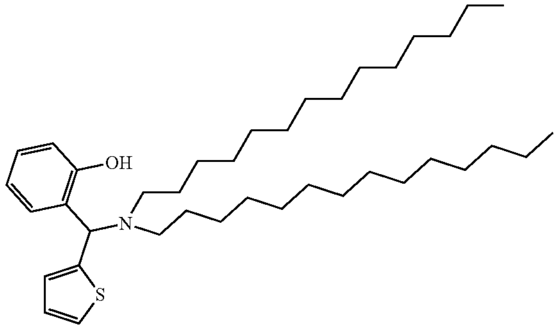
;
-continued
(IIIm)
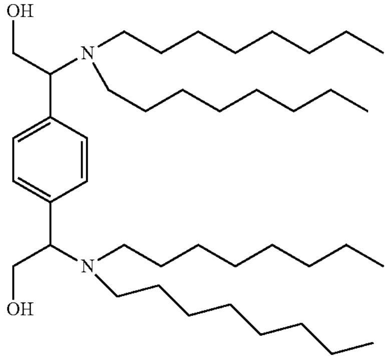
;
(IIIn)
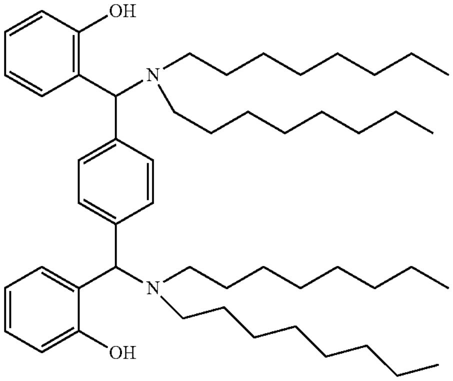
;
(IIIo)
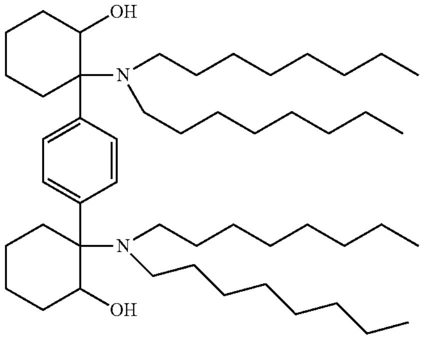
;
(IIIp)
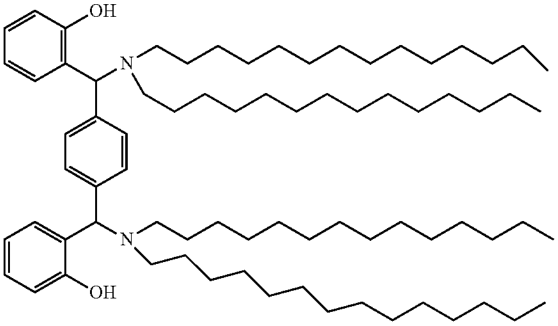
;

-continued
(IIIt)
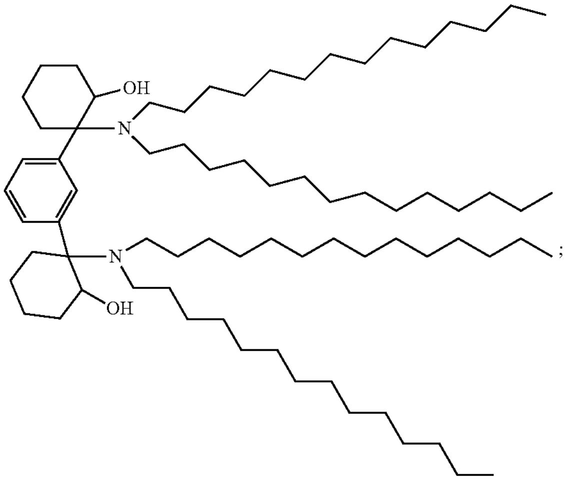
;
(IIIu)
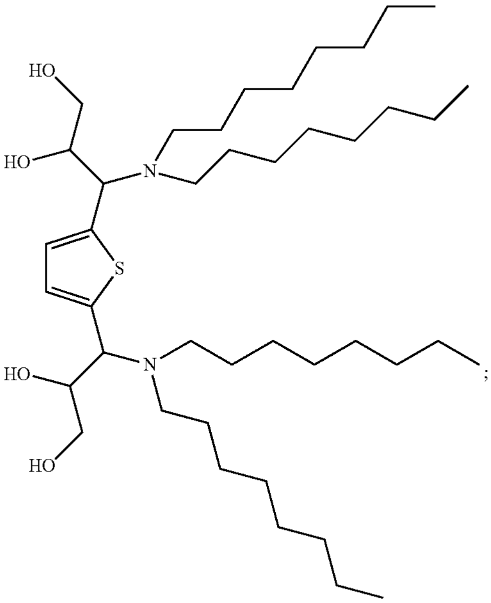
;
-continued
(IIIv)
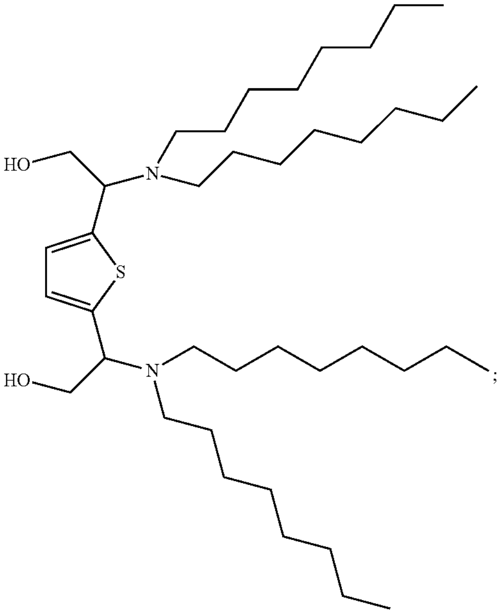
;
(IIIw)
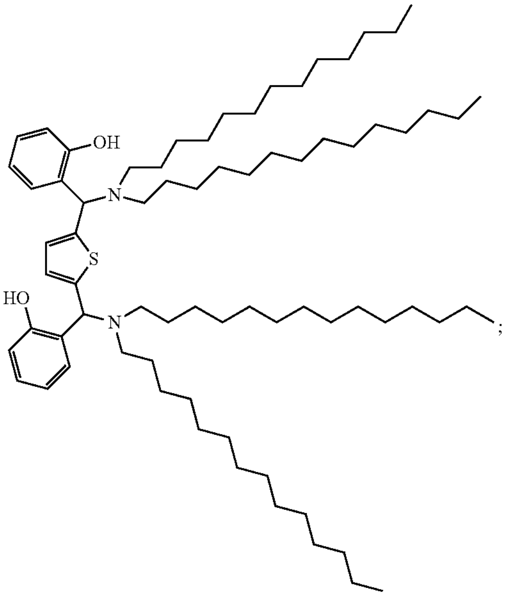
;
(IIIx)
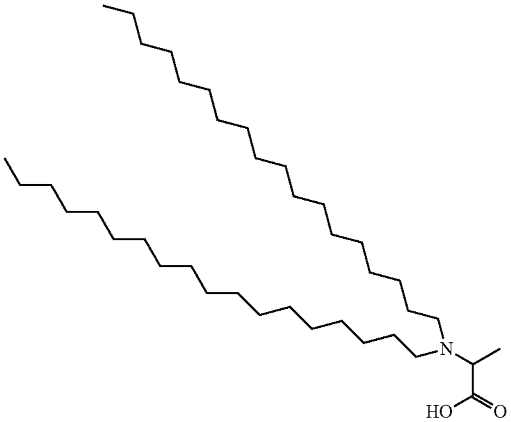

-continued
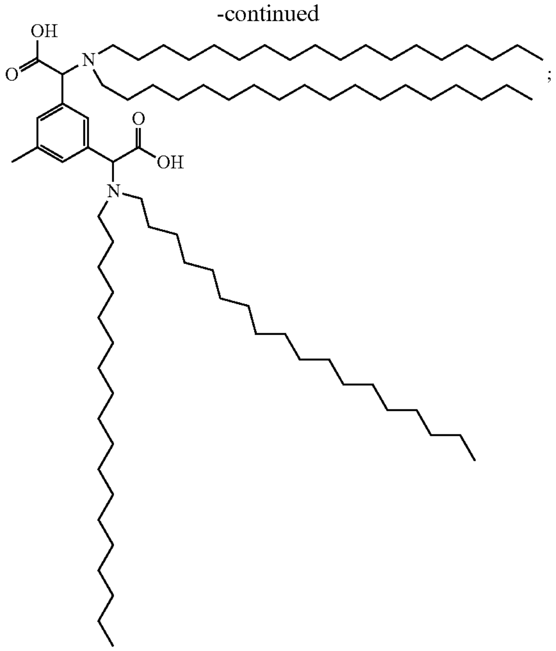
(IIIy)
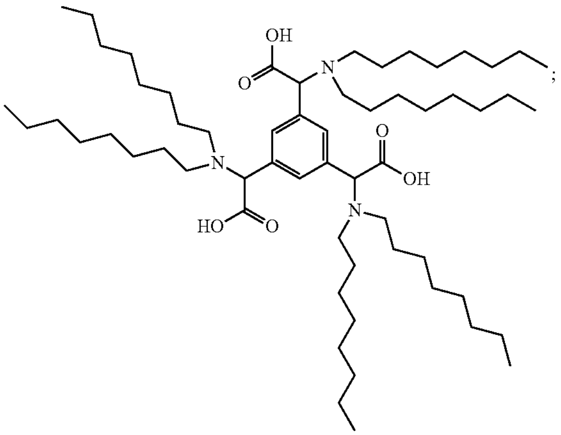
(IIIz)
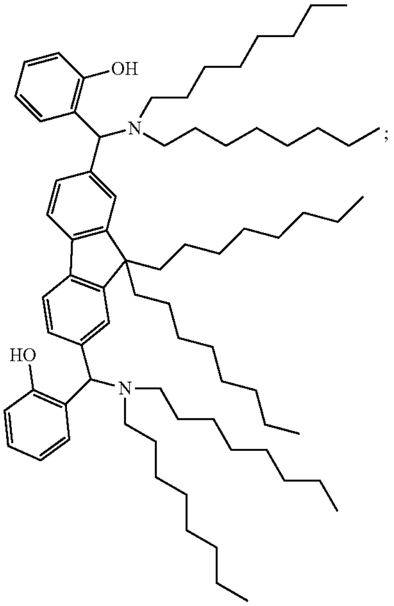
-continued
(III-2)
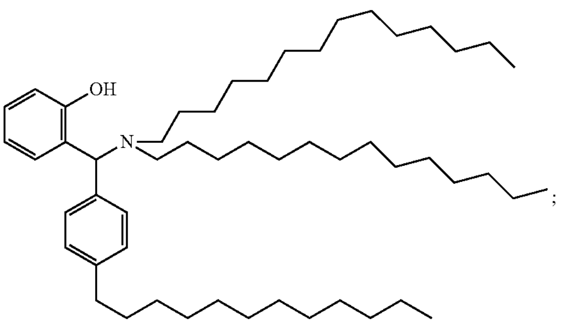
(III-3)
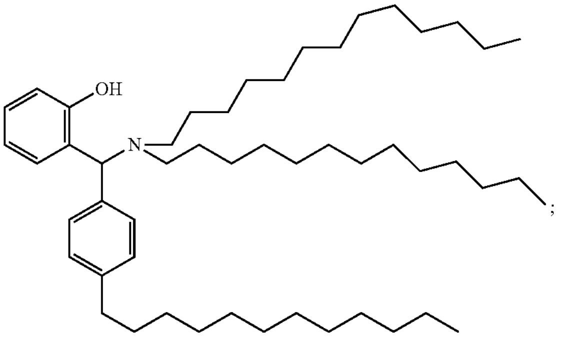
(III-4)
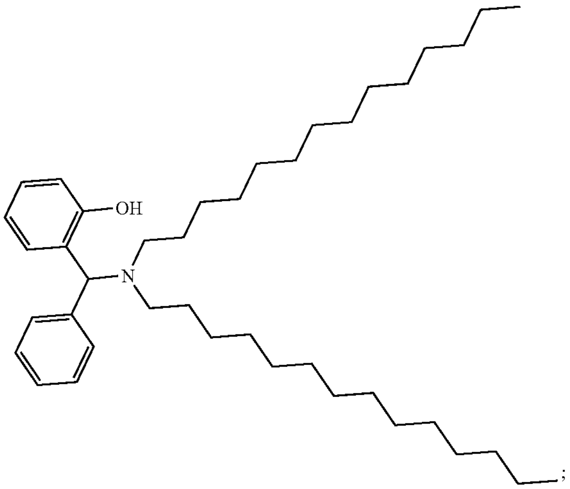
(Iva)
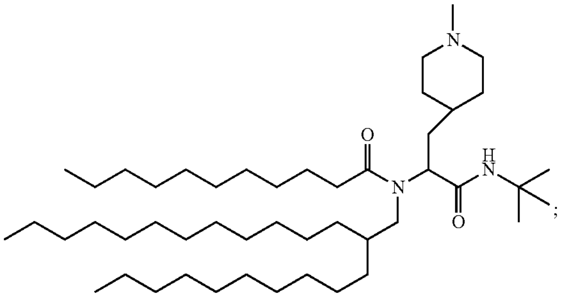

-continued
(Ivb)
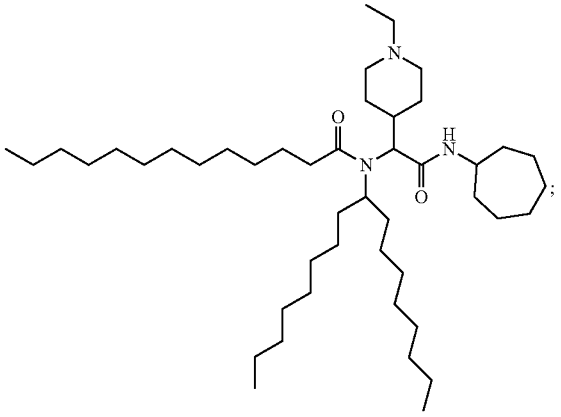
(Ivc)
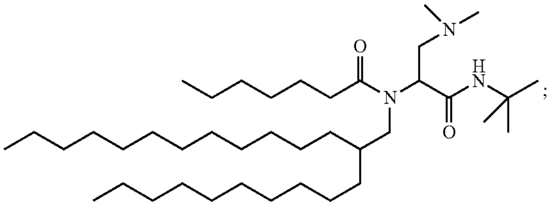
(Ivd)
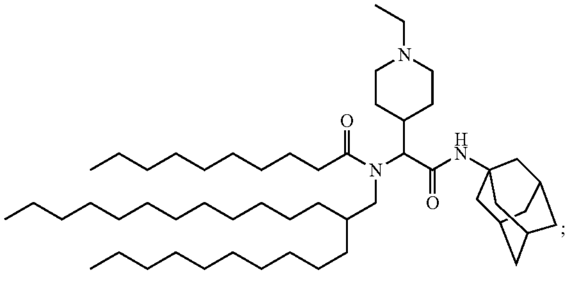
(Ive)
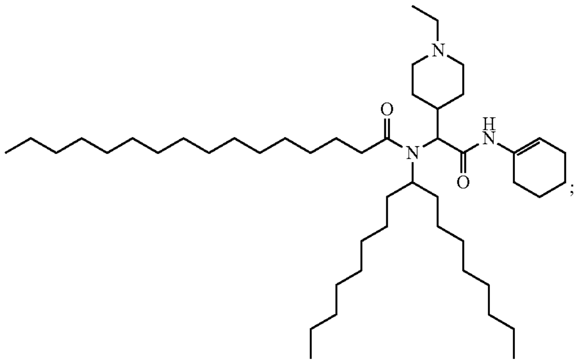
-continued
(Ivf)
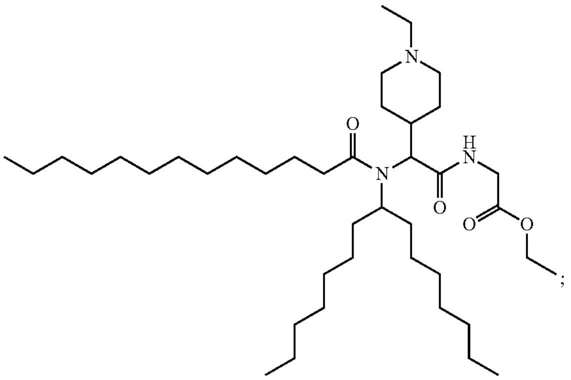
(Ivg)
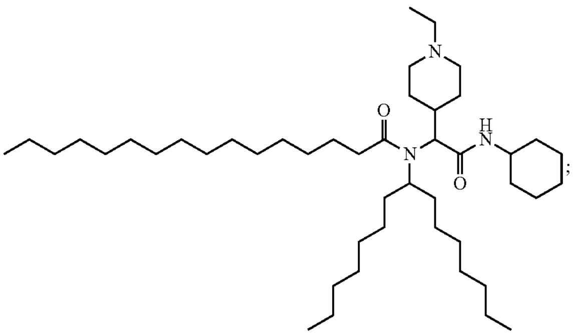
(Ivh)
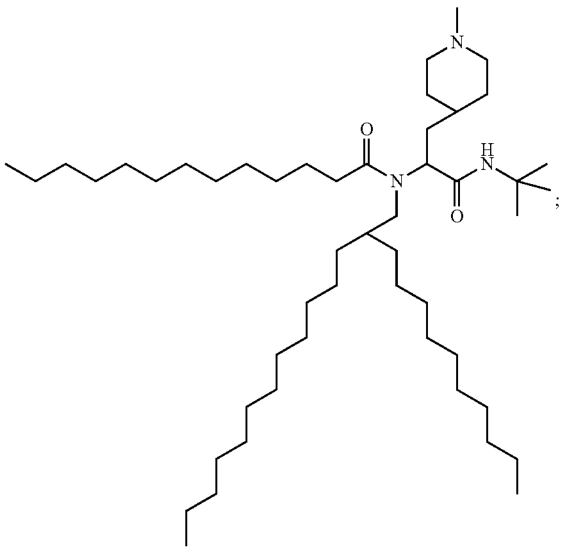

-continued
(Ivi)
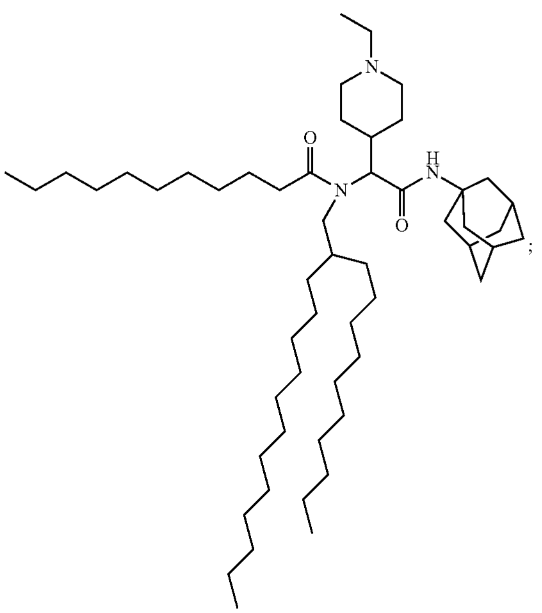
(Ivj)
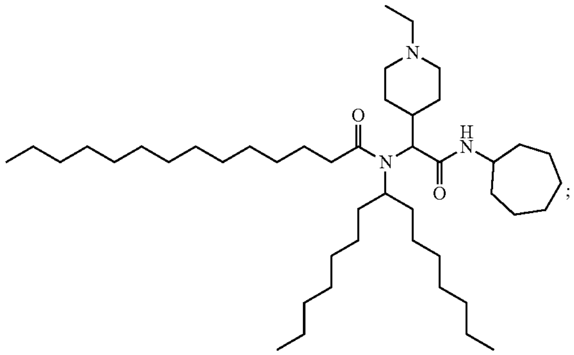
(Ivk)
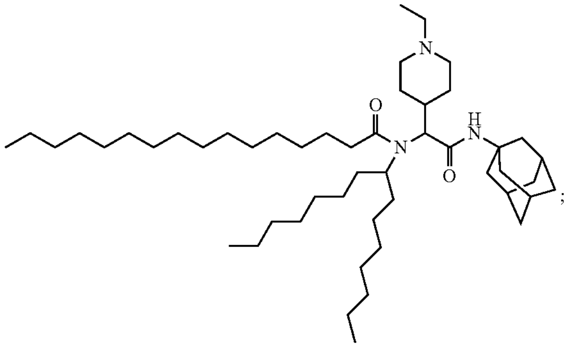
-continued
(Ivl)
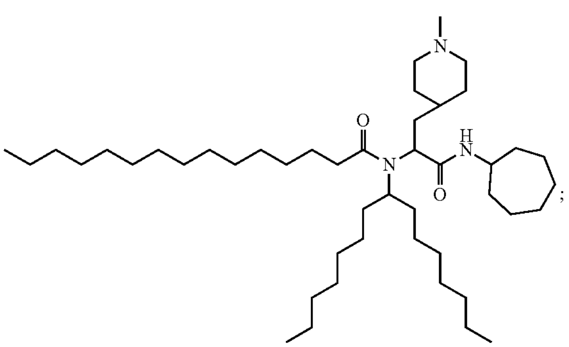
(Ivm)
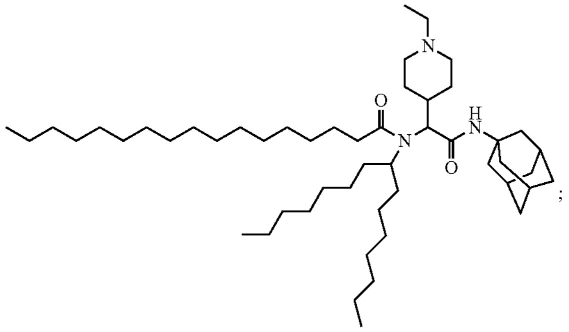
(Ivn)
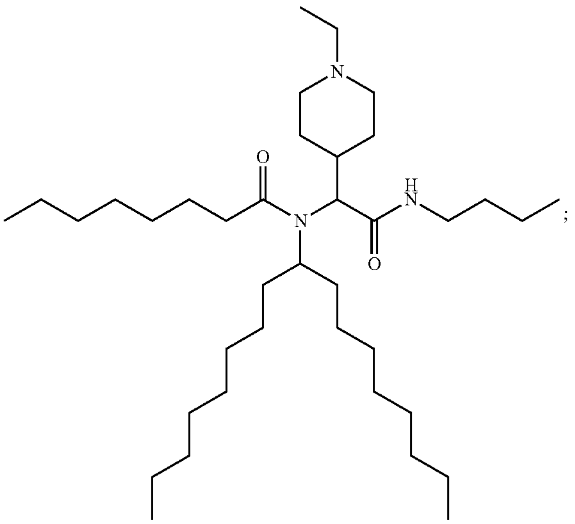

-continued
(Ivo)
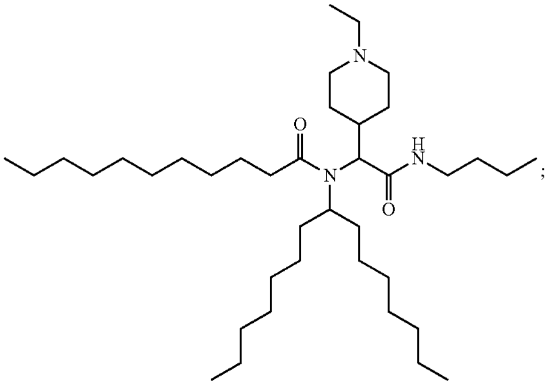
;
(Ivp)
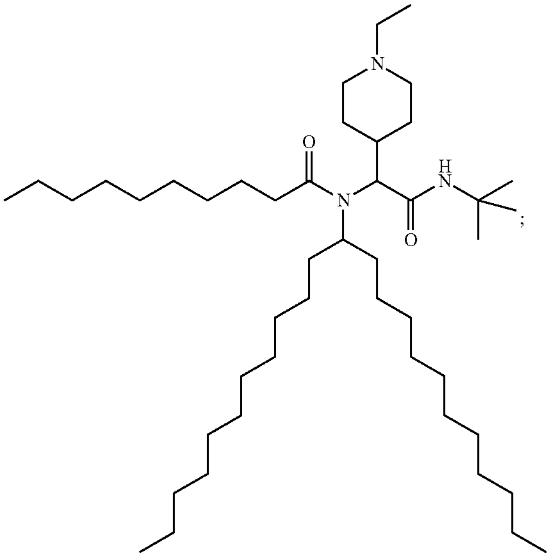
;
(Ivq)
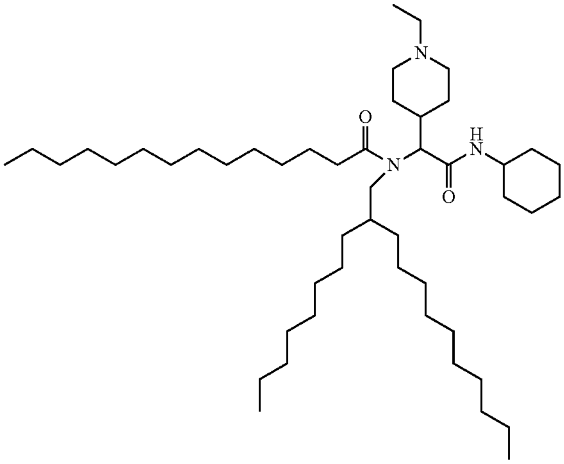
;
-continued
(Ivr)
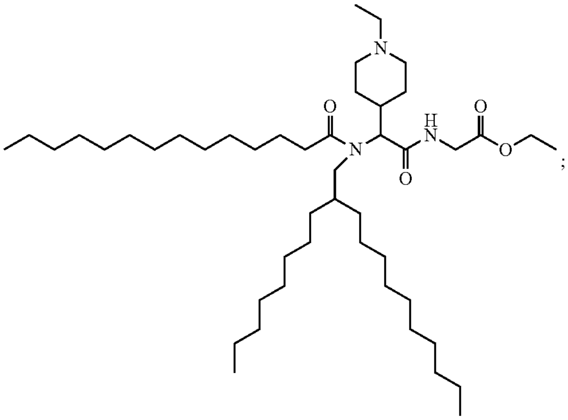
;
(Ivs)
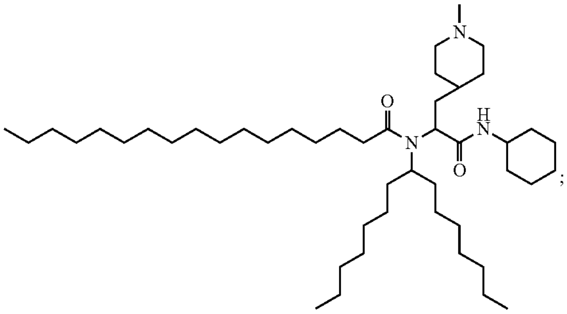
;
(Ivt)
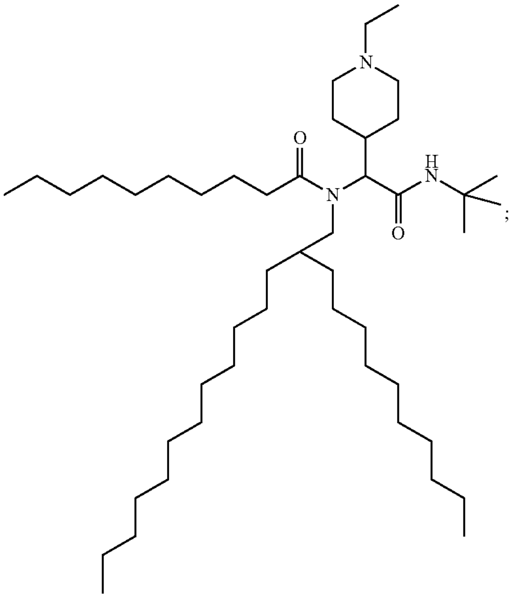
;
(Ivu)
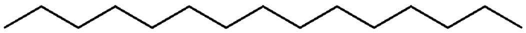

-continued
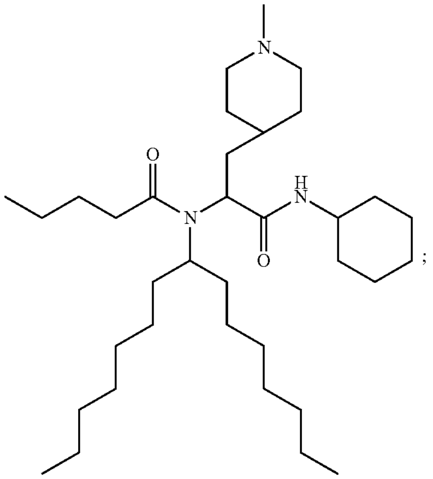
(Ivv)
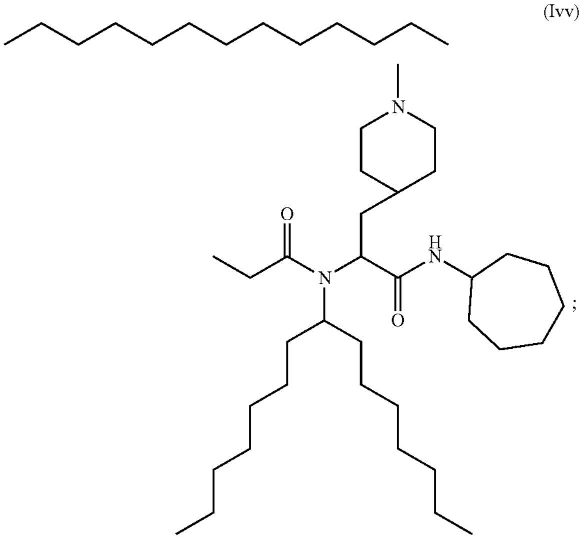
(Ivw)
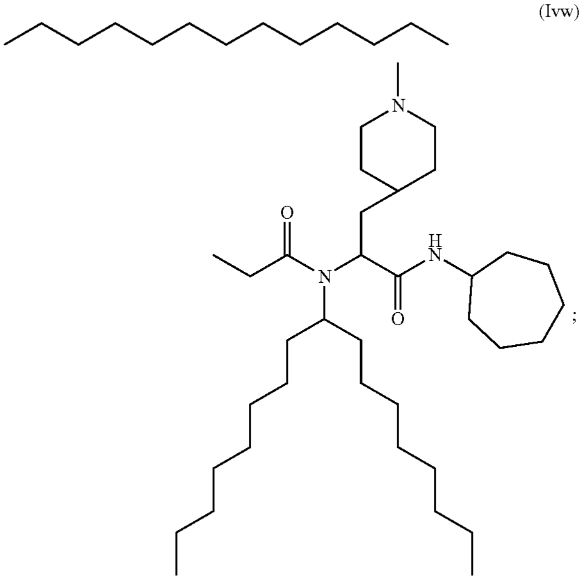
-continued
(Ivx)
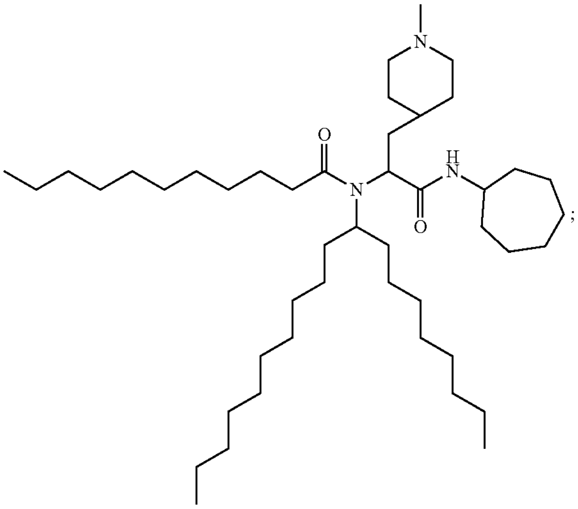
(Ivy)
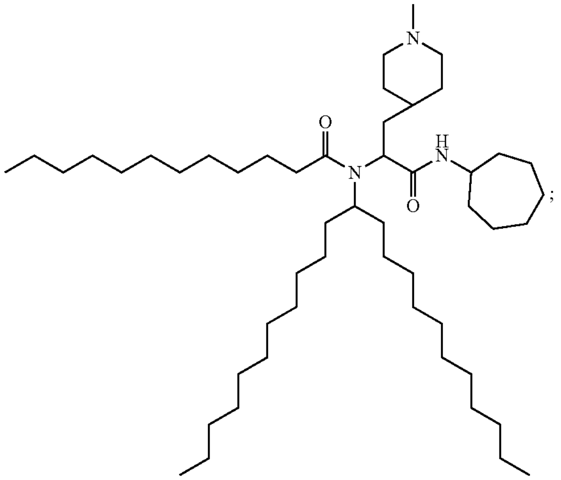
(Ivz)
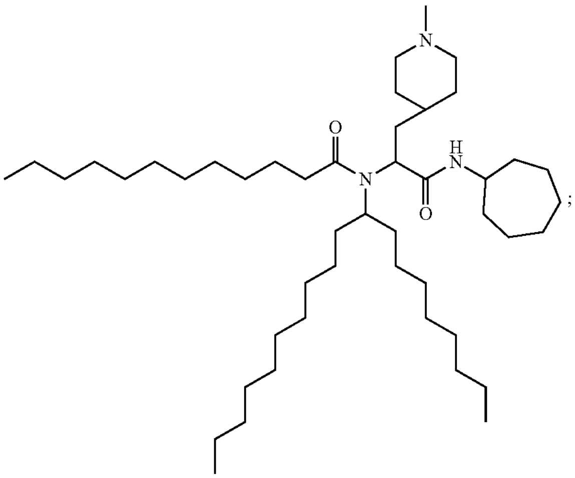

-continued
(Ivaa)
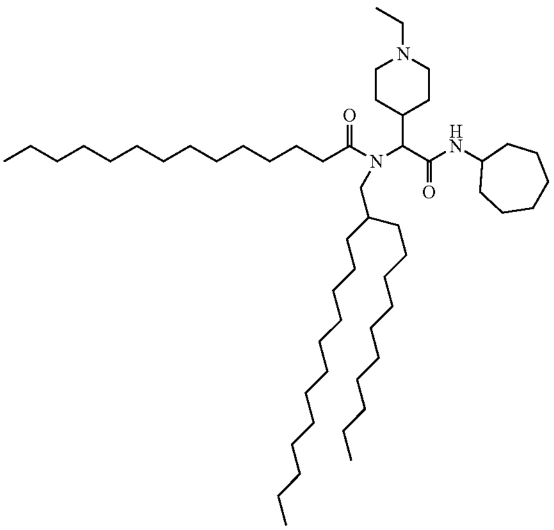
;
(Ivab)
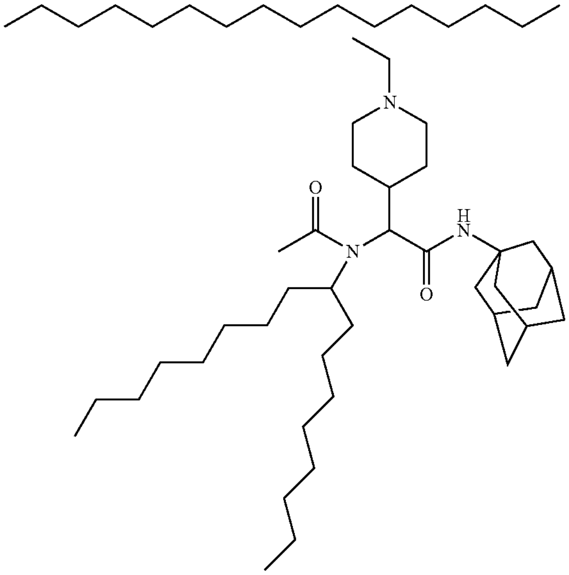
;
(Ivac)
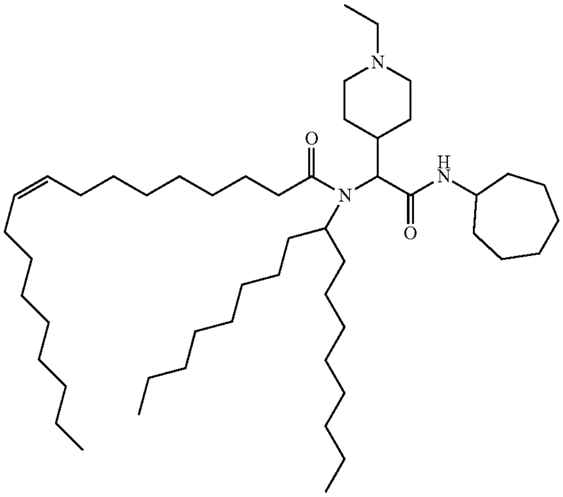
;
-continued
(Ivad)
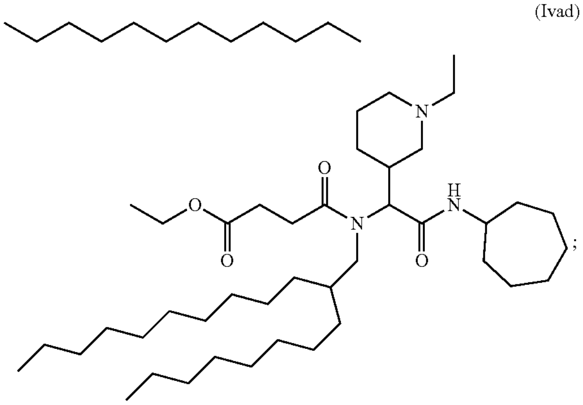
;
(Va)
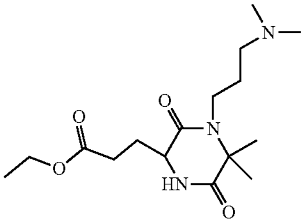
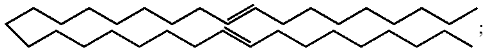
;
(Vb)
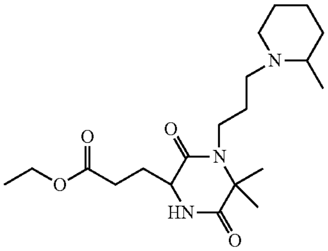
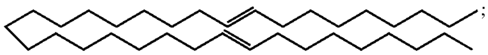
;
(VIa)
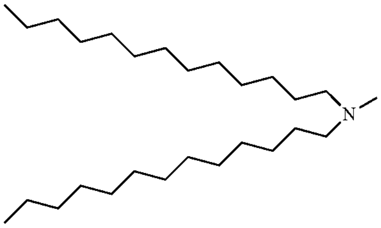

-continued
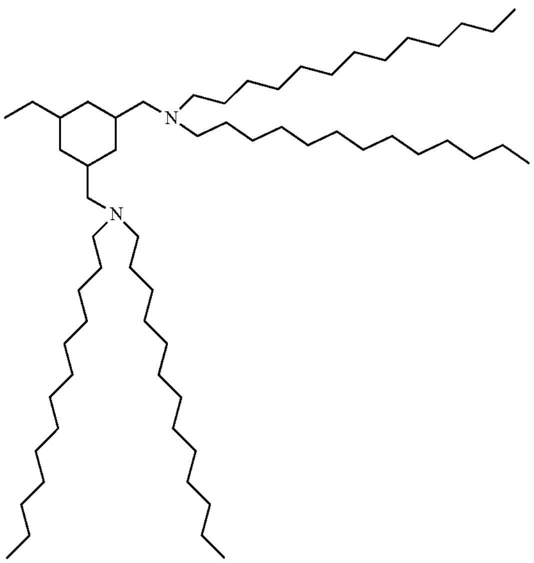
;
(Vib)
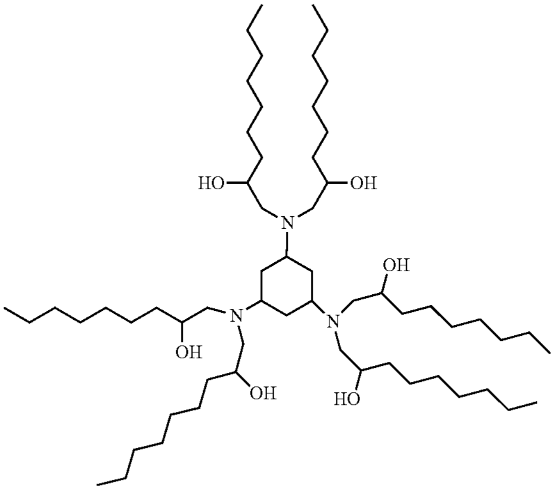
;
(VIc)
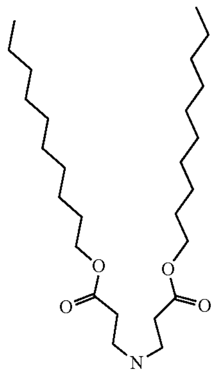
-continued
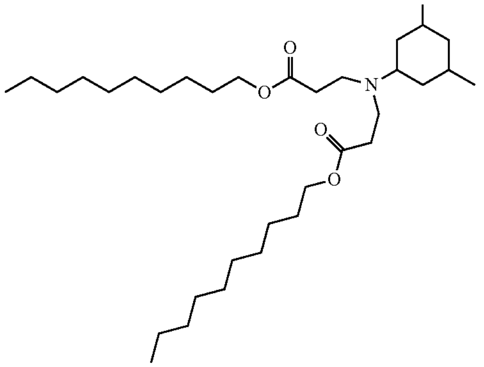
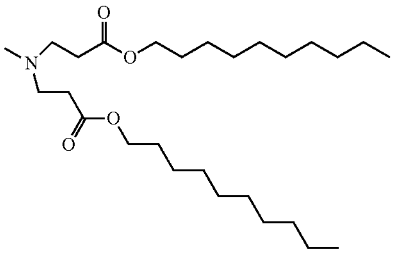
;
(VIIa)
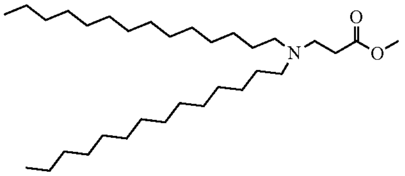
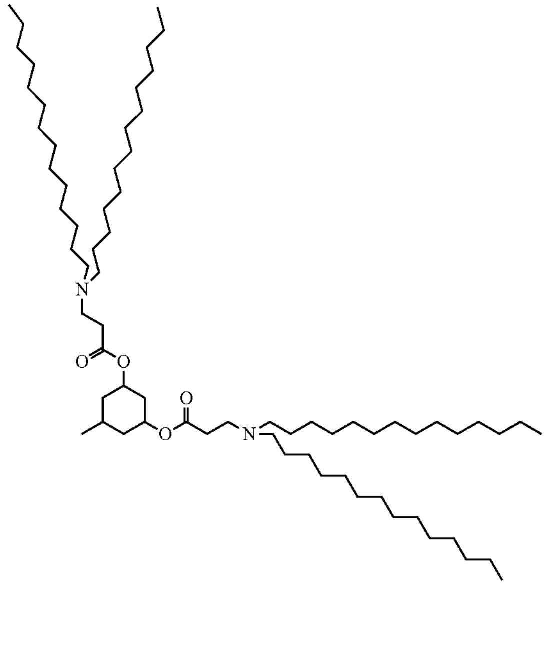
;

-continued (VIIb)

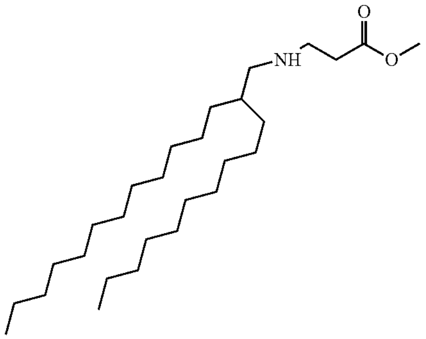

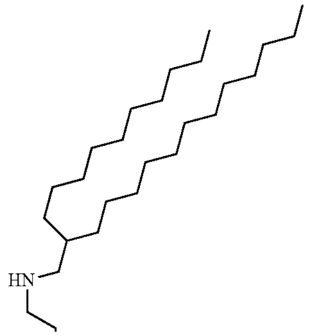

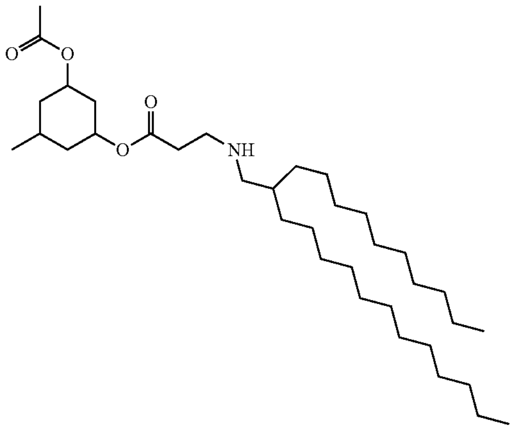

;

or a salt or isomer thereof.

2. The compound of claim 1, wherein the compound is IVr.

3. The compound of claim 1, wherein the compound is IVh.

4. The compound of claim 1, wherein the compound is IIa.

5. The compound of claim 1, wherein the compound is IIb.

6. The compound of claim 1, wherein the compound is Ia.

7. A compound of Formula IV-1

IV-1

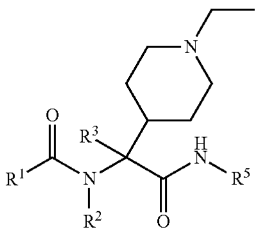

or a salt or isomer thereof, wherein each $R^1$, $R^2$, and $R^5$ is independently selected from $C_3$-$C_{24}$ alkyl, $C_3$-$C_{24}$ alkenyl, $C_3$-$C_{24}$ alkynyl, substituted alkenyl, substituted alkynyl, acyl, substituted carbocyclyl, heterocyclyl, aryl, heteroaryl, and

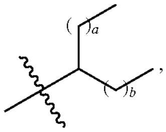,
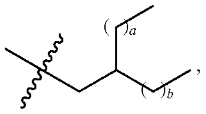,
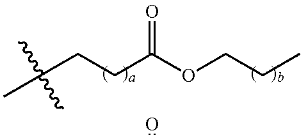,
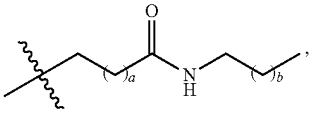,
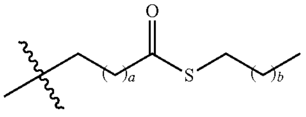,
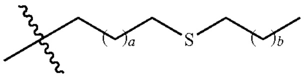,
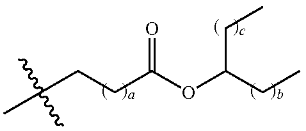,
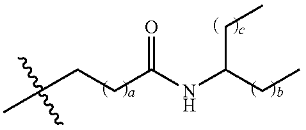,
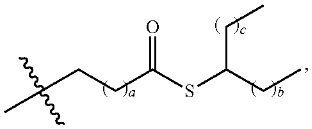,
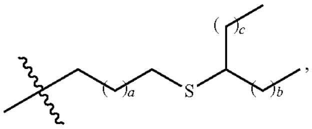,
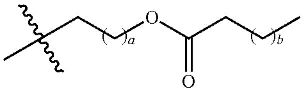, -continued
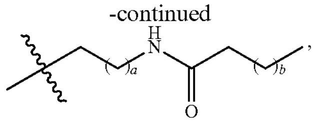
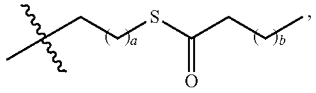
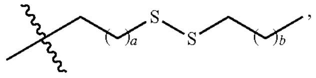
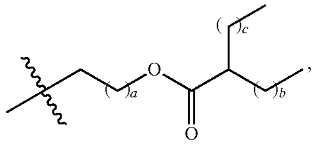
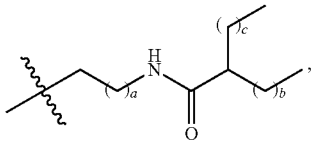
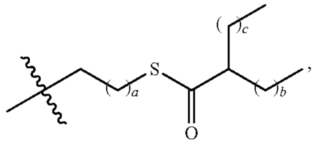
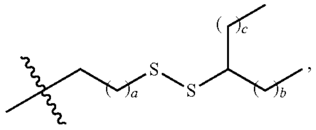
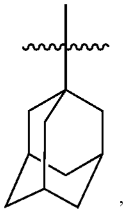
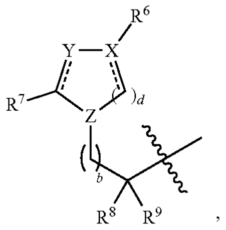
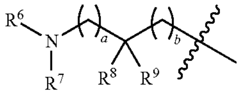
a, b and c are each independently an integer from 0-24, and
d is an integer from 0-10, wherein when $R^5$ is
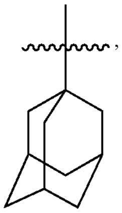
then $R^2$ is selected from $C_3$-$C_{22}$ alkyl, $C_{24}$ alkyl, $C_3$-$C_{24}$ alkenyl, $C_3$-$C_{24}$ alkynyl, substituted $C_3$-$C_{24}$ alkyl, substituted alkenyl, substituted alkynyl, acyl, carbocyclyl, heterocyclyl, aryl, heteroaryl, and
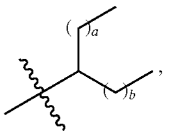
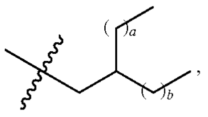
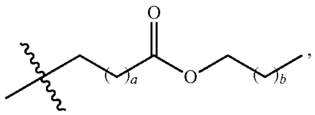
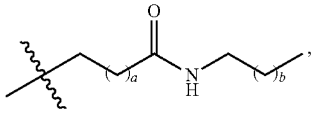
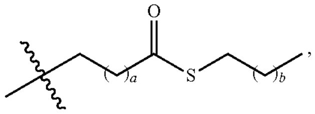
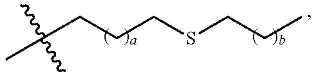
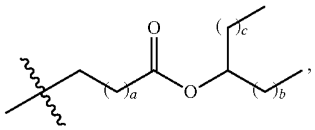
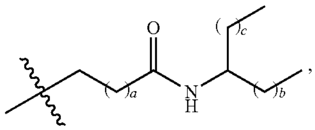
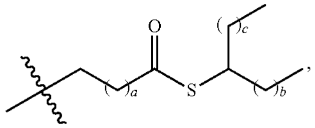
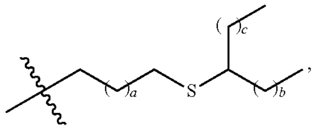
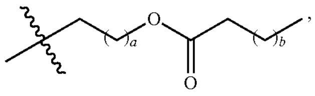
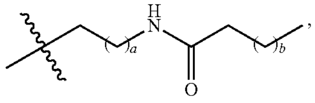
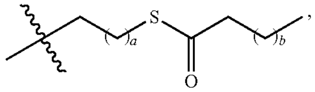
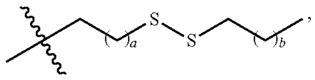
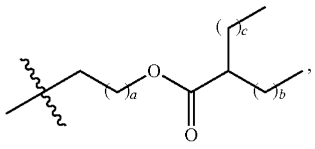

-continued
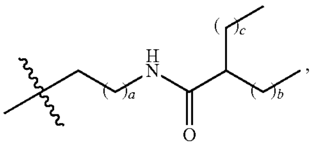
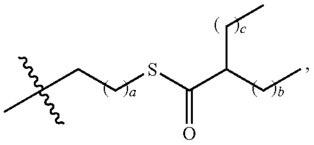
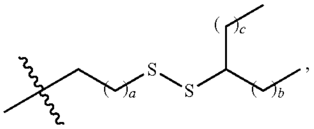
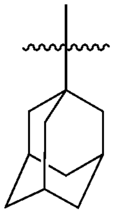
,
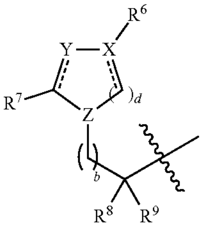
,
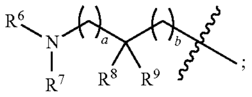
$R^3$ is independently selected from H, $C_3$-$C_{24}$ alkyl, $C_3$-$C_{24}$ alkenyl, $C_3$-$C_{24}$ alkynyl, substituted alkenyl, substituted alkynyl, acyl, carbocyclyl, heterocyclyl, aryl, heteroaryl, and
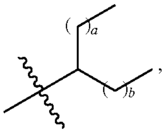
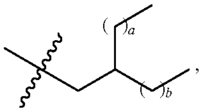
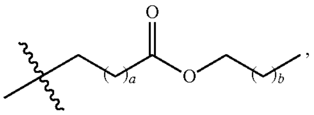
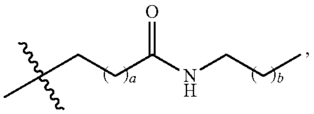
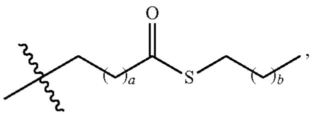
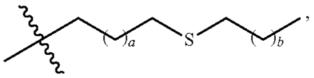
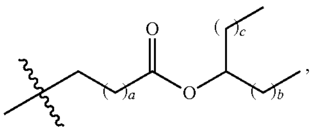
-continued
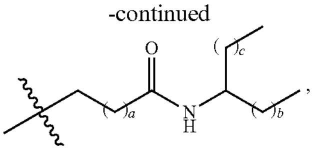
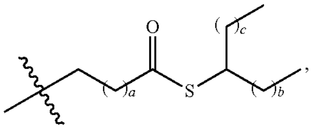
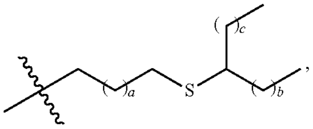
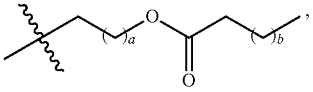
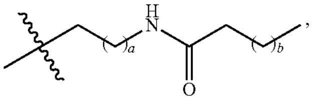
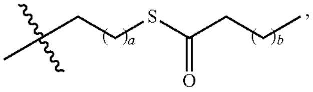
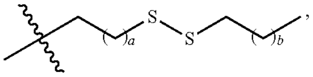
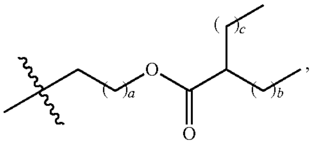
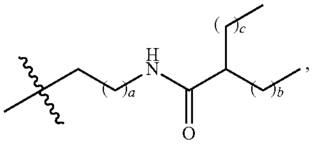
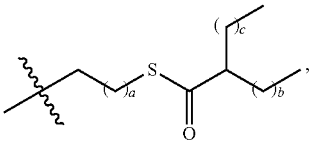
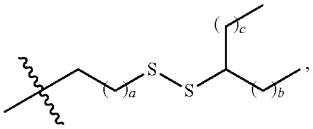
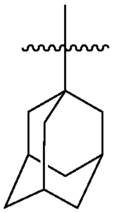
,
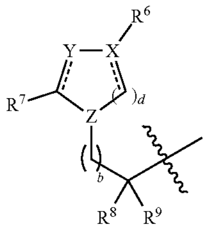
,
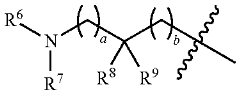

a, b and c are each independently an integer from 0-24, and d is an integer from 0-10;

each $R^6$, $R^7$, $R^8$ and $R^9$ is independently selected from H, $C_1$-$C_{24}$ alkyl, $C_2$-$C_{24}$ alkenyl, $C_2$-$C_{24}$ alkynyl, substituted alkyl, substituted alkenyl, substituted alkynyl, acyl, carbocyclyl, heterocyclyl, aryl, heteroaryl,

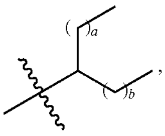,
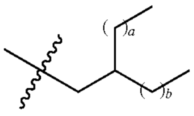,

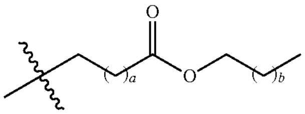,

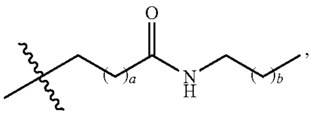,

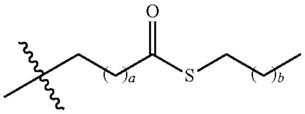,

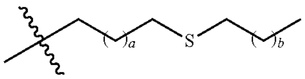,

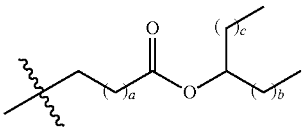,

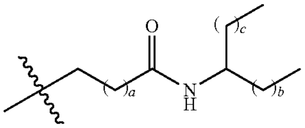,

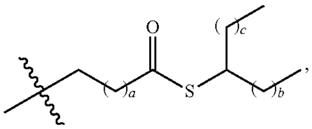,

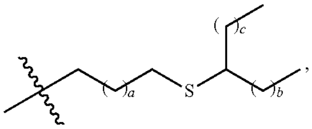,

-continued

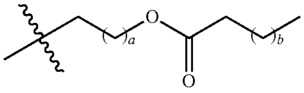,

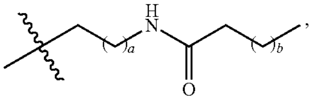,

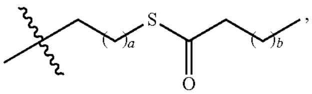,

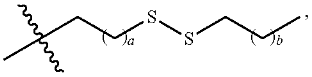,

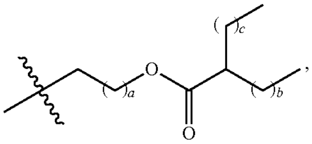,

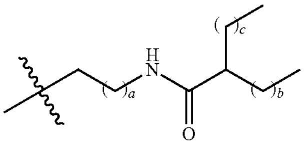,

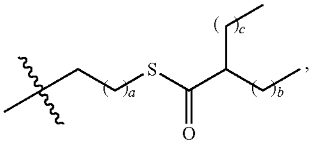,

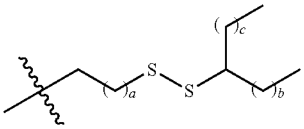,

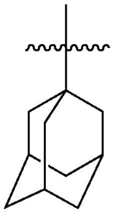, a, b and c are each independently an integer from 0-24;

each X is independently selected from CH, or N;

each Y is independently selected from $CH_2$, NH, O, or S;

each Z is independently selected from CH or N.

8. A nanoparticle composition comprising the compound of claim 7 and a biologically active agent, a phospholipid, a steroid, a polyethylene glycol (PEG) lipid, or a combination thereof.

9. The compound of claim 7, wherein the compound is

IVe

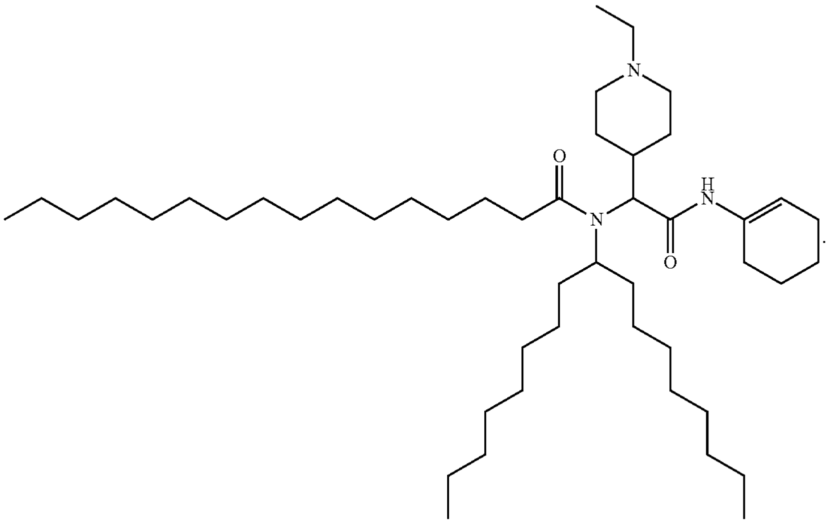

10. A nanoparticle composition comprising the compound of claim 9 and a biologically active agent, a phospholipid, a steroid, a polyethylene glycol (PEG) lipid, or a combination thereof.

11. A compound of Formula IV-2

IV-2

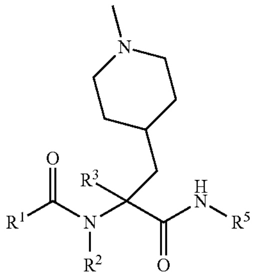

or a salt or isomer thereof, wherein each $R^1$, $R^2$ and $R^5$ is independently selected from $C_3$-$C_{24}$ alkyl, $C_3$-$C_{24}$ alkenyl, $C_3$-$C_{24}$ alkynyl, substituted alkenyl, substituted alkynyl, acyl, carbocyclyl, heterocyclyl, aryl, heteroaryl, and

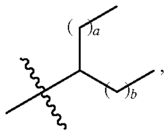,
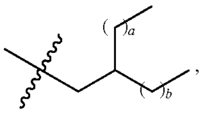,
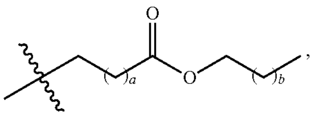,
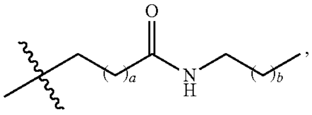,

-continued

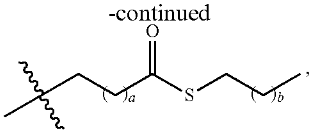,
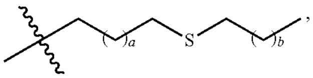,
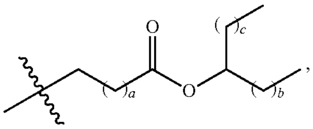,
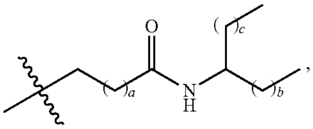,
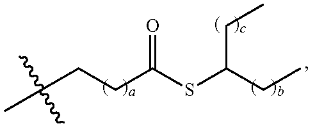,
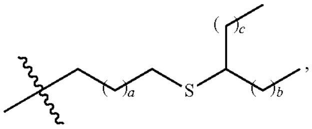,
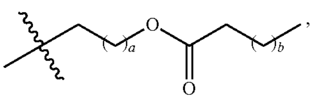,
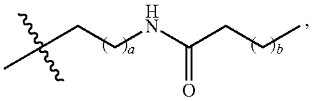,
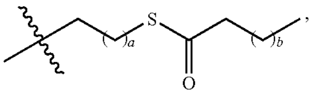, -continued
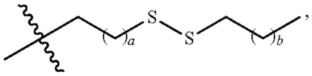
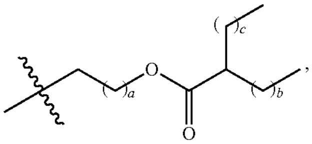
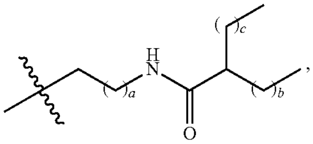
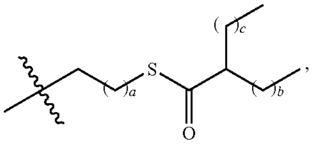
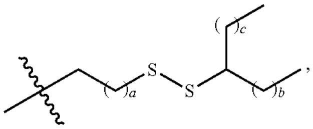
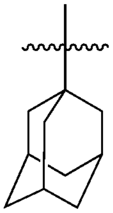
,
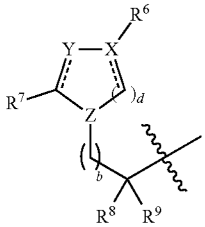
,
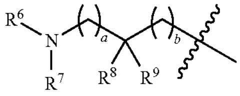
a, b and c are each independently an integer from 0-24, and
d is an integer from 0-10, wherein when $R^5$ is
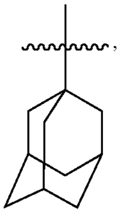 [SMILES: *C12CC3CC(CC(C3)C1)C2]
then $R^2$ is selected from $C_3$-$C_{18}$ alkyl, $C_{20}$-$C_{24}$ alkyl, $C_3$-$C_{24}$ alkenyl, $C_3$-$C_{24}$ alkynyl, substituted $C_2$-$C_{24}$ alkyl, substituted alkenyl, substituted alkynyl, acyl, carbocyclyl, heterocyclyl, aryl, heteroaryl, and
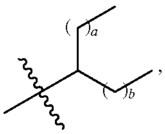
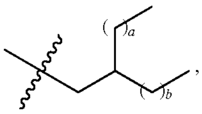
-continued
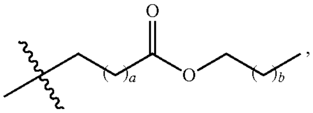
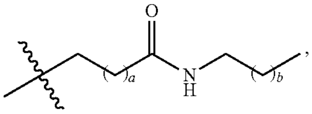
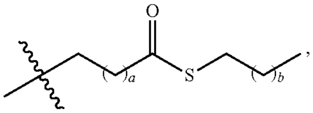
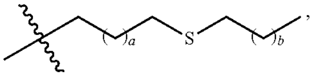
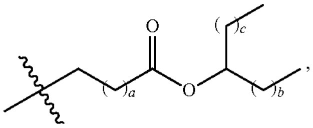
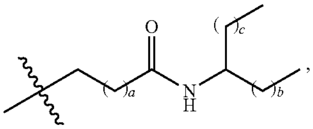
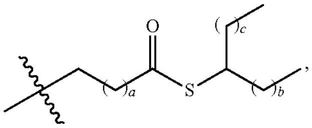
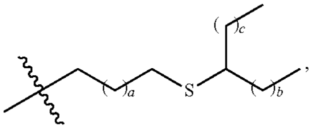
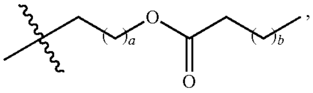
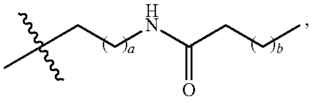
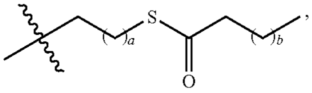
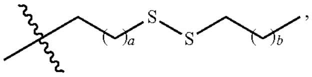
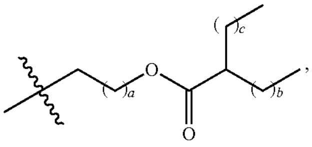
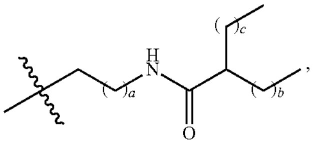

-continued

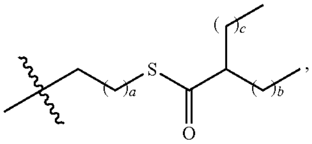

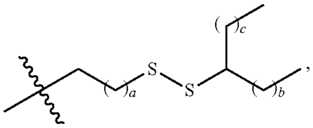

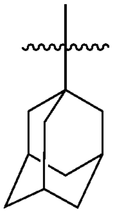

,

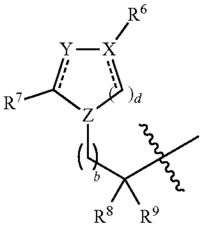

,

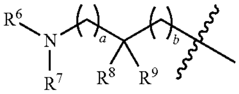

;

$R^3$ is independently selected from H, $C_3$-$C_{24}$ alkyl, $C_3$-$C_{24}$ alkenyl, $C_3$-$C_{24}$ alkynyl, substituted alkenyl, substituted alkynyl, acyl, carbocyclyl, heterocyclyl, aryl, heteroaryl, and

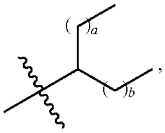

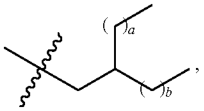

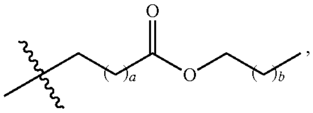

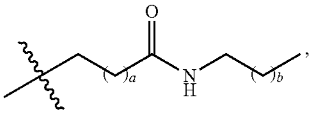

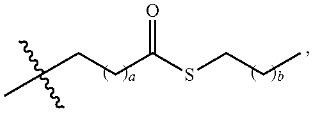

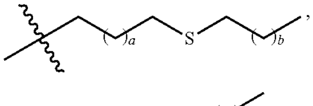

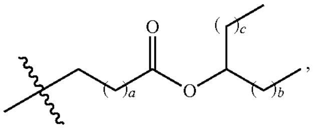

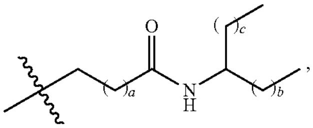

-continued

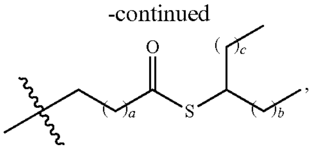

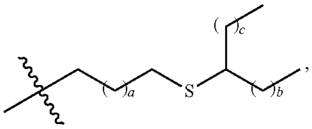

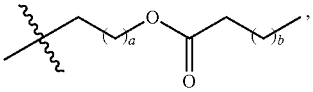

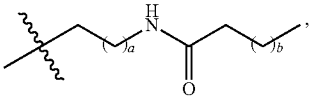

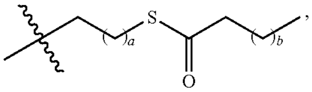

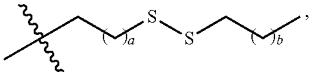

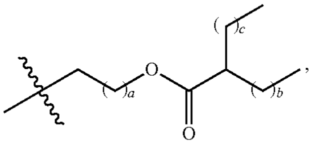

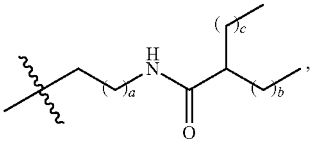

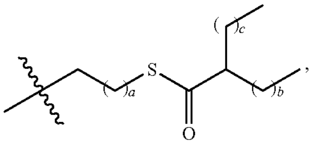

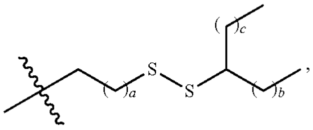

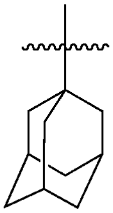

,

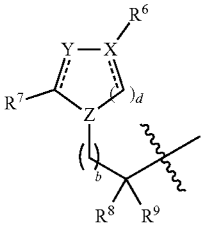

,

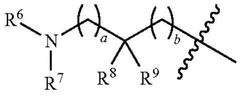

a, b and c are each independently an integer from 0-24, and d is an integer from 0-10;

each $R^6$, $R^7$, $R^8$ and $R^9$ is independently selected from H, $C_1$-$C_{24}$ alkyl, $C_2$-$C_{24}$ alkenyl, $C_2$-$C_{24}$ alkynyl, substituted alkyl, substituted alkenyl, substituted alkynyl, acyl, carbocyclyl, heterocyclyl, aryl, heteroaryl,

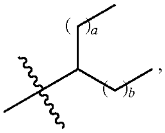
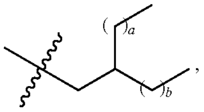
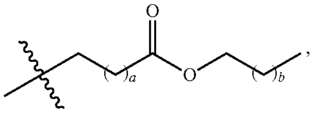
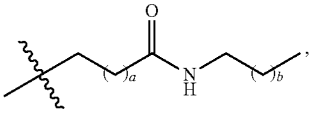
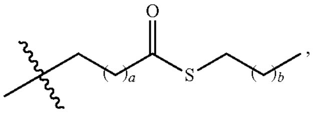
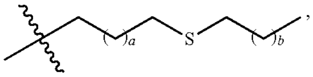
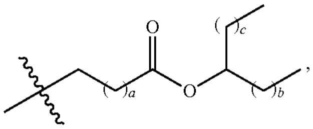
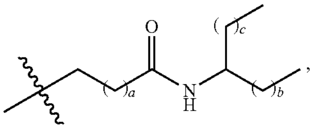
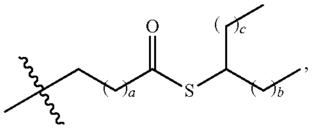
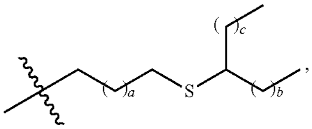
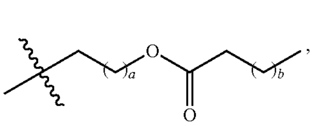
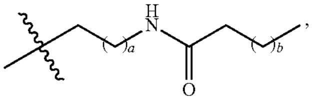
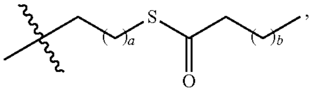
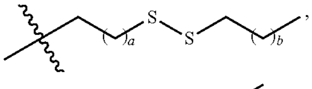
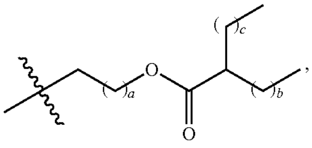

-continued

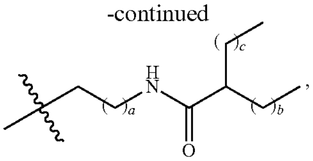
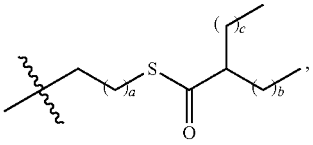
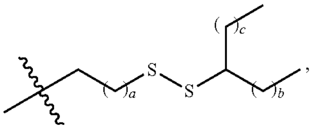
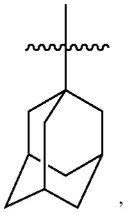

a, b and c are each independently an integer from 0-24;

each X is independently selected from CH, or N;

each Y is independently selected from $CH_2$, NH, O, or S;

each Z is independently selected from CH or N.

12. A nanoparticle composition comprising the compound of claim 11 and a biologically active agent, a phospholipid, a steroid, a polyethylene glycol (PEG) lipid, or a combination thereof.

13. A compound of Formula IV-3

IV-3

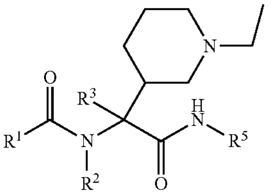

or a salt or isomer thereof, wherein each $R^1$, $R^2$, and $R^5$ is independently selected from $C_3$-$C_{24}$ alkyl, $C_3$-$C_{24}$ alkenyl, $C_3$-$C_{24}$ alkynyl, substituted alkenyl, substituted alkynyl, acyl, carbocyclyl, heterocyclyl, aryl, heteroaryl, and

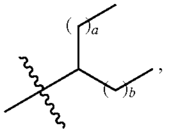
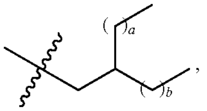
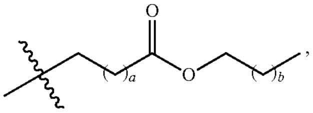

-continued
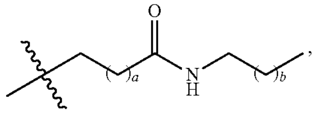
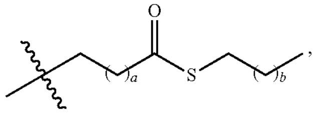
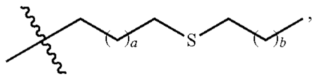
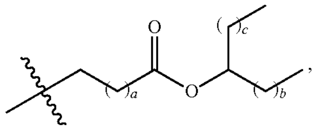
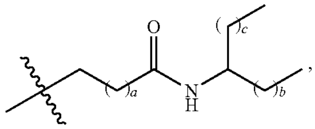
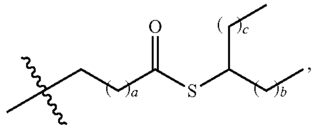
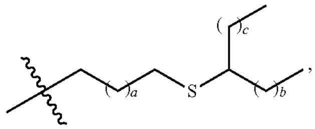
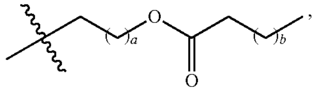
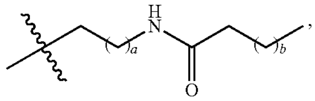
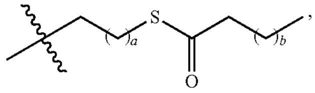
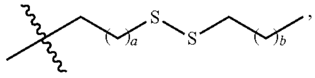
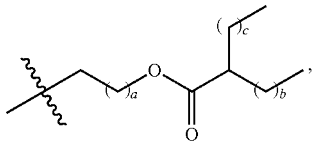
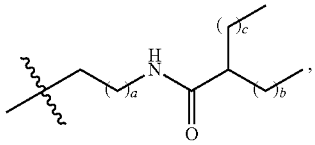
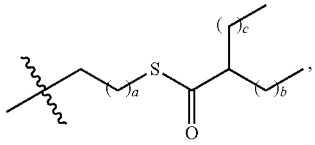
-continued
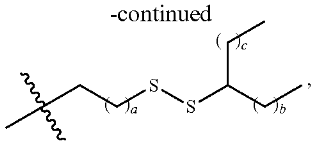
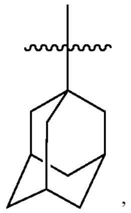
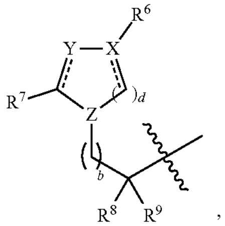
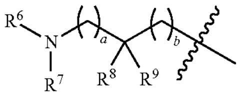
a, b and c are each independently an integer from 0-24, and
d is an integer from 0-10, wherein when $R^5$ is
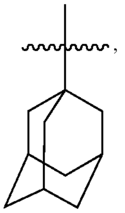 [SMILES: *C12CC3CC(CC(C3)C1)C2]
then $R^2$ is selected from $C_3$-$C_{18}$ alkyl, $C_{20}$-$C_{24}$ alkyl, $C_3$-$C_{24}$ alkenyl, $C_3$-$C_{24}$ alkynyl, substituted $C_3$-$C_{24}$ alkyl, substituted alkenyl, substituted alkynyl, acyl, carbocyclyl, heterocyclyl, aryl, heteroaryl, and
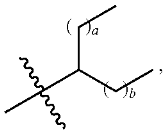
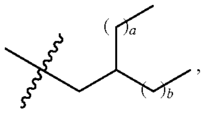
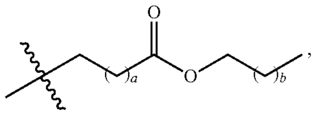
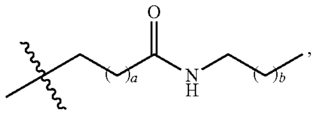
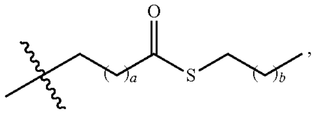
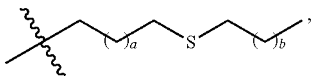
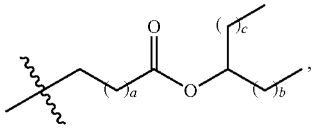

-continued
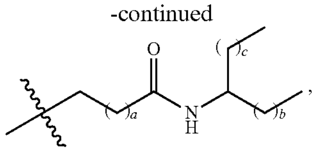
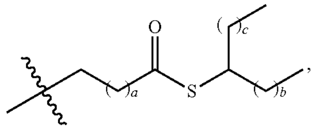
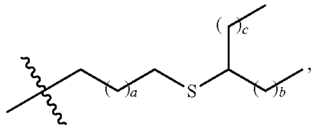
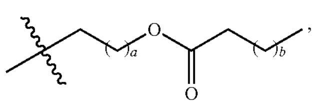
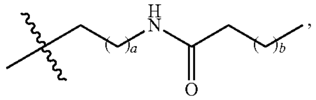
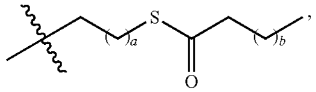
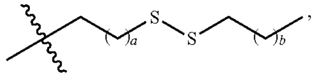
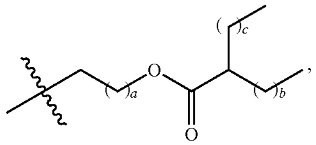
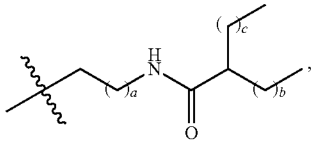
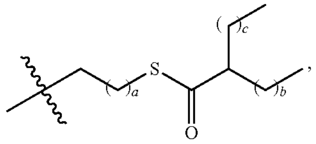
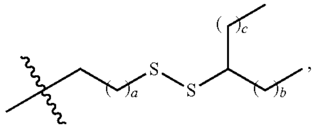
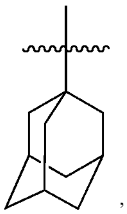
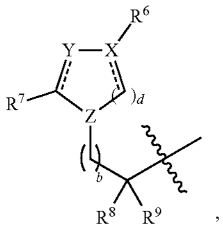
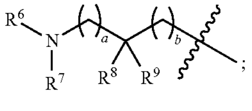
$R^3$ is independently selected from H, $C_3$-$C_{24}$ alkyl, $C_3$-$C_{24}$ alkenyl, $C_3$-$C_{24}$ alkynyl, substituted alkenyl, alkynyl, acyl, carbocyclyl, heterocyclyl, aryl, heteroaryl, and
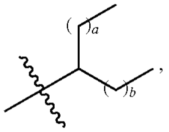
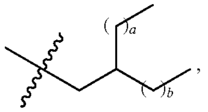
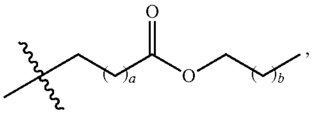
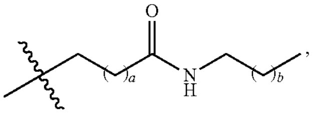
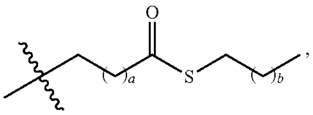
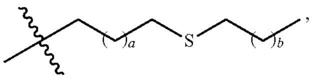
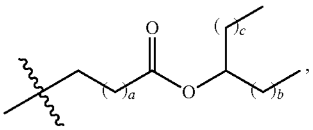
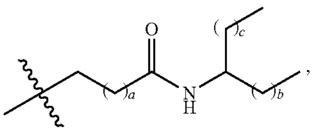
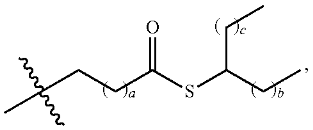
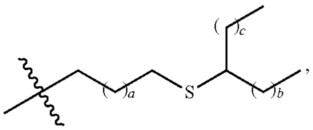
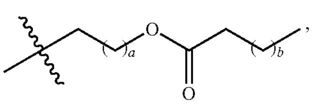
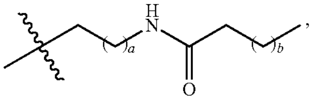
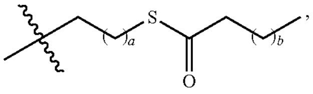
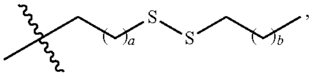

-continued
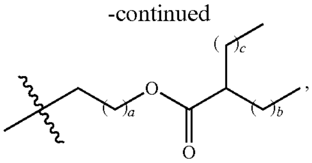,
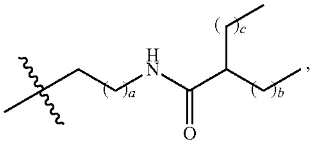,
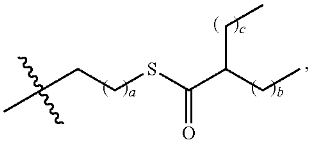,
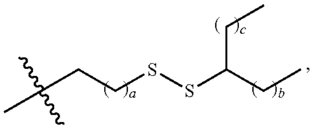,
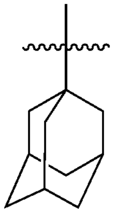,
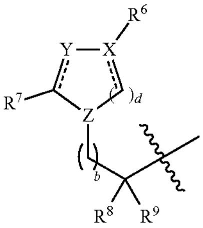,
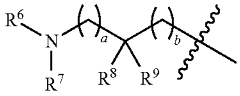
a, b and c are each independently an integer from 0-24, and
d is an integer from 0-10;
each $R^6$, $R^7$, $R^8$ and $R^9$ is independently selected from H, $C_1$-$C_{24}$ alkyl, $C_2$-$C_{24}$ alkenyl, $C_2$-$C_{24}$ alkynyl, substituted alkyl, substituted alkenyl, substituted alkynyl, acyl, carbocyclyl, heterocyclyl, aryl, heteroaryl,
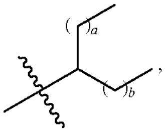,
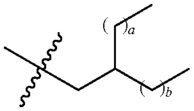,
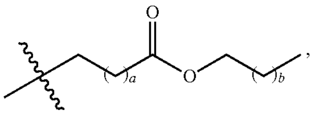,
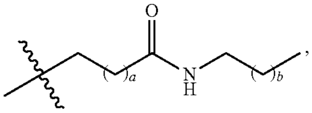,
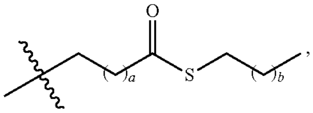,
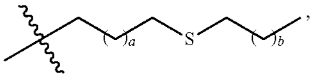,
-continued
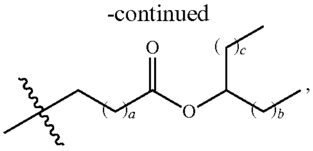,
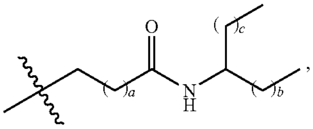,
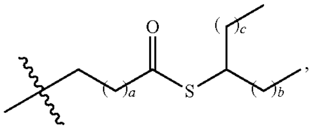,
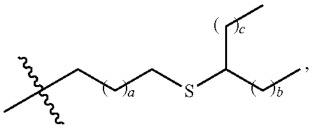,
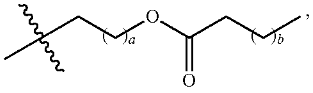,
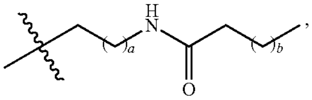,
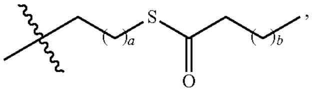,
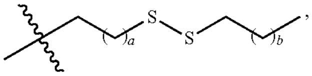,
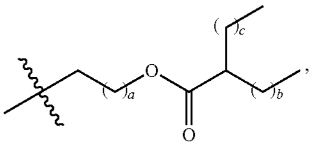,
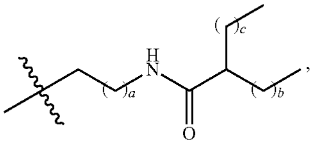,
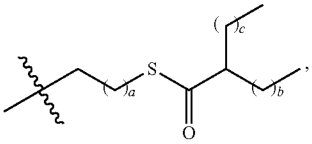,
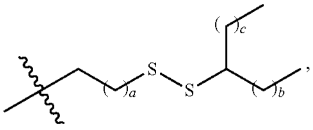,
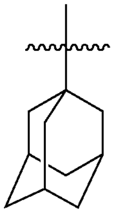, a, b and c are each independently an integer from 0-24;

each X is independently selected from CH, or N;

each Y is independently selected from $CH_2$, NH, O, or S;

each Z is independently selected from CH or N.

14. A nanoparticle composition comprising the compound of claim 13 and a biologically active agent, a phospholipid, a steroid, a polyethylene glycol (PEG) lipid, or a combination thereof.

15. A compound of Formula IV-4

IV-4

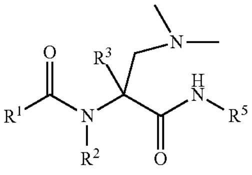

or a salt or isomer thereof, wherein each $R^1$ and $R^5$ is independently selected from $C_3$-$C_{24}$ alkyl, $C_3$-$C_{24}$ alkenyl, $C_3$-$C_{24}$ alkynyl, substituted alkenyl, substituted alkynyl, acyl, carbocyclyl, heterocyclyl, aryl, heteroaryl, and

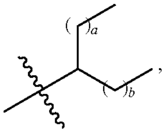
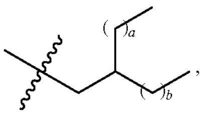
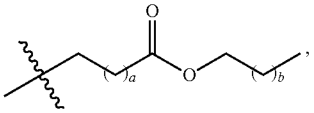
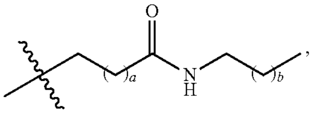
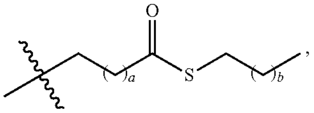
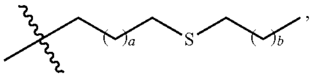
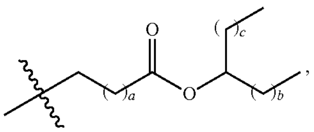
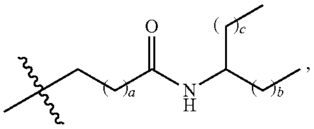
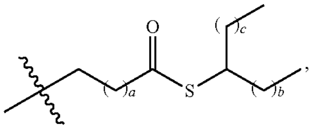

-continued

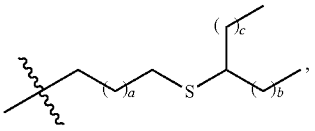
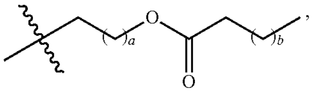
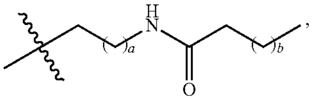
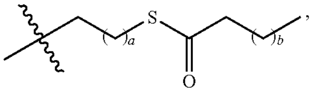
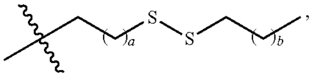
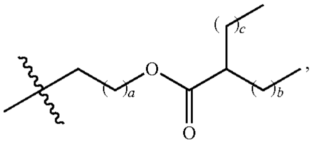
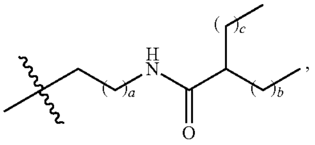
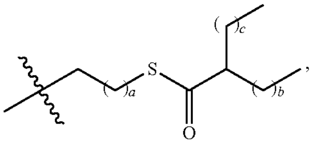
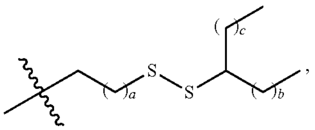
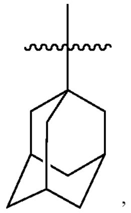
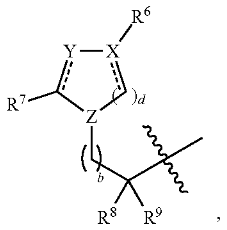
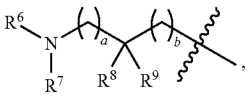

a, b and c are each independently an integer from 0-24, and d is an integer from 0-10;

each $R^2$ is $C_3$-$C_{24}$ alkenyl, $C_3$-$C_{24}$ alkynyl, substituted alkenyl, substituted alkynyl, acyl, carbocyclyl, heterocyclyl, aryl, heteroaryl,

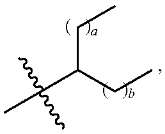
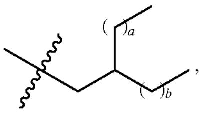
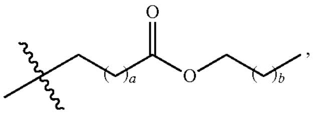
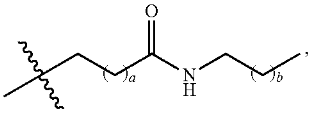
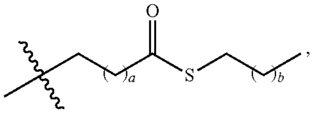
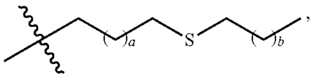
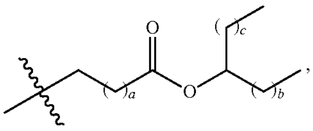
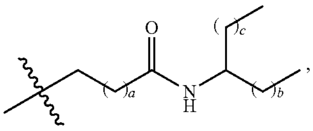
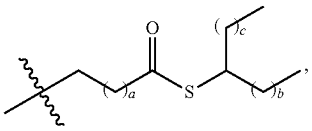
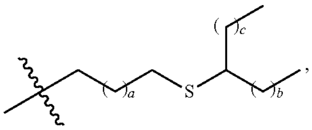
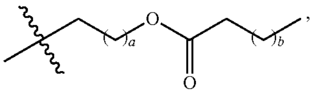
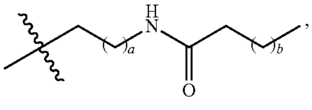
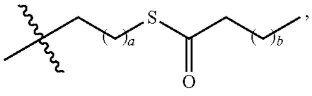
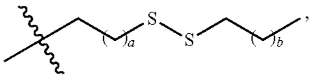
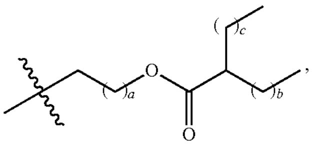
-continued
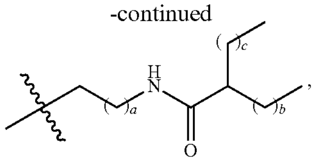
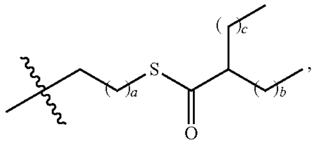
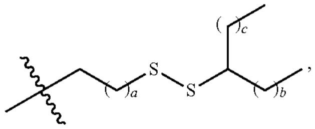
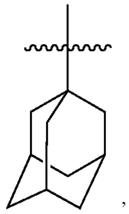
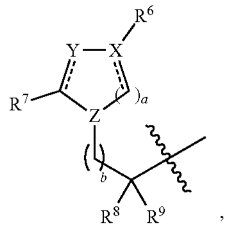
a, b and c are each independently an integer from 0-24, and
d is an integer from 0-10;
$R^3$ is independently selected from H, $C_3$-$C_{24}$ alkyl, $C_3$-$C_{24}$ alkenyl, $C_3$-$C_{24}$ alkynyl, substituted alkenyl, substituted alkynyl, acyl, carbocyclyl, heterocyclyl, aryl, heteroaryl, and
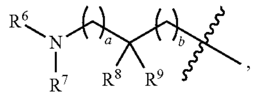
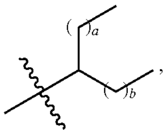
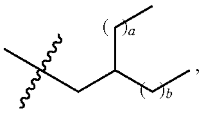
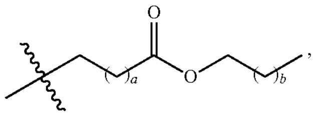
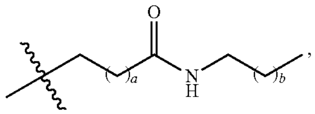
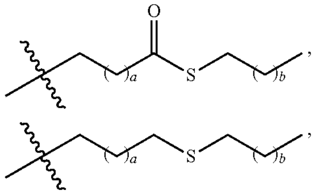
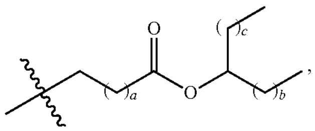

-continued
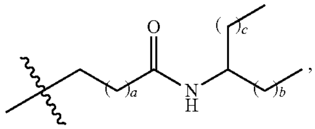
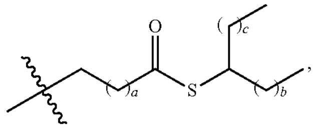
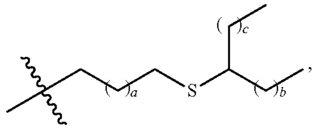
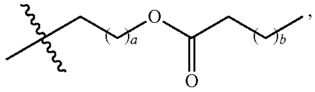
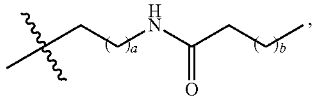
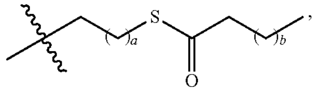
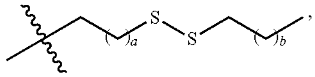
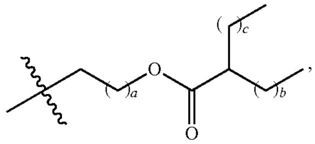
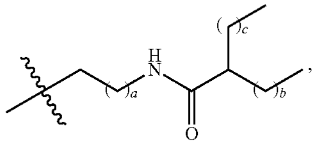
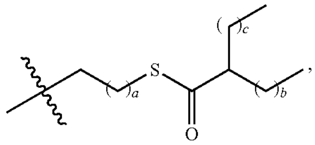
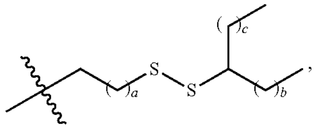
-continued
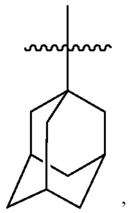
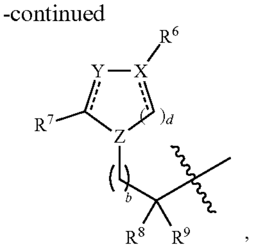
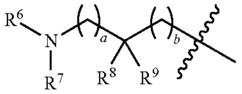
a, b and c are each independently an integer from 0-24, and
d is an integer from 0-10;
each $R^6$, $R^7$, $R^8$ and $R^9$ is independently selected from H, $C_1$-$C_{24}$ alkyl, $C_2$-$C_{24}$ alkenyl, $C_2$-$C_{24}$ alkynyl, substituted alkyl, substituted alkenyl, substituted alkynyl, acyl, carbocyclyl, heterocyclyl, aryl, heteroaryl,
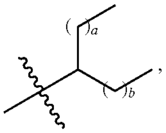
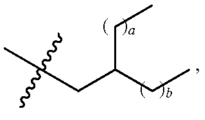
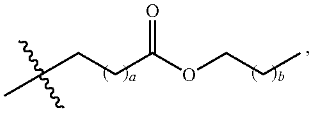
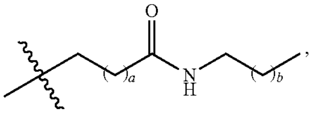
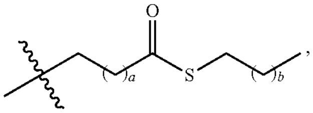
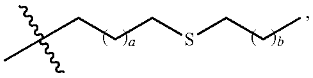
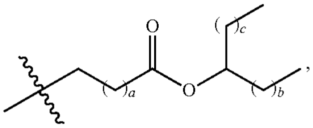
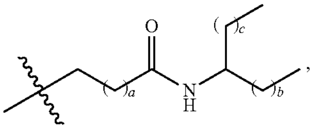
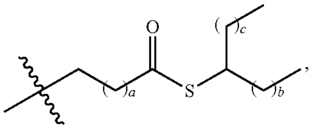
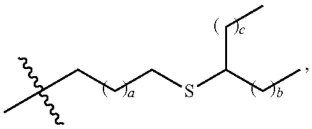

-continued

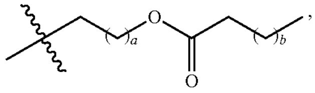

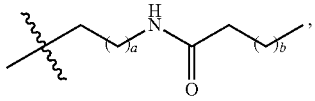

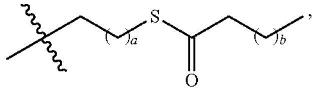

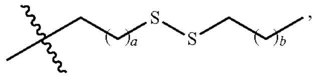

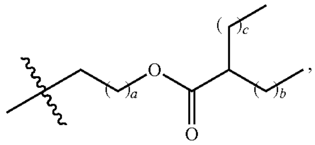

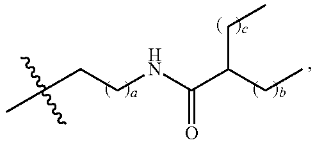

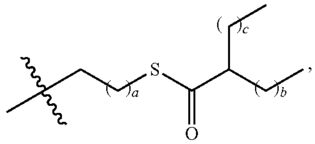

-continued

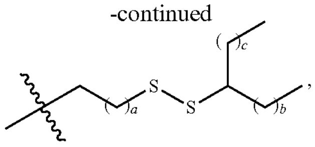

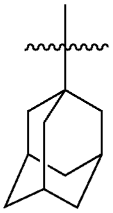

, each X is independently selected from CH, or N;

each Y is independently selected from $CH_2$, NH, O, or S;

each Z is independently selected from CH or N.

16. A nanoparticle composition comprising the compound of claim 15 and a biologically active agent, a phospholipid, a steroid, a polyethylene glycol (PEG) lipid, or a combination thereof.

17. A nanoparticle composition comprising a compound of (Ia)

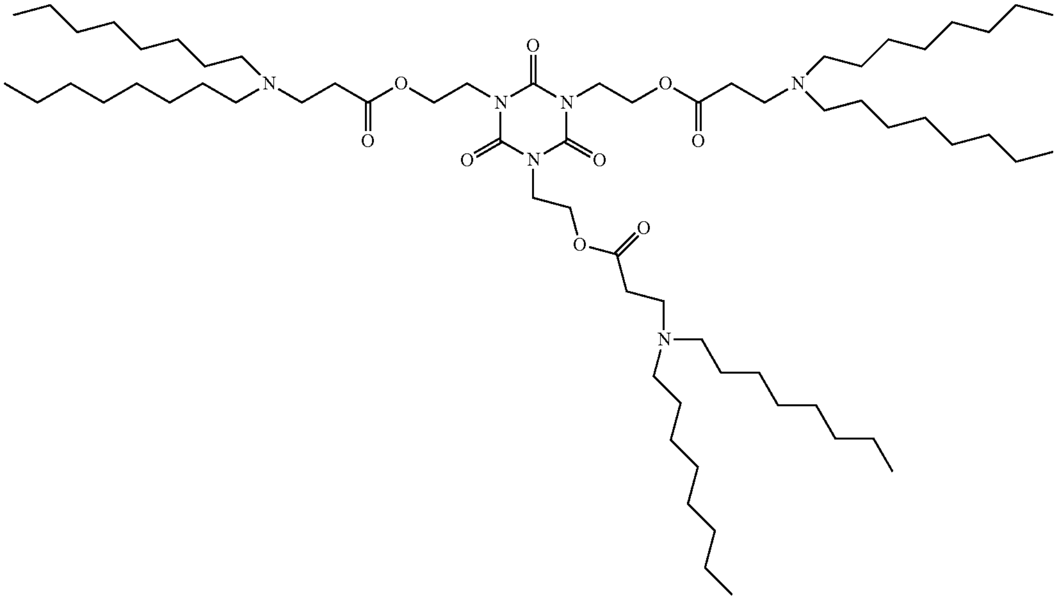

,

-continued
(Ib)
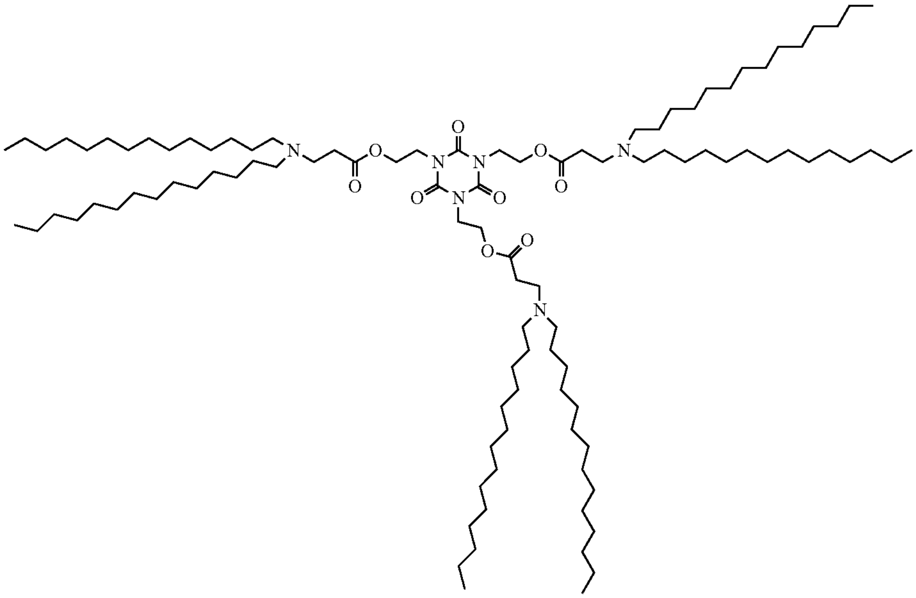
,
(IIa)
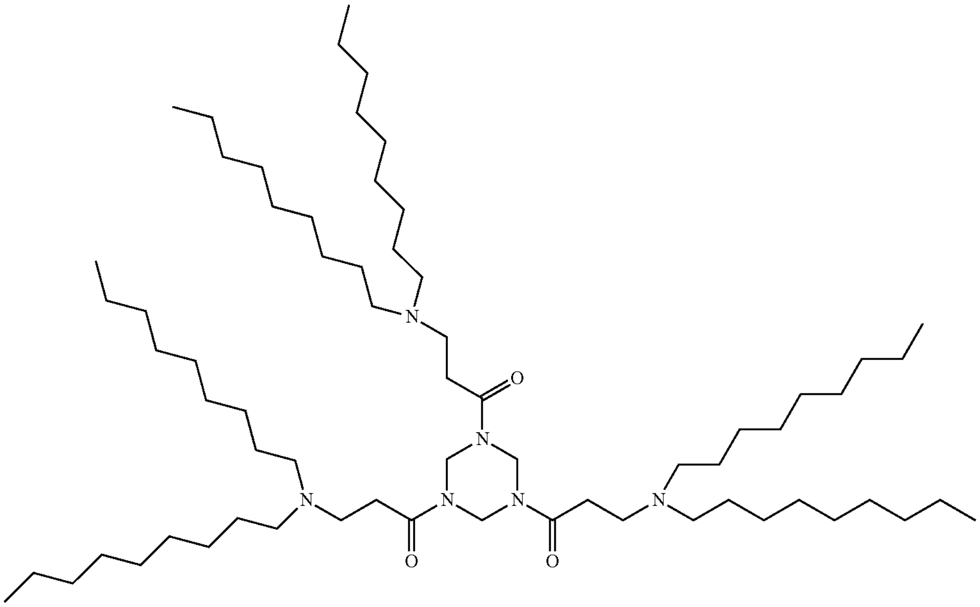
,

-continued
(IIb)
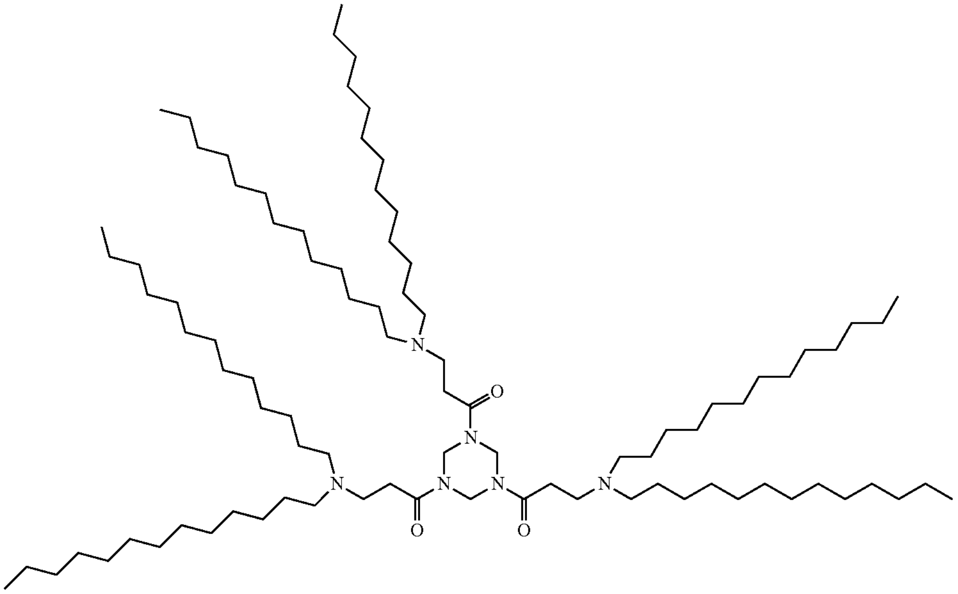
,
(IIIa)
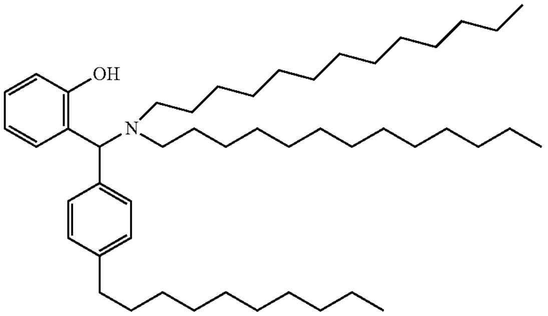
,
(IIIb)
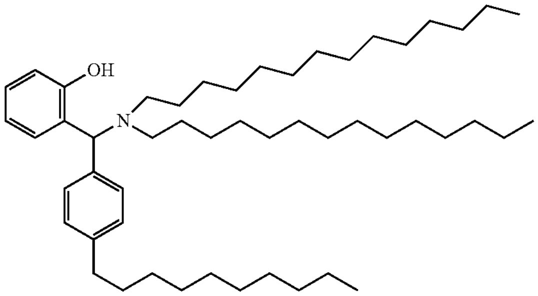
,
(IIIc)
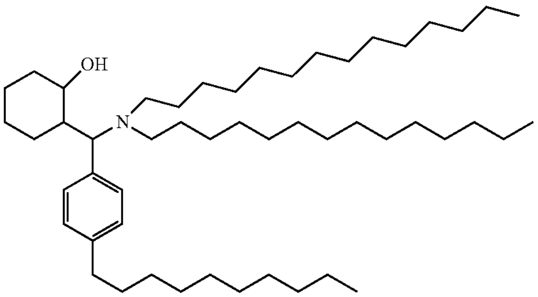
,
(IIId)
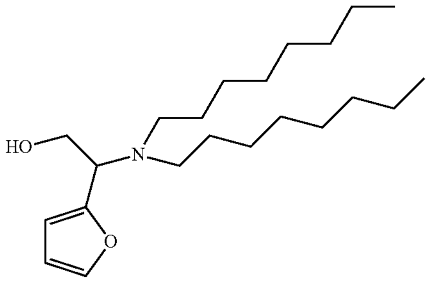
,
(IIIe)
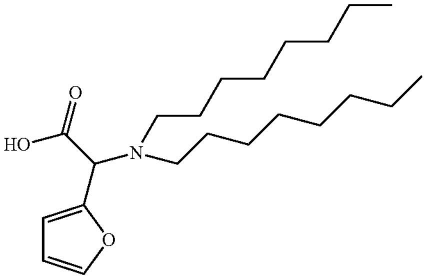
,
(IIIf)
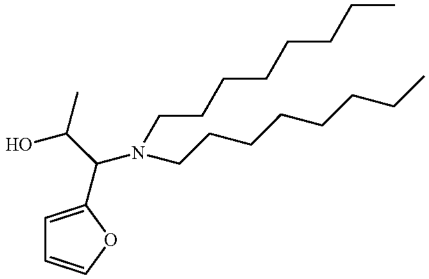
, -continued
(IIIg)
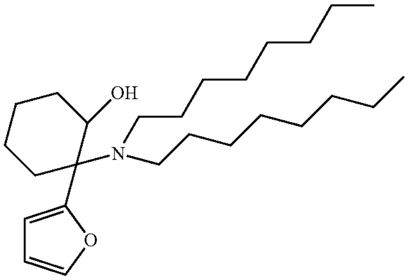
,
(IIIh)
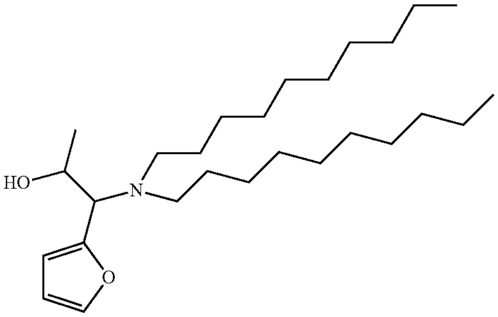
,
(IIIi)
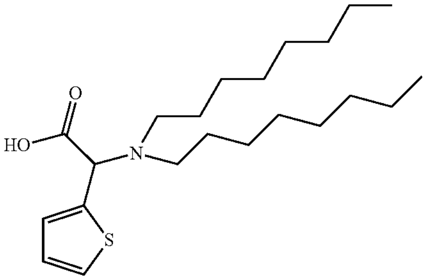
,
(IIIj)
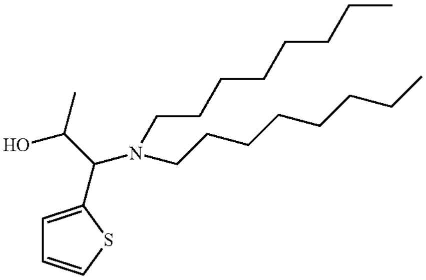
,
(IIIk)
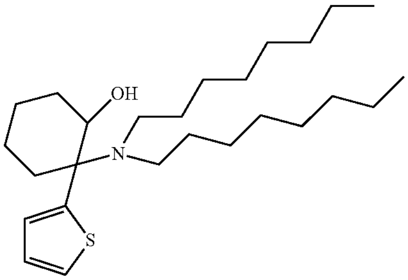
,
(IIIl)
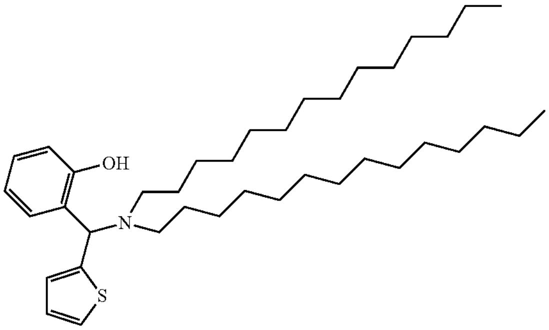
,
(IIIm)
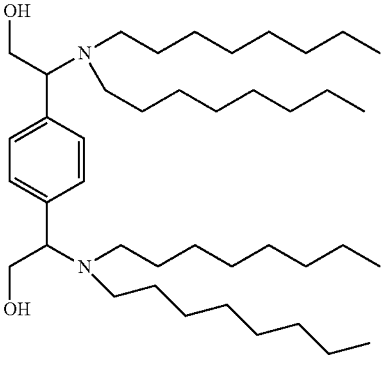
,
(IIIn)
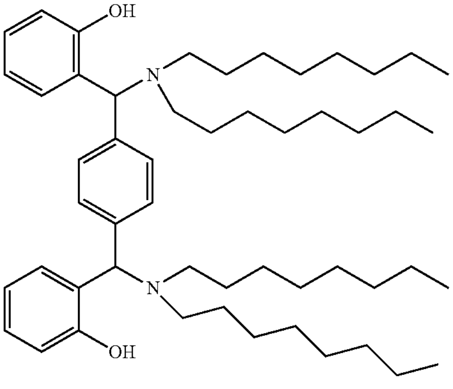
, -continued
(IIIo)
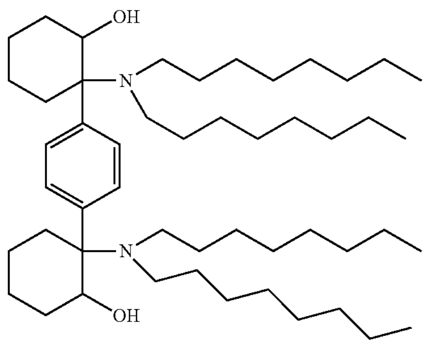
,
(IIIp)
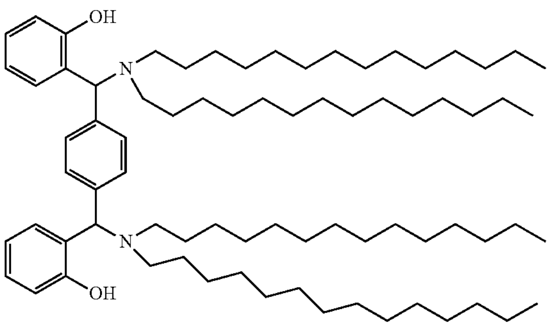
,
(IIIt)
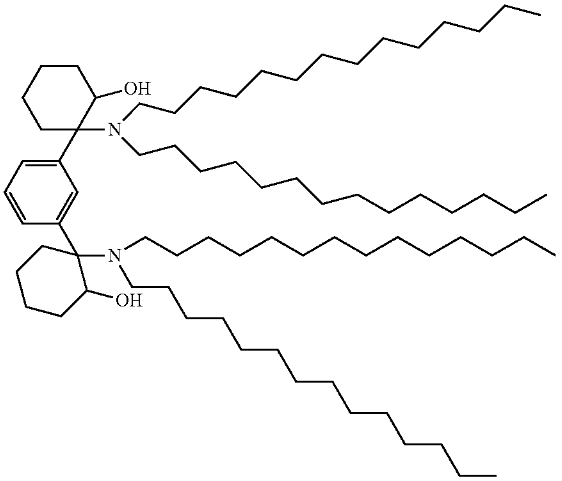
,
(IIIu)
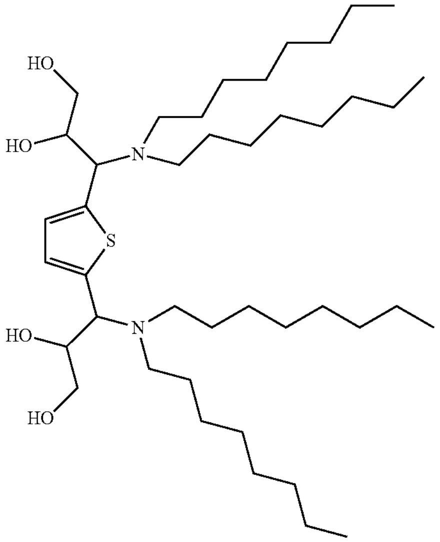
,
(IIIv)
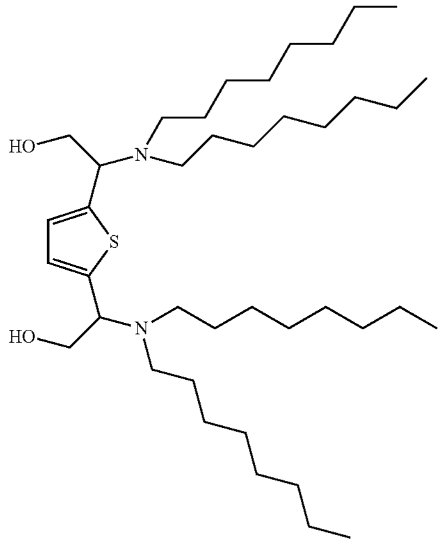
,
(IIIw)
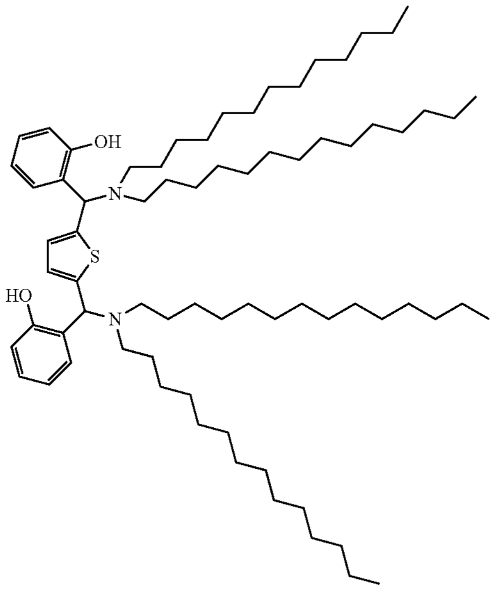
, -continued
(IIIx)
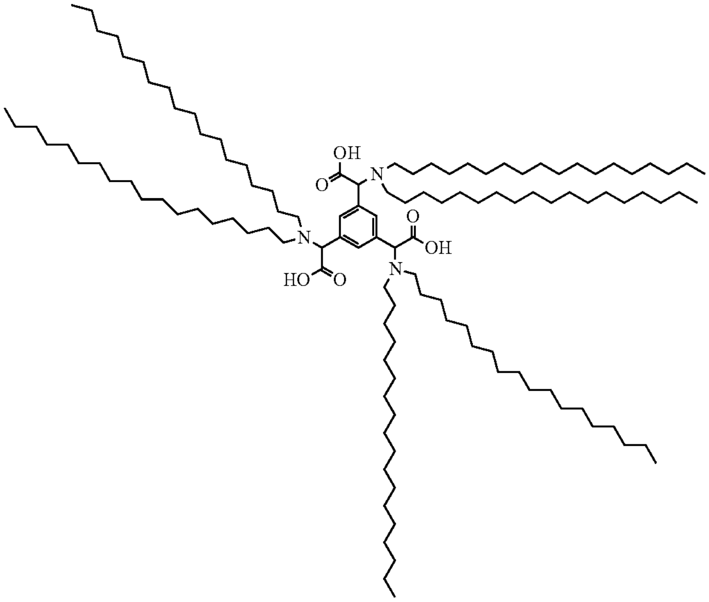
,
(IIIy)
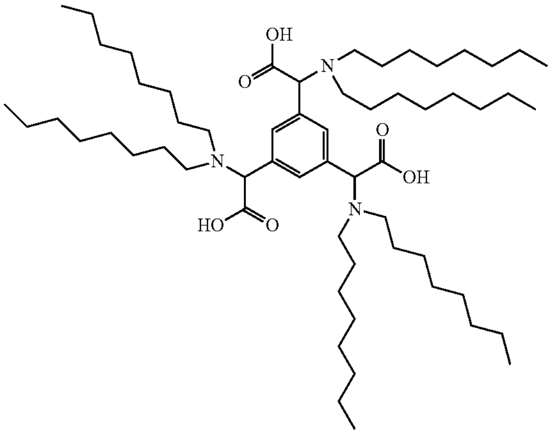
,
(IIIz)
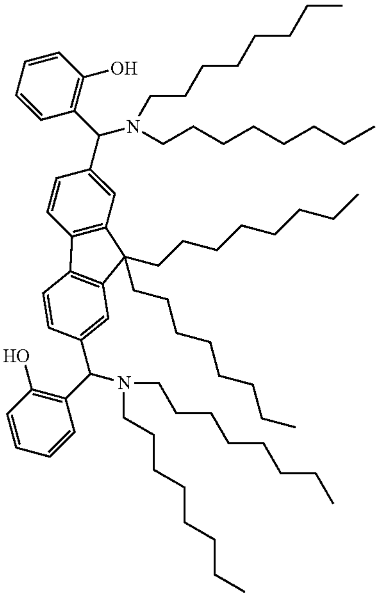
,
(III2)
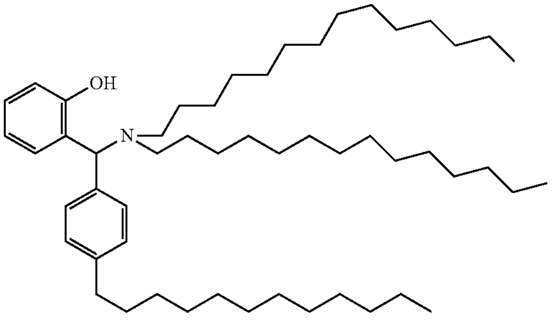
,
(III3)
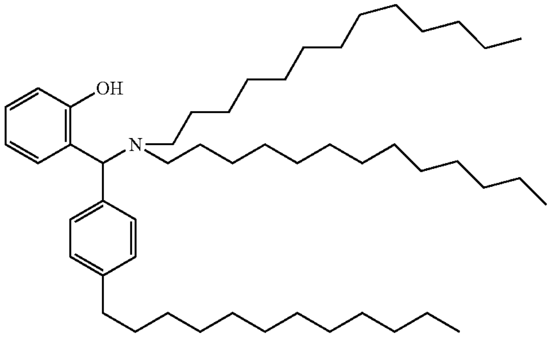
, -continued
(III4)
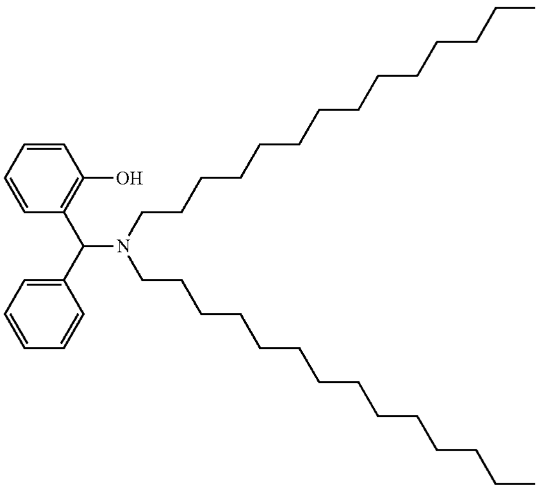
,
(IVa)
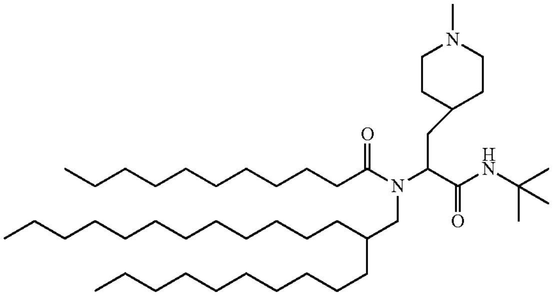
,
(IVb)
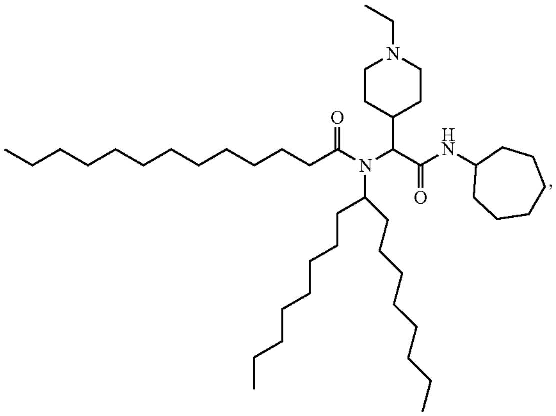
,
(IVc)
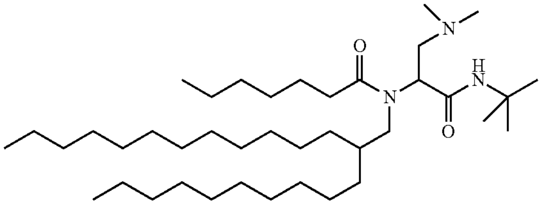
,
(IVd)
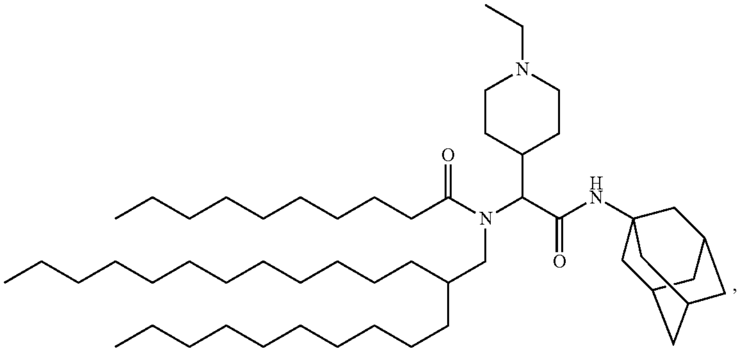
, -continued
(IVe)
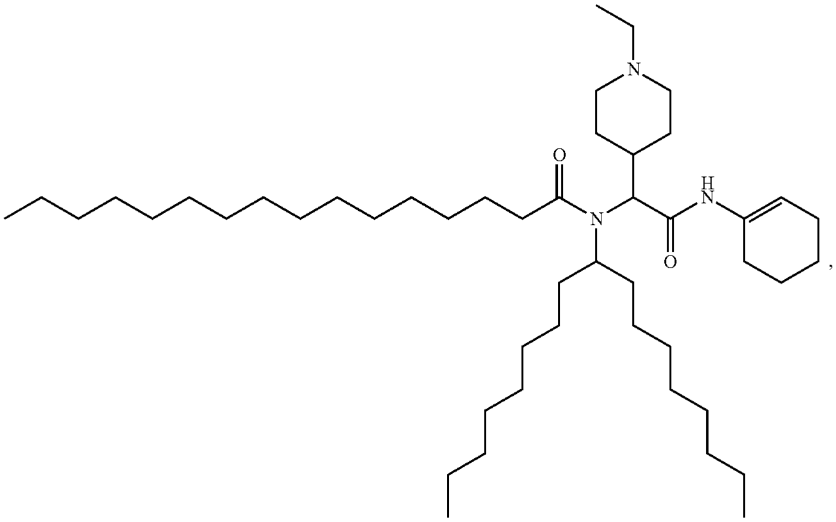
,
(IVf)
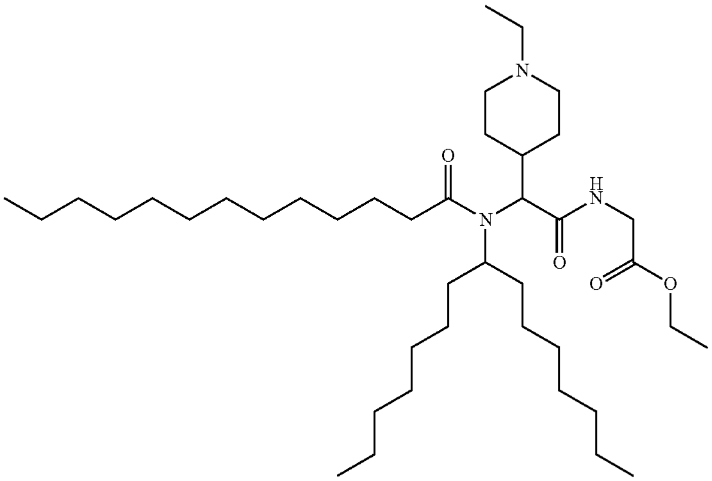
,
(IVg)
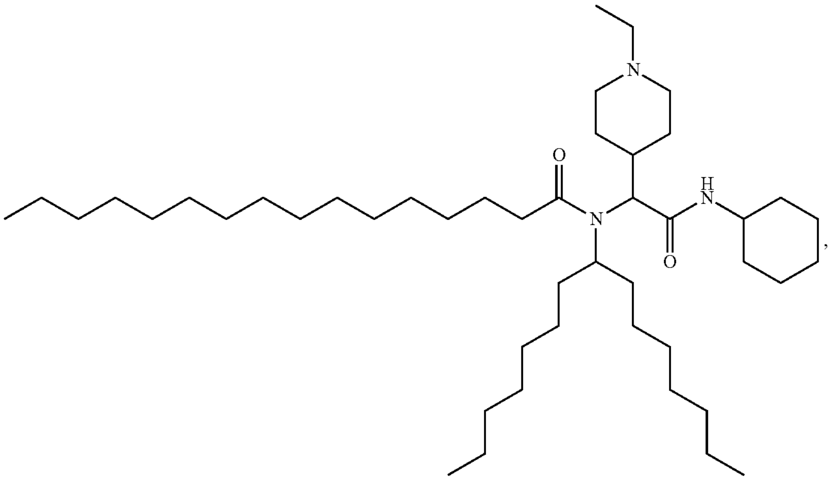
, -continued
(IVh)
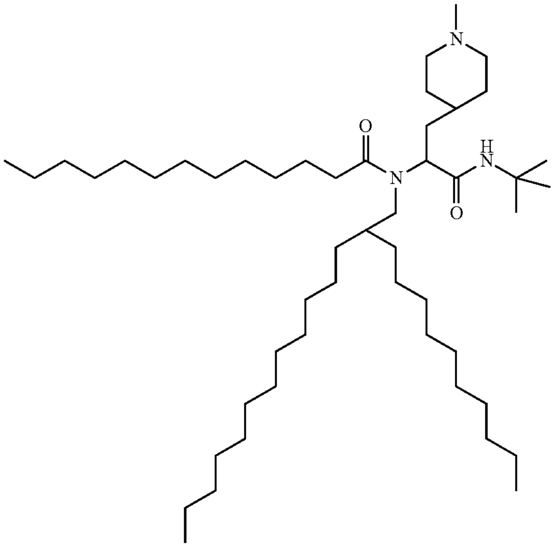
,
(IVi)
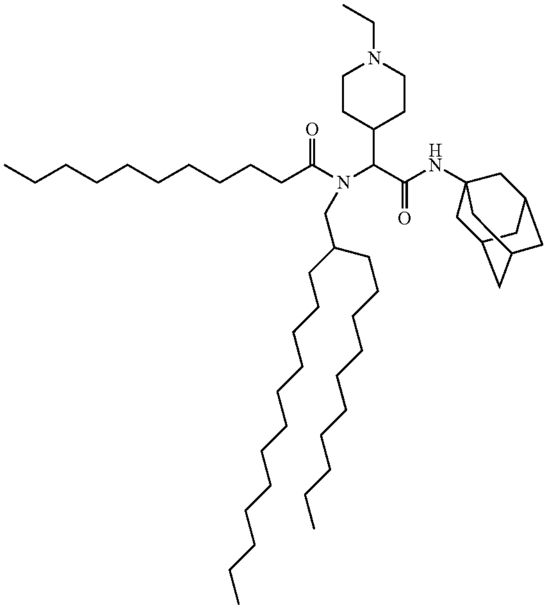
,
(IVj)
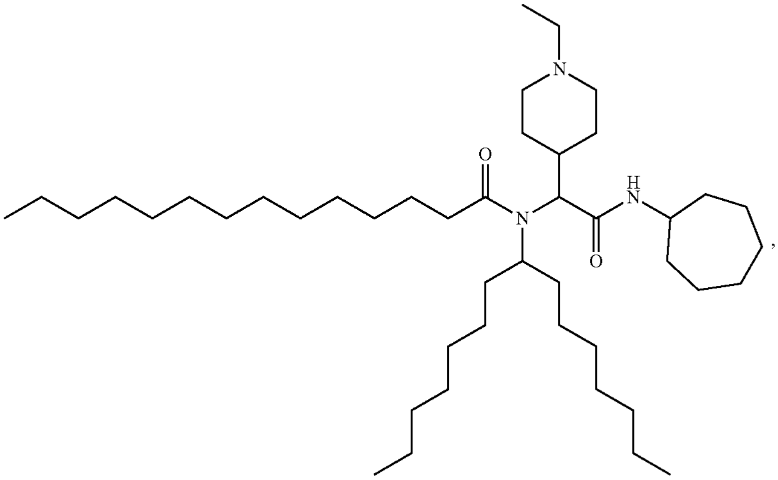
,
(IVk)
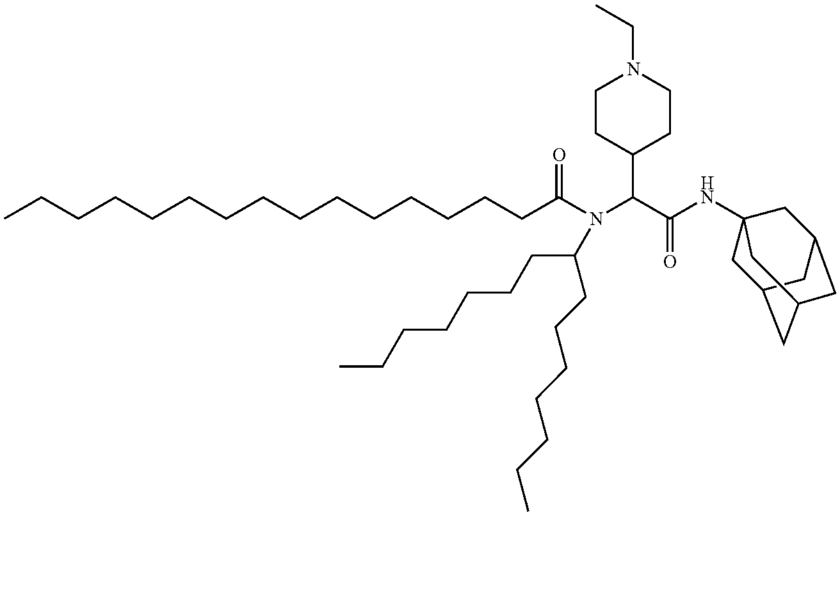
, -continued
(IVl)
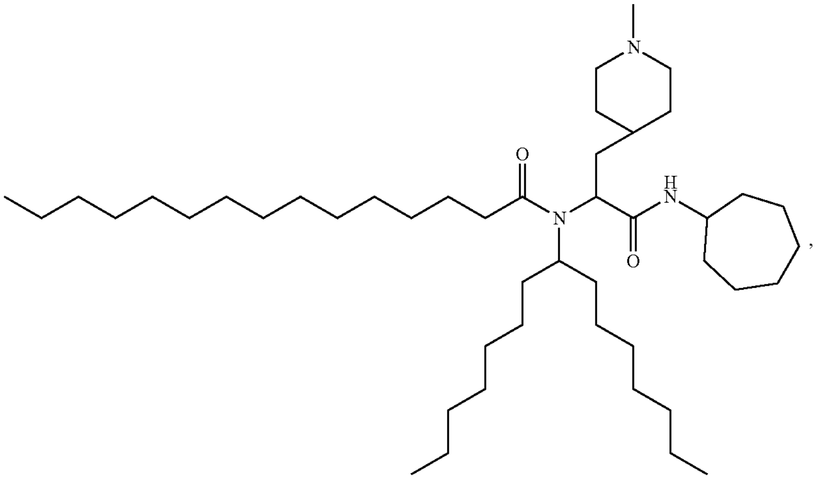
,
(IVm)
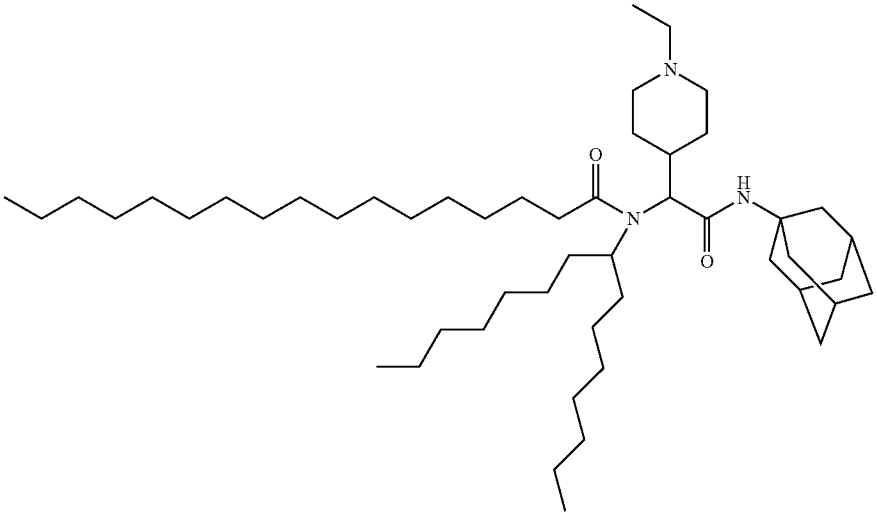
,
(IVn)
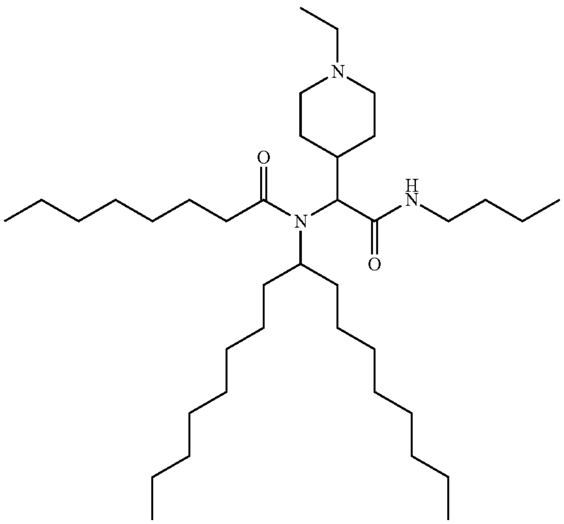
,
(IVo)
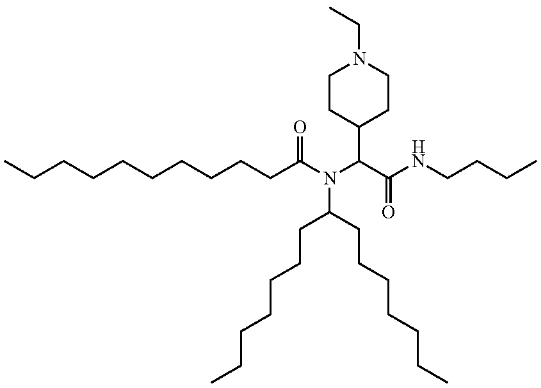
, -continued
(IVp)
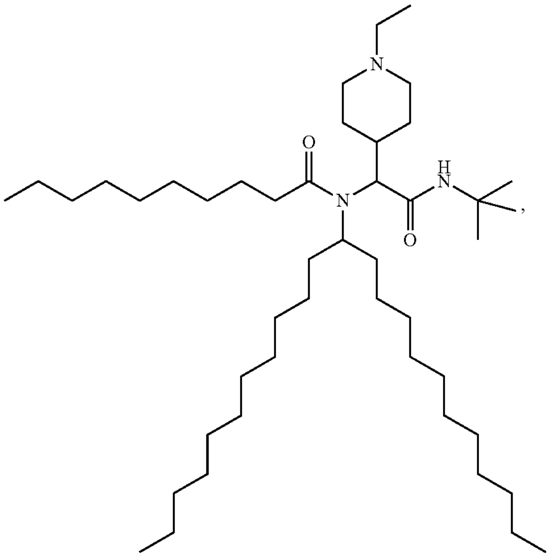
(IVq)
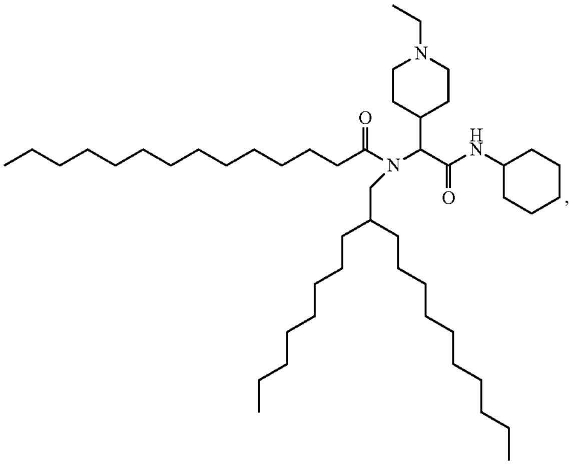
(IVr)
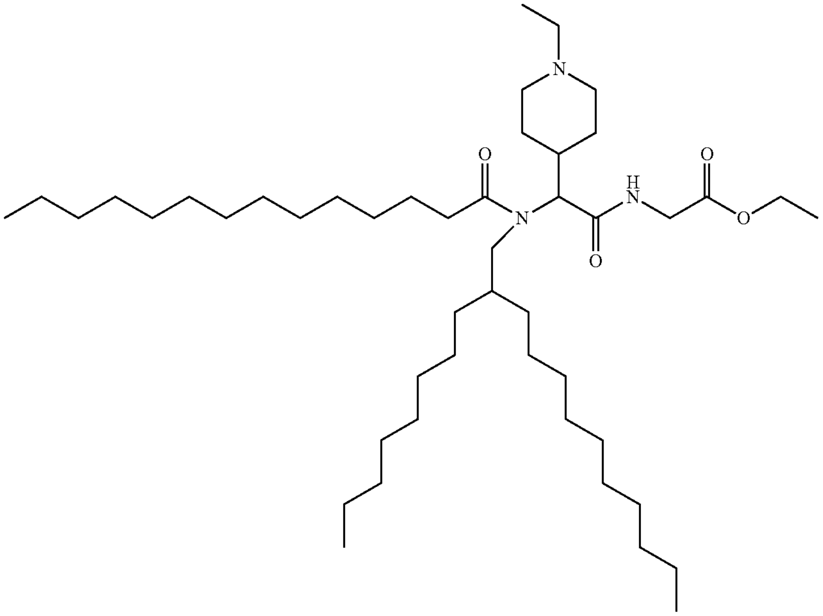
, -continued
(IVs)
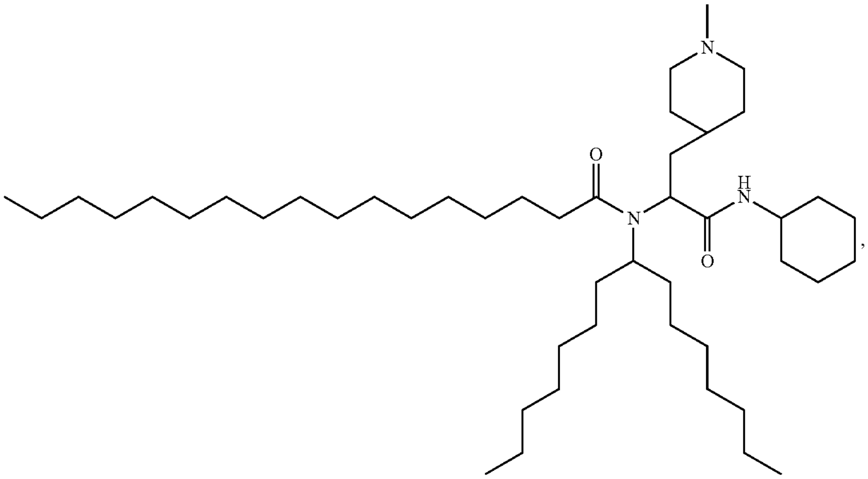
,
(IVt)
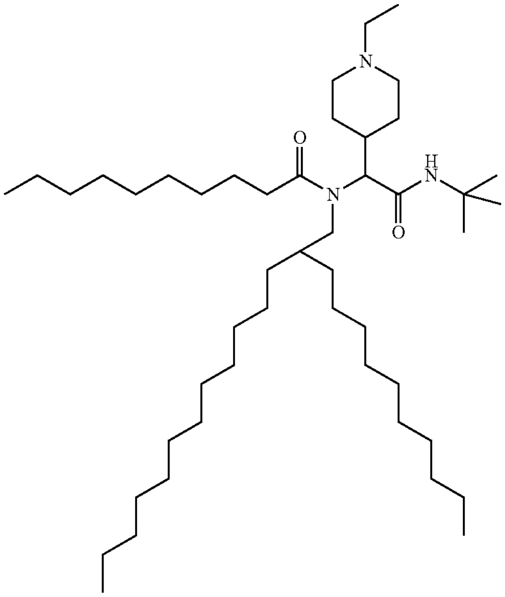
,
(IVu)
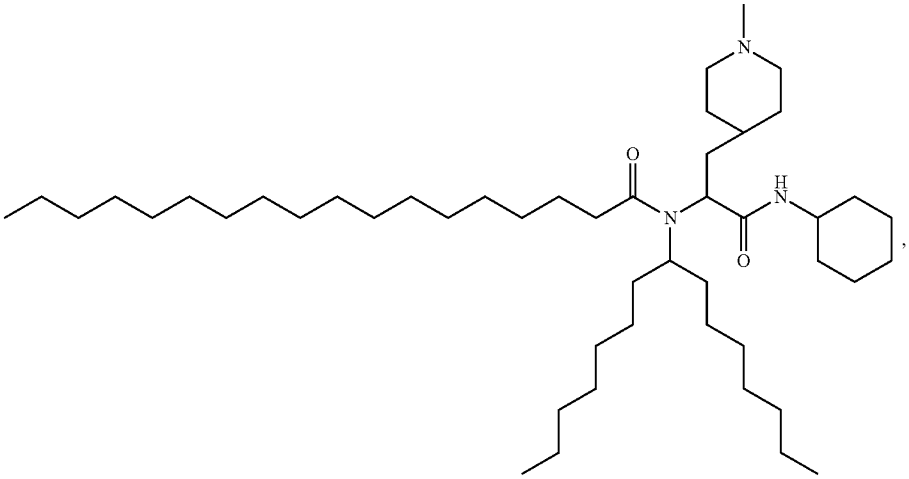
, -continued
(IVv)
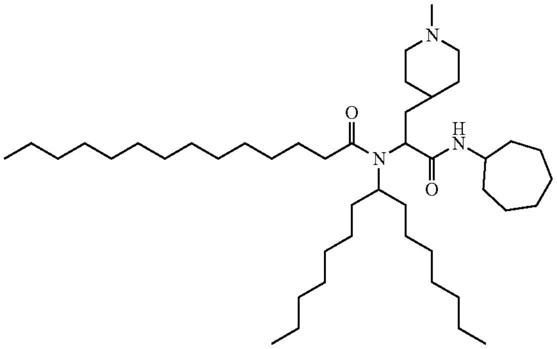
,
(IVw)
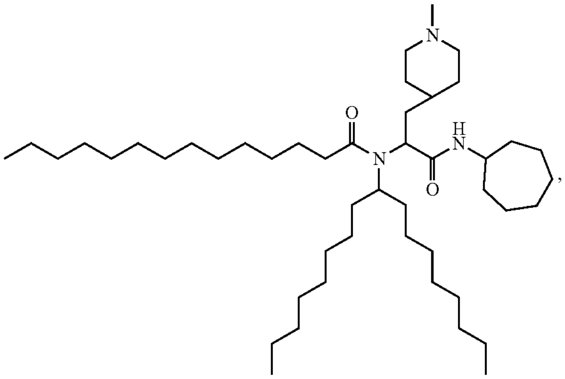
,
(IVx)
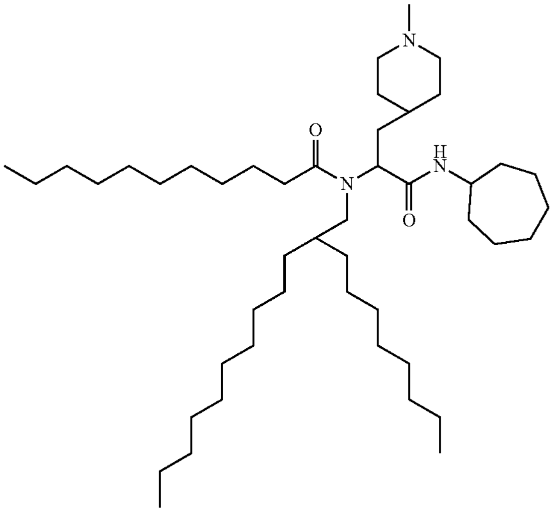
,
(IVy)
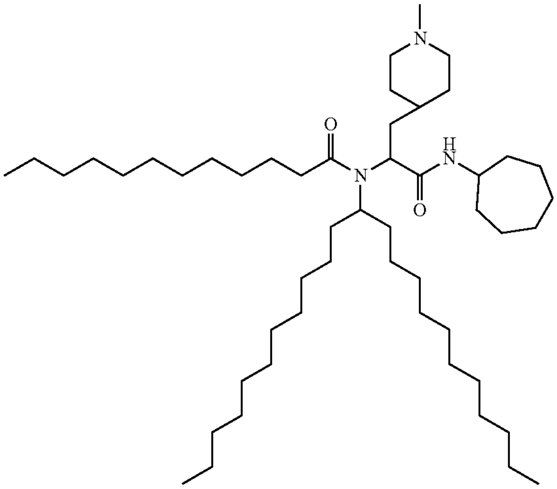
,
(IVz)
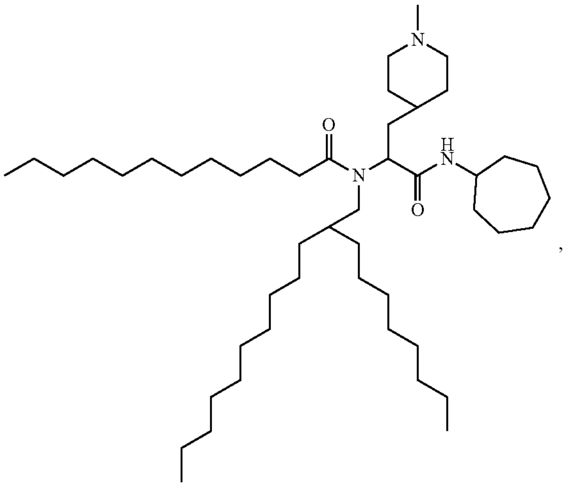
,
(IVaa)
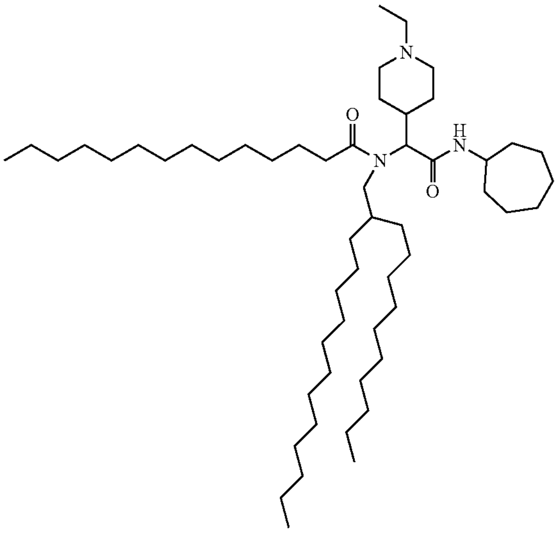
, -continued
(IVAb)
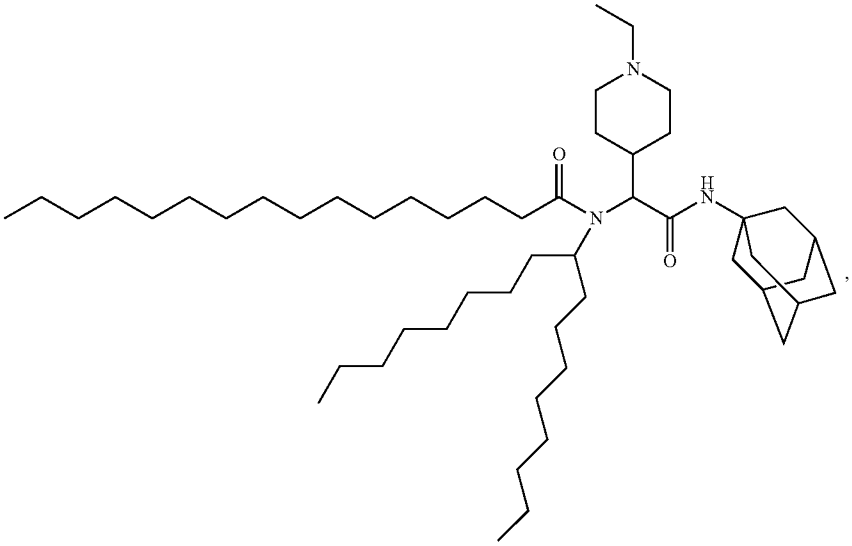
,
(IVac)
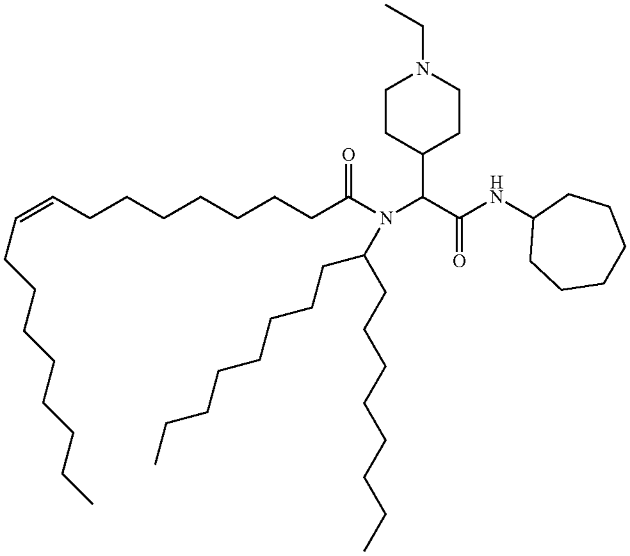
,
(IVad)
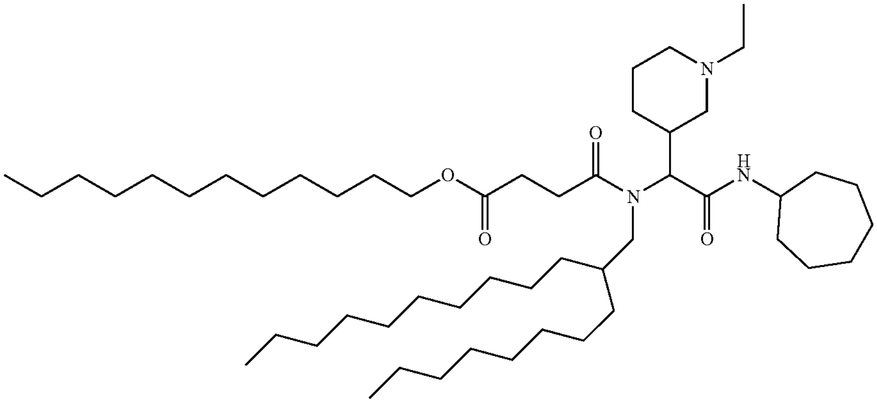
, -continued
(Va)
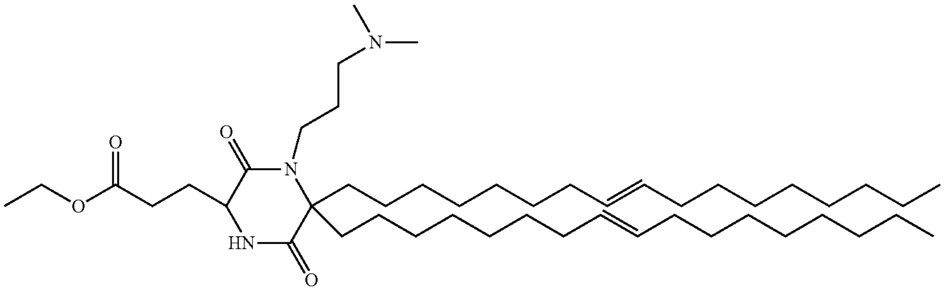
,
(Vb)
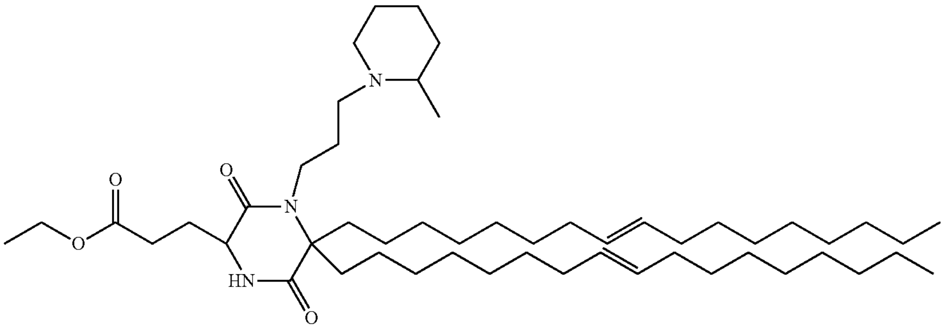
,
(VIa)
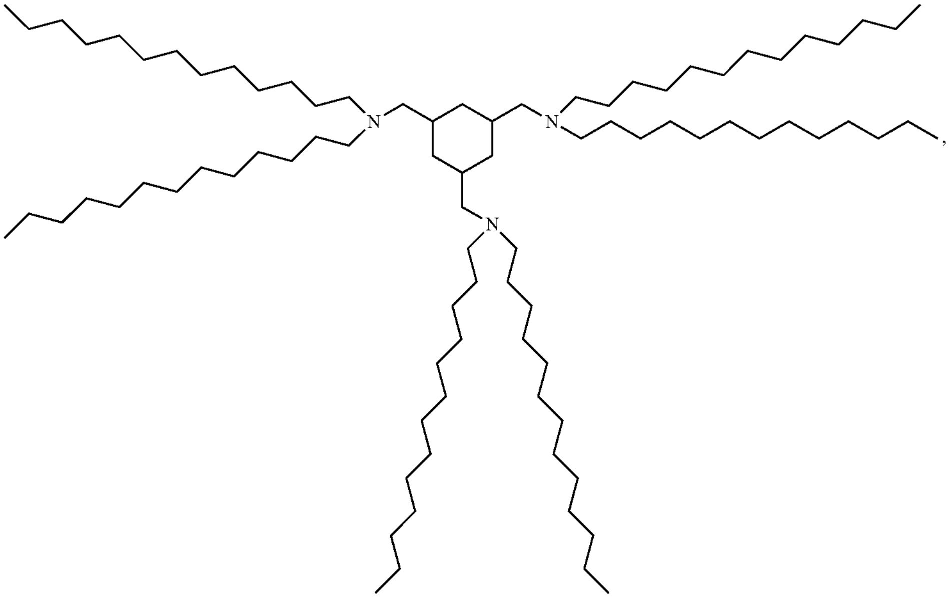
, -continued
(VIb)
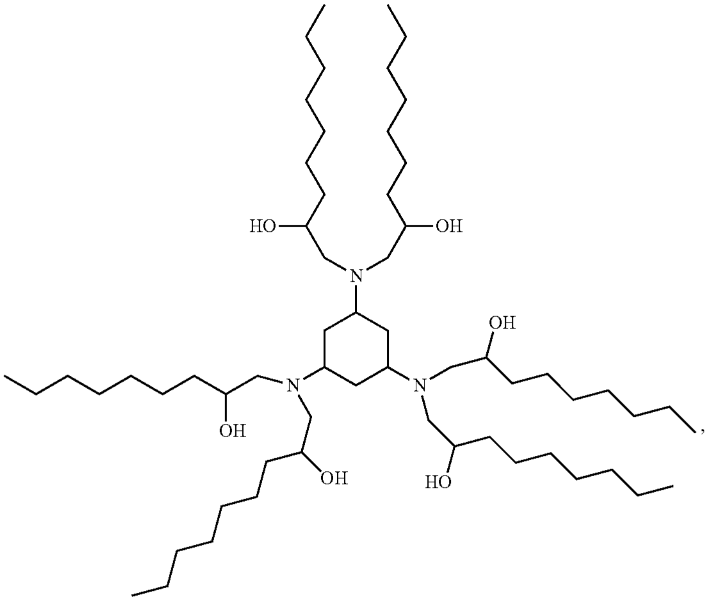
,
(VIc)
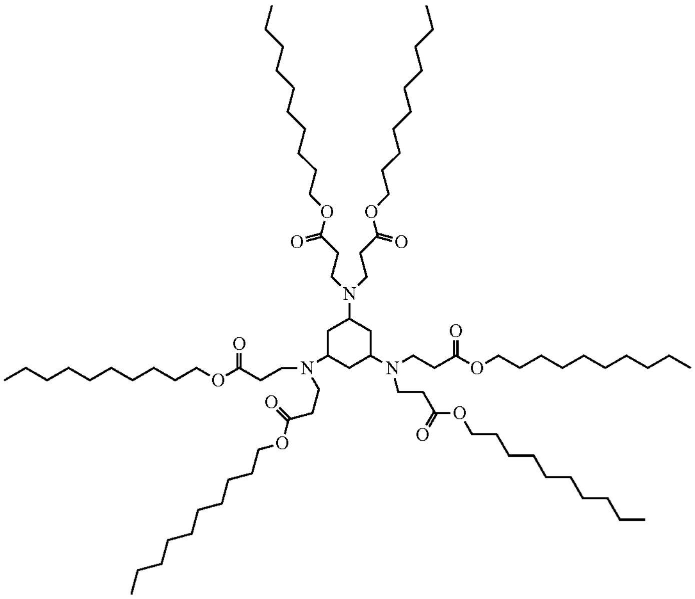
, -continued (VIIa)

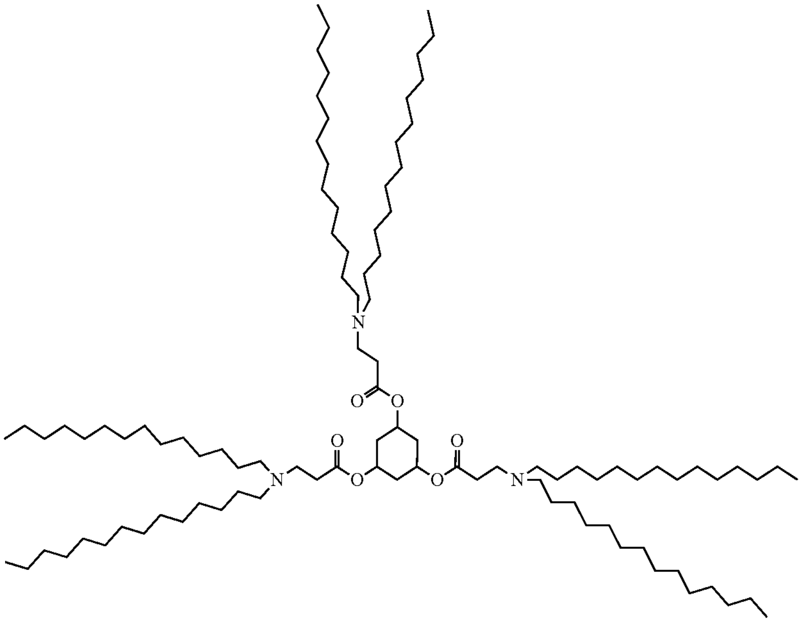

or (VIIb)

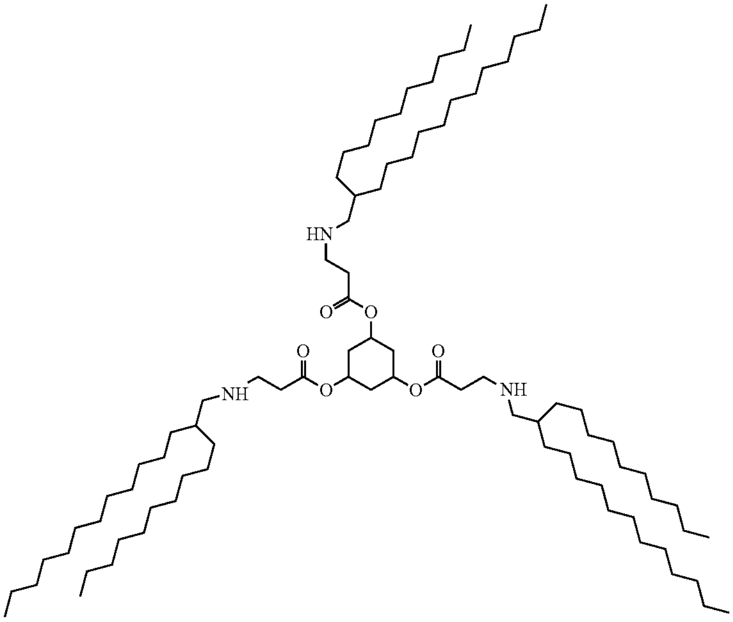

and a biologically active agent, a phospholipid, a steroid, a polyethylene glycol (PEG) lipid, or a combination thereof.

18. The nanoparticle composition of claim 17, comprising a phospholipid selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

19. The nanoparticle composition of claim 17, comprising a steroid selected from the group consisting of cholesterol, fecosterol, sitosterol, ergosterol, campesterol, stigmasterol, brassicasterol, tomatidine, tomatine, ursolic acid, alpha-tocopherol, and mixtures thereof.

20. The nanoparticle composition of claim 17, comprising a PEG lipid selected from the group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof.

21. A method of delivering a biologically active agent to a cell comprising contacting the cell with the nanoparticle composition of claim 17, wherein the nanoparticle composition comprises the biologically active agent, whereby the biologically active agent is delivered to the cell.

* * * * *